(12) United States Patent
Canney et al.

(10) Patent No.: US 12,338,247 B2
(45) Date of Patent: *Jun. 24, 2025

(54) MODULATORS OF THE 5-HYDROXYTRYPTAMINE RECEPTOR 7 AND THEIR METHOD OF USE

(71) Applicants: Temple University-Of The Commonwealth System of Higher Education, Philadelphia, PA (US); Praeventix, LLC, Exton, PA (US)

(72) Inventors: Daniel J. Canney, Ambler, PA (US); Benjamin E. Blass, Eagleville, PA (US); Kevin M. Blattner, Folsom, PA (US); Douglas A. Pippin, Chester Springs, PA (US)

(73) Assignees: Temple University-Of The Commonwealth System of Higher Education, Philadelphia, PA (US); Praeventix, LLC, Exton, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/709,847

(22) Filed: Mar. 31, 2022

(65) Prior Publication Data

US 2023/0112888 A1 Apr. 13, 2023

Related U.S. Application Data

(63) Continuation of application No. 17/015,696, filed on Sep. 9, 2020, now Pat. No. 11,319,327, which is a continuation of application No. 16/349,811, filed as application No. PCT/US2017/061677 on Nov. 15, 2017, now Pat. No. 10,858,368.

(60) Provisional application No. 62/422,344, filed on Nov. 15, 2016.

(51) Int. Cl.
*C07D 491/107* (2006.01)
*C07D 221/00* (2006.01)
*C07D 295/073* (2006.01)
*C07D 309/08* (2006.01)
*C07D 413/10* (2006.01)
*C07D 493/10* (2006.01)
*C07D 513/04* (2006.01)
*C07F 7/10* (2006.01)

(52) U.S. Cl.
CPC ....... *C07D 491/107* (2013.01); *C07D 221/00* (2013.01); *C07D 295/073* (2013.01); *C07D 309/08* (2013.01); *C07D 413/10* (2013.01); *C07D 493/10* (2013.01); *C07D 513/04* (2013.01); *C07F 7/10* (2013.01)

(58) Field of Classification Search
None
See application file for complete search history.

(56) References Cited

U.S. PATENT DOCUMENTS

| | | | |
|---|---|---|---|
| 8,637,263 B1 | 1/2014 | Helton et al. | |
| 10,858,368 B2 | 12/2020 | Canney et al. | |
| 11,319,327 B2 * | 5/2022 | Canney | C07D 519/00 |
| 2004/0229874 A1 | 11/2004 | Bright et al. | |
| 2010/0069390 A1 | 3/2010 | Breder et al. | |
| 2010/0197700 A1 | 8/2010 | Badescu et al. | |
| 2015/0291539 A1 | 10/2015 | Canney et al. | |
| 2016/0016941 A1 | 1/2016 | Canney et al. | |
| 2017/0298037 A1 | 10/2017 | Canney et al. | |
| 2018/0221365 A1 | 8/2018 | Canney et al. | |
| 2019/0367528 A1 | 12/2019 | Canney et al. | |
| 2020/0039985 A1 | 2/2020 | Blass et al. | |
| 2020/0331915 A1 | 10/2020 | Canney et al. | |

FOREIGN PATENT DOCUMENTS

| | | | |
|---|---|---|---|
| EP | 1875899 A1 | 1/2008 | |
| WO | 2005067933 A1 | 7/2005 | |
| WO | 2007019083 A1 | 2/2007 | |
| WO | WO 2012/058769 A1 | 5/2012 | |
| WO | 2013154513 A1 | 10/2013 | |
| WO | 2014164756 A1 | 10/2014 | |
| WO | WO 2016/040554 A1 | 3/2016 | |
| WO | WO 2018/093818 A1 | 5/2018 | |
| WO | WO 2018/175190 A1 | 9/2018 | |
| WO | WO 2019/217890 A1 | 11/2019 | |

OTHER PUBLICATIONS

Bhandare et al., "Modifications to five-substituted 3,3-diethyl-4,5-dihydro-2(3H)-furanones en route to novel muscarinic receptor ligands.", Medicinal Chemistry Research, vol. 20, No. 5, 2011, pp. 558-565, XP055283393 (8 pages).

Bhandare et al., "Bioisosteric Replacement and Related Analogs in the Design, Synthesis and Evaluation of Ligands for Muscarinic Acetylcholine Receptors," Med. Chem., vol. 10, 2014, pp. 361-375 (15 pages).

Chen et al., "Rational Drug Design Leading to the Identification of a Potent 5-HT2C Agonist Lacking 5-HT2B Activity", ACS Medicinal Chemistry Letters, vol. 2, 2011, pp. 929-932 (4 pages).

Cowen et al., "Serotonin revisited", Psychopharmacology, vol. 213, 2011, pp. 167-169 (3 pages).

Gao et al., "Homologation as a lead modification approach en route to a series of lactone-based muscarinic ligands", Medicinal Chemistry Research, vol. 23, No. 2, Aug. 22, 2013, pp. 1023-1030, XP055305444, US, ISSN: 1054-2523, DOI: 10.1007/s00044-013-0692-3 (8 pages).

Hauser et al. "The 5-HT7 receptor as a potential target for treating drug and alcohol abuse", Frontiers in Neuroscience, vol. 8, 2015, pp. 1-9 (9 pages).

(Continued)

*Primary Examiner* — Erich A Leeser
(74) *Attorney, Agent, or Firm* — Proskauer Rose LLP

(57) ABSTRACT

Pharmaceutical compositions of the invention comprise functionalized lactone derivatives having a disease-modifying action in the treatment of diseases associated with dysregulation of 5-hydroxytryptamine receptor 7 activity.

15 Claims, No Drawings

(56) References Cited

OTHER PUBLICATIONS

Hedlund et al., "Functional, molecular and pharmacological advances in 5-HT7 receptor research", Trends in Pharmacological Sciences, vol. 25, No. 9, Sep. 2004, pp. 481-486 (6 pages).

International Preliminary Report on Patentability dated May 21, 2019 for PCT/US2017/061677 (7 pages).

International Search Report dated Feb. 23, 2018 for PCT/US2017/061677 (4 pages).

Kim et al., "Targeted inhibition of serotonin type 7 (5-HT7) receptor function modulates immune responses and reduces the severity of intestinal inflammation", The Journal of Immunology, vol. 190, No. 9, 2013, pp. 4795-4804 (11 pages).

Naumenko et al. "Interplay between Serotonin 5-HT1A and 5-HT7 Receptors in Depressive Disorders", CNS Neuroscience & Therapy, Jun. 30, 2014, pp. 582-590 (9 pages).

Pytliak et al. "Serotonin receptors-from molecular biology to clinical applications", Physiological Research, vol. 60, No. 1, 2011, pp. 15-25 (11 pages).

Vanhoenacker et al. "5-HT7 receptors: current knowledge and future prospects", Trends in pharmacological sciences, vol. 21, No. 2, 2000, pp. 70-77 (8 pages).

Witkin et al., "Constitutive deletion of the serotonin-7 (5-HT7) receptor decreases electrical and chemical seizure thresholds", Epilepsy research, vol. 75, No. 1, 2007, pp. 39-45 (7 pages).

Written Opinion of the International Searching Authority dated Feb. 23, 2018 for PCT/US2017/061677 (6 pages).

Ma, Xinrong et al., "Frondoside A inhibits breast cancer metastasis and antagonizes prostaglandin E receptors EP4 and EP2", Xinrong et al., "Frondoside A inhibits breast cancer metastasis and antagonizes prostaglandin E receptors EP4 and EP2", Breast Cancer Res Treat, vol. 132, No. 3, Apr. 2012, pp. 1001-1008, DOI: 10.1007/s10549-011-1675-z (15 pages).

Silchenko, Alexandra S. et al., Colochirosides B1, B2, B3 and C, Novel Sulfated Triterpene Glycosides from the Sea Cucumber *Colochirus robustus* (Cucumariidae, Dendrochirotida), Natural Product Communications, vol. 10, No. 10, 2015, pp. 1687-1694 DOI: 10.1177/1934578X1501001014, 2015 (8 pages).

\* cited by examiner

MODULATORS OF THE 5-HYDROXYTRYPTAMINE RECEPTOR 7 AND THEIR METHOD OF USE

CROSS REFERENCE TO RELATED APPLICATIONS

This application is a continuation application of U.S. patent application Ser. No. 17/015,696, filed on Sep. 9, 2020, which is a continuation application of U.S. patent application Ser. No. 16/349,811, filed on May 14, 2019, which issued as U.S. Pat. No. 10,858,368 on Dec. 8, 2020, which is a 35 U.S.C. § 371 National Stage Application of International Application No. PCT/US2017/061677, filed Nov. 15, 2017, which claims the benefit of U.S. provisional application No. 62/422,344, filed Nov. 15, 2016, which is are herein incorporated by reference in their entireties.

STATEMENT OF FEDERALLY FUNDED RESEARCH

This invention was made with government support under HHSN-271-2008-00025-C awarded by the National Institutes of Health. The government has certain rights in the invention.

FIELD OF INVENTION

Embodiments of the invention are directed to novel compounds useful as modulators of 5-hydroxytryptamine receptor 7 (5-$HT_7$) activity and their method of use. Embodiments are further directed to a novel chemotype useful for the treatment diseases that are associated with dysregulation of 5-hydroxytryptamine receptor 7 activity.

BACKGROUND OF THE INVENTION

Scrotonin was discovered in the late 1940s and is present in both the peripheral and central nervous systems [Physiol. Res, 60 (2011) 15-25; Psychopharmacology 213 (2011) 167-169]. Scrotonin or 5-hydroxytryptamine (5-HT) is a monoamine neurotransmitter of the indolalkylamine group that acts at synapses of nerve cells. Seven distinct families of scrotonin receptors have been identified and at least 20 subpopulations have been cloned on the basis of sequence similarity, signal transduction coupling and pharmacological characteristics. The seven families of 5-HT receptor are named 5-$HT_1$, 5-$HT_2$, 5-$HT_3$ 5-$HT_4$ 5-$HT_5$ 5-$HT_6$ and 5-$HT_7$ and each of these receptors in turn has subfamilies or subpopulations. The signal transduction mechanism for all seven families have been studied and it is known that activation of 5-$HT_1$ and 5-$HT_5$ receptors causes a decrease in intracellular cAMP whereas activation of 5-$HT_2$, 5-$HT_3$ 5-$HT_4$, 5-$HT_6$, and 5-$HT_7$ results in an increase in intracellular IP3 and DAG. The 5-HT pathways in the brain are important targets for drug development in the area of CNS disorders. The neurotransmitter binds to its a G-protein coupled receptor and is involved in a wide variety of actions including cognition, mood, anxiety, attention, appetite, cardiovascular function, vasoconstriction, sleep (ACS Medicinal Chemistry Letters, 2011, 2, 929-932; Physiological Research, 2011, 60, 15-25), inflammatory bowel disease (IBD), and intestinal inflammation (WO 2012058769, Khan, W. I., et. al. Journal of Immunology, 2013, 190, 4795-4804), epilepsy, seizure disorders (Epilepsy Research (2007) 75, 39), drug addiction, and alcohol addiction (Hauser, S. R. et. al. Frontiers in Neuroscience, 2015, 8, 1-9) among others.

BRIEF SUMMARY OF THE INVENTION

The present invention is directed toward novel 5-hydroxytryptamine receptor 7 (5-HT7) activity modulators, compounds of formula (1),

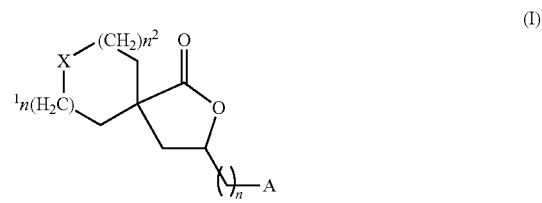

Including hydrates, solvates, pharmaceutically acceptable salts, prodrugs and complexes thereof, wherein:
A is selected from a group consisting of

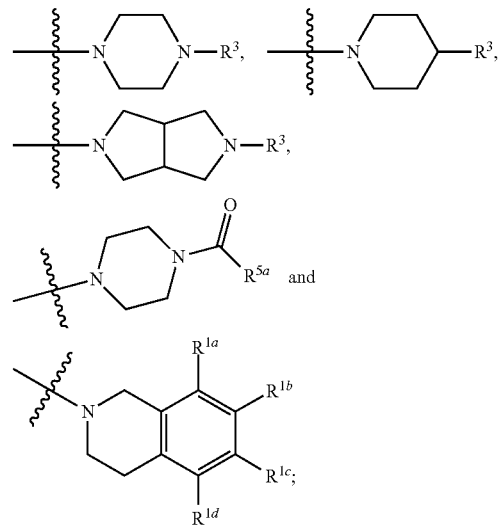

X is selected from the group consisting of O, S, SO, $SO_2$, NR;
$n^1$ is 0, 1, 2:
$n^2$ is 0, 1, 2:
R is selected from the group consisting of H, $C_{1-6}$ linear alkyl, $C_{3-7}$ branched alkyl, $C_{3-7}$ cycloalkyl,

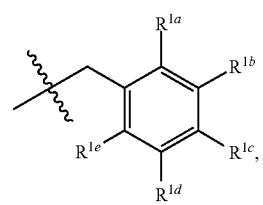

$COR^2$, $CO_2R^{2a}$, $CONR^{2b}R^{2c}$, $SO_2NR^{2b}R^{2c}$, and $SO_2R^{2d}$; $R^{1a}$, $R^{1b}$, $R^{1c}$, $R^{1d}$, and $R^{1e}$ are at each occurrence independently selected from the group consisting of H, OH, $NO_2$, halogen, CN, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, —S($C_{1-6}$ linear alkyl), S($C_{3-7}$ branched alkyl), —S($C_{3-7}$ cycloalkyl), $COR^6$, $CO_2R^7$, $CONR^{8a}R^{8b}$, $SO_2NR^{8a}R^{8b}$, $NR^{9a}R^{9b}$, $NR^{9a}COR^{10}$, $NR^{9a}SO_2R^{11}$, and $NR^{9a}SO_2NR^{12a}R^{12b}$, $R^2$ is selected from the group consisting of H, $C_{1-6}$ linear alkyl, $C_{3-7}$ branched alkyl, and $C_{3-7}$ cycloalkyl:

$R^{2a}$ is selected from the group consisting of $C_{1-6}$ linear alkyl, $C_{3-7}$ branched alkyl, and $C_{3-7}$ cycloalkyl;

$R^{2b}$ is selected from the group consisting of H, $C_{1-6}$ linear alkyl, $C_{3-7}$ branched alkyl, and $C_{3-7}$ cycloalkyl;

$R^{2c}$ is selected from the group consisting of H, $C_{1-6}$ linear alkyl, $C_{3-7}$ branched alkyl, and $C_{3-7}$ cycloalkyl;

$R^{2d}$ is selected from the group consisting of $C_{1-6}$ linear alkyl, $C_{3-7}$ branched alkyl, $C_{3-7}$ cycloalkyl, $C_{1-6}$ linear haloalkyl, $C_{3-7}$ branched haloalkyl, —$(CH_2)_qCN$, —$(CH_2)_qSO_2R^{13}$, —$(CH_2)_qOR^{14}$, $R^3$ is selected from a group consisting of $C_{1-6}$ linear alkyl, $C_{3-7}$ branched alkyl, $C_{1-7}$ cycloalkyl, optionally substituted aryl,

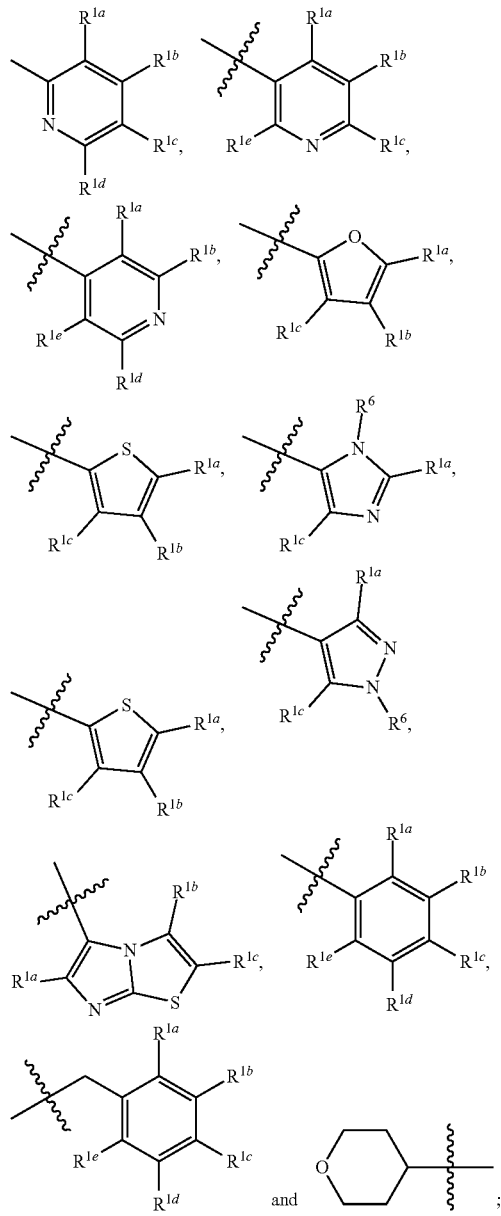
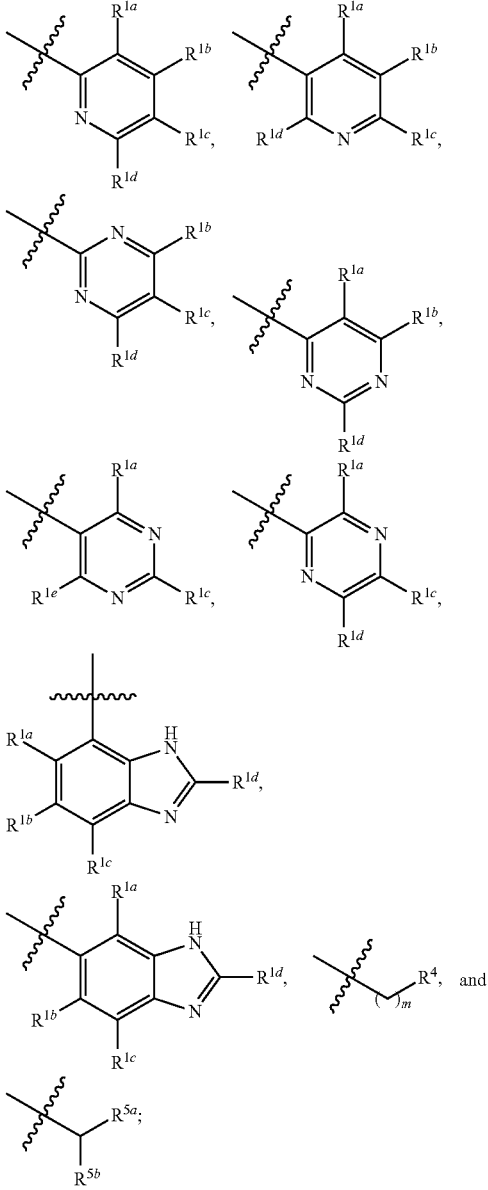

$R^4$ is an optionally substituted aryl:

$R^{5a}$ and $R^{5b}$ are each independently optionally substituted aryl:

$R^6$ is at each occurrence independently selected from the group consisting of H, $C_{1-6}$ linear alkyl, $C_{3-7}$ branched alkyl, and $C_{3-7}$ cycloalkyl:

$R^7$ is at each occurrence independently selected from the group consisting of $C_{1-6}$ linear alkyl, $C_{3-7}$ branched alkyl, and $C_{3-7}$ cycloalkyl;

$R^{8a}$ is at each occurrence independently selected from the group consisting of H, $C_{1-6}$ linear alkyl, $C_{3-7}$ branched alkyl, and $C_{3-7}$ cycloalkyl;

$R^{8b}$ is at each occurrence independently selected from the group consisting of H, $C_{1-6}$ linear alkyl, $C_{3-7}$ branched alkyl, and $C_{3-7}$ cycloalkyl;

$R^{9a}$ is at each occurrence independently selected from the group consisting of H, $C_{1-6}$ linear alkyl, $C_{3-7}$ branched alkyl, and $C_{3-7}$ cycloalkyl;

$R^{9b}$ is at each occurrence independently selected from the group consisting of H, $C_{1-6}$ linear alkyl, $C_{3-7}$ branched alkyl, and $C_{3-7}$ cycloalkyl;

$R^{10}$ is at each occurrence independently selected from the group consisting of H, $C_{1-6}$ linear alkyl, $C_{3-7}$ branched alkyl, and $C_{3-7}$ cycloalkyl:

$R^{11}$ is at each occurrence independently selected from the group consisting of $C_{1-6}$ linear alkyl, $C_{3-7}$ branched alkyl, and $C_{3-7}$ cycloalkyl;

$R^{12a}$ is at each occurrence independently selected from the group consisting of $C_{1-6}$ linear alkyl, $C_{3-7}$ branched alkyl, and $C_{3-7}$ cycloalkyl;

$R^{12b}$ is at each occurrence independently selected from the group consisting of $C_{1-6}$ linear alkyl, $C_{3-7}$ branched alkyl, and $C_{3-7}$ cycloalkyl;

$R^{13}$ is selected from the group consisting of $C_{1-6}$ linear alkyl, $C_{3-7}$ branched alkyl, and $C_{3-7}$ cycloalkyl;

$R^{14}$ is selected from the group consisting of $C_{1-6}$ linear alkyl, $C_{3-7}$ branched alkyl, and $C_{3-7}$ cycloalkyl;

n is 1, 2, or 3;

m is 1 or 2;

and q is 1, 2, or 3:

The present invention further relates to compositions comprising: an effective amount of one or more compounds according to the present invention and an excipient.

The present invention also relates to a method for treating or preventing diseases that involve dysregulation of 5-hydroxytryptamine receptor 7 activity, including, for example, circadian rhythm disorder, depression, schizophrenia, neurogenic inflammation, hypertension, peripheral, vascular diseases, migraine, neuropathic pain, peripheral pain, allodynia, thermoregulation disorder, learning disorder, memory disorder, hippocampal signaling disorder, sleep disorder, attention deficit/hyperactivity disorder, anxiety, avoidant personality disorder, premature ejaculation, eating disorder, premenstrual syndrome, premenstrual dysphonic disorder, seasonal affective disorder, bipolar disorder, inflammatory bowel disease (IBD), intestinal inflammation, epilepsy, seizure disorders, drug addiction, and alcohol addiction said method comprising administering to a subject an effective amount of a compound or composition according to the present invention.

The present invention yet further relates to a method for treating or preventing diseases that involve dysregulation of 5-hydroxytryptamine receptor 7 activity, including, for example, circadian rhythm disorder, depression, schizophrenia, neurogenic inflammation, hypertension, peripheral, vascular diseases, migraine, neuropathic pain, peripheral pain, allodynia, thermoregulation disorder, learning disorder, memory disorder, hippocampal signaling disorder, sleep disorder, attention deficit/hyperactivity disorder, anxiety, avoidant personality disorder, premature ejaculation, eating disorder, premenstrual syndrome, premenstrual dysphonic disorder, seasonal affective disorder, bipolar, disorder inflammatory bowel disease (IBD), intestinal inflammation, epilepsy, seizure disorders, drug addiction, and alcohol addiction wherein said method comprises administering to a subject a composition comprising an effective amount of one or more compounds according to the present invention and an excipient.

The present invention also relates to a method for treating or preventing diseases or conditions associated with circadian rhythm disorder, depression, schizophrenia, neurogenic inflammation, hypertension, peripheral, vascular diseases, migraine, neuropathic pain, peripheral pain, allodynia, thermoregulation disorder, learning disorder, memory disorder, hippocampal signaling disorder, sleep disorder, attention deficit/hyperactivity disorder, anxiety, avoidant personality disorder, premature ejaculation, eating disorder, premenstrual syndrome, premenstrual dysphonic disorder, seasonal affective disorder, bipolar disorder, inflammatory bowel disease (IBD), intestinal inflammation, epilepsy, seizure disorders, drug addiction, alcohol addiction and diseases that involve dysregulation of 5-hydroxytryptamine receptor 7 activity. Said methods comprise administering to a subject an effective amount of a compound or composition according to the present invention.

The present invention yet further relates to a method for treating or preventing diseases or conditions associated with circadian rhythm disorder, depression, schizophrenia, neurogenic inflammation, hypertension, peripheral, vascular diseases, migraine, neuropathic pain, peripheral pain, allodynia, thermoregulation disorder, learning disorder, memory disorder, hippocampal signaling disorder, sleep disorder, attention deficit/hyperactivity disorder, anxiety, avoidant personality disorder, premature ejaculation, eating disorder, premenstrual syndrome, premenstrual dysphonic disorder, seasonal affective disorder, and bipolar disorder, inflammatory bowel disease (IBD), intestinal inflammation, epilepsy, seizure disorders, drug addiction, alcohol addiction and diseases that involve dysregulation of 5-hydroxytryptamine receptor 7 activity, wherein said method comprises administering to a subject a composition comprising an effective amount of one or more compounds according to the present invention and an excipient.

The present invention also relates to a method for treating or preventing diseases or conditions associated with dysregulation of 5-hydroxytryptamine receptor 7 activity. Said methods comprise administering to a subject an effective amount of a compound or composition according to the present invention.

The present invention yet further relates to a method for treating or preventing diseases or conditions associated with dysregulation of 5-hydroxytryptamine receptor 7 activity, wherein said method comprises administering to a subject a composition comprising an effective amount of one or more compounds according to the present invention and an excipient.

The present invention further relates to a process for preparing the 5-hydroxytryptamine receptor 7 activity modulators of the present invention.

These and other objects, features, and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified. All documents cited are in relevant part, incorporated herein by reference; the citation of any document is not to be construed as an admission that it is prior art with respect to the present invention.

DETAILED DESCRIPTION OF THE INVENTION

There is evidence that suggests a role for the $5-HT_7$ receptor in a number of medical disorders, $5-HT_7$ receptor activity modulators are likely to have a beneficial effect on patients suffering from these disorders. The disorders in which $5-HT_7$ dysregulation plays a role and modulation of $5-HT_7$ receptor activity by a therapeutic agent may be a viable approach to therapeutic relief include, but are not limited to, circadian rhythm disorder, depression, schizophrenia, neurogenic inflammation, hypertension, peripheral, vascular diseases, migraine (Vanhoenacker, P. et al. Trends in Pharmacological Sciences, 2000, 21, 2, 70-77), neuropathic pain, peripheral pain, allodynia (EP1875899), thermoregulation disorder, learning disorder, memory disorder, hippocampal signaling disorder, sleep disorder (WO20100197700) attention deficit/hyperactivity disorder (ADHD) (WO20100069390), anxiety, avoidant personality disorder, premature ejaculation, eating disorder, premenstrual syndrome, premenstrual dysphonic disorder, seasonal affective disorder, bipolar disorder (WO20040229874), inflammatory bowel disease (IBD), intestinal inflammation (WO 2012058769, Khan, W. I., et. al. Journal of Immunology, 2013, 190, 4795-4804), epilepsy, seizure disorders (Epilepsy Research (2007) 75, 39), drug addiction, and alcohol addiction (Hauser, S. R. et. al. Frontiers in Neuroscience, 2015, 8, 1-9).

There is a long felt need for new 5-HT₇ modulators that will provide therapeutic relief from patients suffering from diseases associated with dysregulation of 5-hydroxytryptamine receptor 7 activity. The invention addresses the need to identify novel 5-HT7 modulators capable of treating disease associated with dysregulation of 5-hydroxytryptamine receptor 7 activity. The present invention addresses the need to develop new therapeutic agents for the treatment and prevention of circadian rhythm disorder, depression, schizophrenia, neurogenic inflammation, hypertension, peripheral, vascular diseases, migraine, neuropathic pain, peripheral pain, allodynia, thermoregulation disorder, learning disorder, memory disorder, hippocampal signaling disorder, sleep disorder, attention deficit/hyperactivity disorder, anxiety, avoidant personality disorder, premature ejaculation, eating disorder, premenstrual syndrome, premenstrual dysphonic disorder, seasonal affective disorder, bipolar disorder, inflammatory bowel disease (IBD), intestinal inflammation epilepsy, seizure disorders, drug addiction, and alcohol addiction.

The 5-hydroxytryptamine receptor 7 activity modulators of the present invention are capable of treating and preventing diseases associated with dysregulation of 5-hydroxytryptamine receptor 7 activity, for example circadian rhythm disorder, depression, schizophrenia, neurogenic inflammation, hypertension, peripheral, vascular diseases, migraine, neuropathic pain, peripheral pain, allodynia, thermoregulation disorder, learning disorder, memory disorder, hippocampal signaling disorder, sleep disorder, attention deficit/hyperactivity disorder, anxiety, avoidant personality disorder, premature ejaculation, eating disorder, premenstrual syndrome, premenstrual dysphonic disorder, seasonal affective disorder, bipolar disorder, inflammatory bowel disease (IBD), intestinal inflammation, epilepsy, seizure disorders, drug addiction, and alcohol addiction. It has been discovered that the 5-hydroxytryptamine receptor 7 play a role in a number of medical disorders, and therefore, 5-HT₇ receptor activity modulators are likely to have a beneficial effect on patients suffering from these disorders. The disorders in which 5-HT7 dysregulation plays a role and modulation of 5-HT₇ receptor activity by a therapeutic agent may be a viable approach to therapeutic relief include, but are not limited to, circadian rhythm disorder, depression, schizophrenia, neurogenic inflammation, hypertension, peripheral, vascular diseases, migraine (Vanhoenacker, P. et. al. Trends in Pharmacological Sciences, 2000, 21, 2, 70-77), neuropathic pain, peripheral pain, allodynia (EP1875899), thermoregulation disorder, learning disorder, memory disorder, hippocampal signaling disorder, sleep disorder (WO20100197700) attention deficit/hyperactivity disorder (ADHD) (WO20100069390), anxiety, avoidant personality disorder, premature ejaculation, eating disorder, premenstrual syndrome, premenstrual dysphonic disorder, seasonal affective disorder, bipolar disorder (WO20040229874), inflammatory bowel disease (IBD), intestinal inflammation (WO 2012058769) epilepsy, seizure disorders (Epilepsy Research (2007) 75, 39), drug addiction, and alcohol addiction (Hauser, S. R. et. al. Frontiers in Neuroscience, 2015, 8, 1-9).

Without wishing to be limited by theory, it is believed that 5-hydroxytryptamine receptor 7 receptor activity modulators of the present invention can ameliorate, abate, otherwise cause to be controlled, diseases associated with dysregulation of 5-hydroxytryptamine receptor 7 activity. The diseases include, but are not limited to circadian rhythm disorder, depression, schizophrenia, neurogenic inflammation, hypertension, peripheral, vascular diseases, migraine, neuropathic pain, peripheral pain, allodynia, thermoregulation disorder, learning disorder, memory disorder, hippocampal signaling disorder, sleep disorder, attention deficit/hyperactivity disorder, anxiety, avoidant personality disorder, premature ejaculation, eating disorder, premenstrual syndrome, premenstrual dysphonic disorder, seasonal affective disorder, bipolar disorder, inflammatory bowel disease (IBD), intestinal inflammation, epilepsy, seizure disorders, drug addiction, and alcohol addiction.

Throughout the description, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited processing steps.

In the application, where an element or component is said to be included in and/or selected from a list of recited elements or components, it should be understood that the element or component can be any one of the recited elements or components and can be selected from a group consisting of two or more of the recited elements or components.

The use of the singular herein includes the plural (and vice versa) unless specifically stated otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions can be conducted simultaneously.

As used herein, the term "halogen" shall mean chlorine, bromine, fluorine and iodine.

As used herein, unless otherwise noted, "alkyl" and/or "aliphatic" whether used alone or as part of a substituent group refers to straight and branched carbon chains having 1 to 20 carbon atoms or any number within this range, for example 1 to 6 carbon atoms or 1 to 4 carbon atoms. Designated numbers of carbon atoms (e.g. $C_{1-6}$) shall refer independently to the number of carbon atoms in an alkyl moiety or to the alkyl portion of a larger alkyl-containing substituent. Non-limiting examples of alkyl groups include methyl, ethyl, n-propyl, iso-propyl, n-butyl, sec-butyl, iso-butyl, tert-butyl, and the like. Alkyl groups can be optionally substituted. Non-limiting examples of substituted alkyl groups include hydroxymethyl, chloromethyl, trifluoromethyl, aminomethyl, I-chloroethyl, 2-hydroxyethyl, 1,2-difluoroethyl, 3-carboxypropyl, and the like. In substituent groups with multiple alkyl groups such as ($C_{1-6}$ alkyl)$_2$amino, the alkyl groups may be the same or different.

As used herein, the terms "alkenyl" and "alkynyl" groups, whether used alone or as part of a substituent group, refer to straight and branched carbon chains having 2 or more carbon atoms, preferably 2 to 20, wherein an alkenyl chain has at least one double bond in the chain and an alkynyl chain has at least one triple bond in the chain. Alkenyl and alkynyl groups can be optionally substituted. Nonlimiting examples of alkenyl groups include ethenyl, 3-propenyl, 1-propenyl (also 2-methylethenyl), isopropenyl (also 2-methylethen-2-yl), buten-4-yl, and the like. Nonlimiting examples of substituted alkenyl groups include 2-chloroethenyl (also 2-chlorovinyl), 4-hydroxybuten-1-yl, 7-hydroxy-7-methyloct-4-en-2-yl, 7-hydroxy-7-methyloct-3,5-dien-2-yl, and the like. Nonlimiting examples of alkynyl groups include ethynyl, prop-2-ynyl (also propargyl), propyn-1-yl, and 2-methyl-hex-4-yn-1-yl. Nonlimiting examples of substituted alkynyl groups include, 5-hydroxy-5-methylhex-3-ynyl, 6-hydroxy-6-methylhept-3-yn-2-yl, 5-hydroxy-5-ethylhept-3-ynyl, and the like.

As used herein, "cycloalkyl," whether used alone or as part of another group, refers to a non-aromatic carbon-containing ring including cyclized alkyl, alkenyl, and alkynyl groups, e.g., having from 3 to 14 ring carbon atoms, preferably from 3 to 7 or 3 to 6 ring carbon atoms, or even 3 to 4 ring carbon atoms, and optionally containing one or more (e.g., 1, 2, or 3) double or triple bond. Cycloalkyl groups can be monocyclic (e.g., cyclohexyl) or polycyclic (e.g., containing fused, bridged, and/or spiro ring systems), wherein the carbon atoms arc located inside or outside of the ring system. Any suitable ring position of the cycloalkyl group can be covalently linked to the defined chemical structure. Cycloalkyl rings can be optionally substituted. Nonlimiting examples of cycloalkyl groups include: cyclopropyl, 2-methyl-cyclopropyl, cyclopropenyl, cyclobutyl, 2,3-dihydroxycyclobutyl, cyclobutenyl, cyclopentyl, cyclopentenyl, cyclopentadienyl, cyclohexyl, cyclohexenyl, cycloheptyl, cyclooctanyl, decalinyl, 2,5-dimethylcyclopentyl, 3,5-dichlorocyclohexyl, 4-hydroxycyclohexyl, 3,3,5-trimethylcyclohex-1-yl, octahydropentalenyl, octahydro-1H-indenyl, 3a,4,5,6,7,7a-hexahydro-3H-inden-4-yl, decahydroazulenyl; bicyclo[6.2.0]decanyl, decahydronaphthalenyl, and dodecahydro-1H-fluorenyl. The term "cycloalkyl" also includes carbocyclic rings which are bicyclic hydrocarbon rings, non-limiting examples of which include, bicyclo-[2.1.1]hexanyl, bicyclo[2.2.1]heptanyl, bicyclo[3.1.1]heptanyl, 1,3-dimethyl[2.2.1]heptan-2-yl, bicyclo[2.2.2]octanyl, and bicyclo[3.3.3]undecanyl.

"Haloalkyl" is intended to include both branched and straight-chain saturated aliphatic hydrocarbon groups having the specified number of carbon atoms, substituted with 1 or more halogen. Haloalkyl groups include perhaloalkyl groups, wherein all hydrogens of an alkyl group have been replaced with halogens (e.g., —$CF_3$, —$CF_2CF_3$). Haloalkyl groups can optionally be substituted with one or more substituents in addition to halogen. Examples of haloalkyl groups include, but are not limited to, fluoromethyl, dichloroethyl, trifluoromethyl, trichloromethyl, pentafluoroethyl, and pentachloroethyl groups.

The term "alkoxy" refers to the group —O-alkyl, wherein the alkyl group is as defined above. Alkoxy groups optionally may be substituted. The term $C_3$-$C_6$ cyclic alkoxy refers to a ring containing 3 to 6 carbon atoms and at least one oxygen atom (e.g., tetrahydrofuran, tetrahydro-2H-pyran). $C_3$-$C_6$ cyclic alkoxy groups optionally may be substituted.

The term "haloalkoxy" refers to the group —O-haloalkyl, wherein the haloalkyl group is as defined above. Examples of haloalkoxy groups include, but are not limited to, fluoromethoxy, difluoromethoxy, trifluoromethoxy, and pentafluoroethoxyl.

The term "aryl," wherein used alone or as part of another group, is defined herein as an unsaturated, aromatic monocyclic ring of 6 carbon members or to an unsaturated, aromatic polycyclic ring of from 10 to 14 carbon members. Aryl rings can be, for example, phenyl or naphthyl ring each optionally substituted with one or more moieties capable of replacing one or more hydrogen atoms. Non-limiting examples of aryl groups include: phenyl, naphthylen-1-yl, naphthylen-2-yl, 4-fluorophenyl, 2-hydroxyphenyl, 3-methylphenyl, 2-amino-4-fluorophenyl, 2-(N,N-diethylamino) phenyl, 2-cyanophenyl, 2,6-di-tert-butylphenyl, 3-methoxyphenyl, 8-hydroxynaphthylen-2-yl 4,5-dimethoxynaphthylen-1-yl, and 6-cyano-naphthylen-1-yl. Aryl groups also include, for example, phenyl or naphthyl rings fused with one or more saturated or partially saturated carbon rings (e.g., bicyclo[4.2.0]octa-1,3,5-trienyl, indanyl), which can be substituted at one or more carbon atoms of the aromatic and/or saturated or partially saturated rings.

The term "arylalkyl" or "aralkyl" refers to the group -alkyl-aryl, where the alkyl and aryl groups are as defined herein. Aralkyl groups of the present invention arc optionally substituted. Examples of arylalkyl groups include, for example, benzyl, 1-phenylethyl, 2-phenylethyl, 3-phenylpropyl, 2-phenylpropyl, fluorenylmethyl and the like.

The terms "heterocyclic" and/or "heterocycle" and/or "heterocylyl," whether used alone or as part of another group, are defined herein as one or more ring having from 3 to 20 atoms wherein at least one atom in at least one ring is a heteroatom selected from nitrogen (N), oxygen (O), or sulfur (S), and wherein further the ring that includes the heteroatom is non-aromatic. In heterocycle groups that include 2 or more fused rings, the non-heteroatom bearing ring may be aryl (e.g., indolinyl, tetrahydroquinolinyl, chromanyl). Exemplary heterocycle groups have from 3 to 14 ring atoms of which from 1 to 5 are heteroatoms independently selected from nitrogen (N), oxygen (O), or sulfur (S). One or more N or S atoms in a heterocycle group can be oxidized. Heterocycle groups can be optionally substituted.

Non-limiting examples of heterocyclic units having a single ring include: diazirinyl, aziridinyl, urazolyl, azetidinyl, pyrazolidinyl, imidazolidinyl, oxazolidinyl, isoxazolinyl, isoxazolyl, thiazolidinyl, isothiazolyl, isothiazolinyl oxathiazolidinonyl, oxazolidinonyl, hydantoinyl, tetrahydrofuranyl, pyrrolidinyl, morpholinyl, piperazinyl, piperidinyl, dihydropyranyl, tetrahydropyranyl, piperidin-2-onyl (valcrolactam), 2,3,4,5-tetrahydro-1H-azepinyl, 2,3-dihydro-1H-indole, and 1,2,3,4-tetrahydro-quinoline. Non-limiting examples of heterocyclic units having 2 or more rings include: hexahydro-1H-pyrrolizinyl, 3a,4,5,6,7,7a-hexahydro-1H-benzo[d]imidazolyl, 3a,4,5,6,7,7a-hexahydro-1H-indolyl, 1,2,3,4-tetrahydroquinolinyl, chromanyl, isochromanyl, indolinyl, isoindolinyl, and decahydro-1H-cycloocta[b]pyrrolyl.

The term "heteroaryl," whether used alone or as part of another group, is defined herein as one or more rings having from 5 to 20 atoms wherein at least one atom in at least one ring is a heteroatom chosen from nitrogen (N), oxygen (O), or sulfur (S), and wherein further at least one of the rings that includes a heteroatom is aromatic. In heteroaryl groups that include 2 or more fused rings, the non-heteroatom bearing ring may be a carbocycle (e.g., 6,7-Dihydro-5H-cyclopentapyrimidine) or aryl (e.g., benzofuranyl, benzothiophenyl, indolyl). Exemplary heteroaryl groups have from 5 to 14 ring atoms and contain from 1 to 5 ring heteroatoms independently selected from nitrogen (N), oxygen (O), or sulfur (S). One or more N or S atoms in a heteroaryl group can be oxidized. Heteroaryl groups can be substituted. Non-limiting examples of heteroaryl rings containing a single ring include: 1,2,3,4-tetrazolyl, [1,2,3]triazolyl, [1,2,4]triazolyl, triazinyl, thiazolyl, 1H-imidazolyl, oxazolyl, furanyl, thiophenyl, pyrimidinyl, 2-phenylpyrimidinyl, pyridinyl, 3-methylpyridinyl, and 4-dimethylaminopyridinyl. Non-limiting examples of heteroaryl rings containing 2 or more fused rings include: benzofuranyl, benzothiophenyl, benzoxazolyl, benzthiazolyl, benztriazolyl, cinnolinyl, naphthyridinyl, phenanthridinyl, 7H-purinyl, 9H-purinyl, 6-amino-9H-purinyl, 5H-pyrrolo[3,2-d]pyrimidinyl, 7H-pyrrolo[2,3-d]pyrimidinyl, pyrido[2,3-d]pyrimidinyl, 2-phenylbenzo[d]thiazolyl, 1H-indolyl, 4,5,6,7-tetrahydro-1-H-indolyl, quinoxalinyl, 5-methylquinoxalinyl, quinazolinyl, quinolinyl, 8-hydroxy-quinolinyl, 1H-benzo[d]imidazol-2(3H)-onyl, 1H-benzo[d]imidazolyl, and isoquinolinyl.

One non-limiting example of a heteroaryl group as described above is $C_1$-$C_5$ heteroaryl, which has 1 to 5 carbon ring atoms and at least one additional ring atom that is a heteroatom (preferably 1 to 4 additional ring atoms that are heteroatoms) independently selected from nitrogen (N), oxygen (O), or sulfur (S). Examples of $C_1$-$C_5$ heteroaryl include, but arc not limited to, triazinyl, thiazol-2-yl, thiazol-4-yl, imidazol-1-yl, 1H-imidazol-2-yl, 1H-imidazol-4-yl, isoxazolin-5-yl, furan-2-yl, furan-3-yl, thiophen-2-yl, thiophen-4-yl, pyrimidin-2-yl, pyrimidin-4-yl, pyrimidin-5-yl, pyridin-2-yl, pyridin-3-yl, and pyridin-4-yl.

Unless otherwise noted, when two substituents are taken together to form a ring having a specified number of ring atoms (e.g., $R^2$ and $R^3$ taken together with the nitrogen (N) to which they are attached to form a ring having from 3 to 7 ring members), the ring can have carbon atoms and optionally one or more (e.g., 1 to 3) additional heteroatoms independently selected from nitrogen (N), oxygen (O), or sulfur (S). The ring can be saturated or partially saturated and can be optionally substituted.

For the purposed of the present invention fused ring units, as well as spirocyclic rings, bicyclic rings and the like, which comprise a single heteroatom will be considered to belong to the cyclic family corresponding to the heteroatom containing ring. For example, 1,2,3,4-tetrahydroquinoline having the formula:

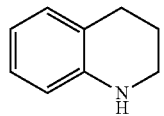

is, for the purposes of the present invention, considered a heterocyclic unit, 6,7-Dihydro-5H-cyclopentapyrimidine having the formula:

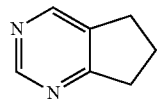

is, for the purposes of the present invention, considered a heteroaryl unit. When a fused ring unit contains heteroatoms in both a saturated and an aryl ring, the aryl ring will predominate and determine the type of category to which the ring is assigned. For example, 1,2,3,4-tetrahydro-[1,8]naphthyridine having the formula:

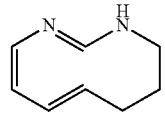

is, for the purposes of the present invention, considered a heteroaryl unit.

Whenever a term or either of their prefix roots appear in a name of a substituent the name is to be interpreted as including those limitations provided herein. For example, whenever the term "alkyl" or "aryl" or either of their prefix roots appear in a name of a substituent (e.g., arylalkyl, alkylamino) the name is to be interpreted as including those limitations given above for "alkyl" and "aryl."

The term "substituted" is used throughout the specification. The term "substituted" is defined herein as a moiety, whether acyclic or cyclic, which has one or more hydrogen atoms replaced by a substituent or several (e.g., 1 to 10) substituents as defined herein below. The substituents are capable of replacing one or two hydrogen atoms of a single moiety at a time. In addition, these substituents can replace two hydrogen atoms on two adjacent carbons to form said substituent, new moiety or unit. For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. The term "substituted" is used throughout the present specification to indicate that a moiety can have one or more of the hydrogen atoms replaced by a substituent. When a moiety is described as "substituted" any number of the hydrogen atoms may be replaced. For example, difluoromethyl is a substituted $C_1$ alkyl; trifluoromethyl is a substituted $C_1$ alkyl; 4-hydroxyphenyl is a substituted aromatic ring; (N,N-dimethyl-5-amino)octanyl is a substituted $C_5$ alkyl; 3-guanidinopropyl is a substituted $C_3$ alkyl; and 2-carboxypyridinyl is a substituted heteroaryl.

The variable groups defined herein, e.g., alkyl, alkenyl, alkynyl, cycloalkyl, alkoxy, aryloxy, aryl, heterocycle and heteroaryl groups defined herein, whether used alone or as part of another group, can be optionally substituted. Optionally substituted groups will be so indicated.

The following are non-limiting examples of substituents which can substitute for hydrogen atoms on a moiety: halogen (chlorine (Cl), bromine (Br), fluorine (F) and iodine (I), —CN, —NO$_2$, oxo (=O), —OR$^{15}$, —SR$^{15}$, —N(R$^{15}$)$_2$, —NR$^{15}$C(O)R$^{15}$, —SO$_2$R$^{15}$, —SO$_2$OR$^{15}$, —SO$_2$N(R$^{15}$)$_2$, —C(O)R$^{15}$, —C(O)OR$^{15}$, —C(O)N(R$^{15}$)$_2$, $C_{3-6}$ alkyl, $C_{1-6}$ haloalkyl, $C_{1-6}$ alkoxy, $C_{2-8}$ alkenyl, $C_{2-8}$ alkynyl, $C_{2-8}$ cycloalkyl, aryl, heterocycle, or heteroaryl, wherein each of the alkyl, haloalkyl, alkenyl, alkynyl, alkoxy, cycloalkyl, aryl, heterocycle, and heteroaryl groups is optionally substituted with 1-10 (e.g., 1-6 or 1-4) groups selected independently from halogen, —CN, —NO$_2$, oxo, and R$^{15}$; wherein R$^{15}$, at each occurrence, independently is hydrogen, —OR$^{16}$, —SR$^{16}$, —C(O)R$^{16}$, —C(O)OR$^{16}$, —C(O)N(R$^{16}$)$_2$, —SO$_2$R$^{16}$, —S(O)$_2$OR$^{16}$, —N(R$^{16}$)$_2$, —NR$^{16}$C(O)R$^{16}$, $C_{1-6}$ alkyl, $C_{1-6}$ haloalkyl, $C_{2-8}$ alkenyl, $C_{2-8}$ alkynyl, cycloalkyl (e.g., C cycloalkyl), aryl, heterocycle, or heteroaryl, or two R$^{15}$ units taken together with the atom(s) to which they are bound form an optionally substituted carbocycle or heterocycle wherein said carbocycle or heterocycle has 3 to 7 ring atoms; wherein $R^{16}$, at each occurrence, independently is hydrogen, $C_{1-6}$ alkyl, $C_{1-6}$ haloalkyl, $C_{2-8}$ alkenyl, $C_{2-8}$ alkynyl, cycloalkyl (e.g., $C_{3-6}$ cycloalkyl), aryl, heterocycle, or heteroaryl, or two $R^{16}$ units taken together with the atom(s) to which they are bound form an optionally substituted carbocycle or heterocycle wherein said carbocycle or heterocycle preferably has 3 to 7 ring atoms.

In some embodiments, the substituents are selected from
i) —$OR^{17}$; for example, —OH, —$OCH_3$, —$OCH_2CH_3$, —$OCH_2CH_2CH_3$;
ii) —$C(O)R^{17}$; for example, —$COCH_3$, —$COCH_2CH_3$, —$COCH_2CH_2CH_3$;
iii) —$C(O)OR^1$, for example, —$CO_2CH$, —$CO_2CH_2CH_3$, —$CO_2CH_2CH_2CH_3$;
iv) —$C(O)N(R^{17})_2$; for example, —$CONH_2$, —$CONHCH_3$, —$CON(CH_3)_2$;
v) —$N(R^{17})_2$; for example, —$NH_2$, —$NHCH_3$, —$N(CH_3)_2$, —$NH(CH_2CH_3)$;
vi) halogen: —F, —Cl, —Br, and —I;
vii) —$CH_eX_g$; wherein X is halogen, in is from 0 to 2, e+g=3; for example, —$CH_2F$, —$CHF_2$, —$CF_3$. —$CCl_3$, or —$CBr_3$;
viii) —$SO_2R^{17}$; for example, —$SO_2H$: —$SO_2CH_3$; —$SO_2C_6H_5$;
ix) $C_1$-$C_6$ linear, branched, or cyclic alkyl;
x) Cyano
xi) Nitro;
xii) $N(R^{17})C(O)R^{17}$;
xiii) Oxo (=O);
xiv) Heterocycle: and
xv) Heteroaryl.

wherein each $R^{17}$ is independently hydrogen, optionally substituted $C_1$-$C_6$ linear or branched alkyl (e.g., optionally substituted $C_1$-$C_4$ linear or branched alkyl), or optionally substituted $C_3$-$C_6$cycloalkyl (e.g optionally substituted $C_3$-$C_4$ cycloalkyl); or two $R^{17}$ units can be taken together to form a ring comprising 3-7 ring atoms. In certain aspects, each $R^{17}$ is independently hydrogen, $C_1$-$C_6$ linear or branched alkyl optionally substituted with halogen or $C_1$-$C_6$ cycloalkyl or $C_3$-$C_6$ cycloalkyl.

At various places in the present specification, substituents of compounds are disclosed in groups or in ranges. It is specifically intended that the description include each and every individual subcombination of the members of such groups and ranges. For example, the term "$C_{1-6}$ alkyl" is specifically intended to individually disclose $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$, alkyl.

For the purposes of the present invention the terms "compound," "analog," and "composition of matter" stand equally well for the 5-hydroxytryptamine receptor 7 activity modulators described herein, including all enantiomeric forms, diasteromeric forms, salts, and the like, and the terms "compound," "analog," and "composition of matter" are used interchangeably throughout the present specification.

Compounds described herein can contain an asymmetric atom (also referred as a chiral center), and some of the compounds can contain one or more asymmetric atoms or centers, which can thus give rise to optical isomers (enantiomers) and diastereomers. The present teachings and compounds disclosed herein include such enantiomers and diastereomers, as well as the racemic and resolved, enantiomerically pure R and S stereoisomers, as well as other mixtures of the R and S stereoisomers and pharmaceutically acceptable salts thereof. Optical isomers can be obtained in pure form by standard procedures known to those skilled in the art, which include, but are not limited to, diastereomeric salt fonnation, kinetic resolution, and asymmetric synthesis. The present teachings also encompass cis and trans isomers of compounds containing alkenyl moieties (e.g., alkenes and imines). It is also understood that the present teachings encompass all possible rcgioisomcrs, and mixtures thereof, which can be obtained in pure form by standard separation procedures known to those skilled in the art, and include, but are not limited to, column chromatography, thin-layer chromatography, and high-performance liquid chromatography.

Pharmaceutically acceptable salts of compounds of the present teachings, which can have an acidic moiety, can be formed using organic and inorganic bases. Both mono and polyanionic salts are contemplated, depending on the number of acidic hydrogens available for deprotonation. Suitable salts formed with bases include metal salts, such as alkali metal or alkaline earth metal salts, for example sodium, potassium, or magnesium salts: ammonia salts and organic amine salts, such as those formed with morpholine, thiomorpholine, piperidine, pyrrolidine, a mono-, di- or tri-lower alkylamine (e.g., ethyl-tert-butyl-, diethyl-, diisopropyl-, triethyl-, tributyl- or dimethylpropylamine), or a mono-, di-, or trihydroxy lower alkylamine (e.g., mono-, di- or triethanolamine). Specific non-limiting examples of inorganic bases include $NaHCO_3$, $Na_2CO_3$, $KHCO_3$, $K_2CO_3$, $Cs_2CO_3$, LiOH, NaOH, KOH, $NaH_2PO_4$, $Na_2HPO_4$, and $Na_3PO_4$. Internal salts also can be formed. Similarly, when a compound disclosed herein contains a basic moiety, salts can be formed using organic and inorganic acids. For example, salts can be formed from the following acids: acetic, propionic, lactic, benzenesulfonic, benzoic, camphorsulfonic, citric, tartaric, succinic, dichloroacetic, ethenesulfonic, formic, fumaric, gluconic, glutamic, hippuric, hydrobromic, hydrochloric, isethionic, lactic, maleic, malic, malonic, mandelic, methanesulfonic, mucic, naphthalenesulfonic, nitric, oxalic, pamoic, pantothenic, phosphoric, phthalic, propionic, succinic, sulfuric, tartaric, toluenesulfonic, and camphorsulfonic as well as other known pharmaceutically acceptable acids.

When any variable occurs more than one time in any constituent or in any formula, its definition in each occurrence is independent of its definition at every other occurrence (e.g., in $N(R^9)_2$, each $R^9$ may be the same or different than the other). Combinations of substituents and/or variables are permissible only if such combinations result in stable compounds.

The terms "treat" and "treating" and "treatment" as used herein, refer to partially or completely alleviating, inhibiting, ameliorating and/or relieving a condition from which a patient is suspected to suffer.

As used herein, "therapeutically effective" and "effective dose" refer to a substance or an amount that elicits a desirable biological activity or effect.

Except when noted, the terms "subject" or "patient" are used interchangeably and refer to mammals such as human patients and non-human primates, as well as experimental animals such as rabbits, rats, and mice, and other animals. Accordingly, the term "subject" or "patient" as used herein means any mammalian patient or subject to which the compounds of the invention can be administered. In an exemplary embodiment of the present invention, to identify subject patients for treatment according to the methods of the invention, accepted screening methods are employed to determine risk factors associated with a targeted or suspected disease or condition or to determine the status of an existing disease or condition in a subject. These screening methods include, for example, conventional work-ups to determine risk factors that may be associated with the targeted or suspected disease or condition. These and other routine methods allow the clinician to select patients in need of therapy using the methods and compounds of the present invention.

The 5-Hydroxytryptamine Receptor 7 Activity Modulators

The 5-hydroxytryptamine receptor 7 activity modulators of the present invention include all enantiomeric and diastereomeric forms alts thereof having the formula

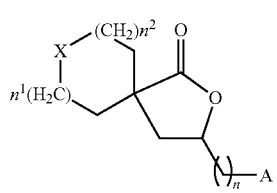

(I)

Including hydrates, solvates, pharmaceutically acceptable salts, prodrugs and complexes thereof, wherein:
A is selected from a group consisting of

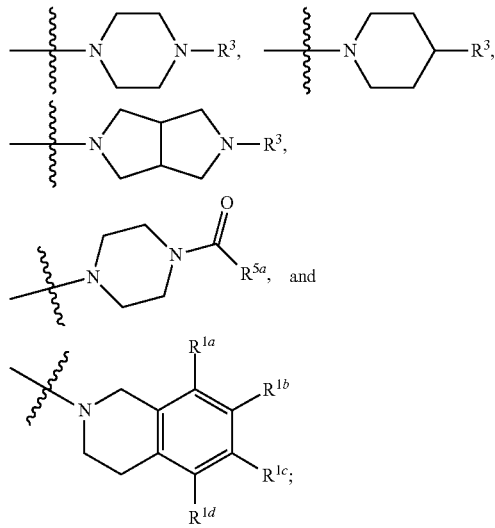

X is selected from the group consisting of O, S, SO, SO$_2$, NR:
$n^1$ is 0, 1, 2;
$n^2$ is 0, 1, 2:
R is selected from the group consisting of H, C$_{1-6}$ linear alkyl, C$_{3-7}$ branched alkyl, C$_{3-7}$ cycloalkyl,

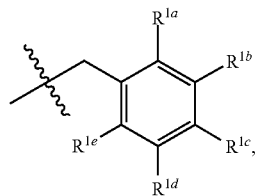

COR$^2$, CO$_2$R$^{2a}$, CONR$^{2b}$R$^{2c}$, SO$_2$NR$^{2b}$R$^{2c}$, and SO$_2$R$^{2d}$:
R$^{1a}$, R$^{1b}$, R$^{1c}$, R$^{1d}$, and R$^{1e}$ are at each occurrence independently selected from the group consisting of H, OH, NO$_2$, halogen, CN, C$_{1-6}$ linear alkyl, C$_{3-7}$ branched alkyl, C$_{1-7}$ cycloalkyl, C$_{1-6}$ linear alkoxy, C$_{1-7}$ branched alkoxy, C$_{3-7}$ cycloalkoxy, C$_{1-6}$ linear haloalkyl, C$_{1-7}$ branched haloalkyl, C$_{1-6}$ linear haloalkoxy, —S(C$_{1-6}$ linear alkyl), S(C$_{3-7}$ branched alkyl), —S(C$_{3-7}$ cycloalkyl), COR$^6$, CO$_2$R$^7$, CONR$^{8a}$R$^{8b}$, SO$_2$NR$^{8a}$R$^{8b}$, NR$^{9a}$R$^{9b}$, NR$^{9a}$COR$^{10}$, NR$^{9a}$SO$_2$R$^{11}$, and NR$^{9a}$SO$_2$NR$^{12a}$R$^{12b}$;

R$^2$ is selected from the group consisting of H, C$_{1-6}$ linear alkyl, C$_{3-7}$ branched alkyl, and C$_{3-7}$ cycloalkyl;

R$^{2a}$ is selected from the group consisting of C$_{1-6}$ linear alkyl, C$_{3-7}$ branched alkyl, and C$_{3-7}$ cycloalkyl;

R$^{2b}$ is selected from the group consisting of H, C$_{1-6}$ linear alkyl, C$_{3-7}$ branched alkyl, and C$_{1-7}$ cycloalkyl;

R$^{2c}$ is selected from the group consisting of H, C$_{1-6}$ linear alkyl, C$_{3-7}$ branched alkyl, and C$_{3-7}$ cycloalkyl;

R$^{2d}$ is selected from the group consisting of C$_{1-6}$ linear alkyl, C$_{3-7}$ branched alkyl, C$_{3-7}$ cycloalkyl, C$_{1-6}$ linear haloalkyl, C$_{3-7}$ branched haloalkyl, —(CH$_2$)$_q$CN, —(CH$_2$)$_q$SO$_2$R$^{13}$, —(CH$_2$)$_q$OR$^{14}$,

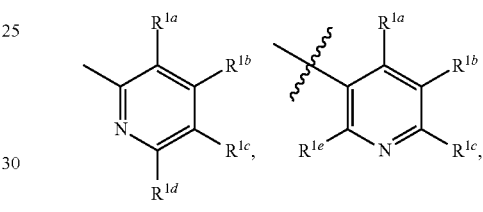

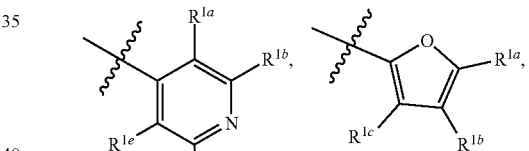

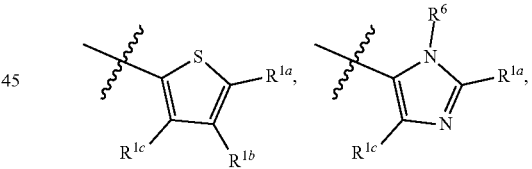

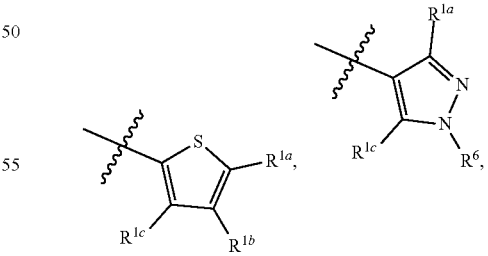

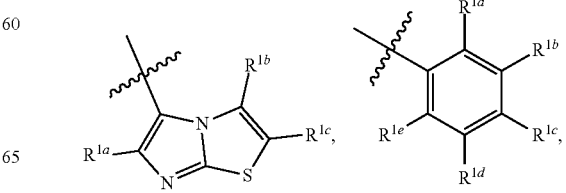

-continued

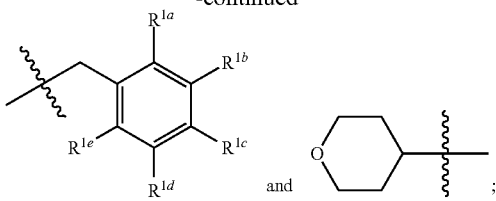

R³ is selected from a group consisting of $C_{1-6}$ linear alkyl, $C_{1-7}$ branched alkyl, $C_{3-7}$ cycloalkyl, optionally substituted aryl,

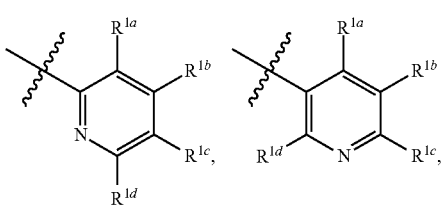

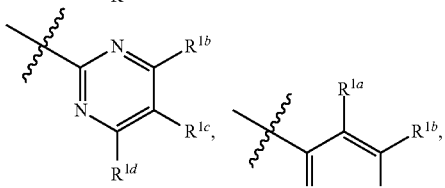

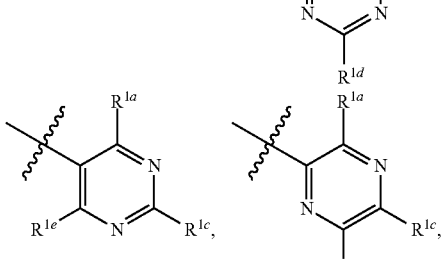

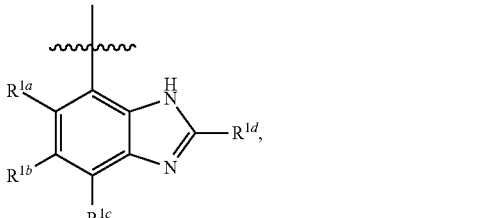

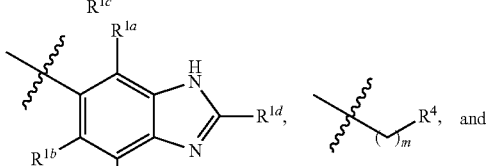

R⁴ is an optionally substituted aryl;
R⁵ᵃ and R⁵ᵇ are each independently optionally substituted aryl;
R⁶ is at each occurrence independently selected from the group consisting of H, $C_{1-6}$ linear alkyl, $C_{3-7}$ branched alkyl, and $C_{3-7}$ cycloalkyl;

R⁷ is at each occurrence independently selected from the group consisting of $C_{1-6}$ linear alkyl, $C_{3-7}$ branched alkyl, and $C_{3-7}$ cycloalkyl:

R⁸ᵃ is at each occurrence independently selected from the group consisting of H, $C_{1-6}$ linear alkyl, $C_{3-7}$ branched alkyl, and $C_{1-7}$ cycloalkyl;

R⁸ᵇ is at each occurrence independently selected from the group consisting of H, $C_{1-6}$ linear alkyl, $C_{3-7}$ branched alkyl, and $C_{3-7}$ cycloalkyl:

R⁹ᵃ is at each occurrence independently selected from the group consisting of H, $C_{1-6}$ linear alkyl, $C_{3-7}$ branched alkyl, and $C_{3-7}$ cycloalkyl:

R⁹ᵇ is at each occurrence independently selected from the group consisting of H, $C_{1-6}$ linear alkyl, $C_{3-7}$ branched alkyl, and $C_{3-7}$ cycloalkyl;

R¹⁰ is at each occurrence independently selected from the group consisting of H, $C_{1-6}$ linear alkyl, $C_{3-7}$ branched alkyl, and $C_{3-7}$ cycloalkyl;

R¹¹ is at each occurrence independently selected from the group consisting of $C_{1-6}$ linear alkyl, $C_{3-7}$ branched alkyl, and $C_{3-7}$ cycloalkyl;

R¹²ᵃ is at each occurrence independently selected from the group consisting of $C_{1-6}$ linear alkyl, $C_{3-7}$ branched alkyl, and $C_{3-7}$ cycloalkyl;

R¹²ᵇ is at each occurrence independently selected from the group consisting of $C_{1-6}$ linear alkyl, $C_{3-7}$ branched alkyl, and $C_{1-7}$ cycloalkyl:

R¹³ is selected from the group consisting of $C_{1-6}$ linear alkyl, $C_{3-7}$ branched alkyl, and $C_{3-7}$ cycloalkyl;

R¹³ is selected from the group consisting of $C_{1-6}$ linear alkyl, $C_{1-7}$ branched alkyl, and $C_{3-7}$ cycloalkyl;

n is 1, 2, or 3;
m is 1 or 2:
and q is 1, 2, or 3;

The embodiments of the present invention include compounds having formula (II):

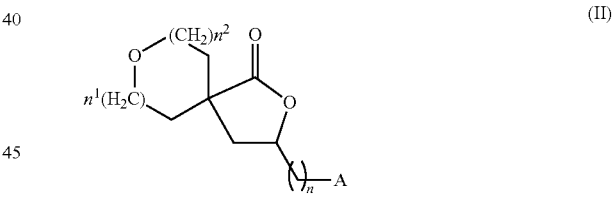

Including hydrates, solvates, enantiomers, diastereomers, pharmaceutically acceptable salts, and complexes thereof.

The embodiments of the present invention include compounds having formula (III):

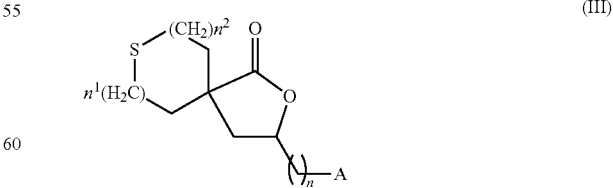

Including hydrates, solvates, enantiomers, diastereomers, pharmaceutically acceptable salts, and complexes thereof.

The embodiments of the present invention include compounds having formula (IV):

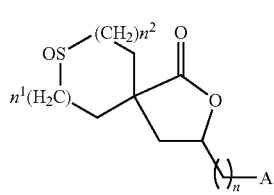
(IV)

Including hydrates, solvates, enantiomers, diastercomers, pharmaceutically acceptable salts, and complexes thereof.

The embodiments of the present invention include compounds having formula (V):

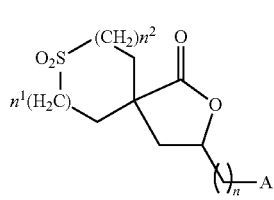
(V)

Including hydrates, solvates, enantiomers, diastercomers, pharmaceutically acceptable salts, and complexes thereof.

The embodiments of the present invention include compounds having formula (VI):

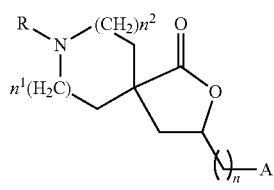
(VI)

Including hydrates, solvates, enantiomers, diastercomers, pharmaceutically acceptable salts, and complexes thereof.

The embodiments of the present invention include compounds having formula (VII):

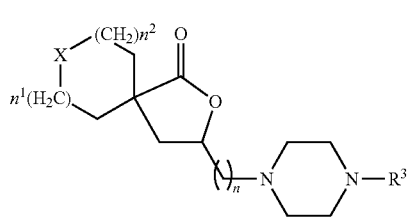
(VII)

Including hydrates, solvates, enantiomers, diastereomers, pharmaceutically acceptable salts, and complexes thereof.

The embodiments of the present invention include compounds having formula (VIII):

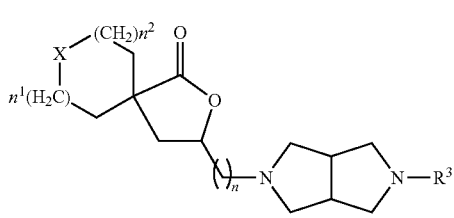
(VIII)

Including hydrates, solvates, enantiomers, diastercomers, pharmaceutically acceptable salts, and complexes thereof.

The embodiments of the present invention include compounds having formula (IX):

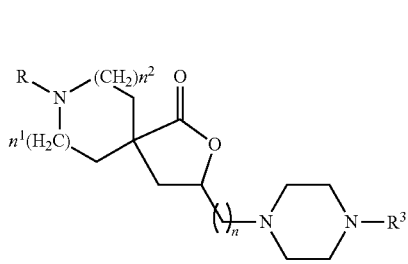
(IX)

Including hydrates, solvates, enantiomers, diastereomers, pharmaceutically acceptable salts, and complexes thereof.

The embodiments of the present invention include compounds having formula (X):

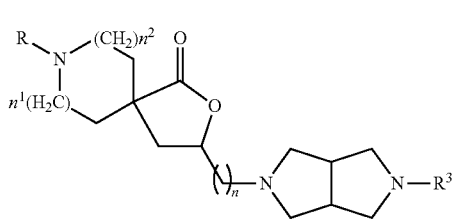
(X)

Including hydrates, solvates, enantiomers, diastereomers, pharmaceutically acceptable salts, and complexes thereof.

The embodiments of the present invention include compounds having formula (XI):

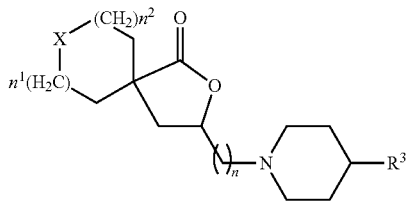
(XI)

Including hydrates, solvates, enantiomers, diastereomers, pharmaceutically acceptable salts, and complexes thereof.

The embodiments of the present invention include compounds having formula (XII):

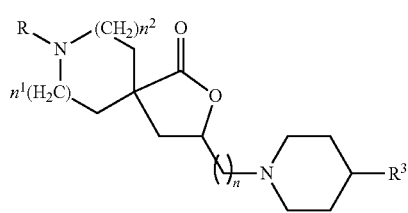

(XII)

Including hydrates, solvates, enantiomers, diastereomers, pharmaceutically acceptable salts, and complexes thereof.

The embodiments of the present invention include compounds having formula (XIII):

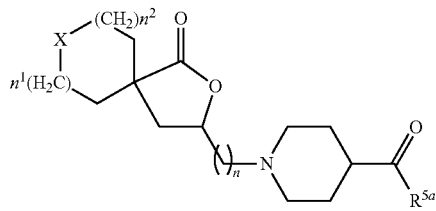

(XIII)

Including hydrates, solvates, enantiomers, diastereomers, pharmaceutically acceptable salts, and complexes thereof.

The embodiments of the present invention include compounds having formula (XIV):

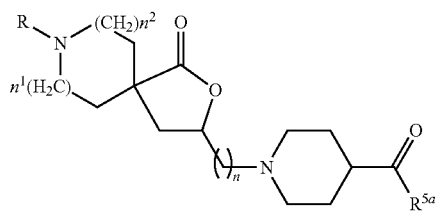

(XIV)

Including hydrates, solvates, enantiomers, diastereomers, pharmaceutically acceptable salts, and complexes thereof.

The embodiments of the present invention include compounds having formula (XV):

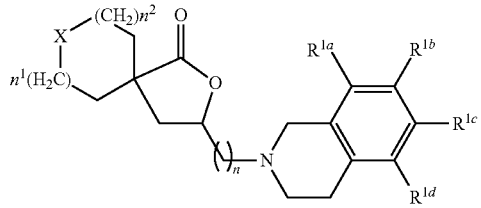

(XV)

Including hydrates, solvates, enantiomers, diastereomers, pharmaceutically acceptable salts, and complexes thereof.

The embodiments of the present invention include compounds having formula (XVI):

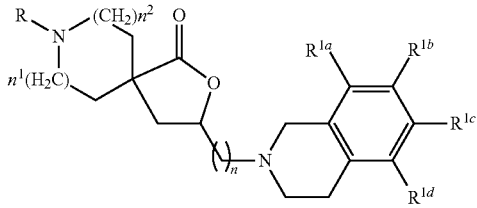

(XVI)

Including hydrates, solvates, enantiomers, diastereomers, pharmaceutically acceptable salts, and complexes thereof.

In some embodiments A is

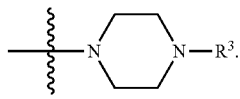

In some embodiments A is

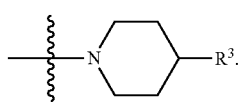

In some embodiments A is

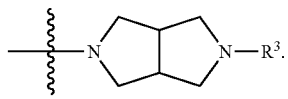

In some embodiments A is

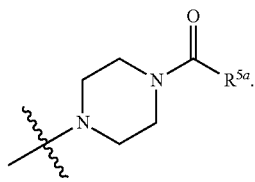

In some embodiments A is

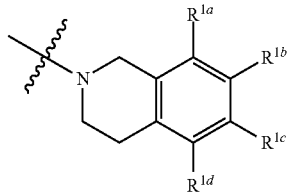

In some embodiments X is O.
In some embodiments X is S.
In some embodiments X is SO.
In some embodiments X is $SO_2$.
In some embodiments X is NR
In some embodiments $n^1$ is 0.

In some embodiments $n^1$ is 1.
In some embodiments $n^1$ is 2.
In some embodiments $n^2$ is 0.
In some embodiments $n^2$ is 1.
In some embodiments $n^2$ is 2.
In some embodiments R is H.
In some embodiments R is $C_{1-6}$ linear alkyl.
In some embodiments R is $C_{3-7}$ branched alkyl.
In some embodiments R is $C_{3-7}$ cycloalkyl.
In some embodiments R is,

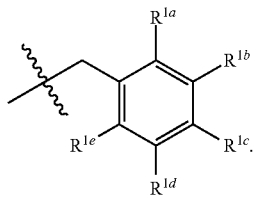

In some embodiments R is $COR^2$.
In some embodiments R is $CO_2R^{2a}$.
In some embodiments R is $CONR^{2b}R^{2c}$.
In some embodiments R is $SO_2NR^{2b}R^{2c}$.
In some embodiments R is $SO_2R^{2d}$.
In some embodiments $R^{1a}$ is H.
In some embodiments $R^{1a}$ is OH.
In some embodiments $R^{1a}$ is $NO_2$.
In some embodiments $R^{1a}$ is halogen.
In some embodiments $R^{1a}$ is CN.
In some embodiments $R^{1a}$ is $C_{1-6}$ linear alkyl.
In some embodiments $R^{1a}$ is $C_{3-7}$ branched alkyl.
In some embodiments $R^{1a}$ is $C_{3-7}$ cycloalkyl.
In some embodiments $R^{1a}$ is $C_{1-6}$ linear alkoxy.
In some embodiments $R^{1a}$ is $C_{3-7}$ branched alkoxy.
In some embodiments $R^{1a}$ is $C_{3-7}$ cycloalkoxy.
In some embodiments $R^{1a}$ is $C_{1-6}$ linear haloalkyl.
In some embodiments $R^{1a}$ is $C_{3-7}$ branched haloalkyl.
In some embodiments $R^{1a}$ is $C_{1-6}$ linear haloalkoxy.
In some embodiments $R^{1a}$ is $-S(C_{1-6}$ linear alkyl$)$.
In some embodiments $R^{1a}$ is $S(C_{3-7}$ branched alkyl$)$.
In some embodiments $R^{1a}$ is $-S(C_{3-7}$ cycloalkyl$)$.
In some embodiments $R^{1a}$ is $COR^6$.
In some embodiments $R^{1a}$ is $CO_2R^7$.
In some embodiments $R^{1a}$ is $CONR^{8a}R^{8b}$.
In some embodiments $R^{1a}$ is $SO_2NR^{8a}R^{8b}$.
In some embodiments $R^{1a}$ is $NR^{8a}R^{8b}$.
In some embodiments $R^{1a}$ is $NR^{8a}COR^{8a}$.
In some embodiments $R^{1a}$ is $NR^{9a}SO_2R^{9b}$.
In some embodiments $R^{1a}$ is $NR^{9a}SO_2NR^{12a}R^{12b}$.
In some embodiments $R^{1b}$ is H.
In some embodiments $R^{1b}$ is OH.
In some embodiments $R^{1b}$ is $NO_2$.
In some embodiments $R^{1b}$ is halogen.
In some embodiments $R^{1b}$ is CN.
In some embodiments $R_{1b}$ is $C_{1-6}$ linear alkyl.
In some embodiments $R^{1b}$ is $C_{3-7}$ branched alkyl.
In some embodiments $R^{1b}$ is $C_{3-7}$ cycloalkyl.
In some embodiments $R^{1b}$ is $C_{1-6}$ linear alkoxy.
In some embodiments $R^{1b}$ is $C_{3-7}$ branched alkoxy.
In some embodiments $R^{1b}$ is $C_{3-7}$ cycloalkoxy.
In some embodiments $R^{1b}$ is $C_{1-6}$ linear haloalkyl.
In some embodiments $R^{1a}$ is $C_{3-7}$ branched haloalkyl.
In some embodiments $R^{1b}$ is $C_{1-6}$ linear haloalkoxy.
In some embodiments $R^{1b}$ is $-S(C_{1-6}$ linear alkyl$)$.
In some embodiments $R^{1b}$ is $S(C_{3-7}$ branched alkyl$)$.

In some embodiments $R^{1b}$ is $-S(C_{1-7}$ cycloalkyl$)$.
In some embodiments $R^{1b}$ is $COR^6$.
In some embodiments $R^{1b}$ is $CO_2R^7$.
In some embodiments $R^{1b}$ is $CONR^{8a}R^{8b}$.
In some embodiments $R^{1b}$ is $SO_2NR^{8a}R^{8b}$.
In some embodiments $R^{1b}$ is $NR^{9a}R^{9b}$.
In some embodiments $R^{1b}$ is $NR^{9a}COR^{10}$.
In some embodiments $R^{1b}$ is $NR^{9a}SO_2R^{11}$.
In some embodiments $R^{1b}$ is $NR^{9a}SO_2NR^{12a}R^{12b}$.
In some embodiments $R^{1c}$ is H.
In some embodiments $R^{1c}$ is OH.
In some embodiments $R^{1c}$ is $NO_2$.
In some embodiments $R^{1c}$ is halogen.
In some embodiments $R^{1c}$ is CN.
In some embodiments $R^{1c}$ is $C_{1-6}$ linear alkyl.
In some embodiments $R^{1c}$ is $C_{3-7}$ branched alkyl.
In some embodiments $R^{1a}$ is $C_{3-7}$ cycloalkyl.
In some embodiments $R^{1c}$ is $C_{1-6}$ linear alkoxy.
In some embodiments $R^{1c}$ is $C_{3-7}$ branched alkoxy.
In some embodiments $R^{1c}$ is $C_{3-7}$ cycloalkoxy.
In some embodiments $R^{1c}$ is $C_{1-6}$ linear haloalkyl.
In some embodiments $R^{1c}$ is $C_{3-7}$ branched haloalkyl.
In some embodiments $R^{1a}$ is $C_{1-6}$ linear haloalkoxy.
In some embodiments $R^{1a}$ is $-S(C_{1-6}$ linear alkyl$)$.
In some embodiments $R^{1c}$ is $S(C_{3-7}$ branched alkyl$)$.
In some embodiments $R^{1c}$ is $-S(C_{3-7}$ cycloalkyl$)$.
In some embodiments $R^{1c}$ is $COR^6$.
In some embodiments $R^{1c}$ is $CO_2R^7$.
In some embodiments $R^{1c}$ is $CONR^{8a}R^{8b}$.
In some embodiments $R^{1c}$ is $SO_2NR^{8a}R^{8b}$.
In some embodiments $R^{1c}$ is $NR^{9a}R^{9b}$.
In some embodiments $R^{1c}$ is $NR^{9a}COR^{10}$.
In some embodiments $R^{1c}$ is $NR^{9a}SO_2R^{11}$.
In some embodiments $R^{1c}$ is $NR^{9a}SO_2NR^{12a}R^{12b}$.
In some embodiments $R^{1d}$ is H.
In some embodiments $R^{1d}$ is OH.
In some embodiments $R^{1d}$ is $NO_2$.
In some embodiments $R^{1d}$ is halogen.
In some embodiments $R^{1d}$ is CN.
In some embodiments $R^{1d}$ is $C_{1-6}$ linear alkyl.
In some embodiments $R^{1d}$ is $C_{3-7}$ branched alkyl.
In some embodiments $R^{1d}$ is $C_{3-7}$ cycloalkyl.
In some embodiments $R^{1d}$ is $C_{1-6}$ linear alkoxy.
In some embodiments $R^{1d}$ is $C_{3-7}$ branched alkoxy.
In some embodiments $R^{1d}$ is $C_{3-7}$ cycloalkoxy.
In some embodiments $R^{1d}$ is $C_{1-6}$ linear haloalkyl.
In some embodiments $R^{1d}$ is $C_{3-7}$ branched haloalkyl.
In some embodiments $R^{1d}$ is $C_{1-6}$ linear haloalkoxy.
In some embodiments $R^{1d}$ is $-S(C_{1-6}$ linear alkyl$)$.
In some embodiments $R^{1d}$ is $S(C_{3-7}$ branched alkyl$)$.
In some embodiments $R^{1d}$ is $-S(C_{3-7}$ cycloalkyl$)$.
In some embodiments $R^{1d}$ is $COR^6$.
In some embodiments $R^{1d}$ is $CO_2R^7$.
In some embodiments $R^{1d}$ is $CONR^{8a}R^{8b}$.
In some embodiments $R^{1d}$ is $SO_2NR^{8a}R^{8b}$.
In some embodiments $R^{1d}$ is $NR^{9a}R^{9b}$.
In some embodiments $R^{1d}$ is $NR^{9a}COR^{10}$.
In some embodiments $R^{1d}$ is $NR^{9a}SO_2R^{11}$.
In some embodiments $R^{1d}$ is $NR^{9a}SO_2NR^{12a}R^{12b}$.
In some embodiments $R^{1e}$ is H.
In some embodiments $R^{1e}$ is OH.
In some embodiments $R^{1e}$ is $NO_2$.
In some embodiments $R^{1e}$ is halogen.
In some embodiments $R^{1e}$ is CN.
In some embodiments $R^{1e}$ is $C_{1-6}$ linear alkyl.
In some embodiments $R^{1e}$ is $C_{3-7}$ branched alkyl.
In some embodiments $R^{1e}$ is $C_{3-7}$ cycloalkyl.

In some embodiments $R^{1e}$ is $C_{1-6}$ linear alkoxy.
In some embodiments $R^{1e}$ is $C_{3-7}$ branched alkoxy.
In some embodiments $R^{1e}$ is $C_{3-7}$ cycloalkoxy.
In some embodiments $R^{1e}$ is $C_{1-6}$ linear haloalkyl.
In some embodiments $R^{1e}$ is $C_{3-7}$ branched haloalkyl.
In some embodiments $R^{1e}$ is $C_{1-6}$ linear haloalkoxy.
In some embodiments $R^{1e}$ is —S($C_{1-6}$ linear alkyl).
In some embodiments $R^{1e}$ is S($C_{3-7}$ branched alkyl).
In some embodiments $R^{1c}$ is —S($C_{3-7}$ cycloalkyl).
In some embodiments $R^{1c}$ is $COR^6$.
In some embodiments $R^{1e}$ is $CO_2R^7$.
In some embodiments $R^{1e}$ is $CONR^{8a}R^{8b}$.
In some embodiments $R^{1e}$ is $SO_2NR^{8a}R^{8b}$.
In some embodiments $R^{1e}$ is $NR^{9a}R^{9b}$.
In some embodiments $R^{1e}$ is $NR^{9a}COR^{10}$.
In some embodiments $R^{1e}$ is $NR^{9a}SO_2R^{11}$.
In some embodiments $R^{1e}$ is $NR^{9a}SO_2NR^{12a}R^{12b}$.
In some embodiments $R^2$ is H.
In some embodiments $R^2$ is $C_{1-6}$ linear alkyl.
In some embodiments $R^2$ is $C_{3-7}$ branched alkyl.
In some embodiments $R^2$ is $C_{3-7}$ cycloalkyl.
In some embodiments $R^{2a}$ is $C_{1-6}$ linear alkyl.
In some embodiments $R^{2a}$ is $C_{3-7}$ branched alkyl.
In some embodiments $R^{2a}$ is $C_{3-7}$ cycloalkyl.
In some embodiments $R^{2a}$ is H.
In some embodiments $R^{2b}$ is $C_{1-6}$ linear alkyl.
In some embodiments $R^{2b}$ is $C_{3-7}$ branched alkyl.
In some embodiments $R^{2b}$ is $C_{3-7}$ cycloalkyl.
In some embodiments $R^{2c}$ is H.
In some embodiments $R^{2c}$ is $C_{1-6}$ linear alkyl.
In some embodiments $R^{2c}$ is, $C_{3-7}$ branched alkyl.
In some embodiments $R^{2c}$ is $C_{3-7}$ cycloalkyl.
In some embodiments $R^{2d}$ is $C_{1-6}$ linear alkyl.
In some embodiments $R^{2d}$ is $C_{1-7}$ branched alkyl.
In some embodiments $R^{2d}$ is $C_{3-7}$ cycloalkyl.
In some embodiments $R^{2d}$ is $C_{1-6}$ linear haloalkyl.
In some embodiments $R^{2d}$ is $C_{1-7}$ branched haloalkyl.
In some embodiments $R^{2d}$ is —$(CH_2)_qCN$.
In some embodiments $R^{2d}$ is —$(CH_2)_qSO_2R^{13}$.
In some embodiments $R^{2d}$ is —$(CH_2)_qOR^{14}$.
In some embodiments $R^{2d}$ is

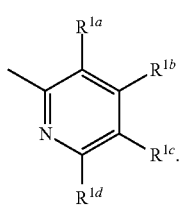

In some embodiments $R^{2d}$ is

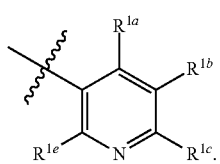

In some embodiments $R^{2d}$ is

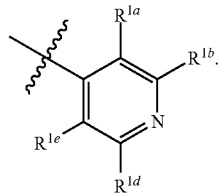

In some embodiments $R^{2d}$ is

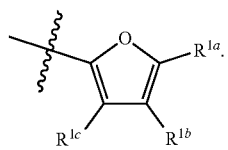

In some embodiments $R^{2d}$ is

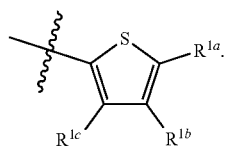

In some embodiments $R^{2d}$ is

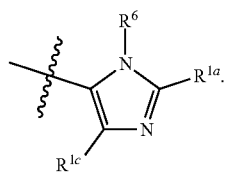

In some embodiments $R^{2d}$ is

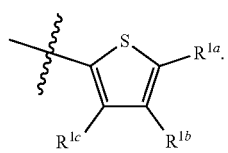

In some embodiments $R^{2d}$ is

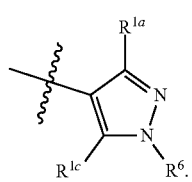

In some embodiments $R^{2d}$ is

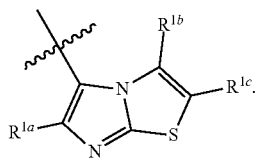

In some embodiments $R^{2d}$ is

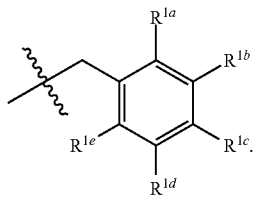

In some embodiments $R^{2d}$ is

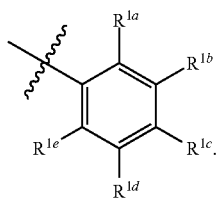

In some embodiments $R^{2d}$ is

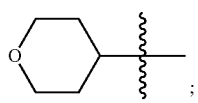

In some embodiments $R^3$ is $C_{1-6}$ linear alkyl.
In some embodiments $R^3$ is $C_{3-7}$ branched alkyl.
In some embodiments $R^3$ is $C_{3-7}$ cycloalkyl.
In some embodiments $R^3$ is optionally substituted aryl.
In some embodiments $R^3$ is phenyl.
In some embodiments $R^3$ is an optionally aryl substituted with 1 to 4 units independently selected from the group consisting of OH, $NO_2$, halogen, CN, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, —S($C_{1-6}$ linear alkyl), S($C_{3-7}$ branched alkyl), —S($C_{3-7}$ cycloalkyl), $COR^6$, $CO_2R^7$, $CONR^{8a}R^{8b}$, $SO_2NR^{8a}R^{8b}$, $NR^{9a}R^{9b}$, $NR^{9a}COR^{10}$, $NR^{9a}SO_2R^{11}$, $NR^{9a}SO_2NR^{12a}R^{12b}$,

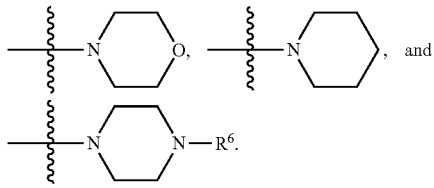

In some embodiments $R^3$ is

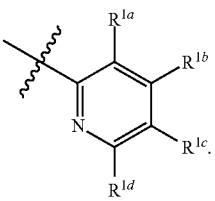

In some embodiments $R^3$ is

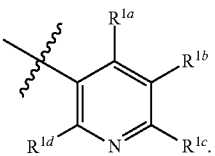

In some embodiments $R^3$ is

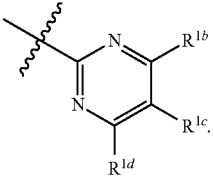

In some embodiments $R^3$ is

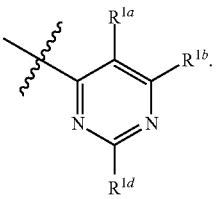

In some embodiments $R^3$ is

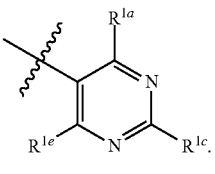

In some embodiments $R^3$ is

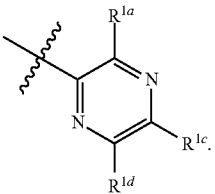

In some embodiments $R^3$ is

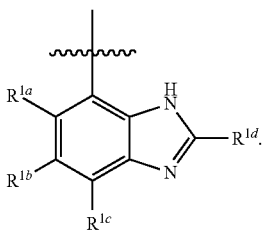

In some embodiments $R^3$ is

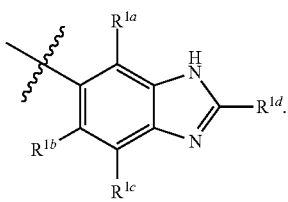

In some embodiments $R^3$ is

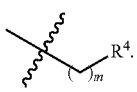

In some embodiments $R^3$ is

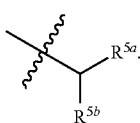

In some embodiments $R^4$ is optionally substituted aryl.
In some embodiments $R^4$ is an optionally substituted aryl substituted with 1 to 4 units independently selected from the group consisting of OH NO$_2$, halogen, CN, C$_{1-6}$ linear alkyl, C$_{1-7}$ branched alkyl, C$_{3-7}$ cycloalkyl, C$_{1-6}$ linear alkoxy, C$_{3-7}$ branched alkoxy, C$_{3-7}$ cycloalkoxy, C$_{1-6}$ linear haloalkyl, C$_{3-7}$ branched haloalkyl, C$_{1-6}$ linear haloalkoxy, —S(C$_{1-6}$ linear alkyl), S(C$_{3-7}$ branched alkyl), —S(C$_{3-7}$ cycloalkyl), COR$^6$, CO$_2$R$^7$, CONR$^{8a}$R$^{8b}$, SO$_2$NR$^{8a}$R$^{8b}$, NR$^{9a}$R$^{9b}$, NR$^{9a}$R$^{9b}$, NR$^{9a}$COR$^{10}$, NR$^{9a}$SO$_2$R$^{11}$, NR$^{9a}$SO$_2$NR$^{12a}$R$^{12b}$,

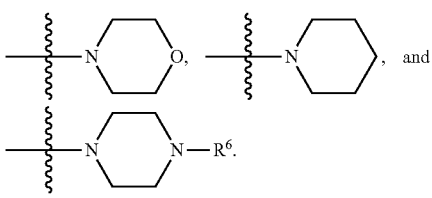

and

In some embodiments $R^5$ is optionally substituted aryl.
In some embodiments $R^5$ is optionally substituted aryl.
In some embodiments $R^6$ is H.
In some embodiments $R^6$ is C$_{1-6}$ linear alkyl.
In some embodiments $R^6$ is C$_{3-7}$ branched alkyl.
In some embodiments $R^6$ is C$_{3-7}$ cycloalkyl.
In some embodiments $R^7$ is C$_{1-6}$ linear alkyl.
In some embodiments $R^7$ is C$_{3-7}$ branched alkyl.
In some embodiments $R^7$ is C$_{3-7}$ cycloalkyl.
In some embodiments $R^{8a}$ is H.
In some embodiments $R^{8a}$ is C$_{1-6}$ linear alkyl.
In some embodiments $R^{8a}$ is C$_{3-7}$ branched alkyl.
In some embodiments $R^{8a}$ is C$_{3-7}$ cycloalkyl.
In some embodiments $R^{8b}$ is H.
In some embodiments $R^{8b}$ is C$_{1-6}$ linear alkyl.
In some embodiments $R^{8b}$ is C$_{3-7}$ branched alkyl.
In some embodiments $R^{8b}$ is C$_{3-7}$ cycloalkyl.
In some embodiments $R^{9a}$ is H.
In some embodiments $R^{9a}$ is C$_{1-6}$ linear alkyl.
In some embodiments $R^{9a}$ is C$_{3-7}$ branched alkyl.
In some embodiments $R^{9a}$ is C$_{3-7}$ cycloalkyl.
In some embodiments $R^{9b}$ is H.
In some embodiments $R^{9b}$ is C$_{1-6}$ linear alkyl.
In some embodiments $R^{9b}$ is C$_{3-7}$ branched alkyl.
In some embodiments $R^{9b}$ is C$_{3-7}$ cycloalkyl.
In some embodiments $R^{10}$ is H.
In some embodiments $R^{10}$ is C$_{1-6}$ linear alkyl.
In some embodiments $R^{10}$ is C$_{3-7}$ branched alkyl.
In some embodiments $R^{10}$ is C$_{3-7}$ cycloalkyl.
In some embodiments $R^{11}$ is C$_{1-6}$ linear alkyl.
In some embodiments $R^{11}$ is C$_{3-7}$ branched alkyl.
In some embodiments $R^{11}$ is C$_{3-7}$ cycloalkyl.
In some embodiments $R^{10}$ is C$_{1-6}$ linear alkyl.
In some embodiments $R^{10}$ is C$_{3-7}$ branched alkyl.
In some embodiments $R^{12a}$ is C$_{3-7}$ cycloalkyl.
In some embodiments $R^{12a}$ is C$_{1-6}$ linear alkyl.
In some embodiments $R^{12a}$ is C$_{3-7}$ branched alkyl.
In some embodiments $R^{12b}$ is C$_{3-7}$ cycloalkyl.
In some embodiments $R^{12b}$ is C$_{1-6}$ linear alkyl.
In some embodiments $R^{12b}$ is C$_{3-7}$ branched alkyl.
In some embodiments $R^{12b}$ is C$_{3-7}$ cycloalkyl.
In some embodiments $R^{13}$ is C$_{1-6}$ linear alkyl.
In some embodiments $R^{13}$ is C$_{3-7}$ branched alkyl.
In some embodiments $R^{13}$ is C$_{3-7}$ cycloalkyl.
In some embodiments $R^{14}$ is C$_{1-6}$ linear alkyl.
In some embodiments $R^{14}$ is C$_{3-7}$ branched alkyl.
In some embodiments $R^{14}$ is C$_{3-7}$ cycloalkyl.
In some embodiments n is 1.
In some embodiments n is 2.
In some embodiments n is 3.
In some embodiments m is 1.
In some embodiments m is 2.
In some embodiments q is 1.
In some embodiments q is 2.
In some embodiments q is 3.
Exemplary embodiments include compounds having the formula (XVII)

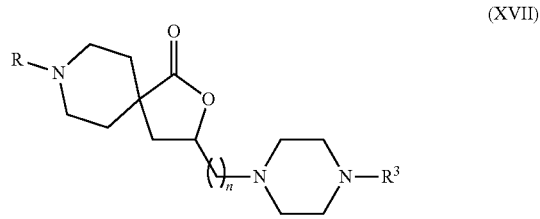

(XVII)

or a pharmaceutically acceptable salt form thereof defined herein below in Table 1.

TABLE 1

| Entry | n | R | R³ |
|---|---|---|---|
| 1 | 1 | H | Phenyl |
| 2 | 2 | H | Phenyl |
| 3 | 3 | H | Phenyl |
| 4 | 1 | Me | Phenyl |
| 5 | 2 | Me | Phenyl |
| 6 | 3 | Me | Phenyl |
| 7 | 1 | CH₂Ph | Phenyl |
| 8 | 2 | CH₂Ph | Phenyl |
| 9 | 3 | CH₂Ph | Phenyl |
| 10 | 1 | COMe | Phenyl |
| 11 | 2 | COMe | Phenyl |
| 12 | 3 | COMe | Phenyl |
| 13 | 1 | CO₂Me | Phenyl |
| 14 | 2 | CO₂Me | Phenyl |
| 15 | 3 | CO₂Me | Phenyl |
| 16 | 1 | CO₂tBu | Phenyl |
| 17 | 2 | CO₂tBu | Phenyl |
| 18 | 3 | CO₂tBu | Phenyl |
| 19 | 1 | CONHMe | Phenyl |
| 20 | 2 | CONHMe | Phenyl |
| 21 | 3 | CONHMe | Phenyl |
| 22 | 1 | SO₂Me | Phenyl |
| 23 | 2 | SO₂Me | Phenyl |
| 24 | 3 | SO₂Me | Phenyl |
| 25 | 1 | SO₂NH₂ | Phenyl |
| 26 | 2 | SO₂NH₂ | Phenyl |
| 27 | 3 | SO₂NH₂ | Phenyl |
| 28 | 1 | H | 3-OH-Phenyl |
| 29 | 2 | H | 3-OH-Phenyl |
| 30 | 3 | H | 3-OH-Phenyl |
| 31 | 1 | Me | 3-OH-Phenyl |
| 32 | 2 | Me | 3-OH-Phenyl |
| 33 | 3 | Me | 3-OH-Phenyl |
| 34 | 1 | CH₂Ph | 3-OH-Phenyl |
| 35 | 2 | CH₂Ph | 3-OH-Phenyl |
| 36 | 3 | CH₂Ph | 3-OH-Phenyl |
| 37 | 1 | COMe | 3-OH-Phenyl |
| 38 | 2 | COMe | 3-OH-Phenyl |
| 39 | 3 | COMe | 3-OH-Phenyl |
| 40 | 1 | CO₂Me | 3-OH-Phenyl |
| 41 | 2 | CO₂Me | 3-OH-Phenyl |
| 42 | 3 | CO₂Me | 3-OH-Phenyl |
| 43 | 1 | CO₂tBu | 3-OH-Phenyl |
| 44 | 2 | CO₂tBu | 3-OH-Phenyl |
| 45 | 3 | CO₂tBu | 3-OH-Phenyl |
| 46 | 1 | CONHMe | 3-OH-Phenyl |
| 47 | 2 | CONHMe | 3-OH-Phenyl |
| 48 | 3 | CONHMe | 3-OH-Phenyl |
| 49 | 1 | SO₂Me | 3-OH-Phenyl |
| 50 | 2 | SO₂Me | 3-OH-Phenyl |
| 51 | 3 | SO₂Me | 3-OH-Phenyl |
| 52 | 1 | SO₂NH₂ | 3-OH-Phenyl |
| 53 | 2 | SO₂NH₂ | 3-OH-Phenyl |
| 54 | 3 | SO₂NH₂ | 3-OH-Phenyl |
| 55 | 1 | H | 4-NO₂-Phenyl |
| 56 | 2 | H | 4-NO₂-Phenyl |
| 57 | 3 | H | 4-NO₂-Phenyl |
| 58 | 1 | Me | 4-NO₂-Phenyl |
| 59 | 2 | Me | 4-NO₂-Phenyl |
| 60 | 3 | Me | 4-NO₂-Phenyl |
| 61 | 1 | CH₂Ph | 4-NO₂-Phenyl |
| 62 | 2 | CH₂Ph | 4-NO₂-Phenyl |
| 63 | 3 | CH₂Ph | 4-NO₂-Phenyl |
| 64 | 1 | COMe | 4-NO₂-Phenyl |
| 65 | 2 | COMe | 4-NO₂-Phenyl |
| 66 | 3 | COMe | 4-NO₂-Phenyl |
| 67 | 1 | CO₂Me | 4-NO₂-Phenyl |
| 68 | 2 | CO₂Me | 4-NO₂-Phenyl |
| 69 | 3 | CO₂Me | 4-NO₂-Phenyl |
| 70 | 1 | CO₂tBu | 4-NO₂-Phenyl |
| 71 | 2 | CO₂tBu | 4-NO₂-Phenyl |
| 72 | 3 | CO₂tBu | 4-NO₂-Phenyl |
| 73 | 1 | CONHMe | 4-NO₂-Phenyl |
| 74 | 2 | CONHMe | 4-NO₂-Phenyl |
| 75 | 3 | CONHMe | 4-NO₂-Phenyl |
| 76 | 1 | SO₂Me | 4-NO₂-Phenyl |
| 77 | 2 | SO₂Me | 4-NO₂-Phenyl |
| 78 | 3 | SO₂Me | 4-NO₂-Phenyl |
| 79 | 1 | SO₂NH₂ | 4-NO₂-Phenyl |
| 80 | 2 | SO₂NH₂ | 4-NO₂-Phenyl |
| 81 | 3 | SO₂NH₂ | 4-NO₂-Phenyl |
| 82 | 1 | H | 3-OMe-Phenyl |
| 83 | 2 | H | 3-OMe-Phenyl |
| 84 | 3 | H | 3-OMe-Phenyl |
| 85 | 1 | Me | 3-OMe-Phenyl |
| 86 | 2 | Me | 3-OMe-Phenyl |
| 87 | 3 | Me | 3-OMe-Phenyl |
| 88 | 1 | CH₂Ph | 3-OMe-Phenyl |
| 89 | 2 | CH₂Ph | 3-OMe-Phenyl |
| 90 | 3 | CH₂Ph | 3-OMe-Phenyl |
| 91 | 1 | COMe | 3-OMe-Phenyl |
| 92 | 2 | COMe | 3-OMe-Phenyl |
| 93 | 3 | COMe | 3-OMe-Phenyl |
| 94 | 1 | CO₂Me | 3-OMe-Phenyl |
| 95 | 2 | CO₂Me | 3-OMe-Phenyl |
| 96 | 3 | CO₂Me | 3-OMe-Phenyl |
| 97 | 1 | CO₂tBu | 3-OMe-Phenyl |
| 98 | 2 | CO₂tBu | 3-OMe-Phenyl |
| 99 | 3 | CO₂tBu | 3-OMe-Phenyl |
| 100 | 1 | CONHMe | 3-OMe-Phenyl |
| 101 | 2 | CONHMe | 3-OMe-Phenyl |
| 102 | 3 | CONHMe | 3-OMe-Phenyl |
| 103 | 1 | SO₂Me | 3-OMe-Phenyl |
| 104 | 2 | SO₂Me | 3-OMe-Phenyl |
| 105 | 3 | SO₂Me | 3-OMe-Phenyl |
| 106 | 1 | SO₂NH₂ | 3-OMe-Phenyl |
| 107 | 2 | SO₂NH₂ | 3-OMe-Phenyl |
| 108 | 3 | SO₂NH₂ | 3-OMe-Phenyl |
| 109 | 1 | H | 4-CN-Phenyl |
| 110 | 2 | H | 4-CN-Phenyl |
| 111 | 3 | H | 4-CN-Phenyl |
| 112 | 1 | Me | 4-CN-Phenyl |
| 113 | 2 | Me | 4-CN-Phenyl |
| 114 | 3 | Me | 4-CN-Phenyl |
| 115 | 1 | CH₂Ph | 4-CN-Phenyl |
| 116 | 2 | CH₂Ph | 4-CN-Phenyl |
| 117 | 3 | CH₂Ph | 4-CN-Phenyl |
| 118 | 1 | COMe | 4-CN-Phenyl |
| 119 | 2 | COMe | 4-CN-Phenyl |
| 120 | 3 | COMe | 4-CN-Phenyl |
| 121 | 1 | CO₂Me | 4-CN-Phenyl |
| 122 | 2 | CO₂Me | 4-CN-Phenyl |
| 123 | 3 | CO₂Me | 4-CN-Phenyl |
| 124 | 1 | CO₂tBu | 4-CN-Phenyl |
| 125 | 2 | CO₂tBu | 4-CN-Phenyl |
| 126 | 3 | CO₂tBu | 4-CN-Phenyl |
| 127 | 1 | CONHMe | 4-CN-Phenyl |
| 128 | 2 | CONHMe | 4-CN-Phenyl |
| 129 | 3 | CONHMe | 4-CN-Phenyl |
| 130 | 1 | SO₂Me | 4-CN-Phenyl |
| 131 | 2 | SO₂Me | 4-CN-Phenyl |
| 132 | 3 | SO₂Me | 4-CN-Phenyl |
| 133 | 1 | SO₂NH₂ | 4-CN-Phenyl |
| 134 | 2 | SO₂NH₂ | 4-CN-Phenyl |
| 135 | 3 | SO₂NH₂ | 4-CN-Phenyl |
| 136 | 1 | H | 2-CN-Phenyl |
| 137 | 2 | H | 2-CN-Phenyl |
| 138 | 3 | H | 2-CN-Phenyl |
| 139 | 1 | Me | 2-CN-Phenyl |
| 140 | 2 | Me | 2-CN-Phenyl |
| 141 | 3 | Me | 2-CN-Phenyl |
| 142 | 1 | CH₂Ph | 2-CN-Phenyl |
| 143 | 2 | CH₂Ph | 2-CN-Phenyl |
| 144 | 3 | CH₂Ph | 2-CN-Phenyl |
| 145 | 1 | COMe | 2-CN-Phenyl |
| 146 | 2 | COMe | 2-CN-Phenyl |
| 147 | 3 | COMe | 2-CN-Phenyl |
| 148 | 1 | CO₂Me | 2-CN-Phenyl |
| 149 | 2 | CO₂Me | 2-CN-Phenyl |
| 150 | 3 | CO₂Me | 2-CN-Phenyl |
| 151 | 1 | CO₂tBu | 2-CN-Phenyl |
| 152 | 2 | CO₂tBu | 2-CN-Phenyl |
| 153 | 3 | CO₂tBu | 2-CN-Phenyl |
| 154 | 1 | CONHMe | 2-CN-Phenyl |
| 155 | 2 | CONHMe | 2-CN-Phenyl |
| 156 | 3 | CONHMe | 2-CN-Phenyl |

TABLE 1-continued

| Entry | n | R | R³ |
|---|---|---|---|
| 157 | 1 | SO₂Me | 2-CN-Phenyl |
| 158 | 2 | SO₂Me | 2-CN-Phenyl |
| 159 | 3 | SO₂Me | 2-CN-Phenyl |
| 160 | 1 | SO₂NH₂ | 2-CN-Phenyl |
| 161 | 2 | SO₂NH₂ | 2-CN-Phenyl |
| 162 | 3 | SO₂NH₂ | 2-CN-Phenyl |
| 163 | 1 | H | 3-Me-Phenyl |
| 164 | 2 | H | 3-Me-Phenyl |
| 165 | 3 | H | 3-Me-Phenyl |
| 166 | 1 | Me | 3-Me-Phenyl |
| 167 | 2 | Me | 3-Me-Phenyl |
| 168 | 3 | Me | 3-Me-Phenyl |
| 169 | 1 | CH₂Ph | 3-Me-Phenyl |
| 170 | 2 | CH₂Ph | 3-Me-Phenyl |
| 171 | 3 | CH₂Ph | 3-Me-Phenyl |
| 172 | 1 | COMe | 3-Me-Phenyl |
| 173 | 2 | COMe | 3-Me-Phenyl |
| 174 | 3 | COMe | 3-Me-Phenyl |
| 175 | 1 | CO₂Me | 3-Me-Phenyl |
| 176 | 2 | CO₂Me | 3-Me-Phenyl |
| 177 | 3 | CO₂Me | 3-Me-Phenyl |
| 178 | 1 | CO₂tBu | 3-Me-Phenyl |
| 179 | 2 | CO₂tBu | 3-Me-Phenyl |
| 180 | 3 | CO₂tBu | 3-Me-Phenyl |
| 181 | 1 | CONHMe | 3-Me-Phenyl |
| 182 | 2 | CONHMe | 3-Me-Phenyl |
| 183 | 3 | CONHMe | 3-Me-Phenyl |
| 184 | 1 | SO₂Me | 3-Me-Phenyl |
| 185 | 2 | SO₂Me | 3-Me-Phenyl |
| 186 | 3 | SO₂Me | 3-Me-Phenyl |
| 187 | 1 | SO₂NH₂ | 3-Me-Phenyl |
| 188 | 2 | SO₂NH₂ | 3-Me-Phenyl |
| 189 | 3 | SO₂NH₂ | 3-Me-Phenyl |
| 190 | 1 | H | 2-F-Phenyl |
| 191 | 2 | H | 2-F-Phenyl |
| 192 | 3 | H | 2-F-Phenyl |
| 193 | 1 | Me | 2-F-Phenyl |
| 194 | 2 | Me | 2-F-Phenyl |
| 195 | 3 | Me | 2-F-Phenyl |
| 196 | 1 | CH₂Ph | 2-F-Phenyl |
| 197 | 2 | CH₂Ph | 2-F-Phenyl |
| 198 | 3 | CH₂Ph | 2-F-Phenyl |
| 199 | 1 | COMe | 2-F-Phenyl |
| 200 | 2 | COMe | 2-F-Phenyl |
| 201 | 3 | COMe | 2-F-Phenyl |
| 202 | 1 | CO₂Me | 2-F-Phenyl |
| 203 | 2 | CO₂Me | 2-F-Phenyl |
| 204 | 3 | CO₂Me | 2-F-Phenyl |
| 205 | 1 | CO₂tBu | 2-F-Phenyl |
| 206 | 2 | CO₂tBu | 2-F-Phenyl |
| 207 | 3 | CO₂tBu | 2-F-Phenyl |
| 208 | 1 | CONHMe | 2-F-Phenyl |
| 209 | 2 | CONHMe | 2-F-Phenyl |
| 210 | 3 | CONHMe | 2-F-Phenyl |
| 211 | 1 | SO₂Me | 2-F-Phenyl |
| 212 | 2 | SO₂Me | 2-F-Phenyl |
| 213 | 3 | SO₂Me | 2-F-Phenyl |
| 214 | 1 | SO₂NH₂ | 2-F-Phenyl |
| 215 | 2 | SO₂NH₂ | 2-F-Phenyl |
| 216 | 3 | SO₂NH₂ | 2-F-Phenyl |
| 217 | 1 | H | 4-F-Phenyl |
| 218 | 2 | H | 4-F-Phenyl |
| 219 | 3 | H | 4-F-Phenyl |
| 220 | 1 | Me | 4-F-Phenyl |
| 221 | 2 | Me | 4-F-Phenyl |
| 222 | 3 | Me | 4-F-Phenyl |
| 223 | 1 | CH₂Ph | 4-F-Phenyl |
| 224 | 2 | CH₂Ph | 4-F-Phenyl |
| 225 | 3 | CH₂Ph | 4-F-Phenyl |
| 226 | 1 | COMe | 4-F-Phenyl |
| 227 | 2 | COMe | 4-F-Phenyl |
| 228 | 3 | COMe | 4-F-Phenyl |
| 229 | 1 | CO₂Me | 4-F-Phenyl |
| 230 | 2 | CO₂Me | 4-F-Phenyl |
| 231 | 3 | CO₂Me | 4-F-Phenyl |
| 232 | 1 | CO₂tBu | 4-F-Phenyl |
| 233 | 2 | CO₂tBu | 4-F-Phenyl |
| 234 | 3 | CO₂tBu | 4-F-Phenyl |
| 235 | 1 | CONHMe | 4-F-Phenyl |
| 236 | 2 | CONHMe | 4-F-Phenyl |
| 237 | 3 | CONHMe | 4-F-Phenyl |
| 238 | 1 | SO₂Me | 4-F-Phenyl |
| 239 | 2 | SO₂Me | 4-F-Phenyl |
| 240 | 3 | SO₂Me | 4-F-Phenyl |
| 241 | 1 | SO₂NH₂ | 4-F-Phenyl |
| 242 | 2 | SO₂NH₂ | 4-F-Phenyl |
| 243 | 3 | SO₂NH₂ | 4-F-Phenyl |
| 244 | 1 | H | 3-Cl-Phenyl |
| 245 | 2 | H | 3-Cl-Phenyl |
| 246 | 3 | H | 3-Cl-Phenyl |
| 247 | 1 | Me | 3-Cl-Phenyl |
| 248 | 2 | Me | 3-Cl-Phenyl |
| 249 | 3 | Me | 3-Cl-Phenyl |
| 250 | 1 | CH₂Ph | 3-Cl-Phenyl |
| 251 | 2 | CH₂Ph | 3-Cl-Phenyl |
| 252 | 3 | CH₂Ph | 3-Cl-Phenyl |
| 253 | 1 | COMe | 3-Cl-Phenyl |
| 254 | 2 | COMe | 3-Cl-Phenyl |
| 255 | 3 | COMe | 3-Cl-Phenyl |
| 256 | 1 | CO₂Me | 3-Cl-Phenyl |
| 257 | 2 | CO₂Me | 3-Cl-Phenyl |
| 258 | 3 | CO₂Me | 3-Cl-Phenyl |
| 259 | 1 | CO₂tBu | 3-Cl-Phenyl |
| 260 | 2 | CO₂tBu | 3-Cl-Phenyl |
| 261 | 3 | CO₂tBu | 3-Cl-Phenyl |
| 262 | 1 | CONHMe | 3-Cl-Phenyl |
| 263 | 2 | CONHMe | 3-Cl-Phenyl |
| 264 | 3 | CONHMe | 3-Cl-Phenyl |
| 265 | 1 | SO₂Me | 3-Cl-Phenyl |
| 266 | 2 | SO₂Me | 3-Cl-Phenyl |
| 267 | 3 | SO₂Me | 3-Cl-Phenyl |
| 268 | 1 | SO₂NH₂ | 3-Cl-Phenyl |
| 269 | 2 | SO₂NH₂ | 3-Cl-Phenyl |
| 270 | 3 | SO₂NH₂ | 3-Cl-Phenyl |
| 271 | 1 | H | 2-Br-Phenyl |
| 272 | 2 | H | 2-Br-Phenyl |
| 273 | 3 | H | 2-Br-Phenyl |
| 274 | 1 | Me | 2-Br-Phenyl |
| 275 | 2 | Me | 2-Br-Phenyl |
| 276 | 3 | Me | 2-Br-Phenyl |
| 277 | 1 | CH₂Ph | 2-Br-Phenyl |
| 278 | 2 | CH₂Ph | 2-Br-Phenyl |
| 279 | 3 | CH₂Ph | 2-Br-Phenyl |
| 280 | 1 | COMe | 2-Br-Phenyl |
| 281 | 2 | COMe | 2-Br-Phenyl |
| 282 | 3 | COMe | 2-Br-Phenyl |
| 283 | 1 | CO₂Me | 2-Br-Phenyl |
| 284 | 2 | CO₂Me | 2-Br-Phenyl |
| 285 | 3 | CO₂Me | 2-Br-Phenyl |
| 286 | 1 | CO₂tBu | 2-Br-Phenyl |
| 287 | 2 | CO₂tBu | 2-Br-Phenyl |
| 288 | 3 | CO₂tBu | 2-Br-Phenyl |
| 289 | 1 | CONHMe | 2-Br-Phenyl |
| 290 | 2 | CONHMe | 2-Br-Phenyl |
| 291 | 3 | CONHMe | 2-Br-Phenyl |
| 292 | 1 | SO₂Me | 2-Br-Phenyl |
| 293 | 2 | SO₂Me | 2-Br-Phenyl |
| 294 | 3 | SO₂Me | 2-Br-Phenyl |
| 295 | 1 | SO₂NH₂ | 2-Br-Phenyl |
| 296 | 2 | SO₂NH₂ | 2-Br-Phenyl |
| 297 | 3 | SO₂NH₂ | 2-Br-Phenyl |
| 298 | 1 | H | 4-Br-Phenyl |
| 299 | 2 | H | 4-Br-Phenyl |
| 300 | 3 | H | 4-Br-Phenyl |
| 301 | 1 | Me | 4-Br-Phenyl |
| 302 | 2 | Me | 4-Br-Phenyl |
| 303 | 3 | Me | 4-Br-Phenyl |
| 304 | 1 | CH₂Ph | 4-Br-Phenyl |
| 305 | 2 | CH₂Ph | 4-Br-Phenyl |
| 306 | 3 | CH₂Ph | 4-Br-Phenyl |
| 307 | 1 | COMe | 4-Br-Phenyl |
| 308 | 2 | COMe | 4-Br-Phenyl |
| 309 | 3 | COMe | 4-Br-Phenyl |
| 310 | 1 | CO₂Me | 4-Br-Phenyl |
| 311 | 2 | CO₂Me | 4-Br-Phenyl |
| 312 | 3 | CO₂Me | 4-Br-Phenyl |

TABLE 1-continued

| Entry | n | R | R³ |
|---|---|---|---|
| 313 | 1 | CO₂tBu | 4-Br-Phenyl |
| 314 | 2 | CO₂tBu | 4-Br-Phenyl |
| 315 | 3 | CO₂tBu | 4-Br-Phenyl |
| 316 | 1 | CONHMe | 4-Br-Phenyl |
| 317 | 2 | CONHMe | 4-Br-Phenyl |
| 318 | 3 | CONHMe | 4-Br-Phenyl |
| 319 | 1 | SO₂Me | 4-Br-Phenyl |
| 320 | 2 | SO₂Me | 4-Br-Phenyl |
| 321 | 3 | SO₂Me | 4-Br-Phenyl |
| 322 | 1 | SO₂NH₂ | 4-Br-Phenyl |
| 323 | 2 | SO₂NH₂ | 4-Br-Phenyl |
| 324 | 3 | SO₂NH₂ | 4-Br-Phenyl |
| 325 | 1 | H | 3-CF₃-Phenyl |
| 326 | 2 | H | 3-CF₃-Phenyl |
| 327 | 3 | H | 3-CF₃-Phenyl |
| 328 | 1 | Me | 3-CF₃-Phenyl |
| 329 | 2 | Me | 3-CF₃-Phenyl |
| 330 | 3 | Me | 3-CF₃-Phenyl |
| 331 | 1 | CH₂Ph | 3-CF₃-Phenyl |
| 332 | 2 | CH₂Ph | 3-CF₃-Phenyl |
| 333 | 3 | CH₂Ph | 3-CF₃-Phenyl |
| 334 | 1 | COMe | 3-CF₃-Phenyl |
| 335 | 2 | COMe | 3-CF₃-Phenyl |
| 336 | 3 | COMe | 3-CF₃-Phenyl |
| 337 | 1 | CO₂Me | 3-CF₃-Phenyl |
| 338 | 2 | CO₂Me | 3-CF₃-Phenyl |
| 339 | 3 | CO₂Me | 3-CF₃-Phenyl |
| 340 | 1 | CO₂tBu | 3-CF₃-Phenyl |
| 341 | 2 | CO₂tBu | 3-CF₃-Phenyl |
| 342 | 3 | CO₂tBu | 3-CF₃-Phenyl |
| 343 | 1 | CONHMe | 3-CF₃-Phenyl |
| 344 | 2 | CONHMe | 3-CF₃-Phenyl |
| 345 | 3 | CONHMe | 3-CF₃-Phenyl |
| 346 | 1 | SO₂Me | 3-CF₃-Phenyl |
| 347 | 2 | SO₂Me | 3-CF₃-Phenyl |
| 348 | 3 | SO₂Me | 3-CF₃-Phenyl |
| 349 | 1 | SO₂NH₂ | 3-CF₃-Phenyl |
| 350 | 2 | SO₂NH₂ | 3-CF₃-Phenyl |
| 351 | 3 | SO₂NH₂ | 3-CF₃-Phenyl |
| 352 | 1 | H | 2-iPr-Phenyl |
| 353 | 2 | H | 2-iPr-Phenyl |
| 354 | 3 | H | 2-iPr-Phenyl |
| 355 | 1 | Me | 2-iPr-Phenyl |
| 356 | 2 | Me | 2-iPr-Phenyl |
| 357 | 3 | Me | 2-iPr-Phenyl |
| 358 | 1 | CH₂Ph | 2-iPr-Phenyl |
| 359 | 2 | CH₂Ph | 2-iPr-Phenyl |
| 360 | 3 | CH₂Ph | 2-iPr-Phenyl |
| 361 | 1 | COMe | 2-iPr-Phenyl |
| 362 | 2 | COMe | 2-iPr-Phenyl |
| 363 | 3 | COMe | 2-iPr-Phenyl |
| 364 | 1 | CO₂Me | 2-iPr-Phenyl |
| 365 | 2 | CO₂Me | 2-iPr-Phenyl |
| 366 | 3 | CO₂Me | 2-iPr-Phenyl |
| 367 | 1 | CO₂tBu | 2-iPr-Phenyl |
| 368 | 2 | CO₂tBu | 2-iPr-Phenyl |
| 369 | 3 | CO₂tBu | 2-iPr-Phenyl |
| 370 | 1 | CONHMe | 2-iPr-Phenyl |
| 371 | 2 | CONHMe | 2-iPr-Phenyl |
| 372 | 3 | CONHMe | 2-iPr-Phenyl |
| 373 | 1 | SO₂Me | 2-iPr-Phenyl |
| 374 | 2 | SO₂Me | 2-iPr-Phenyl |
| 375 | 3 | SO₂Me | 2-iPr-Phenyl |
| 376 | 1 | SO₂NH₂ | 2-iPr-Phenyl |
| 377 | 2 | SO₂NH₂ | 2-iPr-Phenyl |
| 378 | 3 | SO₂NH₂ | 2-iPr-Phenyl |
| 379 | 1 | H | 4-iPr-Phenyl |
| 380 | 2 | H | 4-iPr-Phenyl |
| 381 | 3 | H | 4-iPr-Phenyl |
| 382 | 1 | Me | 4-iPr-Phenyl |
| 383 | 2 | Me | 4-iPr-Phenyl |
| 384 | 3 | Me | 4-iPr-Phenyl |
| 385 | 1 | CH₂Ph | 4-iPr-Phenyl |
| 386 | 2 | CH₂Ph | 4-iPr-Phenyl |
| 387 | 3 | CH₂Ph | 4-iPr-Phenyl |
| 388 | 1 | COMe | 4-iPr-Phenyl |
| 389 | 2 | COMe | 4-iPr-Phenyl |
| 390 | 3 | COMe | 4-iPr-Phenyl |
| 391 | 1 | CO₂Me | 4-iPr-Phenyl |
| 392 | 2 | CO₂Me | 4-iPr-Phenyl |
| 393 | 3 | CO₂Me | 4-iPr-Phenyl |
| 394 | 1 | CO₂tBu | 4-iPr-Phenyl |
| 395 | 2 | CO₂tBu | 4-iPr-Phenyl |
| 396 | 3 | CO₂tBu | 4-iPr-Phenyl |
| 397 | 1 | CONHMe | 4-iPr-Phenyl |
| 398 | 2 | CONHMe | 4-iPr-Phenyl |
| 399 | 3 | CONHMe | 4-iPr-Phenyl |
| 400 | 1 | SO₂Me | 4-iPr-Phenyl |
| 401 | 2 | SO₂Me | 4-iPr-Phenyl |
| 402 | 3 | SO₂Me | 4-iPr-Phenyl |
| 403 | 1 | SO₂NH₂ | 4-iPr-Phenyl |
| 404 | 2 | SO₂NH₂ | 4-iPr-Phenyl |
| 405 | 3 | SO₂NH₂ | 4-iPr-Phenyl |
| 406 | 1 | H | 3-NH₂-Phenyl |
| 407 | 2 | H | 3-NH₂-Phenyl |
| 408 | 3 | H | 3-NH₂-Phenyl |
| 409 | 1 | Me | 3-NH₂-Phenyl |
| 410 | 2 | Me | 3-NH₂-Phenyl |
| 411 | 3 | Me | 3-NH₂-Phenyl |
| 412 | 1 | CH₂Ph | 3-NH₂-Phenyl |
| 413 | 2 | CH₂Ph | 3-NH₂-Phenyl |
| 414 | 3 | CH₂Ph | 3-NH₂-Phenyl |
| 415 | 1 | COMe | 3-NH₂-Phenyl |
| 416 | 2 | COMe | 3-NH₂-Phenyl |
| 417 | 3 | COMe | 3-NH₂-Phenyl |
| 418 | 1 | CO₂Me | 3-NH₂-Phenyl |
| 419 | 2 | CO₂Me | 3-NH₂-Phenyl |
| 420 | 3 | CO₂Me | 3-NH₂-Phenyl |
| 421 | 1 | CO₂tBu | 3-NH₂-Phenyl |
| 422 | 2 | CO₂tBu | 3-NH₂-Phenyl |
| 423 | 3 | CO₂tBu | 3-NH₂-Phenyl |
| 424 | 1 | CONHMe | 3-NH₂-Phenyl |
| 425 | 2 | CONHMe | 3-NH₂-Phenyl |
| 426 | 3 | CONHMe | 3-NH₂-Phenyl |
| 427 | 1 | SO₂Me | 3-NH₂-Phenyl |
| 428 | 2 | SO₂Me | 3-NH₂-Phenyl |
| 429 | 3 | SO₂Me | 3-NH₂-Phenyl |
| 430 | 1 | SO₂NH₂ | 3-NH₂-Phenyl |
| 431 | 2 | SO₂NH₂ | 3-NH₂-Phenyl |
| 432 | 3 | SO₂NH₂ | 3-NH₂-Phenyl |
| 433 | 1 | H | 2,4-di-Me-Phenyl |
| 434 | 2 | H | 2,4-di-Me-Phenyl |
| 435 | 3 | H | 2,4-di-Me-Phenyl |
| 436 | 1 | Me | 2,4-di-Me-Phenyl |
| 437 | 2 | Me | 2,4-di-Me-Phenyl |
| 438 | 3 | Me | 2,4-di-Me-Phenyl |
| 439 | 1 | CH₂Ph | 2,4-di-Me-Phenyl |
| 440 | 2 | CH₂Ph | 2,4-di-Me-Phenyl |
| 441 | 3 | CH₂Ph | 2,4-di-Me-Phenyl |
| 442 | 1 | COMe | 2,4-di-Me-Phenyl |
| 443 | 2 | COMe | 2,4-di-Me-Phenyl |
| 444 | 3 | COMe | 2,4-di-Me-Phenyl |
| 445 | 1 | CO₂Me | 2,4-di-Me-Phenyl |
| 446 | 2 | CO₂Me | 2,4-di-Me-Phenyl |
| 447 | 3 | CO₂Me | 2,4-di-Me-Phenyl |
| 448 | 1 | CO₂tBu | 2,4-di-Me-Phenyl |
| 449 | 2 | CO₂tBu | 2,4-di-Me-Phenyl |
| 450 | 3 | CO₂tBu | 2,4-di-Me-Phenyl |
| 451 | 1 | CONHMe | 2,4-di-Me-Phenyl |
| 452 | 2 | CONHMe | 2,4-di-Me-Phenyl |
| 453 | 3 | CONHMe | 2,4-di-Me-Phenyl |
| 454 | 1 | SO₂Me | 2,4-di-Me-Phenyl |
| 455 | 2 | SO₂Me | 2,4-di-Me-Phenyl |
| 456 | 3 | SO₂Me | 2,4-di-Me-Phenyl |
| 457 | 1 | SO₂NH₂ | 2,4-di-Me-Phenyl |
| 458 | 2 | SO₂NH₂ | 2,4-di-Me-Phenyl |
| 459 | 3 | SO₂NH₂ | 2,4-di-Me-Phenyl |
| 460 | 1 | H | 2,6-di-iPr-Phenyl |
| 461 | 2 | H | 2,6-di-iPr-Phenyl |
| 462 | 3 | H | 2,6-di-iPr-Phenyl |
| 463 | 1 | Me | 2,6-di-iPr-Phenyl |
| 464 | 2 | Me | 2,6-di-iPr-Phenyl |
| 465 | 3 | Me | 2,6-di-iPr-Phenyl |
| 466 | 1 | CH₂Ph | 2,6-di-iPr-Phenyl |
| 467 | 2 | CH₂Ph | 2,6-di-iPr-Phenyl |
| 468 | 3 | CH₂Ph | 2,6-di-iPr-Phenyl |

TABLE 1-continued

| Entry | n | R | R³ |
|---|---|---|---|
| 469 | 1 | COMe | 2,6-di-iPr-Phenyl |
| 470 | 2 | COMe | 2,6-di-iPr-Phenyl |
| 471 | 3 | COMe | 2,6-di-iPr-Phenyl |
| 472 | 1 | CO₂Me | 2,6-di-iPr-Phenyl |
| 473 | 2 | CO₂Me | 2,6-di-iPr-Phenyl |
| 474 | 3 | CO₂Me | 2,6-di-iPr-Phenyl |
| 475 | 1 | CO₂tBu | 2,6-di-iPr-Phenyl |
| 476 | 2 | CO₂tBu | 2,6-di-iPr-Phenyl |
| 477 | 3 | CO₂tBu | 2,6-di-iPr-Phenyl |
| 478 | 1 | CONHMe | 2,6-di-iPr-Phenyl |
| 479 | 2 | CONHMe | 2,6-di-iPr-Phenyl |
| 480 | 3 | CONHMe | 2,6-di-iPr-Phenyl |
| 481 | 1 | SO₂Me | 2,6-di-iPr-Phenyl |
| 482 | 2 | SO₂Me | 2,6-di-iPr-Phenyl |
| 483 | 3 | SO₂Me | 2,6-di-iPr-Phenyl |
| 484 | 1 | SO₂NH₂ | 2,6-di-iPr-Phenyl |
| 485 | 2 | SO₂NH₂ | 2,6-di-iPr-Phenyl |
| 486 | 3 | SO₂NH₂ | 2,6-di-iPr-Phenyl |
| 487 | 1 | H | 3-Ph-Phenyl |
| 488 | 2 | H | 3-Ph-Phenyl |
| 489 | 3 | H | 3-Ph-Phenyl |
| 490 | 1 | Me | 3-Ph-Phenyl |
| 491 | 2 | Me | 3-Ph-Phenyl |
| 492 | 3 | Me | 3-Ph-Phenyl |
| 493 | 1 | CH₂Ph | 3-Ph-Phenyl |
| 494 | 2 | CH₂Ph | 3-Ph-Phenyl |
| 495 | 3 | CH₂Ph | 3-Ph-Phenyl |
| 496 | 1 | COMe | 3-Ph-Phenyl |
| 497 | 2 | COMe | 3-Ph-Phenyl |
| 498 | 3 | COMe | 3-Ph-Phenyl |
| 499 | 1 | CO₂Me | 3-Ph-Phenyl |
| 500 | 2 | CO₂Me | 3-Ph-Phenyl |
| 501 | 3 | CO₂Me | 3-Ph-Phenyl |
| 502 | 1 | CO₂tBu | 3-Ph-Phenyl |
| 503 | 2 | CO₂tBu | 3-Ph-Phenyl |
| 504 | 3 | CO₂tBu | 3-Ph-Phenyl |
| 505 | 1 | CONHMe | 3-Ph-Phenyl |
| 506 | 2 | CONHMe | 3-Ph-Phenyl |
| 507 | 3 | CONHMe | 3-Ph-Phenyl |
| 508 | 1 | SO₂Me | 3-Ph-Phenyl |
| 509 | 2 | SO₂Me | 3-Ph-Phenyl |
| 510 | 3 | SO₂Me | 3-Ph-Phenyl |
| 511 | 1 | SO₂NH₂ | 3-Ph-Phenyl |
| 512 | 2 | SO₂NH₂ | 3-Ph-Phenyl |
| 513 | 3 | SO₂NH₂ | 3-Ph-Phenyl |
| 514 | 1 | H | 2-morpholino-phenyl |
| 515 | 2 | H | 2-morpholino-phenyl |
| 516 | 3 | H | 2-morpholino-phenyl |
| 517 | 1 | Me | 2-morpholino-phenyl |
| 518 | 2 | Me | 2-morpholino-phenyl |
| 519 | 3 | Me | 2-morpholino-phenyl |
| 520 | 1 | CH₂Ph | 2-morpholino-phenyl |
| 521 | 2 | CH₂Ph | 2-morpholino-phenyl |
| 522 | 3 | CH₂Ph | 2-morpholino-phenyl |
| 523 | 1 | COMe | 2-morpholino-phenyl |
| 524 | 2 | COMe | 2-morpholino-phenyl |
| 525 | 3 | COMe | 2-morpholino-phenyl |
| 526 | 1 | CO₂Me | 2-morpholino-phenyl |
| 527 | 2 | CO₂Me | 2-morpholino-phenyl |
| 528 | 3 | CO₂Me | 2-morpholino-phenyl |
| 529 | 1 | CO₂tBu | 2-morpholino-phenyl |
| 530 | 2 | CO₂tBu | 2-morpholino-phenyl |
| 531 | 3 | CO₂tBu | 2-morpholino-phenyl |
| 532 | 1 | CONHMe | 2-morpholino-phenyl |
| 533 | 2 | CONHMe | 2-morpholino-phenyl |
| 534 | 3 | CONHMe | 2-morpholino-phenyl |
| 535 | 1 | SO₂Me | 2-morpholino-phenyl |
| 536 | 2 | SO₂Me | 2-morpholino-phenyl |
| 537 | 3 | SO₂Me | 2-morpholino-phenyl |
| 538 | 1 | SO₂NH₂ | 2-morpholino-phenyl |
| 539 | 2 | SO₂NH₂ | 2-morpholino-phenyl |
| 540 | 3 | SO₂NH₂ | 2-morpholino-phenyl |
| 541 | 1 | H | 4-morpholino-phenyl |
| 542 | 2 | H | 4-morpholino-phenyl |
| 543 | 3 | H | 4-morpholino-phenyl |
| 544 | 1 | Me | 4-morpholino-phenyl |
| 545 | 2 | Me | 4-morpholino-phenyl |
| 546 | 3 | Me | 4-morpholino-phenyl |
| 547 | 1 | CH₂Ph | 4-morpholino-phenyl |
| 548 | 2 | CH₂Ph | 4-morpholino-phenyl |
| 549 | 3 | CH₂Ph | 4-morpholino-phenyl |
| 550 | 1 | COMe | 4-morpholino-phenyl |
| 551 | 2 | COMe | 4-morpholino-phenyl |
| 552 | 3 | COMe | 4-morpholino-phenyl |
| 553 | 1 | CO₂Me | 4-morpholino-phenyl |
| 554 | 2 | CO₂Me | 4-morpholino-phenyl |
| 555 | 3 | CO₂Me | 4-morpholino-phenyl |
| 556 | 1 | CO₂tBu | 4-morpholino-phenyl |
| 557 | 2 | CO₂tBu | 4-morpholino-phenyl |
| 558 | 3 | CO₂tBu | 4-morpholino-phenyl |
| 559 | 1 | CONHMe | 4-morpholino-phenyl |
| 560 | 2 | CONHMe | 4-morpholino-phenyl |
| 561 | 3 | CONHMe | 4-morpholino-phenyl |
| 562 | 1 | SO₂Me | 4-morpholino-phenyl |
| 563 | 2 | SO₂Me | 4-morpholino-phenyl |
| 564 | 3 | SO₂Me | 4-morpholino-phenyl |
| 565 | 1 | SO₂NH₂ | 4-morpholino-phenyl |
| 566 | 2 | SO₂NH₂ | 4-morpholino-phenyl |
| 567 | 3 | SO₂NH₂ | 4-morpholino-phenyl |
| 568 | 1 | H | 2-pyrimidinyl |
| 569 | 2 | H | 2-pyrimidinyl |
| 570 | 3 | H | 2-pyrimidinyl |
| 571 | 1 | Me | 2-pyrimidinyl |
| 572 | 2 | Me | 2-pyrimidinyl |
| 573 | 3 | Me | 2-pyrimidinyl |
| 574 | 1 | CH₂Ph | 2-pyrimidinyl |
| 575 | 2 | CH₂Ph | 2-pyrimidinyl |
| 576 | 3 | CH₂Ph | 2-pyrimidinyl |
| 577 | 1 | COMe | 2-pyrimidinyl |
| 578 | 2 | COMe | 2-pyrimidinyl |
| 579 | 3 | COMe | 2-pyrimidinyl |
| 580 | 1 | CO₂Me | 2-pyrimidinyl |
| 581 | 2 | CO₂Me | 2-pyrimidinyl |
| 582 | 3 | CO₂Me | 2-pyrimidinyl |
| 583 | 1 | CO₂tBu | 2-pyrimidinyl |
| 584 | 2 | CO₂tBu | 2-pyrimidinyl |
| 585 | 3 | CO₂tBu | 2-pyrimidinyl |
| 586 | 1 | CONHMe | 2-pyrimidinyl |
| 587 | 2 | CONHMe | 2-pyrimidinyl |
| 588 | 3 | CONHMe | 2-pyrimidinyl |
| 589 | 1 | SO₂Me | 2-pyrimidinyl |
| 590 | 2 | SO₂Me | 2-pyrimidinyl |
| 591 | 3 | SO₂Me | 2-pyrimidinyl |
| 592 | 1 | SO₂NH₂ | 2-pyrimidinyl |
| 593 | 2 | SO₂NH₂ | 2-pyrimidinyl |
| 594 | 3 | SO₂NH₂ | 2-pyrimidinyl |
| 595 | 1 | H | 2-methyl-1H-benzo[d]imidazol-4-yl |
| 596 | 2 | H | 2-methyl-1H-benzo[d]imidazol-4-yl |
| 597 | 3 | H | 2-methyl-1H-benzo[d]imidazol-4-yl |
| 598 | 1 | Me | 2-methyl-1H-benzo[d]imidazol-4-yl |
| 599 | 2 | Me | 2-methyl-1H-benzo[d]imidazol-4-yl |
| 600 | 3 | Me | 2-methyl-1H-benzo[d]imidazol-4-yl |
| 601 | 1 | CH₂Ph | 2-methyl-1H-benzo[d]imidazol-4-yl |
| 602 | 2 | CH₂Ph | 2-methyl-1H-benzo[d]imidazol-4-yl |
| 603 | 3 | CH₂Ph | 2-methyl-1H-benzo[d]imidazol-4-yl |
| 604 | 1 | COMe | 2-methyl-1H-benzo[d]imidazol-4-yl |
| 605 | 2 | COMe | 2-methyl-1H-benzo[d]imidazol-4-yl |
| 606 | 3 | COMe | 2-methyl-1H-benzo[d]imidazol-4-yl |
| 607 | 1 | CO₂Me | 2-methyl-1H-benzo[d]imidazol-4-yl |
| 608 | 2 | CO₂Me | 2-methyl-1H-benzo[d]imidazol-4-yl |
| 609 | 3 | CO₂Me | 2-methyl-1H-benzo[d]imidazol-4-yl |

TABLE 1-continued

| Entry | n | R | R³ |
|---|---|---|---|
| 610 | 1 | CO₂tBu | 2-methyl-1H-benzo[d]imidazol-4-yl |
| 611 | 2 | CO₂tBu | 2-methyl-1H-benzo[d]imidazol-4-yl |
| 612 | 3 | CO₂tBu | 2-methyl-1H-benzo[d]imidazol-4-yl |
| 613 | 1 | CONHMe | 2-methyl-1H-benzo[d]imidazol-4-yl |
| 614 | 2 | CONHMe | 2-methyl-1H-benzo[d]imidazol-4-yl |
| 615 | 3 | CONHMe | 2-methyl-1H-benzo[d]imidazol-4-yl |
| 616 | 1 | SO₂Me | 2-methyl-1H-benzo[d]imidazol-4-yl |
| 617 | 2 | SO₂Me | 2-methyl-1H-benzo[d]imidazol-4-yl |
| 618 | 3 | SO₂Me | 2-methyl-1H-benzo[d]imidazol-4-yl |
| 619 | 1 | SO₂NH₂ | 2-methyl-1H-benzo[d]imidazol-4-yl |
| 620 | 2 | SO₂NH₂ | 2-methyl-1H-benzo[d]imidazol-4-yl |
| 621 | 3 | SO₂NH₂ | 2-methyl-1H-benzo[d]imidazol-4-yl |
| 622 | 1 | H | 4-OH-Phenyl |
| 623 | 2 | H | 4-OH-Phenyl |
| 624 | 3 | H | 4-OH-Phenyl |
| 625 | 1 | Me | 4-OH-Phenyl |
| 626 | 2 | Me | 4-OH-Phenyl |
| 627 | 3 | Me | 4-OH-Phenyl |
| 628 | 1 | CH₂Ph | 4-OH-Phenyl |
| 629 | 2 | CH₂Ph | 4-OH-Phenyl |
| 630 | 3 | CH₂Ph | 4-OH-Phenyl |
| 631 | 1 | COMe | 4-OH-Phenyl |
| 632 | 2 | COMe | 4-OH-Phenyl |
| 633 | 3 | COMe | 4-OH-Phenyl |
| 634 | 1 | CO₂Me | 4-OH-Phenyl |
| 635 | 2 | CO₂Me | 4-OH-Phenyl |
| 636 | 3 | CO₂Me | 4-OH-Phenyl |
| 637 | 1 | CO₂tBu | 4-OH-Phenyl |
| 638 | 2 | CO₂tBu | 4-OH-Phenyl |
| 639 | 3 | CO₂tBu | 4-OH-Phenyl |
| 640 | 1 | CONHMe | 4-OH-Phenyl |
| 641 | 2 | CONHMe | 4-OH-Phenyl |
| 642 | 3 | CONHMe | 4-OH-Phenyl |
| 643 | 1 | SO₂Me | 4-OH-Phenyl |
| 644 | 2 | SO₂Me | 4-OH-Phenyl |
| 645 | 3 | SO₂Me | 4-OH-Phenyl |
| 646 | 1 | SO₂NH₂ | 4-OH-Phenyl |
| 647 | 2 | SO₂NH₂ | 4-OH-Phenyl |
| 648 | 3 | SO₂NH₂ | 4-OH-Phenyl |
| 649 | 1 | H | 2-OH-Phenyl |
| 650 | 2 | H | 2-OH-Phenyl |
| 651 | 3 | H | 2-OH-Phenyl |
| 652 | 1 | Me | 2-OH-Phenyl |
| 653 | 2 | Me | 2-OH-Phenyl |
| 654 | 3 | Me | 2-OH-Phenyl |
| 655 | 1 | CH₂Ph | 2-OH-Phenyl |
| 656 | 2 | CH₂Ph | 2-OH-Phenyl |
| 657 | 3 | CH₂Ph | 2-OH-Phenyl |
| 658 | 1 | COMe | 2-OH-Phenyl |
| 659 | 2 | COMe | 2-OH-Phenyl |
| 660 | 3 | COMe | 2-OH-Phenyl |
| 661 | 1 | CO₂Me | 2-OH-Phenyl |
| 662 | 2 | CO₂Me | 2-OH-Phenyl |
| 663 | 3 | CO₂Me | 2-OH-Phenyl |
| 664 | 1 | CO₂tBu | 2-OH-Phenyl |
| 665 | 2 | CO₂tBu | 2-OH-Phenyl |
| 666 | 3 | CO₂tBu | 2-OH-Phenyl |
| 667 | 1 | CONHMe | 2-OH-Phenyl |
| 668 | 2 | CONHMe | 2-OH-Phenyl |
| 669 | 3 | CONHMe | 2-OH-Phenyl |
| 670 | 1 | SO₂Me | 2-OH-Phenyl |
| 671 | 2 | SO₂Me | 2-OH-Phenyl |
| 672 | 3 | SO₂Me | 2-OH-Phenyl |
| 673 | 1 | SO₂NH₂ | 2-OH-Phenyl |
| 674 | 2 | SO₂NH₂ | 2-OH-Phenyl |
| 675 | 3 | SO₂NH₂ | 2-OH-Phenyl |
| 676 | 1 | H | 4-OMe-Phenyl |
| 677 | 2 | H | 4-OMe-Phenyl |
| 678 | 3 | H | 4-OMe-Phenyl |
| 679 | 1 | Me | 4-OMe-Phenyl |
| 680 | 2 | Me | 4-OMe-Phenyl |
| 681 | 3 | Me | 4-OMe-Phenyl |
| 682 | 1 | CH₂Ph | 4-OMe-Phenyl |
| 683 | 2 | CH₂Ph | 4-OMe-Phenyl |
| 684 | 3 | CH₂Ph | 4-OMe-Phenyl |
| 685 | 1 | COMe | 4-OMe-Phenyl |
| 686 | 2 | COMe | 4-OMe-Phenyl |
| 687 | 3 | COMe | 4-OMe-Phenyl |
| 688 | 1 | CO₂Me | 4-OMe-Phenyl |
| 689 | 2 | CO₂Me | 4-OMe-Phenyl |
| 690 | 3 | CO₂Me | 4-OMe-Phenyl |
| 691 | 1 | CO₂tBu | 4-OMe-Phenyl |
| 692 | 2 | CO₂tBu | 4-OMe-Phenyl |
| 693 | 3 | CO₂tBu | 4-OMe-Phenyl |
| 694 | 1 | CONHMe | 4-OMe-Phenyl |
| 695 | 2 | CONHMe | 4-OMe-Phenyl |
| 696 | 3 | CONHMe | 4-OMe-Phenyl |
| 697 | 1 | SO₂Me | 4-OMe-Phenyl |
| 698 | 2 | SO₂Me | 4-OMe-Phenyl |
| 699 | 3 | SO₂Me | 4-OMe-Phenyl |
| 700 | 1 | SO₂NH₂ | 4-OMe-Phenyl |
| 701 | 2 | SO₂NH₂ | 4-OMe-Phenyl |
| 702 | 3 | SO₂NH₂ | 4-OMe-Phenyl |
| 703 | 1 | H | 2-OMe-Phenyl |
| 704 | 2 | H | 2-OMe-Phenyl |
| 705 | 3 | H | 2-OMe-Phenyl |
| 706 | 1 | Me | 2-OMe-Phenyl |
| 707 | 2 | Me | 2-OMe-Phenyl |
| 708 | 3 | Me | 2-OMe-Phenyl |
| 709 | 1 | CH₂Ph | 2-OMe-Phenyl |
| 710 | 2 | CH₂Ph | 2-OMe-Phenyl |
| 711 | 3 | CH₂Ph | 2-OMe-Phenyl |
| 712 | 1 | COMe | 2-OMe-Phenyl |
| 713 | 2 | COMe | 2-OMe-Phenyl |
| 714 | 3 | COMe | 2-OMe-Phenyl |
| 715 | 1 | CO₂Me | 2-OMe-Phenyl |
| 716 | 2 | CO₂Me | 2-OMe-Phenyl |
| 717 | 3 | CO₂Me | 2-OMe-Phenyl |
| 718 | 1 | CO₂tBu | 2-OMe-Phenyl |
| 719 | 2 | CO₂tBu | 2-OMe-Phenyl |
| 720 | 3 | CO₂tBu | 2-OMe-Phenyl |
| 721 | 1 | CONHMe | 2-OMe-Phenyl |
| 722 | 2 | CONHMe | 2-OMe-Phenyl |
| 723 | 3 | CONHMe | 2-OMe-Phenyl |
| 724 | 1 | SO₂Me | 2-OMe-Phenyl |
| 725 | 2 | SO₂Me | 2-OMe-Phenyl |
| 726 | 3 | SO₂Me | 2-OMe-Phenyl |
| 727 | 1 | SO₂NH₂ | 2-OMe-Phenyl |
| 728 | 2 | SO₂NH₂ | 2-OMe-Phenyl |
| 729 | 3 | SO₂NH₂ | 2-OMe-Phenyl |
| 730 | 1 | H | 3-CN-Phenyl |
| 731 | 2 | H | 3-CN-Phenyl |
| 732 | 3 | H | 3-CN-Phenyl |
| 733 | 1 | Me | 3-CN-Phenyl |
| 734 | 2 | Me | 3-CN-Phenyl |
| 735 | 3 | Me | 3-CN-Phenyl |
| 736 | 1 | CH₂Ph | 3-CN-Phenyl |
| 737 | 2 | CH₂Ph | 3-CN-Phenyl |
| 738 | 3 | CH₂Ph | 3-CN-Phenyl |
| 739 | 1 | COMe | 3-CN-Phenyl |
| 740 | 2 | COMe | 3-CN-Phenyl |
| 741 | 3 | COMe | 3-CN-Phenyl |
| 742 | 1 | CO₂Me | 3-CN-Phenyl |
| 743 | 2 | CO₂Me | 3-CN-Phenyl |
| 744 | 3 | CO₂Me | 3-CN-Phenyl |
| 745 | 1 | CO₂tBu | 3-CN-Phenyl |
| 746 | 2 | CO₂tBu | 3-CN-Phenyl |
| 747 | 3 | CO₂tBu | 3-CN-Phenyl |
| 748 | 1 | CONHMe | 3-CN-Phenyl |
| 749 | 2 | CONHMe | 3-CN-Phenyl |
| 750 | 3 | CONHMe | 3-CN-Phenyl |
| 751 | 1 | SO₂Me | 3-CN-Phenyl |
| 752 | 2 | SO₂Me | 3-CN-Phenyl |
| 753 | 3 | SO₂Me | 3-CN-Phenyl |

TABLE 1-continued

| Entry | n | R | R³ |
|---|---|---|---|
| 754 | 1 | SO₂NH₂ | 3-CN-Phenyl |
| 755 | 2 | SO₂NH₂ | 3-CN-Phenyl |
| 756 | 3 | SO₂NH₂ | 3-CN-Phenyl |
| 757 | 1 | H | 2-Me-Phenyl |
| 758 | 2 | H | 2-Me-Phenyl |
| 759 | 3 | H | 2-Me-Phenyl |
| 760 | 1 | Me | 2-Me-Phenyl |
| 761 | 2 | Me | 2-Me-Phenyl |
| 762 | 3 | Me | 2-Me-Phenyl |
| 763 | 1 | CH₂Ph | 2-Me-Phenyl |
| 764 | 2 | CH₂Ph | 2-Me-Phenyl |
| 765 | 3 | CH₂Ph | 2-Me-Phenyl |
| 766 | 1 | COMe | 2-Me-Phenyl |
| 767 | 2 | COMe | 2-Me-Phenyl |
| 768 | 3 | COMe | 2-Me-Phenyl |
| 769 | 1 | CO₂Me | 2-Me-Phenyl |
| 770 | 2 | CO₂Me | 2-Me-Phenyl |
| 771 | 3 | CO₂Me | 2-Me-Phenyl |
| 772 | 1 | CO₂tBu | 2-Me-Phenyl |
| 773 | 2 | CO₂tBu | 2-Me-Phenyl |
| 774 | 3 | CO₂tBu | 2-Me-Phenyl |
| 775 | 1 | CONHMe | 2-Me-Phenyl |
| 776 | 2 | CONHMe | 2-Me-Phenyl |
| 777 | 3 | CONHMe | 2-Me-Phenyl |
| 778 | 1 | SO₂Me | 2-Me-Phenyl |
| 779 | 2 | SO₂Me | 2-Me-Phenyl |
| 780 | 3 | SO₂Me | 2-Me-Phenyl |
| 781 | 1 | SO₂NH₂ | 2-Me-Phenyl |
| 782 | 2 | SO₂NH₂ | 2-Me-Phenyl |
| 783 | 3 | SO₂NH₂ | 2-Me-Phenyl |
| 784 | 1 | H | 4-Me-Phenyl |
| 785 | 2 | H | 4-Me-Phenyl |
| 786 | 3 | H | 4-Me-Phenyl |
| 787 | 1 | Me | 4-Me-Phenyl |
| 788 | 2 | Me | 4-Me-Phenyl |
| 789 | 3 | Me | 4-Me-Phenyl |
| 790 | 1 | CH₂Ph | 4-Me-Phenyl |
| 791 | 2 | CH₂Ph | 4-Me-Phenyl |
| 792 | 3 | CH₂Ph | 4-Me-Phenyl |
| 793 | 1 | COMe | 4-Me-Phenyl |
| 794 | 2 | COMe | 4-Me-Phenyl |
| 795 | 3 | COMe | 4-Me-Phenyl |
| 796 | 1 | CO₂Me | 4-Me-Phenyl |
| 797 | 2 | CO₂Me | 4-Me-Phenyl |
| 798 | 3 | CO₂Me | 4-Me-Phenyl |
| 799 | 1 | CO₂tBu | 4-Me-Phenyl |
| 800 | 2 | CO₂tBu | 4-Me-Phenyl |
| 801 | 3 | CO₂tBu | 4-Me-Phenyl |
| 802 | 1 | CONHMe | 4-Me-Phenyl |
| 803 | 2 | CONHMe | 4-Me-Phenyl |
| 804 | 3 | CONHMe | 4-Me-Phenyl |
| 805 | 1 | SO₂Me | 4-Me-Phenyl |
| 806 | 2 | SO₂Me | 4-Me-Phenyl |
| 807 | 3 | SO₂Me | 4-Me-Phenyl |
| 808 | 1 | SO₂NH₂ | 4-Me-Phenyl |
| 809 | 2 | SO₂NH₂ | 4-Me-Phenyl |
| 810 | 3 | SO₂NH₂ | 4-Me-Phenyl |
| 811 | 1 | H | 3-F-Phenyl |
| 812 | 2 | H | 3-F-Phenyl |
| 813 | 3 | H | 3-F-Phenyl |
| 814 | 1 | Me | 3-F-Phenyl |
| 815 | 2 | Me | 3-F-Phenyl |
| 816 | 3 | Me | 3-F-Phenyl |
| 817 | 1 | CH₂Ph | 3-F-Phenyl |
| 818 | 2 | CH₂Ph | 3-F-Phenyl |
| 819 | 3 | CH₂Ph | 3-F-Phenyl |
| 820 | 1 | COMe | 3-F-Phenyl |
| 821 | 2 | COMe | 3-F-Phenyl |
| 822 | 3 | COMe | 3-F-Phenyl |
| 823 | 1 | CO₂Me | 3-F-Phenyl |
| 824 | 2 | CO₂Me | 3-F-Phenyl |
| 825 | 3 | CO₂Me | 3-F-Phenyl |
| 826 | 1 | CO₂tBu | 3-F-Phenyl |
| 827 | 2 | CO₂tBu | 3-F-Phenyl |
| 828 | 3 | CO₂tBu | 3-F-Phenyl |
| 829 | 1 | CONHMe | 3-F-Phenyl |
| 830 | 2 | CONHMe | 3-F-Phenyl |
| 831 | 3 | CONHMe | 3-F-Phenyl |
| 832 | 1 | SO₂Me | 3-F-Phenyl |
| 833 | 2 | SO₂Me | 3-F-Phenyl |
| 834 | 3 | SO₂Me | 3-F-Phenyl |
| 835 | 1 | SO₂NH₂ | 3-F-Phenyl |
| 836 | 2 | SO₂NH₂ | 3-F-Phenyl |
| 837 | 3 | SO₂NH₂ | 3-F-Phenyl |
| 838 | 1 | H | 2-Cl-Phenyl |
| 839 | 2 | H | 2-Cl-Phenyl |
| 840 | 3 | H | 2-Cl-Phenyl |
| 841 | 1 | Me | 2-Cl-Phenyl |
| 842 | 2 | Me | 2-Cl-Phenyl |
| 843 | 3 | Me | 2-Cl-Phenyl |
| 844 | 1 | CH₂Ph | 2-Cl-Phenyl |
| 845 | 2 | CH₂Ph | 2-Cl-Phenyl |
| 846 | 3 | CH₂Ph | 2-Cl-Phenyl |
| 847 | 1 | COMe | 2-Cl-Phenyl |
| 848 | 2 | COMe | 2-Cl-Phenyl |
| 849 | 3 | COMe | 2-Cl-Phenyl |
| 850 | 1 | CO₂Me | 2-Cl-Phenyl |
| 851 | 2 | CO₂Me | 2-Cl-Phenyl |
| 852 | 3 | CO₂Me | 2-Cl-Phenyl |
| 853 | 1 | CO₂tBu | 2-Cl-Phenyl |
| 854 | 2 | CO₂tBu | 2-Cl-Phenyl |
| 855 | 3 | CO₂tBu | 2-Cl-Phenyl |
| 856 | 1 | CONHMe | 2-Cl-Phenyl |
| 857 | 2 | CONHMe | 2-Cl-Phenyl |
| 858 | 3 | CONHMe | 2-Cl-Phenyl |
| 859 | 1 | SO₂Me | 2-Cl-Phenyl |
| 860 | 2 | SO₂Me | 2-Cl-Phenyl |
| 861 | 3 | SO₂Me | 2-Cl-Phenyl |
| 862 | 1 | SO₂NH₂ | 2-Cl-Phenyl |
| 863 | 2 | SO₂NH₂ | 2-Cl-Phenyl |
| 864 | 3 | SO₂NH₂ | 2-Cl-Phenyl |
| 865 | 1 | H | 4-Cl-Phenyl |
| 866 | 2 | H | 4-Cl-Phenyl |
| 867 | 3 | H | 4-Cl-Phenyl |
| 868 | 1 | Me | 4-Cl-Phenyl |
| 869 | 2 | Me | 4-Cl-Phenyl |
| 870 | 3 | Me | 4-Cl-Phenyl |
| 871 | 1 | CH₂Ph | 4-Cl-Phenyl |
| 872 | 2 | CH₂Ph | 4-Cl-Phenyl |
| 873 | 3 | CH₂Ph | 4-Cl-Phenyl |
| 874 | 1 | COMe | 4-Cl-Phenyl |
| 875 | 2 | COMe | 4-Cl-Phenyl |
| 876 | 3 | COMe | 4-Cl-Phenyl |
| 877 | 1 | CO₂Me | 4-Cl-Phenyl |
| 878 | 2 | CO₂Me | 4-Cl-Phenyl |
| 879 | 3 | CO₂Me | 4-Cl-Phenyl |
| 880 | 1 | CO₂tBu | 4-Cl-Phenyl |
| 881 | 2 | CO₂tBu | 4-Cl-Phenyl |
| 882 | 3 | CO₂tBu | 4-Cl-Phenyl |
| 883 | 1 | CONHMe | 4-Cl-Phenyl |
| 884 | 2 | CONHMe | 4-Cl-Phenyl |
| 885 | 3 | CONHMe | 4-Cl-Phenyl |
| 886 | 1 | SO₂Me | 4-Cl-Phenyl |
| 887 | 2 | SO₂Me | 4-Cl-Phenyl |
| 888 | 3 | SO₂Me | 4-Cl-Phenyl |
| 889 | 1 | SO₂NH₂ | 4-Cl-Phenyl |
| 890 | 2 | SO₂NH₂ | 4-Cl-Phenyl |
| 891 | 3 | SO₂NH₂ | 4-Cl-Phenyl |
| 892 | 1 | H | 3-Br-Phenyl |
| 893 | 2 | H | 3-Br-Phenyl |
| 894 | 3 | H | 3-Br-Phenyl |
| 895 | 1 | Me | 3-Br-Phenyl |
| 896 | 2 | Me | 3-Br-Phenyl |
| 897 | 3 | Me | 3-Br-Phenyl |
| 898 | 1 | CH₂Ph | 3-Br-Phenyl |
| 899 | 2 | CH₂Ph | 3-Br-Phenyl |
| 900 | 3 | CH₂Ph | 3-Br-Phenyl |
| 901 | 1 | COMe | 3-Br-Phenyl |
| 902 | 2 | COMe | 3-Br-Phenyl |
| 903 | 3 | COMe | 3-Br-Phenyl |
| 904 | 1 | CO₂Me | 3-Br-Phenyl |
| 905 | 2 | CO₂Me | 3-Br-Phenyl |
| 906 | 3 | CO₂Me | 3-Br-Phenyl |
| 907 | 1 | CO₂tBu | 3-Br-Phenyl |
| 908 | 2 | CO₂tBu | 3-Br-Phenyl |
| 909 | 3 | CO₂tBu | 3-Br-Phenyl |

TABLE 1-continued

| Entry | n | R | R³ |
|---|---|---|---|
| 910 | 1 | CONHMe | 3-Br-Phenyl |
| 911 | 2 | CONHMe | 3-Br-Phenyl |
| 912 | 3 | CONHMe | 3-Br-Phenyl |
| 913 | 1 | $SO_2Me$ | 3-Br-Phenyl |
| 914 | 2 | $SO_2Me$ | 3-Br-Phenyl |
| 915 | 3 | $SO_2Me$ | 3-Br-Phenyl |
| 916 | 1 | $SO_2NH_2$ | 3-Br-Phenyl |
| 917 | 2 | $SO_2NH_2$ | 3-Br-Phenyl |
| 918 | 3 | $SO_2NH_2$ | 3-Br-Phenyl |
| 919 | 1 | H | 2-$CF_3$-Phenyl |
| 920 | 2 | H | 2-$CF_3$-Phenyl |
| 921 | 3 | H | 2-$CF_3$-Phenyl |
| 922 | 1 | Me | 2-$CF_3$-Phenyl |
| 923 | 2 | Me | 2-$CF_3$-Phenyl |
| 924 | 3 | Me | 2-$CF_3$-Phenyl |
| 925 | 1 | $CH_2Ph$ | 2-$CF_3$-Phenyl |
| 926 | 2 | $CH_2Ph$ | 2-$CF_3$-Phenyl |
| 927 | 3 | $CH_2Ph$ | 2-$CF_3$-Phenyl |
| 928 | 1 | COMe | 2-$CF_3$-Phenyl |
| 929 | 2 | COMe | 2-$CF_3$-Phenyl |
| 930 | 3 | COMe | 2-$CF_3$-Phenyl |
| 931 | 1 | $CO_2Me$ | 2-$CF_3$-Phenyl |
| 932 | 2 | $CO_2Me$ | 2-$CF_3$-Phenyl |
| 933 | 3 | $CO_2Me$ | 2-$CF_3$-Phenyl |
| 934 | 1 | $CO_2tBu$ | 2-$CF_3$-Phenyl |
| 935 | 2 | $CO_2tBu$ | 2-$CF_3$-Phenyl |
| 936 | 3 | $CO_2tBu$ | 2-$CF_3$-Phenyl |
| 937 | 1 | CONHMe | 2-$CF_3$-Phenyl |
| 938 | 2 | CONHMe | 2-$CF_3$-Phenyl |
| 939 | 3 | CONHMe | 2-$CF_3$-Phenyl |
| 940 | 1 | $SO_2Me$ | 2-$CF_3$-Phenyl |
| 941 | 2 | $SO_2Me$ | 2-$CF_3$-Phenyl |
| 942 | 3 | $SO_2Me$ | 2-$CF_3$-Phenyl |
| 943 | 1 | $SO_2NH_2$ | 2-$CF_3$-Phenyl |
| 944 | 2 | $SO_2NH_2$ | 2-$CF_3$-Phenyl |
| 945 | 3 | $SO_2NH_2$ | 2-$CF_3$-Phenyl |
| 946 | 1 | H | 4-$CF_3$-Phenyl |
| 947 | 2 | H | 4-$CF_3$-Phenyl |
| 948 | 3 | H | 4-$CF_3$-Phenyl |
| 949 | 1 | Me | 4-$CF_3$-Phenyl |
| 950 | 2 | Me | 4-$CF_3$-Phenyl |
| 951 | 3 | Me | 4-$CF_3$-Phenyl |
| 952 | 1 | $CH_2Ph$ | 4-$CF_3$-Phenyl |
| 953 | 2 | $CH_2Ph$ | 4-$CF_3$-Phenyl |
| 954 | 3 | $CH_2Ph$ | 4-$CF_3$-Phenyl |
| 955 | 1 | COMe | 4-$CF_3$-Phenyl |
| 956 | 2 | COMe | 4-$CF_3$-Phenyl |
| 957 | 3 | COMe | 4-$CF_3$-Phenyl |
| 958 | 1 | $CO_2Me$ | 4-$CF_3$-Phenyl |
| 959 | 2 | $CO_2Me$ | 4-$CF_3$-Phenyl |
| 960 | 3 | $CO_2Me$ | 4-$CF_3$-Phenyl |
| 961 | 1 | $CO_2tBu$ | 4-$CF_3$-Phenyl |
| 962 | 2 | $CO_2tBu$ | 4-$CF_3$-Phenyl |
| 963 | 3 | $CO_2tBu$ | 4-$CF_3$-Phenyl |
| 964 | 1 | CONHMe | 4-$CF_3$-Phenyl |
| 965 | 2 | CONHMe | 4-$CF_3$-Phenyl |
| 966 | 3 | CONHMe | 4-$CF_3$-Phenyl |
| 967 | 1 | $SO_2Me$ | 4-$CF_3$-Phenyl |
| 968 | 2 | $SO_2Me$ | 4-$CF_3$-Phenyl |
| 969 | 3 | $SO_2Me$ | 4-$CF_3$-Phenyl |
| 970 | 1 | $SO_2NH_2$ | 4-$CF_3$-Phenyl |
| 971 | 2 | $SO_2NH_2$ | 4-$CF_3$-Phenyl |
| 972 | 3 | $SO_2NH_2$ | 4-$CF_3$-Phenyl |
| 973 | 1 | H | 3-iPr-Phenyl |
| 974 | 2 | H | 3-iPr-Phenyl |
| 975 | 3 | H | 3-iPr-Phenyl |
| 976 | 1 | Me | 3-iPr-Phenyl |
| 977 | 2 | Me | 3-iPr-Phenyl |
| 978 | 3 | Me | 3-iPr-Phenyl |
| 979 | 1 | $CH_2Ph$ | 3-iPr-Phenyl |
| 980 | 2 | $CH_2Ph$ | 3-iPr-Phenyl |
| 981 | 3 | $CH_2Ph$ | 3-iPr-Phenyl |
| 982 | 1 | COMe | 3-iPr-Phenyl |
| 983 | 2 | COMe | 3-iPr-Phenyl |
| 984 | 3 | COMe | 3-iPr-Phenyl |
| 985 | 1 | $CO_2Me$ | 3-iPr-Phenyl |
| 986 | 2 | $CO_2Me$ | 3-iPr-Phenyl |
| 987 | 3 | $CO_2Me$ | 3-iPr-Phenyl |
| 988 | 1 | $CO_2tBu$ | 3-iPr-Phenyl |
| 989 | 2 | $CO_2tBu$ | 3-iPr-Phenyl |
| 990 | 3 | $CO_2tBu$ | 3-iPr-Phenyl |
| 991 | 1 | CONHMe | 3-iPr-Phenyl |
| 992 | 2 | CONHMe | 3-iPr-Phenyl |
| 993 | 3 | CONHMe | 3-iPr-Phenyl |
| 994 | 1 | $SO_2Me$ | 3-iPr-Phenyl |
| 995 | 2 | $SO_2Me$ | 3-iPr-Phenyl |
| 996 | 3 | $SO_2Me$ | 3-iPr-Phenyl |
| 997 | 1 | $SO_2NH_2$ | 3-iPr-Phenyl |
| 998 | 2 | $SO_2NH_2$ | 3-iPr-Phenyl |
| 999 | 3 | $SO_2NH_2$ | 3-iPr-Phenyl |
| 1000 | 1 | H | 4-$NH_2$-Phenyl |
| 1001 | 2 | H | 4-$NH_2$-Phenyl |
| 1002 | 3 | H | 4-$NH_2$-Phenyl |
| 1003 | 1 | Me | 4-$NH_2$-Phenyl |
| 1004 | 2 | Me | 4-$NH_2$-Phenyl |
| 1005 | 3 | Me | 4-$NH_2$-Phenyl |
| 1006 | 1 | $CH_2Ph$ | 4-$NH_2$-Phenyl |
| 1007 | 2 | $CH_2Ph$ | 4-$NH_2$-Phenyl |
| 1008 | 3 | $CH_2Ph$ | 4-$NH_2$-Phenyl |
| 1009 | 1 | COMe | 4-$NH_2$-Phenyl |
| 1010 | 2 | COMe | 4-$NH_2$-Phenyl |
| 1011 | 3 | COMe | 4-$NH_2$-Phenyl |
| 1012 | 1 | $CO_2Me$ | 4-$NH_2$-Phenyl |
| 1013 | 2 | $CO_2Me$ | 4-$NH_2$-Phenyl |
| 1014 | 3 | $CO_2Me$ | 4-$NH_2$-Phenyl |
| 1015 | 1 | $CO_2tBu$ | 4-$NH_2$-Phenyl |
| 1016 | 2 | $CO_2tBu$ | 4-$NH_2$-Phenyl |
| 1017 | 3 | $CO_2tBu$ | 4-$NH_2$-Phenyl |
| 1018 | 1 | CONHMe | 4-$NH_2$-Phenyl |
| 1019 | 2 | CONHMe | 4-$NH_2$-Phenyl |
| 1020 | 3 | CONHMe | 4-$NH_2$-Phenyl |
| 1021 | 1 | $SO_2Me$ | 4-$NH_2$-Phenyl |
| 1022 | 2 | $SO_2Me$ | 4-$NH_2$-Phenyl |
| 1023 | 3 | $SO_2Me$ | 4-$NH_2$-Phenyl |
| 1024 | 1 | $SO_2NH_2$ | 4-$NH_2$-Phenyl |
| 1025 | 2 | $SO_2NH_2$ | 4-$NH_2$-Phenyl |
| 1026 | 3 | $SO_2NH_2$ | 4-$NH_2$-Phenyl |
| 1027 | 1 | H | 2-$NH_2$-Phenyl |
| 1028 | 2 | H | 2-$NH_2$-Phenyl |
| 1029 | 3 | H | 2-$NH_2$-Phenyl |
| 1030 | 1 | Me | 2-$NH_2$-Phenyl |
| 1031 | 2 | Me | 2-$NH_2$-Phenyl |
| 1032 | 3 | Me | 2-$NH_2$-Phenyl |
| 1033 | 1 | $CH_2Ph$ | 2-$NH_2$-Phenyl |
| 1034 | 2 | $CH_2Ph$ | 2-$NH_2$-Phenyl |
| 1035 | 3 | $CH_2Ph$ | 2-$NH_2$-Phenyl |
| 1036 | 1 | COMe | 2-$NH_2$-Phenyl |
| 1037 | 2 | COMe | 2-$NH_2$-Phenyl |
| 1038 | 3 | COMe | 2-$NH_2$-Phenyl |
| 1039 | 1 | $CO_2Me$ | 2-$NH_2$-Phenyl |
| 1040 | 2 | $CO_2Me$ | 2-$NH_2$-Phenyl |
| 1041 | 3 | $CO_2Me$ | 2-$NH_2$-Phenyl |
| 1042 | 1 | $CO_2tBu$ | 2-$NH_2$-Phenyl |
| 1043 | 2 | $CO_2tBu$ | 2-$NH_2$-Phenyl |
| 1044 | 3 | $CO_2tBu$ | 2-$NH_2$-Phenyl |
| 1045 | 1 | CONHMe | 2-$NH_2$-Phenyl |
| 1046 | 2 | CONHMe | 2-$NH_2$-Phenyl |
| 1047 | 3 | CONHMe | 2-$NH_2$-Phenyl |
| 1048 | 1 | $SO_2Me$ | 2-$NH_2$-Phenyl |
| 1049 | 2 | $SO_2Me$ | 2-$NH_2$-Phenyl |
| 1050 | 3 | $SO_2Me$ | 2-$NH_2$-Phenyl |
| 1051 | 1 | $SO_2NH_2$ | 2-$NH_2$-Phenyl |
| 1052 | 2 | $SO_2NH_2$ | 2-$NH_2$-Phenyl |
| 1053 | 3 | $SO_2NH_2$ | 2-$NH_2$-Phenyl |
| 1054 | 1 | H | 2,6-di-Me-Phenyl |
| 1055 | 2 | H | 2,6-di-Me-Phenyl |
| 1056 | 3 | H | 2,6-di-Me-Phenyl |
| 1057 | 1 | Me | 2,6-di-Me-Phenyl |
| 1058 | 2 | Me | 2,6-di-Me-Phenyl |
| 1059 | 3 | Me | 2,6-di-Me-Phenyl |
| 1060 | 1 | $CH_2Ph$ | 2,6-di-Me-Phenyl |
| 1061 | 2 | $CH_2Ph$ | 2,6-di-Me-Phenyl |
| 1062 | 3 | $CH_2Ph$ | 2,6-di-Me-Phenyl |
| 1063 | 1 | COMe | 2,6-di-Me-Phenyl |
| 1064 | 2 | COMe | 2,6-di-Me-Phenyl |
| 1065 | 3 | COMe | 2,6-di-Me-Phenyl |

TABLE 1-continued

| Entry | n | R | R³ |
|---|---|---|---|
| 1066 | 1 | CO₂Me | 2,6-di-Me-Phenyl |
| 1067 | 2 | CO₂Me | 2,6-di-Me-Phenyl |
| 1068 | 3 | CO₂Me | 2,6-di-Me-Phenyl |
| 1069 | 1 | CO₂tBu | 2,6-di-Me-Phenyl |
| 1070 | 2 | CO₂tBu | 2,6-di-Me-Phenyl |
| 1071 | 3 | CO₂tBu | 2,6-di-Me-Phenyl |
| 1072 | 1 | CONHMe | 2,6-di-Me-Phenyl |
| 1073 | 2 | CONHMe | 2,6-di-Me-Phenyl |
| 1074 | 3 | CONHMe | 2,6-di-Me-Phenyl |
| 1075 | 1 | SO₂Me | 2,6-di-Me-Phenyl |
| 1076 | 2 | SO₂Me | 2,6-di-Me-Phenyl |
| 1077 | 3 | SO₂Me | 2,6-di-Me-Phenyl |
| 1078 | 1 | SO₂NH₂ | 2,6-di-Me-Phenyl |
| 1079 | 2 | SO₂NH₂ | 2,6-di-Me-Phenyl |
| 1080 | 3 | SO₂NH₂ | 2,6-di-Me-Phenyl |
| 1081 | 1 | H | 2-Ph-Phenyl |
| 1082 | 2 | H | 2-Ph-Phenyl |
| 1083 | 3 | H | 2-Ph-Phenyl |
| 1084 | 1 | Me | 2-Ph-Phenyl |
| 1085 | 2 | Me | 2-Ph-Phenyl |
| 1086 | 3 | Me | 2-Ph-Phenyl |
| 1087 | 1 | CH₂Ph | 2-Ph-Phenyl |
| 1088 | 2 | CH₂Ph | 2-Ph-Phenyl |
| 1089 | 3 | CH₂Ph | 2-Ph-Phenyl |
| 1090 | 1 | COMe | 2-Ph-Phenyl |
| 1091 | 2 | COMe | 2-Ph-Phenyl |
| 1092 | 3 | COMe | 2-Ph-Phenyl |
| 1093 | 1 | CO₂Me | 2-Ph-Phenyl |
| 1094 | 2 | CO₂Me | 2-Ph-Phenyl |
| 1095 | 3 | CO₂Me | 2-Ph-Phenyl |
| 1096 | 1 | CO₂tBu | 2-Ph-Phenyl |
| 1097 | 2 | CO₂tBu | 2-Ph-Phenyl |
| 1098 | 3 | CO₂tBu | 2-Ph-Phenyl |
| 1099 | 1 | CONHMe | 2-Ph-Phenyl |
| 1100 | 2 | CONHMe | 2-Ph-Phenyl |
| 1101 | 3 | CONHMe | 2-Ph-Phenyl |
| 1102 | 1 | SO₂Me | 2-Ph-Phenyl |
| 1103 | 2 | SO₂Me | 2-Ph-Phenyl |
| 1104 | 3 | SO₂Me | 2-Ph-Phenyl |
| 1105 | 1 | SO₂NH₂ | 2-Ph-Phenyl |
| 1106 | 2 | SO₂NH₂ | 2-Ph-Phenyl |
| 1107 | 3 | SO₂NH₂ | 2-Ph-Phenyl |
| 1108 | 1 | H | 4-Ph-Phenyl |
| 1109 | 2 | H | 4-Ph-Phenyl |
| 1110 | 3 | H | 4-Ph-Phenyl |
| 1111 | 1 | Me | 4-Ph-Phenyl |
| 1112 | 2 | Me | 4-Ph-Phenyl |
| 1113 | 3 | Me | 4-Ph-Phenyl |
| 1114 | 1 | CH₂Ph | 4-Ph-Phenyl |
| 1115 | 2 | CH₂Ph | 4-Ph-Phenyl |
| 1116 | 3 | CH₂Ph | 4-Ph-Phenyl |
| 1117 | 1 | COMe | 4-Ph-Phenyl |
| 1118 | 2 | COMe | 4-Ph-Phenyl |
| 1119 | 3 | COMe | 4-Ph-Phenyl |
| 1120 | 1 | CO₂Me | 4-Ph-Phenyl |
| 1121 | 2 | CO₂Me | 4-Ph-Phenyl |
| 1122 | 3 | CO₂Me | 4-Ph-Phenyl |
| 1123 | 1 | CO₂tBu | 4-Ph-Phenyl |
| 1124 | 2 | CO₂tBu | 4-Ph-Phenyl |
| 1125 | 3 | CO₂tBu | 4-Ph-Phenyl |
| 1126 | 1 | CONHMe | 4-Ph-Phenyl |
| 1127 | 2 | CONHMe | 4-Ph-Phenyl |
| 1128 | 3 | CONHMe | 4-Ph-Phenyl |
| 1129 | 1 | SO₂Me | 4-Ph-Phenyl |
| 1130 | 2 | SO₂Me | 4-Ph-Phenyl |
| 1131 | 3 | SO₂Me | 4-Ph-Phenyl |
| 1132 | 1 | SO₂NH₂ | 4-Ph-Phenyl |
| 1133 | 2 | SO₂NH₂ | 4-Ph-Phenyl |
| 1134 | 3 | SO₂NH₂ | 4-Ph-Phenyl |
| 1135 | 1 | H | 3-morpholino-phenyl |
| 1136 | 2 | H | 3-morpholino-phenyl |
| 1137 | 3 | H | 3-morpholino-phenyl |
| 1138 | 1 | Me | 3-morpholino-henyl |
| 1139 | 2 | Me | 3-morpholino-phenyl |
| 1140 | 3 | Me | 3-morpholino-phenyl |
| 1141 | 1 | CH₂Ph | 3-morpholino-phenyl |
| 1142 | 2 | CH₂Ph | 3-morpholino-phenyl |
| 1143 | 3 | CH₂Ph | 3-morpholino-phenyl |
| 1144 | 1 | COMe | 3-morpholino-phenyl |
| 1145 | 2 | COMe | 3-morpholino-phenyl |
| 1146 | 3 | COMe | 3-morpholino-phenyl |
| 1147 | 1 | CO₂Me | 3-morpholino-phenyl |
| 1148 | 2 | CO₂Me | 3-morpholino-phenyl |
| 1149 | 3 | CO₂Me | 3-morpholino-phenyl |
| 1150 | 1 | CO₂tBu | 3-morpholino-phenyl |
| 1151 | 2 | CO₂tBu | 3-morpholino-phenyl |
| 1152 | 3 | CO₂tBu | 3-morpholino-phenyl |
| 1153 | 1 | CONHMe | 3-morpholino-phenyl |
| 1154 | 2 | CONHMe | 3-morpholino-phenyl |
| 1155 | 3 | CONHMe | 3-morpholino-phenyl |
| 1156 | 1 | SO₂Me | 3-morpholino-phenyl |
| 1157 | 2 | SO₂Me | 3-morpholino-phenyl |
| 1158 | 3 | SO₂Me | 3-morpholino-phenyl |
| 1159 | 1 | SO₂NH₂ | 3-morpholino-phenyl |
| 1160 | 2 | SO₂NH₂ | 3-morpholino-phenyl |
| 1161 | 3 | SO₂NH₂ | 3-morpholino-phenyl |
| 1162 | 1 | H | 2-pyrazinyl |
| 1163 | 2 | H | 2-pyrazinyl |
| 1164 | 3 | H | 2-pyrazinyl |
| 1165 | 1 | Me | 2-pyrazinyl |
| 1166 | 2 | Me | 2-pyrazinyl |
| 1167 | 3 | Me | 2-pyrazinyl |
| 1168 | 1 | CH₂Ph | 2-pyrazinyl |
| 1169 | 2 | CH₂Ph | 2-pyrazinyl |
| 1170 | 3 | CH₂Ph | 2-pyrazinyl |
| 1171 | 1 | COMe | 2-pyrazinyl |
| 1172 | 2 | COMe | 2-pyrazinyl |
| 1173 | 3 | COMe | 2-pyrazinyl |
| 1174 | 1 | CO₂Me | 2-pyrazinyl |
| 1175 | 2 | CO₂Me | 2-pyrazinyl |
| 1176 | 3 | CO₂Me | 2-pyrazinyl |
| 1177 | 1 | CO₂tBu | 2-pyrazinyl |
| 1178 | 2 | CO₂tBu | 2-pyrazinyl |
| 1179 | 3 | CO₂tBu | 2-pyrazinyl |
| 1180 | 1 | CONHMe | 2-pyrazinyl |
| 1181 | 2 | CONHMe | 2-pyrazinyl |
| 1182 | 3 | CONHMe | 2-pyrazinyl |
| 1183 | 1 | SO₂Me | 2-pyrazinyl |
| 1184 | 2 | SO₂Me | 2-pyrazinyl |
| 1185 | 3 | SO₂Me | 2-pyrazinyl |
| 1186 | 1 | SO₂NH₂ | 2-pyrazinyl |
| 1187 | 2 | SO₂NH₂ | 2-pyrazinyl |
| 1188 | 3 | SO₂NH₂ | 2-pyrazinyl |
| 1189 | 1 | H | 5-indolyl |
| 1190 | 2 | H | 5-indolyl |
| 1191 | 3 | H | 5-indolyl |
| 1192 | 1 | Me | 5-indolyl |
| 1193 | 2 | Me | 5-indolyl |
| 1194 | 3 | Me | 5-indolyl |
| 1195 | 1 | CH₂Ph | 5-indolyl |
| 1196 | 2 | CH₂Ph | 5-indolyl |
| 1197 | 3 | CH₂Ph | 5-indolyl |
| 1198 | 1 | COMe | 5-indolyl |
| 1199 | 2 | COMe | 5-indolyl |
| 1200 | 3 | COMe | 5-indolyl |
| 1201 | 1 | CO₂Me | 5-indolyl |
| 1202 | 2 | CO₂Me | 5-indolyl |
| 1203 | 3 | CO₂Me | 5-indolyl |
| 1204 | 1 | CO₂tBu | 5-indolyl |
| 1205 | 2 | CO₂tBu | 5-indolyl |
| 1206 | 3 | CO₂tBu | 5-indolyl |
| 1207 | 1 | CONHMe | 5-indolyl |
| 1208 | 2 | CONHMe | 5-indolyl |
| 1209 | 3 | CONHMe | 5-indolyl |
| 1210 | 1 | SO₂Me | 5-indolyl |
| 1211 | 2 | SO₂Me | 5-indolyl |
| 1212 | 3 | SO₂Me | 5-indolyl |
| 1213 | 1 | SO₂NH₂ | 5-indolyl |
| 1214 | 2 | SO₂NH₂ | 5-indolyl |
| 1215 | 3 | SO₂NH₂ | 5-indolyl |
| 1216 | 1 | H | 1H-benzo[d]imidazol-4-yl |
| 1217 | 2 | H | 1H-benzo[d]imidazol-4-yl |
| 1218 | 3 | H | 1H-benzo[d]imidazol-4-yl |

TABLE 1-continued

| Entry | n | R | R³ |
|---|---|---|---|
| 1219 | 1 | Me | 1H-benzo[d]imidazol-4-yl |
| 1220 | 2 | Me | 1H-benzo[d]imidazol-4-yl |
| 1221 | 3 | Me | 1H-benzo[d]imidazol-4-yl |
| 1222 | 1 | CH₂Ph | 1H-benzo[d]imidazol-4-yl |
| 1223 | 2 | CH₂Ph | 1H-benzo[d]imidazol-4-yl |
| 1224 | 3 | CH₂Ph | 1H-benzo[d]imidazol-4-yl |
| 1225 | 1 | COMe | 1H-benzo[d]imidazol-4-yl |
| 1226 | 2 | COMe | 1H-benzo[d]imidazol-4-yl |
| 1227 | 3 | COMe | 1H-benzo[d]imidazol-4-yl |
| 1228 | 1 | CO₂Me | 1H-benzo[d]imidazol-4-yl |
| 1229 | 2 | CO₂Me | 1H-benzo[d]imidazol-4-yl |
| 1230 | 3 | CO₂Me | 1H-benzo[d]imidazol-4-yl |
| 1231 | 1 | CO₂tBu | 1H-benzo[d]imidazol-4-yl |
| 1232 | 2 | CO₂tBu | 1H-benzo[d]imidazol-4-yl |
| 1233 | 3 | CO₂tBu | 1H-benzo[d]imidazol-4-yl |
| 1234 | 1 | CONHMe | 1H-benzo[d]imidazol-4-yl |
| 1235 | 2 | CONHMe | 1H-benzo[d]imidazol-4-yl |
| 1236 | 3 | CONHMe | 1H-benzo[d]imidazol-4-yl |
| 1237 | 1 | SO₂Me | 1H-benzo[d]imidazol-4-yl |
| 1238 | 2 | SO₂Me | 1H-benzo[d]imidazol-4-yl |
| 1239 | 3 | SO₂Me | 1H-benzo[d]imidazol-4-yl |
| 1240 | 1 | SO₂NH₂ | 1H-benzo[d]imidazol-4-yl |
| 1241 | 2 | SO₂NH₂ | 1H-benzo[d]imidazol-4-yl |
| 1242 | 3 | SO₂NH₂ | 1H-benzo[d]imidazol-4-yl |

Exemplary embodiments include compounds having the formula (XVIII)

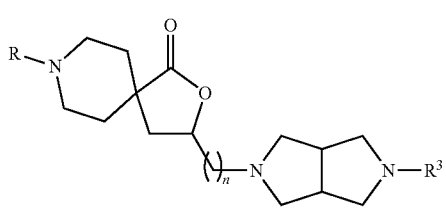

(XVIII)

or a pharmaceutically acceptable salt form thereof defined herein below in Table 2.

TABLE 2

| Entry | n | R | R³ |
|---|---|---|---|
| 1 | 1 | H | Phenyl |
| 2 | 2 | H | Phenyl |
| 3 | 3 | H | Phenyl |
| 4 | 1 | Me | Phenyl |
| 5 | 2 | Me | Phenyl |
| 6 | 3 | Me | Phenyl |
| 7 | 1 | CH₂Ph | Phenyl |
| 8 | 2 | CH₂Ph | Phenyl |
| 9 | 3 | CH₂Ph | Phenyl |
| 10 | 1 | COMe | Phenyl |
| 11 | 2 | COMe | Phenyl |
| 12 | 3 | COMe | Phenyl |
| 13 | 1 | CO₂Me | Phenyl |
| 14 | 2 | CO₂Me | Phenyl |
| 15 | 3 | CO₂Me | Phenyl |
| 16 | 1 | CO₂tBu | Phenyl |
| 17 | 2 | CO₂tBu | Phenyl |
| 18 | 3 | CO₂tBu | Phenyl |
| 19 | 1 | CONHMe | Phenyl |
| 20 | 2 | CONHMe | Phenyl |
| 21 | 3 | CONHMe | Phenyl |
| 22 | 1 | SO₂Me | Phenyl |
| 23 | 2 | SO₂Me | Phenyl |
| 24 | 3 | SO₂Me | Phenyl |
| 25 | 1 | SO₂NH₂ | Phenyl |
| 26 | 2 | SO₂NH₂ | Phenyl |
| 27 | 3 | SO₂NH₂ | Phenyl |
| 28 | 1 | H | 3-OH-Phenyl |
| 29 | 2 | H | 3-OH-Phenyl |
| 30 | 3 | H | 3-OH-Phenyl |
| 31 | 1 | Me | 3-OH-Phenyl |
| 32 | 2 | Me | 3-OH-Phenyl |
| 33 | 3 | Me | 3-OH-Phenyl |
| 34 | 1 | CH₂Ph | 3-OH-Phenyl |
| 35 | 2 | CH₂Ph | 3-OH-Phenyl |
| 36 | 3 | CH₂Ph | 3-OH-Phenyl |
| 37 | 1 | COMe | 3-OH-Phenyl |
| 38 | 2 | COMe | 3-OH-Phenyl |
| 39 | 3 | COMe | 3-OH-Phenyl |
| 40 | 1 | CO₂Me | 3-OH-Phenyl |
| 41 | 2 | CO₂Me | 3-OH-Phenyl |
| 42 | 3 | CO₂Me | 3-OH-Phenyl |
| 43 | 1 | CO₂tBu | 3-OH-Phenyl |
| 44 | 2 | CO₂tBu | 3-OH-Phenyl |
| 45 | 3 | CO₂tBu | 3-OH-Phenyl |
| 46 | 1 | CONHMe | 3-OH-Phenyl |
| 47 | 2 | CONHMe | 3-OH-Phenyl |
| 48 | 3 | CONHMe | 3-OH-Phenyl |
| 49 | 1 | SO₂Me | 3-OH-Phenyl |
| 50 | 2 | SO₂Me | 3-OH-Phenyl |
| 51 | 3 | SO₂Me | 3-OH-Phenyl |
| 52 | 1 | SO₂NH₂ | 3-OH-Phenyl |
| 53 | 2 | SO₂NH₂ | 3-OH-Phenyl |
| 54 | 3 | SO₂NH₂ | 3-OH-Phenyl |
| 55 | 1 | H | 4-NO₂-Phenyl |
| 56 | 2 | H | 4-NO₂-Phenyl |
| 57 | 3 | H | 4-NO₂-Phenyl |
| 58 | 1 | Me | 4-NO₂-Phenyl |
| 59 | 2 | Me | 4-NO₂-Phenyl |
| 60 | 3 | Me | 4-NO₂-Phenyl |
| 61 | 1 | CH₂Ph | 4-NO₂-Phenyl |
| 62 | 2 | CH₂Ph | 4-NO₂-Phenyl |
| 63 | 3 | CH₂Ph | 4-NO₂-Phenyl |
| 64 | 1 | COMe | 4-NO₂-Phenyl |
| 65 | 2 | COMe | 4-NO₂-Phenyl |
| 66 | 3 | COMe | 4-NO₂-Phenyl |
| 67 | 1 | CO₂Me | 4-NO₂-Phenyl |
| 68 | 2 | CO₂Me | 4-NO₂-Phenyl |
| 69 | 3 | CO₂Me | 4-NO₂-Phenyl |
| 70 | 1 | CO₂tBu | 4-NO₂-Phenyl |
| 71 | 2 | CO₂tBu | 4-NO₂-Phenyl |
| 72 | 3 | CO₂tBu | 4-NO₂-Phenyl |
| 73 | 1 | CONHMe | 4-NO₂-Phenyl |
| 74 | 2 | CONHMe | 4-NO₂-Phenyl |
| 75 | 3 | CONHMe | 4-NO₂-Phenyl |
| 76 | 1 | SO₂Me | 4-NO₂-Phenyl |
| 77 | 2 | SO₂Me | 4-NO₂-Phenyl |
| 78 | 3 | SO₂Me | 4-NO₂-Phenyl |
| 79 | 1 | SO₂NH₂ | 4-NO₂-Phenyl |
| 80 | 2 | SO₂NH₂ | 4-NO₂-Phenyl |
| 81 | 3 | SO₂NH₂ | 4-NO₂-Phenyl |

TABLE 2-continued

| Entry | n | R | R³ |
|---|---|---|---|
| 82 | 1 | H | 3-OMe-Phenyl |
| 83 | 2 | H | 3-OMe-Phenyl |
| 84 | 3 | H | 3-OMe-Phenyl |
| 85 | 1 | Me | 3-OMe-Phenyl |
| 86 | 2 | Me | 3-OMe-Phenyl |
| 87 | 3 | Me | 3-OMe-Phenyl |
| 88 | 1 | CH₂Ph | 3-OMe-Phenyl |
| 89 | 2 | CH₂Ph | 3-OMe-Phenyl |
| 90 | 3 | CH₂Ph | 3-OMe-Phenyl |
| 91 | 1 | COMe | 3-OMe-Phenyl |
| 92 | 2 | COMe | 3-OMe-Phenyl |
| 93 | 3 | COMe | 3-OMe-Phenyl |
| 94 | 1 | CO₂Me | 3-OMe-Phenyl |
| 95 | 2 | CO₂Me | 3-OMe-Phenyl |
| 96 | 3 | CO₂Me | 3-OMe-Phenyl |
| 97 | 1 | CO₂tBu | 3-OMe-Phenyl |
| 98 | 2 | CO₂tBu | 3-OMe-Phenyl |
| 99 | 3 | CO₂tBu | 3-OMe-Phenyl |
| 100 | 1 | CONHMe | 3-OMe-Phenyl |
| 101 | 2 | CONHMe | 3-OMe-Phenyl |
| 102 | 3 | CONHMe | 3-OMe-Phenyl |
| 103 | 1 | SO₂Me | 3-OMe-Phenyl |
| 104 | 2 | SO₂Me | 3-OMe-Phenyl |
| 105 | 3 | SO₂Me | 3-OMe-Phenyl |
| 106 | 1 | SO₂NH₂ | 3-OMe-Phenyl |
| 107 | 2 | SO₂NH₂ | 3-OMe-Phenyl |
| 108 | 3 | SO₂NH₂ | 3-OMe-Phenyl |
| 109 | 1 | H | 4-CN-Phenyl |
| 110 | 2 | H | 4-CN-Phenyl |
| 111 | 3 | H | 4-CN-Phenyl |
| 112 | 1 | Me | 4-CN-Phenyl |
| 113 | 2 | Me | 4-CN-Phenyl |
| 114 | 3 | Me | 4-CN-Phenyl |
| 115 | 1 | CH₂Ph | 4-CN-Phenyl |
| 116 | 2 | CH₂Ph | 4-CN-Phenyl |
| 117 | 3 | CH₂Ph | 4-CN-Phenyl |
| 118 | 1 | COMe | 4-CN-Phenyl |
| 119 | 2 | COMe | 4-CN-Phenyl |
| 120 | 3 | COMe | 4-CN-Phenyl |
| 121 | 1 | CO₂Me | 4-CN-Phenyl |
| 122 | 2 | CO₂Me | 4-CN-Phenyl |
| 123 | 3 | CO₂Me | 4-CN-Phenyl |
| 124 | 1 | CO₂tBu | 4-CN-Phenyl |
| 125 | 2 | CO₂tBu | 4-CN-Phenyl |
| 126 | 3 | CO₂tBu | 4-CN-Phenyl |
| 127 | 1 | CONHMe | 4-CN-Phenyl |
| 128 | 2 | CONHMe | 4-CN-Phenyl |
| 129 | 3 | CONHMe | 4-CN-Phenyl |
| 130 | 1 | SO₂Me | 4-CN-Phenyl |
| 131 | 2 | SO₂Me | 4-CN-Phenyl |
| 132 | 3 | SO₂Me | 4-CN-Phenyl |
| 133 | 1 | SO₂NH₂ | 4-CN-Phenyl |
| 134 | 2 | SO₂NH₂ | 4-CN-Phenyl |
| 135 | 3 | SO₂NH₂ | 4-CN-Phenyl |
| 136 | 1 | H | 2-CN-Phenyl |
| 137 | 2 | H | 2-CN-Phenyl |
| 138 | 3 | H | 2-CN-Phenyl |
| 139 | 1 | Me | 2-CN-Phenyl |
| 140 | 2 | Me | 2-CN-Phenyl |
| 141 | 3 | Me | 2-CN-Phenyl |
| 142 | 1 | CH₂Ph | 2-CN-Phenyl |
| 143 | 2 | CH₂Ph | 2-CN-Phenyl |
| 144 | 3 | CH₂Ph | 2-CN-Phenyl |
| 145 | 1 | COMe | 2-CN-Phenyl |
| 146 | 2 | COMe | 2-CN-Phenyl |
| 147 | 3 | COMe | 2-CN-Phenyl |
| 148 | 1 | CO₂Me | 2-CN-Phenyl |
| 149 | 2 | CO₂Me | 2-CN-Phenyl |
| 150 | 3 | CO₂Me | 2-CN-Phenyl |
| 151 | 1 | CO₂tBu | 2-CN-Phenyl |
| 152 | 2 | CO₂tBu | 2-CN-Phenyl |
| 153 | 3 | CO₂tBu | 2-CN-Phenyl |
| 154 | 1 | CONHMe | 2-CN-Phenyl |
| 155 | 2 | CONHMe | 2-CN-Phenyl |
| 156 | 3 | CONHMe | 2-CN-Phenyl |
| 157 | 1 | SO₂Me | 2-CN-Phenyl |
| 158 | 2 | SO₂Me | 2-CN-Phenyl |
| 159 | 3 | SO₂Me | 2-CN-Phenyl |
| 160 | 1 | SO₂NH₂ | 2-CN-Phenyl |
| 161 | 2 | SO₂NH₂ | 2-CN-Phenyl |
| 162 | 3 | SO₂NH₂ | 2-CN-Phenyl |
| 163 | 1 | H | 3-Me-Phenyl |
| 164 | 2 | H | 3-Me-Phenyl |
| 165 | 3 | H | 3-Me-Phenyl |
| 166 | 1 | Me | 3-Me-Phenyl |
| 167 | 2 | Me | 3-Me-Phenyl |
| 168 | 3 | Me | 3-Me-Phenyl |
| 169 | 1 | CH₂Ph | 3-Me-Phenyl |
| 170 | 2 | CH₂Ph | 3-Me-Phenyl |
| 171 | 3 | CH₂Ph | 3-Me-Phenyl |
| 172 | 1 | COMe | 3-Me-Phenyl |
| 173 | 2 | COMe | 3-Me-Phenyl |
| 174 | 3 | COMe | 3-Me-Phenyl |
| 175 | 1 | CO₂Me | 3-Me-Phenyl |
| 176 | 2 | CO₂Me | 3-Me-Phenyl |
| 177 | 3 | CO₂Me | 3-Me-Phenyl |
| 178 | 1 | CO₂tBu | 3-Me-Phenyl |
| 179 | 2 | CO₂tBu | 3-Me-Phenyl |
| 180 | 3 | CO₂tBu | 3-Me-Phenyl |
| 181 | 1 | CONHMe | 3-Me-Phenyl |
| 182 | 2 | CONHMe | 3-Me-Phenyl |
| 183 | 3 | CONHMe | 3-Me-Phenyl |
| 184 | 1 | SO₂Me | 3-Me-Phenyl |
| 185 | 2 | SO₂Me | 3-Me-Phenyl |
| 186 | 3 | SO₂Me | 3-Me-Phenyl |
| 187 | 1 | SO₂NH₂ | 3-Me-Phenyl |
| 188 | 2 | SO₂NH₂ | 3-Me-Phenyl |
| 189 | 3 | SO₂NH₂ | 3-Me-Phenyl |
| 190 | 1 | H | 2-F-Phenyl |
| 191 | 2 | H | 2-F-Phenyl |
| 192 | 3 | H | 2-F-Phenyl |
| 193 | 1 | Me | 2-F-Phenyl |
| 194 | 2 | Me | 2-F-Phenyl |
| 195 | 3 | Me | 2-F-Phenyl |
| 196 | 1 | CH₂Ph | 2-F-Phenyl |
| 197 | 2 | CH₂Ph | 2-F-Phenyl |
| 198 | 3 | CH₂Ph | 2-F-Phenyl |
| 199 | 1 | COMe | 2-F-Phenyl |
| 200 | 2 | COMe | 2-F-Phenyl |
| 201 | 3 | COMe | 2-F-Phenyl |
| 202 | 1 | CO₂Me | 2-F-Phenyl |
| 203 | 2 | CO₂Me | 2-F-Phenyl |
| 204 | 3 | CO₂Me | 2-F-Phenyl |
| 205 | 1 | CO₂tBu | 2-F-Phenyl |
| 206 | 2 | CO₂tBu | 2-F-Phenyl |
| 207 | 3 | CO₂tBu | 2-F-Phenyl |
| 208 | 1 | CONHMe | 2-F-Phenyl |
| 209 | 2 | CONHMe | 2-F-Phenyl |
| 210 | 3 | CONHMe | 2-F-Phenyl |
| 211 | 1 | SO₂Me | 2-F-Phenyl |
| 212 | 2 | SO₂Me | 2-F-Phenyl |
| 213 | 3 | SO₂Me | 2-F-Phenyl |
| 214 | 1 | SO₂NH₂ | 2-F-Phenyl |
| 215 | 2 | SO₂NH₂ | 2-F-Phenyl |
| 216 | 3 | SO₂NH₂ | 2-F-Phenyl |
| 217 | 1 | H | 4-F-Phenyl |
| 218 | 2 | H | 4-F-Phenyl |
| 219 | 3 | H | 4-F-Phenyl |
| 220 | 1 | Me | 4-F-Phenyl |
| 221 | 2 | Me | 4-F-Phenyl |
| 222 | 3 | Me | 4-F-Phenyl |
| 223 | 1 | CH₂Ph | 4-F-Phenyl |
| 224 | 2 | CH₂Ph | 4-F-Phenyl |
| 225 | 3 | CH₂Ph | 4-F-Phenyl |
| 226 | 1 | COMe | 4-F-Phenyl |
| 227 | 2 | COMe | 4-F-Phenyl |
| 228 | 3 | COMe | 4-F-Phenyl |
| 229 | 1 | CO₂Me | 4-F-Phenyl |
| 230 | 2 | CO₂Me | 4-F-Phenyl |
| 231 | 3 | CO₂Me | 4-F-Phenyl |
| 232 | 1 | CO₂tBu | 4-F-Phenyl |
| 233 | 2 | CO₂tBu | 4-F-Phenyl |
| 234 | 3 | CO₂tBu | 4-F-Phenyl |
| 235 | 1 | CONHMe | 4-F-Phenyl |
| 236 | 2 | CONHMe | 4-F-Phenyl |
| 237 | 3 | CONHMe | 4-F-Phenyl |

TABLE 2-continued

| Entry | n | R | R³ |
|---|---|---|---|
| 238 | 1 | SO₂Me | 4-F-Phenyl |
| 239 | 2 | SO₂Me | 4-F-Phenyl |
| 240 | 3 | SO₂Me | 4-F-Phenyl |
| 241 | 1 | SO₂NH₂ | 4-F-Phenyl |
| 242 | 2 | SO₂NH₂ | 4-F-Phenyl |
| 243 | 3 | SO₂NH₂ | 4-F-Phenyl |
| 244 | 1 | H | 3-Cl-Phenyl |
| 245 | 2 | H | 3-Cl-Phenyl |
| 246 | 3 | H | 3-Cl-Phenyl |
| 247 | 1 | Me | 3-Cl-Phenyl |
| 248 | 2 | Me | 3-Cl-Phenyl |
| 249 | 3 | Me | 3-Cl-Phenyl |
| 250 | 1 | CH₂Ph | 3-Cl-Phenyl |
| 251 | 2 | CH₂Ph | 3-Cl-Phenyl |
| 252 | 3 | CH₂Ph | 3-Cl-Phenyl |
| 253 | 1 | COMe | 3-Cl-Phenyl |
| 254 | 2 | COMe | 3-Cl-Phenyl |
| 255 | 3 | COMe | 3-Cl-Phenyl |
| 256 | 1 | CO₂Me | 3-Cl-Phenyl |
| 257 | 2 | CO₂Me | 3-Cl-Phenyl |
| 258 | 3 | CO₂Me | 3-Cl-Phenyl |
| 259 | 1 | CO₂tBu | 3-Cl-Phenyl |
| 260 | 2 | CO₂tBu | 3-Cl-Phenyl |
| 261 | 3 | CO₂tBu | 3-Cl-Phenyl |
| 262 | 1 | CONHMe | 3-Cl-Phenyl |
| 263 | 2 | CONHMe | 3-Cl-Phenyl |
| 264 | 3 | CONHMe | 3-Cl-Phenyl |
| 265 | 1 | SO₂Me | 3-Cl-Phenyl |
| 266 | 2 | SO₂Me | 3-Cl-Phenyl |
| 267 | 3 | SO₂Me | 3-Cl-Phenyl |
| 268 | 1 | SO₂NH₂ | 3-Cl-Phenyl |
| 269 | 2 | SO₂NH₂ | 3-Cl-Phenyl |
| 270 | 3 | SO₂NH₂ | 3-Cl-Phenyl |
| 271 | 1 | H | 2-Br-Phenyl |
| 272 | 2 | H | 2-Br-Phenyl |
| 273 | 3 | H | 2-Br-Phenyl |
| 274 | 1 | Me | 2-Br-Phenyl |
| 275 | 2 | Me | 2-Br-Phenyl |
| 276 | 3 | Me | 2-Br-Phenyl |
| 277 | 1 | CH₂Ph | 2-Br-Phenyl |
| 278 | 2 | CH₂Ph | 2-Br-Phenyl |
| 279 | 3 | CH₂Ph | 2-Br-Phenyl |
| 280 | 1 | COMe | 2-Br-Phenyl |
| 281 | 2 | COMe | 2-Br-Phenyl |
| 282 | 3 | COMe | 2-Br-Phenyl |
| 283 | 1 | CO₂Me | 2-Br-Phenyl |
| 284 | 2 | CO₂Me | 2-Br-Phenyl |
| 285 | 3 | CO₂Me | 2-Br-Phenyl |
| 286 | 1 | CO₂tBu | 2-Br-Phenyl |
| 287 | 2 | CO₂tBu | 2-Br-Phenyl |
| 288 | 3 | CO₂tBu | 2-Br-Phenyl |
| 289 | 1 | CONHMe | 2-Br-Phenyl |
| 290 | 2 | CONHMe | 2-Br-Phenyl |
| 291 | 3 | CONHMe | 2-Br-Phenyl |
| 292 | 1 | SO₂Me | 2-Br-Phenyl |
| 293 | 2 | SO₂Me | 2-Br-Phenyl |
| 294 | 3 | SO₂Me | 2-Br-Phenyl |
| 295 | 1 | SO₂NH₂ | 2-Br-Phenyl |
| 296 | 2 | SO₂NH₂ | 2-Br-Phenyl |
| 297 | 3 | SO₂NH₂ | 2-Br-Phenyl |
| 298 | 1 | H | 4-Br-Phenyl |
| 299 | 2 | H | 4-Br-Phenyl |
| 300 | 3 | H | 4-Br-Phenyl |
| 301 | 1 | Me | 4-Br-Phenyl |
| 302 | 2 | Me | 4-Br-Phenyl |
| 303 | 3 | Me | 4-Br-Phenyl |
| 304 | 1 | CH₂Ph | 4-Br-Phenyl |
| 305 | 2 | CH₂Ph | 4-Br-Phenyl |
| 306 | 3 | CH₂Ph | 4-Br-Phenyl |
| 307 | 1 | COMe | 4-Br-Phenyl |
| 308 | 2 | COMe | 4-Br-Phenyl |
| 309 | 3 | COMe | 4-Br-Phenyl |
| 310 | 1 | CO₂Me | 4-Br-Phenyl |
| 311 | 2 | CO₂Me | 4-Br-Phenyl |
| 312 | 3 | CO₂Me | 4-Br-Phenyl |
| 313 | 1 | CO₂tBu | 4-Br-Phenyl |
| 314 | 2 | CO₂tBu | 4-Br-Phenyl |
| 315 | 3 | CO₂tBu | 4-Br-Phenyl |
| 316 | 1 | CONHMe | 4-Br-Phenyl |
| 317 | 2 | CONHMe | 4-Br-Phenyl |
| 318 | 3 | CONHMe | 4-Br-Phenyl |
| 319 | 1 | SO₂Me | 4-Br-Phenyl |
| 320 | 2 | SO₂Me | 4-Br-Phenyl |
| 321 | 3 | SO₂Me | 4-Br-Phenyl |
| 322 | 1 | SO₂NH₂ | 4-Br-Phenyl |
| 323 | 2 | SO₂NH₂ | 4-Br-Phenyl |
| 324 | 3 | SO₂NH₂ | 4-Br-Phenyl |
| 325 | 1 | H | 3-CF₃-Phenyl |
| 326 | 2 | H | 3-CF₃-Phenyl |
| 327 | 3 | H | 3-CF₃-Phenyl |
| 328 | 1 | Me | 3-CF₃-Phenyl |
| 329 | 2 | Me | 3-CF₃-Phenyl |
| 330 | 3 | Me | 3-CF₃-Phenyl |
| 331 | 1 | CH₂Ph | 3-CF₃-Phenyl |
| 332 | 2 | CH₂Ph | 3-CF₃-Phenyl |
| 333 | 3 | CH₂Ph | 3-CF₃-Phenyl |
| 334 | 1 | COMe | 3-CF₃-Phenyl |
| 335 | 2 | COMe | 3-CF₃-Phenyl |
| 336 | 3 | COMe | 3-CF₃-Phenyl |
| 337 | 1 | CO₂Me | 3-CF₃-Phenyl |
| 338 | 2 | CO₂Me | 3-CF₃-Phenyl |
| 339 | 3 | CO₂Me | 3-CF₃-Phenyl |
| 340 | 1 | CO₂tBu | 3-CF₃-Phenyl |
| 341 | 2 | CO₂tBu | 3-CF₃-Phenyl |
| 342 | 3 | CO₂tBu | 3-CF₃-Phenyl |
| 343 | 1 | CONHMe | 3-CF₃-Phenyl |
| 344 | 2 | CONHMe | 3-CF₃-Phenyl |
| 345 | 3 | CONHMe | 3-CF₃-Phenyl |
| 346 | 1 | SO₂Me | 3-CF₃-Phenyl |
| 347 | 2 | SO₂Me | 3-CF₃-Phenyl |
| 348 | 3 | SO₂Me | 3-CF₃-Phenyl |
| 349 | 1 | SO₂NH₂ | 3-CF₃-Phenyl |
| 350 | 2 | SO₂NH₂ | 3-CF₃-Phenyl |
| 351 | 3 | SO₂NH₂ | 3-CF₃-Phenyl |
| 352 | 1 | H | 2-iPr-Phenyl |
| 353 | 2 | H | 2-iPr-Phenyl |
| 354 | 3 | H | 2-iPr-Phenyl |
| 355 | 1 | Me | 2-iPr-Phenyl |
| 356 | 2 | Me | 2-iPr-Phenyl |
| 357 | 3 | Me | 2-iPr-Phenyl |
| 358 | 1 | CH₂Ph | 2-iPr-Phenyl |
| 359 | 2 | CH₂Ph | 2-iPr-Phenyl |
| 360 | 3 | CH₂Ph | 2-iPr-Phenyl |
| 361 | 1 | COMe | 2-iPr-Phenyl |
| 362 | 2 | COMe | 2-iPr-Phenyl |
| 363 | 3 | COMe | 2-iPr-Phenyl |
| 364 | 1 | CO₂Me | 2-iPr-Phenyl |
| 365 | 2 | CO₂Me | 2-iPr-Phenyl |
| 366 | 3 | CO₂Me | 2-iPr-Phenyl |
| 367 | 1 | CO₂tBu | 2-iPr-Phenyl |
| 368 | 2 | CO₂tBu | 2-iPr-Phenyl |
| 369 | 3 | CO₂tBu | 2-iPr-Phenyl |
| 370 | 1 | CONHMe | 2-iPr-Phenyl |
| 371 | 2 | CONHMe | 2-iPr-Phenyl |
| 372 | 3 | CONHMe | 2-iPr-Phenyl |
| 373 | 1 | SO₂Me | 2-iPr-Phenyl |
| 374 | 2 | SO₂Me | 2-iPr-Phenyl |
| 375 | 3 | SO₂Me | 2-iPr-Phenyl |
| 376 | 1 | SO₂NH₂ | 2-iPr-Phenyl |
| 377 | 2 | SO₂NH₂ | 2-iPr-Phenyl |
| 378 | 3 | SO₂NH₂ | 2-iPr-Phenyl |
| 379 | 1 | H | 4-iPr-Phenyl |
| 380 | 2 | H | 4-iPr-Phenyl |
| 381 | 3 | H | 4-iPr-Phenyl |
| 382 | 1 | Me | 4-iPr-Phenyl |
| 383 | 2 | Me | 4-iPr-Phenyl |
| 384 | 3 | Me | 4-iPr-Phenyl |
| 385 | 1 | CH₂Ph | 4-iPr-Phenyl |
| 386 | 2 | CH₂Ph | 4-iPr-Phenyl |
| 387 | 3 | CH₂Ph | 4-iPr-Phenyl |
| 388 | 1 | COMe | 4-iPr-Phenyl |
| 389 | 2 | COMe | 4-iPr-Phenyl |
| 390 | 3 | COMe | 4-iPr-Phenyl |
| 391 | 1 | CO₂Me | 4-iPr-Phenyl |
| 392 | 2 | CO₂Me | 4-iPr-Phenyl |
| 393 | 3 | CO₂Me | 4-iPr-Phenyl |

TABLE 2-continued

| Entry | n | R | R³ |
|---|---|---|---|
| 394 | 1 | CO₂tBu | 4-iPr-Phenyl |
| 395 | 2 | CO₂tBu | 4-iPr-Phenyl |
| 396 | 3 | CO₂tBu | 4-iPr-Phenyl |
| 397 | 1 | CONHMe | 4-iPr-Phenyl |
| 398 | 2 | CONHMe | 4-iPr-Phenyl |
| 399 | 3 | CONHMe | 4-iPr-Phenyl |
| 400 | 1 | SO₂Me | 4-iPr-Phenyl |
| 401 | 2 | SO₂Me | 4-iPr-Phenyl |
| 402 | 3 | SO₂Me | 4-iPr-Phenyl |
| 403 | 1 | SO₂NH₂ | 4-iPr-Phenyl |
| 404 | 2 | SO₂NH₂ | 4-iPr-Phenyl |
| 405 | 3 | SO₂NH₂ | 4-iPr-Phenyl |
| 406 | 1 | H | 3-NH₂-Phenyl |
| 407 | 2 | H | 3-NH₂-Phenyl |
| 408 | 3 | H | 3-NH₂-Phenyl |
| 409 | 1 | Me | 3-NH₂-Phenyl |
| 410 | 2 | Me | 3-NH₂-Phenyl |
| 411 | 3 | Me | 3-NH₂-Phenyl |
| 412 | 1 | CH₂Ph | 3-NH₂-Phenyl |
| 413 | 2 | CH₂Ph | 3-NH₂-Phenyl |
| 414 | 3 | CH₂Ph | 3-NH₂-Phenyl |
| 415 | 1 | COMe | 3-NH₂-Phenyl |
| 416 | 2 | COMe | 3-NH₂-Phenyl |
| 417 | 3 | COMe | 3-NH₂-Phenyl |
| 418 | 1 | CO₂Me | 3-NH₂-Phenyl |
| 419 | 2 | CO₂Me | 3-NH₂-Phenyl |
| 420 | 3 | CO₂Me | 3-NH₂-Phenyl |
| 421 | 1 | CO₂tBu | 3-NH₂-Phenyl |
| 422 | 2 | CO₂tBu | 3-NH₂-Phenyl |
| 423 | 3 | CO₂tBu | 3-NH₂-Phenyl |
| 424 | 1 | CONHMe | 3-NH₂-Phenyl |
| 425 | 2 | CONHMe | 3-NH₂-Phenyl |
| 426 | 3 | CONHMe | 3-NH₂-Phenyl |
| 427 | 1 | SO₂Me | 3-NH₂-Phenyl |
| 428 | 2 | SO₂Me | 3-NH₂-Phenyl |
| 429 | 3 | SO₂Me | 3-NH₂-Phenyl |
| 430 | 1 | SO₂NH₂ | 3-NH₂-Phenyl |
| 431 | 2 | SO₂NH₂ | 3-NH₂-Phenyl |
| 432 | 3 | SO₂NH₂ | 3-NH₂-Phenyl |
| 433 | 1 | H | 2,4-di-Me-Phenyl |
| 434 | 2 | H | 2,4-di-Me-Phenyl |
| 435 | 3 | H | 2,4-di-Me-Phenyl |
| 436 | 1 | Me | 2,4-di-Me-Phenyl |
| 437 | 2 | Me | 2,4-di-Me-Phenyl |
| 438 | 3 | Me | 2,4-di-Me-Phenyl |
| 439 | 1 | CH₂Ph | 2,4-di-Me-Phenyl |
| 440 | 2 | CH₂Ph | 2,4-di-Me-Phenyl |
| 441 | 3 | CH₂Ph | 2,4-di-Me-Phenyl |
| 442 | 1 | COMe | 2,4-di-Me-Phenyl |
| 443 | 2 | COMe | 2,4-di-Me-Phenyl |
| 444 | 3 | COMe | 2,4-di-Me-Phenyl |
| 445 | 1 | CO₂Me | 2,4-di-Me-Phenyl |
| 446 | 2 | CO₂Me | 2,4-di-Me-Phenyl |
| 447 | 3 | CO₂Me | 2,4-di-Me-Phenyl |
| 448 | 1 | CO₂tBu | 2,4-di-Me-Phenyl |
| 449 | 2 | CO₂tBu | 2,4-di-Me-Phenyl |
| 450 | 3 | CO₂tBu | 2,4-di-Me-Phenyl |
| 451 | 1 | CONHMe | 2,4-di-Me-Phenyl |
| 452 | 2 | CONHMe | 2,4-di-Me-Phenyl |
| 453 | 3 | CONHMe | 2,4-di-Me-Phenyl |
| 454 | 1 | SO₂Me | 2,4-di-Me-Phenyl |
| 455 | 2 | SO₂Me | 2,4-di-Me-Phenyl |
| 456 | 3 | SO₂Me | 2,4-di-Me-Phenyl |
| 457 | 1 | SO₂NH₂ | 2,4-di-Me-Phenyl |
| 458 | 2 | SO₂NH₂ | 2,4-di-Me-Phenyl |
| 459 | 3 | SO₂NH₂ | 2,4-di-Me-Phenyl |
| 460 | 1 | H | 2,6-di-iPr-Phenyl |
| 461 | 2 | H | 2,6-di-iPr-Phenyl |
| 462 | 3 | H | 2,6-di-iPr-Phenyl |
| 463 | 1 | Me | 2,6-di-iPr-Phenyl |
| 464 | 2 | Me | 2,6-di-iPr-Phenyl |
| 465 | 3 | Me | 2,6-di-iPr-Phenyl |
| 466 | 1 | CH₂Ph | 2,6-di-iPr-Phenyl |
| 467 | 2 | CH₂Ph | 2,6-di-iPr-Phenyl |
| 468 | 3 | CH₂Ph | 2,6-di-iPr-Phenyl |
| 469 | 1 | COMe | 2,6-di-iPr-Phenyl |
| 470 | 2 | COMe | 2,6-di-iPr-Phenyl |
| 471 | 3 | COMe | 2,6-di-iPr-Phenyl |
| 472 | 1 | CO₂Me | 2,6-di-iPr-Phenyl |
| 473 | 2 | CO₂Me | 2,6-di-iPr-Phenyl |
| 474 | 3 | CO₂Me | 2,6-di-iPr-Phenyl |
| 475 | 1 | CO₂tBu | 2,6-di-iPr-Phenyl |
| 476 | 2 | CO₂tBu | 2,6-di-iPr-Phenyl |
| 477 | 3 | CO₂tBu | 2,6-di-iPr-Phenyl |
| 478 | 1 | CONHMe | 2,6-di-iPr-Phenyl |
| 479 | 2 | CONHMe | 2,6-di-iPr-Phenyl |
| 480 | 3 | CONHMe | 2,6-di-iPr-Phenyl |
| 481 | 1 | SO₂Me | 2,6-di-iPr-Phenyl |
| 482 | 2 | SO₂Me | 2,6-di-iPr-Phenyl |
| 483 | 3 | SO₂Me | 2,6-di-iPr-Phenyl |
| 484 | 1 | SO₂NH₂ | 2,6-di-iPr-Phenyl |
| 485 | 2 | SO₂NH₂ | 2,6-di-iPr-Phenyl |
| 486 | 3 | SO₂NH₂ | 2,6-di-iPr-Phenyl |
| 487 | 1 | H | 3-Ph-Phenyl |
| 488 | 2 | H | 3-Ph-Phenyl |
| 489 | 3 | H | 3-Ph-Phenyl |
| 490 | 1 | Me | 3-Ph-Phenyl |
| 491 | 2 | Me | 3-Ph-Phenyl |
| 492 | 3 | Me | 3-Ph-Phenyl |
| 493 | 1 | CH₂Ph | 3-Ph-Phenyl |
| 494 | 2 | CH₂Ph | 3-Ph-Phenyl |
| 495 | 3 | CH₂Ph | 3-Ph-Phenyl |
| 496 | 1 | COMe | 3-Ph-Phenyl |
| 497 | 2 | COMe | 3-Ph-Phenyl |
| 498 | 3 | COMe | 3-Ph-Phenyl |
| 499 | 1 | CO₂Me | 3-Ph-Phenyl |
| 500 | 2 | CO₂Me | 3-Ph-Phenyl |
| 501 | 3 | CO₂Me | 3-Ph-Phenyl |
| 502 | 1 | CO₂tBu | 3-Ph-Phenyl |
| 503 | 2 | CO₂tBu | 3-Ph-Phenyl |
| 504 | 3 | CO₂tBu | 3-Ph-Phenyl |
| 505 | 1 | CONHMe | 3-Ph-Phenyl |
| 506 | 2 | CONHMe | 3-Ph-Phenyl |
| 507 | 3 | CONHMe | 3-Ph-Phenyl |
| 508 | 1 | SO₂Me | 3-Ph-Phenyl |
| 509 | 2 | SO₂Me | 3-Ph-Phenyl |
| 510 | 3 | SO₂Me | 3-Ph-Phenyl |
| 511 | 1 | SO₂NH₂ | 3-Ph-Phenyl |
| 512 | 2 | SO₂NH₂ | 3-Ph-Phenyl |
| 513 | 3 | SO₂NH₂ | 3-Ph-Phenyl |
| 514 | 1 | H | 2-morpholino-phenyl |
| 515 | 2 | H | 2-morpholino-phenyl |
| 516 | 3 | H | 2-morpholino-phenyl |
| 517 | 1 | Me | 2-morpholino-phenyl |
| 518 | 2 | Me | 2-morpholino-phenyl |
| 519 | 3 | Me | 2-morpholino-phenyl |
| 520 | 1 | CH₂Ph | 2-morpholino-phenyl |
| 521 | 2 | CH₂Ph | 2-morpholino-phenyl |
| 522 | 3 | CH₂Ph | 2-morpholino-phenyl |
| 523 | 1 | COMe | 2-morpholino-phenyl |
| 524 | 2 | COMe | 2-morpholino-phenyl |
| 525 | 3 | COMe | 2-morpholino-phenyl |
| 526 | 1 | CO₂Me | 2-morpholino-phenyl |
| 527 | 2 | CO₂Me | 2-morpholino-phenyl |
| 528 | 3 | CO₂Me | 2-morpholino-phenyl |
| 529 | 1 | CO₂tBu | 2-morpholino-phenyl |
| 530 | 2 | CO₂tBu | 2-morpholino-phenyl |
| 531 | 3 | CO₂tBu | 2-morpholino-phenyl |
| 532 | 1 | CONHMe | 2-morpholino-phenyl |
| 533 | 2 | CONHMe | 2-morpholino-phenyl |
| 534 | 3 | CONHMe | 2-morpholino-phenyl |
| 535 | 1 | SO₂Me | 2-morpholino-phenyl |
| 536 | 2 | SO₂Me | 2-morpholino-phenyl |
| 537 | 3 | SO₂Me | 2-morpholino-phenyl |
| 538 | 1 | SO₂NH₂ | 2-morpholino-phenyl |
| 539 | 2 | SO₂NH₂ | 2-morpholino-phenyl |
| 540 | 3 | SO₂NH₂ | 2-morpholino-phenyl |
| 541 | 1 | H | 4-morpholino-phenyl |
| 542 | 2 | H | 4-morpholino-phenyl |
| 543 | 3 | H | 4-morpholino-phenyl |
| 544 | 1 | Me | 4-morpholino-phenyl |
| 545 | 2 | Me | 4-morpholino-phenyl |
| 546 | 3 | Me | 4-morpholino-phenyl |
| 547 | 1 | CH₂Ph | 4-morpholino-phenyl |
| 548 | 2 | CH₂Ph | 4-morpholino-phenyl |
| 549 | 3 | CH₂Ph | 4-morpholino-phenyl |

TABLE 2-continued

| Entry | n | R | R³ |
|---|---|---|---|
| 550 | 1 | COMe | 4-morpholino-phenyl |
| 551 | 2 | COMe | 4-morpholino-phenyl |
| 552 | 3 | COMe | 4-morpholino-phenyl |
| 553 | 1 | CO₂Me | 4-morpholino-phenyl |
| 554 | 2 | CO₂Me | 4-morpholino-phenyl |
| 555 | 3 | CO₂Me | 4-morpholino-phenyl |
| 556 | 1 | CO₂tBu | 4-morpholino-phenyl |
| 557 | 2 | CO₂tBu | 4-morpholino-phenyl |
| 558 | 3 | CO₂tBu | 4-morpholino-phenyl |
| 559 | 1 | CONHMe | 4-morpholino-phenyl |
| 560 | 2 | CONHMe | 4-morpholino-phenyl |
| 561 | 3 | CONHMe | 4-morpholino-phenyl |
| 562 | 1 | SO₂Me | 4-morpholino-phenyl |
| 563 | 2 | SO₂Me | 4-morpholino-phenyl |
| 564 | 3 | SO₂Me | 4-morpholino-phenyl |
| 565 | 1 | SO₂NH₂ | 4-morpholino-phenyl |
| 566 | 2 | SO₂NH₂ | 4-morpholino-phenyl |
| 567 | 3 | SO₂NH₂ | 4-morpholino-phenyl |
| 568 | 1 | H | 2-pyrimidinyl |
| 569 | 2 | H | 2-pyrimidinyl |
| 570 | 3 | H | 2-pyrimidinyl |
| 571 | 1 | Me | 2-pyrimidinyl |
| 572 | 2 | Me | 2-pyrimidinyl |
| 573 | 3 | Me | 2-pyrimidinyl |
| 574 | 1 | CH₂Ph | 2-pyrimidinyl |
| 575 | 2 | CH₂Ph | 2-pyrimidinyl |
| 576 | 3 | CH₂Ph | 2-pyrimidinyl |
| 577 | 1 | COMe | 2-pyrimidinyl |
| 578 | 2 | COMe | 2-pyrimidinyl |
| 579 | 3 | COMe | 2-pyrimidinyl |
| 580 | 1 | CO₂Me | 2-pyrimidinyl |
| 581 | 2 | CO₂Me | 2-pyrimidinyl |
| 582 | 3 | CO₂Me | 2-pyrimidinyl |
| 583 | 1 | CO₂tBu | 2-pyrimidinyl |
| 584 | 2 | CO₂tBu | 2-pyrimidinyl |
| 585 | 3 | CO₂tBu | 2-pyrimidinyl |
| 586 | 1 | CONHMe | 2-pyrimidinyl |
| 587 | 2 | CONHMe | 2-pyrimidinyl |
| 588 | 3 | CONHMe | 2-pyrimidinyl |
| 589 | 1 | SO₂Me | 2-pyrimidinyl |
| 590 | 2 | SO₂Me | 2-pyrimidinyl |
| 591 | 3 | SO₂Me | 2-pyrimidinyl |
| 592 | 1 | SO₂NH₂ | 2-pyrimidinyl |
| 593 | 2 | SO₂NH₂ | 2-pyrimidinyl |
| 594 | 3 | SO₂NH₂ | 2-pyrimidinyl |
| 595 | 1 | H | 2-methyl-1H-benzo[d]imidazol-4-yl |
| 596 | 2 | H | 2-methyl-1H-benzo[d]imidazol-4-yl |
| 597 | 3 | H | 2-methyl-1H-benzo[d]imidazol-4-yl |
| 598 | 1 | Me | 2-methyl-1H-benzo[d]imidazol-4-yl |
| 599 | 2 | Me | 2-methyl-1H-benzo[d]imidazol-4-yl |
| 600 | 3 | Me | 2-methyl-1H-benzo[d]imidazol-4-yl |
| 601 | 1 | CH₂Ph | 2-methyl-1H-benzo[d]imidazol-4-yl |
| 602 | 2 | CH₂Ph | 2-methyl-1H-benzo[d]imidazol-4-yl |
| 603 | 3 | CH₂Ph | 2-methyl-1H-benzo[d]imidazol-4-yl |
| 604 | 1 | COMe | 2-methyl-1H-benzo[d]imidazol-4-yl |
| 605 | 2 | COMe | 2-methyl-1H-benzo[d]imidazol-4-yl |
| 606 | 3 | COMe | 2-methyl-1H-benzo[d]imidazol-4-yl |
| 607 | 1 | CO₂Me | 2-methyl-1H-benzo[d]imidazol-4-yl |
| 608 | 2 | CO₂Me | 2-methyl-1H-benzo[d]imidazol-4-yl |
| 609 | 3 | CO₂Me | 2-methyl-1H-benzo[d]imidazol-4-yl |
| 610 | 1 | CO₂tBu | 2-methyl-1H-benzo[d]imidazol-4-yl |
| 611 | 2 | CO₂tBu | 2-methyl-1H-benzo[d]imidazol-4-yl |
| 612 | 3 | CO₂tBu | 2-methyl-1H-benzo[d]imidazol-4-yl |
| 613 | 1 | CONHMe | 2-methyl-1H-benzo[d]imidazol-4-yl |
| 614 | 2 | CONHMe | 2-methyl-1H-benzo[d]imidazol-4-yl |
| 615 | 3 | CONHMe | 2-methyl-1H-benzo[d]imidazol-4-yl |
| 616 | 1 | SO₂Me | 2-methyl-1H-benzo[d]imidazol-4-yl |
| 617 | 2 | SO₂Me | 2-methyl-1H-benzo[d]imidazol-4-yl |
| 618 | 3 | SO₂Me | 2-methyl-1H-benzo[d]imidazol-4-yl |
| 619 | 1 | SO₂NH₂ | 2-methyl-1H-benzo[d]imidazol-4-yl |
| 620 | 2 | SO₂NH₂ | 2-methyl-1H-benzo[d]imidazol-4-yl |
| 621 | 3 | SO₂NH₂ | 2-methyl-1H-benzo[d]imidazol-4-yl |
| 622 | 1 | H | 4-OH-Phenyl |
| 623 | 2 | H | 4-OH-Phenyl |
| 624 | 3 | H | 4-OH-Phenyl |
| 625 | 1 | Me | 4-OH-Phenyl |
| 626 | 2 | Me | 4-OH-Phenyl |
| 627 | 3 | Me | 4-OH-Phenyl |
| 628 | 1 | CH₂Ph | 4-OH-Phenyl |
| 629 | 2 | CH₂Ph | 4-OH-Phenyl |
| 630 | 3 | CH₂Ph | 4-OH-Phenyl |
| 631 | 1 | COMe | 4-OH-Phenyl |
| 632 | 2 | COMe | 4-OH-Phenyl |
| 633 | 3 | COMe | 4-OH-Phenyl |
| 634 | 1 | CO₂Me | 4-OH-Phenyl |
| 635 | 2 | CO₂Me | 4-OH-Phenyl |
| 636 | 3 | CO₂Me | 4-OH-Phenyl |
| 637 | 1 | CO₂tBu | 4-OH-Phenyl |
| 638 | 2 | CO₂tBu | 4-OH-Phenyl |
| 639 | 3 | CO₂tBu | 4-OH-Phenyl |
| 640 | 1 | CONHMe | 4-OH-Phenyl |
| 641 | 2 | CONHMe | 4-OH-Phenyl |
| 642 | 3 | CONHMe | 4-OH-Phenyl |
| 643 | 1 | SO₂Me | 4-OH-Phenyl |
| 644 | 2 | SO₂Me | 4-OH-Phenyl |
| 645 | 3 | SO₂Me | 4-OH-Phenyl |
| 646 | 1 | SO₂NH₂ | 4-OH-Phenyl |
| 647 | 2 | SO₂NH₂ | 4-OH-Phenyl |
| 648 | 3 | SO₂NH₂ | 4-OH-Phenyl |
| 649 | 1 | H | 2-OH-Phenyl |
| 650 | 2 | H | 2-OH-Phenyl |
| 651 | 3 | H | 2-OH-Phenyl |
| 652 | 1 | Me | 2-OH-Phenyl |
| 653 | 2 | Me | 2-OH-Phenyl |
| 654 | 3 | Me | 2-OH-Phenyl |
| 655 | 1 | CH₂Ph | 2-OH-Phenyl |
| 656 | 2 | CH₂Ph | 2-OH-Phenyl |
| 657 | 3 | CH₂Ph | 2-OH-Phenyl |
| 658 | 1 | COMe | 2-OH-Phenyl |
| 659 | 2 | COMe | 2-OH-Phenyl |
| 660 | 3 | COMe | 2-OH-Phenyl |
| 661 | 1 | CO₂Me | 2-OH-Phenyl |
| 662 | 2 | CO₂Me | 2-OH-Phenyl |
| 663 | 3 | CO₂Me | 2-OH-Phenyl |
| 664 | 1 | CO₂tBu | 2-OH-Phenyl |
| 665 | 2 | CO₂tBu | 2-OH-Phenyl |
| 666 | 3 | CO₂tBu | 2-OH-Phenyl |
| 667 | 1 | CONHMe | 2-OH-Phenyl |
| 668 | 2 | CONHMe | 2-OH-Phenyl |
| 669 | 3 | CONHMe | 2-OH-Phenyl |
| 670 | 1 | SO₂Me | 2-OH-Phenyl |
| 671 | 2 | SO₂Me | 2-OH-Phenyl |
| 672 | 3 | SO₂Me | 2-OH-Phenyl |
| 673 | 1 | SO₂NH₂ | 2-OH-Phenyl |
| 674 | 2 | SO₂NH₂ | 2-OH-Phenyl |
| 675 | 3 | SO₂NH₂ | 2-OH-Phenyl |
| 676 | 1 | H | 4-OMe-Phenyl |
| 677 | 2 | H | 4-OMe-Phenyl |

TABLE 2-continued

| Entry | n | R | R³ |
|---|---|---|---|
| 678 | 3 | H | 4-OMe-Phenyl |
| 679 | 1 | Me | 4-OMe-Phenyl |
| 680 | 2 | Me | 4-OMe-Phenyl |
| 681 | 3 | Me | 4-OMe-Phenyl |
| 682 | 1 | CH₂Ph | 4-OMe-Phenyl |
| 683 | 2 | CH₂Ph | 4-OMe-Phenyl |
| 684 | 3 | CH₂Ph | 4-OMe-Phenyl |
| 685 | 1 | COMe | 4-OMe-Phenyl |
| 686 | 2 | COMe | 4-OMe-Phenyl |
| 687 | 3 | COMe | 4-OMe-Phenyl |
| 688 | 1 | CO₂Me | 4-OMe-Phenyl |
| 689 | 2 | CO₂Me | 4-OMe-Phenyl |
| 690 | 3 | CO₂Me | 4-OMe-Phenyl |
| 691 | 1 | CO₂tBu | 4-OMe-Phenyl |
| 692 | 2 | CO₂tBu | 4-OMe-Phenyl |
| 693 | 3 | CO₂tBu | 4-OMe-Phenyl |
| 694 | 1 | CONHMe | 4-OMe-Phenyl |
| 695 | 2 | CONHMe | 4-OMe-Phenyl |
| 696 | 3 | CONHMe | 4-OMe-Phenyl |
| 697 | 1 | SO₂Me | 4-OMe-Phenyl |
| 698 | 2 | SO₂Me | 4-OMe-Phenyl |
| 699 | 3 | SO₂Me | 4-OMe-Phenyl |
| 700 | 1 | SO₂NH₂ | 4-OMe-Phenyl |
| 701 | 2 | SO₂NH₂ | 4-OMe-Phenyl |
| 702 | 3 | SO₂NH₂ | 4-OMe-Phenyl |
| 703 | 1 | H | 2-OMe-Phenyl |
| 704 | 2 | H | 2-OMe-Phenyl |
| 705 | 3 | H | 2-OMe-Phenyl |
| 706 | 1 | Me | 2-OMe-Phenyl |
| 707 | 2 | Me | 2-OMe-Phenyl |
| 708 | 3 | Me | 2-OMe-Phenyl |
| 709 | 1 | CH₂Ph | 2-OMe-Phenyl |
| 710 | 2 | CH₂Ph | 2-OMe-Phenyl |
| 711 | 3 | CH₂Ph | 2-OMe-Phenyl |
| 712 | 1 | COMe | 2-OMe-Phenyl |
| 713 | 2 | COMe | 2-OMe-Phenyl |
| 714 | 3 | COMe | 2-OMe-Phenyl |
| 715 | 1 | CO₂Me | 2-OMe-Phenyl |
| 716 | 2 | CO₂Me | 2-OMe-Phenyl |
| 717 | 3 | CO₂Me | 2-OMe-Phenyl |
| 718 | 1 | CO₂tBu | 2-OMe-Phenyl |
| 719 | 2 | CO₂tBu | 2-OMe-Phenyl |
| 720 | 3 | CO₂tBu | 2-OMe-Phenyl |
| 721 | 1 | CONHMe | 2-OMe-Phenyl |
| 722 | 2 | CONHMe | 2-OMe-Phenyl |
| 723 | 3 | CONHMe | 2-OMe-Phenyl |
| 724 | 1 | SO₂Me | 2-OMe-Phenyl |
| 725 | 2 | SO₂Me | 2-OMe-Phenyl |
| 726 | 3 | SO₂Me | 2-OMe-Phenyl |
| 727 | 1 | SO₂NH₂ | 2-OMe-Phenyl |
| 728 | 2 | SO₂NH₂ | 2-OMe-Phenyl |
| 729 | 3 | SO₂NH₂ | 2-OMe-Phenyl |
| 730 | 1 | H | 3-CN-Phenyl |
| 731 | 2 | H | 3-CN-Phenyl |
| 732 | 3 | H | 3-CN-Phenyl |
| 733 | 1 | Me | 3-CN-Phenyl |
| 734 | 2 | Me | 3-CN-Phenyl |
| 735 | 3 | Me | 3-CN-Phenyl |
| 736 | 1 | CH₂Ph | 3-CN-Phenyl |
| 737 | 2 | CH₂Ph | 3-CN-Phenyl |
| 738 | 3 | CH₂Ph | 3-CN-Phenyl |
| 739 | 1 | COMe | 3-CN-Phenyl |
| 740 | 2 | COMe | 3-CN-Phenyl |
| 741 | 3 | COMe | 3-CN-Phenyl |
| 742 | 1 | CO₂Me | 3-CN-Phenyl |
| 743 | 2 | CO₂Me | 3-CN-Phenyl |
| 744 | 3 | CO₂Me | 3-CN-Phenyl |
| 745 | 1 | CO₂tBu | 3-CN-Phenyl |
| 746 | 2 | CO₂tBu | 3-CN-Phenyl |
| 747 | 3 | CO₂tBu | 3-CN-Phenyl |
| 748 | 1 | CONHMe | 3-CN-Phenyl |
| 749 | 2 | CONHMe | 3-CN-Phenyl |
| 750 | 3 | CONHMe | 3-CN-Phenyl |
| 751 | 1 | SO₂Me | 3-CN-Phenyl |
| 752 | 2 | SO₂Me | 3-CN-Phenyl |
| 753 | 3 | SO₂Me | 3-CN-Phenyl |
| 754 | 1 | SO₂NH₂ | 3-CN-Phenyl |
| 755 | 2 | SO₂NH₂ | 3-CN-Phenyl |
| 756 | 3 | SO₂NH₂ | 3-CN-Phenyl |
| 757 | 1 | H | 2-Me-Phenyl |
| 758 | 2 | H | 2-Me-Phenyl |
| 759 | 3 | H | 2-Me-Phenyl |
| 760 | 1 | Me | 2-Me-Phenyl |
| 761 | 2 | Me | 2-Me-Phenyl |
| 762 | 3 | Me | 2-Me-Phenyl |
| 763 | 1 | CH₂Ph | 2-Me-Phenyl |
| 764 | 2 | CH₂Ph | 2-Me-Phenyl |
| 765 | 3 | CH₂Ph | 2-Me-Phenyl |
| 766 | 1 | COMe | 2-Me-Phenyl |
| 767 | 2 | COMe | 2-Me-Phenyl |
| 768 | 3 | COMe | 2-Me-Phenyl |
| 769 | 1 | CO₂Me | 2-Me-Phenyl |
| 770 | 2 | CO₂Me | 2-Me-Phenyl |
| 771 | 3 | CO₂Me | 2-Me-Phenyl |
| 772 | 1 | CO₂tBu | 2-Me-Phenyl |
| 773 | 2 | CO₂tBu | 2-Me-Phenyl |
| 774 | 3 | CO₂tBu | 2-Me-Phenyl |
| 775 | 1 | CONHMe | 2-Me-Phenyl |
| 776 | 2 | CONHMe | 2-Me-Phenyl |
| 777 | 3 | CONHMe | 2-Me-Phenyl |
| 778 | 1 | SO₂Me | 2-Me-Phenyl |
| 779 | 2 | SO₂Me | 2-Me-Phenyl |
| 780 | 3 | SO₂Me | 2-Me-Phenyl |
| 781 | 1 | SO₂NH₂ | 2-Me-Phenyl |
| 782 | 2 | SO₂NH₂ | 2-Me-Phenyl |
| 783 | 3 | SO₂NH₂ | 2-Me-Phenyl |
| 784 | 1 | H | 4-Me-Phenyl |
| 785 | 2 | H | 4-Me-Phenyl |
| 786 | 3 | H | 4-Me-Phenyl |
| 787 | 1 | Me | 4-Me-Phenyl |
| 788 | 2 | Me | 4-Me-Phenyl |
| 789 | 3 | Me | 4-Me-Phenyl |
| 790 | 1 | CH₂Ph | 4-Me-Phenyl |
| 791 | 2 | CH₂Ph | 4-Me-Phenyl |
| 792 | 3 | CH₂Ph | 4-Me-Phenyl |
| 793 | 1 | COMe | 4-Me-Phenyl |
| 794 | 2 | COMe | 4-Me-Phenyl |
| 795 | 3 | COMe | 4-Me-Phenyl |
| 796 | 1 | CO₂Me | 4-Me-Phenyl |
| 797 | 2 | CO₂Me | 4-Me-Phenyl |
| 798 | 3 | CO₂Me | 4-Me-Phenyl |
| 799 | 1 | CO₂tBu | 4-Me-Phenyl |
| 800 | 2 | CO₂tBu | 4-Me-Phenyl |
| 801 | 3 | CO₂tBu | 4-Me-Phenyl |
| 802 | 1 | CONHMe | 4-Me-Phenyl |
| 803 | 2 | CONHMe | 4-Me-Phenyl |
| 804 | 3 | CONHMe | 4-Me-Phenyl |
| 805 | 1 | SO₂Me | 4-Me-Phenyl |
| 806 | 2 | SO₂Me | 4-Me-Phenyl |
| 807 | 3 | SO₂Me | 4-Me-Phenyl |
| 808 | 1 | SO₂NH₂ | 4-Me-Phenyl |
| 809 | 2 | SO₂NH₂ | 4-Me-Phenyl |
| 810 | 3 | SO₂NH₂ | 4-Me-Phenyl |
| 811 | 1 | H | 3-F-Phenyl |
| 812 | 2 | H | 3-F-Phenyl |
| 813 | 3 | H | 3-F-Phenyl |
| 814 | 1 | Me | 3-F-Phenyl |
| 815 | 2 | Me | 3-F-Phenyl |
| 816 | 3 | Me | 3-F-Phenyl |
| 817 | 1 | CH₂Ph | 3-F-Phenyl |
| 818 | 2 | CH₂Ph | 3-F-Phenyl |
| 819 | 3 | CH₂Ph | 3-F-Phenyl |
| 820 | 1 | COMe | 3-F-Phenyl |
| 821 | 2 | COMe | 3-F-Phenyl |
| 822 | 3 | COMe | 3-F-Phenyl |
| 823 | 1 | CO₂Me | 3-F-Phenyl |
| 824 | 2 | CO₂Me | 3-F-Phenyl |
| 825 | 3 | CO₂Me | 3-F-Phenyl |
| 826 | 1 | CO₂tBu | 3-F-Phenyl |
| 827 | 2 | CO₂tBu | 3-F-Phenyl |
| 828 | 3 | CO₂tBu | 3-F-Phenyl |
| 829 | 1 | CONHMe | 3-F-Phenyl |
| 830 | 2 | CONHMe | 3-F-Phenyl |
| 831 | 3 | CONHMe | 3-F-Phenyl |
| 832 | 1 | SO₂Me | 3-F-Phenyl |
| 833 | 2 | SO₂Me | 3-F-Phenyl |

TABLE 2-continued

| Entry | n | R | R³ |
|---|---|---|---|
| 834 | 3 | SO₂Me | 3-F-Phenyl |
| 835 | 1 | SO₂NH₂ | 3-F-Phenyl |
| 836 | 2 | SO₂NH₂ | 3-F-Phenyl |
| 837 | 3 | SO₂NH₂ | 3-F-Phenyl |
| 838 | 1 | H | 2-Cl-Phenyl |
| 839 | 2 | H | 2-Cl-Phenyl |
| 840 | 3 | H | 2-Cl-Phenyl |
| 841 | 1 | Me | 2-Cl-Phenyl |
| 842 | 2 | Me | 2-Cl-Phenyl |
| 843 | 3 | Me | 2-Cl-Phenyl |
| 844 | 1 | CH₂Ph | 2-Cl-Phenyl |
| 845 | 2 | CH₂Ph | 2-Cl-Phenyl |
| 846 | 3 | CH₂Ph | 2-Cl-Phenyl |
| 847 | 1 | COMe | 2-Cl-Phenyl |
| 848 | 2 | COMe | 2-Cl-Phenyl |
| 849 | 3 | COMe | 2-Cl-Phenyl |
| 850 | 1 | CO₂Me | 2-Cl-Phenyl |
| 851 | 2 | CO₂Me | 2-Cl-Phenyl |
| 852 | 3 | CO₂Me | 2-Cl-Phenyl |
| 853 | 1 | CO₂tBu | 2-Cl-Phenyl |
| 854 | 2 | CO₂tBu | 2-Cl-Phenyl |
| 855 | 3 | CO₂tBu | 2-Cl-Phenyl |
| 856 | 1 | CONHMe | 2-Cl-Phenyl |
| 857 | 2 | CONHMe | 2-Cl-Phenyl |
| 858 | 3 | CONHMe | 2-Cl-Phenyl |
| 859 | 1 | SO₂Me | 2-Cl-Phenyl |
| 860 | 2 | SO₂Me | 2-Cl-Phenyl |
| 861 | 3 | SO₂Me | 2-Cl-Phenyl |
| 862 | 1 | SO₂NH₂ | 2-Cl-Phenyl |
| 863 | 2 | SO₂NH₂ | 2-Cl-Phenyl |
| 864 | 3 | SO₂NH₂ | 2-Cl-Phenyl |
| 865 | 1 | H | 4-Cl-Phenyl |
| 866 | 2 | H | 4-Cl-Phenyl |
| 867 | 3 | H | 4-Cl-Phenyl |
| 868 | 1 | Me | 4-Cl-Phenyl |
| 869 | 2 | Me | 4-Cl-Phenyl |
| 870 | 3 | Me | 4-Cl-Phenyl |
| 871 | 1 | CH₂Ph | 4-Cl-Phenyl |
| 872 | 2 | CH₂Ph | 4-Cl-Phenyl |
| 873 | 3 | CH₂Ph | 4-Cl-Phenyl |
| 874 | 1 | COMe | 4-Cl-Phenyl |
| 875 | 2 | COMe | 4-Cl-Phenyl |
| 876 | 3 | COMe | 4-Cl-Phenyl |
| 877 | 1 | CO₂Me | 4-Cl-Phenyl |
| 878 | 2 | CO₂Me | 4-Cl-Phenyl |
| 879 | 3 | CO₂Me | 4-Cl-Phenyl |
| 880 | 1 | CO₂tBu | 4-Cl-Phenyl |
| 881 | 2 | CO₂tBu | 4-Cl-Phenyl |
| 882 | 3 | CO₂tBu | 4-Cl-Phenyl |
| 883 | 1 | CONHMe | 4-Cl-Phenyl |
| 884 | 2 | CONHMe | 4-Cl-Phenyl |
| 885 | 3 | CONHMe | 4-Cl-Phenyl |
| 886 | 1 | SO₂Me | 4-Cl-Phenyl |
| 887 | 2 | SO₂Me | 4-Cl-Phenyl |
| 888 | 3 | SO₂Me | 4-Cl-Phenyl |
| 889 | 1 | SO₂NH₂ | 4-Cl-Phenyl |
| 890 | 2 | SO₂NH₂ | 4-Cl-Phenyl |
| 891 | 3 | SO₂NH₂ | 4-Cl-Phenyl |
| 892 | 1 | H | 3-Br-Phenyl |
| 893 | 2 | H | 3-Br-Phenyl |
| 894 | 3 | H | 3-Br-Phenyl |
| 895 | 1 | Me | 3-Br-Phenyl |
| 896 | 2 | Me | 3-Br-Phenyl |
| 897 | 3 | Me | 3-Br-Phenyl |
| 898 | 1 | CH₂Ph | 3-Br-Phenyl |
| 899 | 2 | CH₂Ph | 3-Br-Phenyl |
| 900 | 3 | CH₂Ph | 3-Br-Phenyl |
| 901 | 1 | COMe | 3-Br-Phenyl |
| 902 | 2 | COMe | 3-Br-Phenyl |
| 903 | 3 | COMe | 3-Br-Phenyl |
| 904 | 1 | CO₂Me | 3-Br-Phenyl |
| 905 | 2 | CO₂Me | 3-Br-Phenyl |
| 906 | 3 | CO₂Me | 3-Br-Phenyl |
| 907 | 1 | CO₂tBu | 3-Br-Phenyl |
| 908 | 2 | CO₂tBu | 3-Br-Phenyl |
| 909 | 3 | CO₂tBu | 3-Br-Phenyl |
| 910 | 1 | CONHMe | 3-Br-Phenyl |
| 911 | 2 | CONHMe | 3-Br-Phenyl |
| 912 | 3 | CONHMe | 3-Br-Phenyl |
| 913 | 1 | SO₂Me | 3-Br-Phenyl |
| 914 | 2 | SO₂Me | 3-Br-Phenyl |
| 915 | 3 | SO₂Me | 3-Br-Phenyl |
| 916 | 1 | SO₂NH₂ | 3-Br-Phenyl |
| 917 | 2 | SO₂NH₂ | 3-Br-Phenyl |
| 918 | 3 | SO₂NH₂ | 3-Br-Phenyl |
| 919 | 1 | H | 2-CF₃-Phenyl |
| 920 | 2 | H | 2-CF₃-Phenyl |
| 921 | 3 | H | 2-CF₃-Phenyl |
| 922 | 1 | Me | 2-CF₃-Phenyl |
| 923 | 2 | Me | 2-CF₃-Phenyl |
| 924 | 3 | Me | 2-CF₃-Phenyl |
| 925 | 1 | CH₂Ph | 2-CF₃-Phenyl |
| 926 | 2 | CH₂Ph | 2-CF₃-Phenyl |
| 927 | 3 | CH₂Ph | 2-CF₃-Phenyl |
| 928 | 1 | COMe | 2-CF₃-Phenyl |
| 929 | 2 | COMe | 2-CF₃-Phenyl |
| 930 | 3 | COMe | 2-CF₃-Phenyl |
| 931 | 1 | CO₂Me | 2-CF₃-Phenyl |
| 932 | 2 | CO₂Me | 2-CF₃-Phenyl |
| 933 | 3 | CO₂Me | 2-CF₃-Phenyl |
| 934 | 1 | CO₂tBu | 2-CF₃-Phenyl |
| 935 | 2 | CO₂tBu | 2-CF₃-Phenyl |
| 936 | 3 | CO₂tBu | 2-CF₃-Phenyl |
| 937 | 1 | CONHMe | 2-CF₃-Phenyl |
| 938 | 2 | CONHMe | 2-CF₃-Phenyl |
| 939 | 3 | CONHMe | 2-CF₃-Phenyl |
| 940 | 1 | SO₂Me | 2-CF₃-Phenyl |
| 941 | 2 | SO₂Me | 2-CF₃-Phenyl |
| 942 | 3 | SO₂Me | 2-CF₃-Phenyl |
| 943 | 1 | SO₂NH₂ | 2-CF₃-Phenyl |
| 944 | 2 | SO₂NH₂ | 2-CF₃-Phenyl |
| 945 | 3 | SO₂NH₂ | 2-CF₃-Phenyl |
| 946 | 1 | H | 4-CF₃-Phenyl |
| 947 | 2 | H | 4-CF₃-Phenyl |
| 948 | 3 | H | 4-CF₃-Phenyl |
| 949 | 1 | Me | 4-CF₃-Phenyl |
| 950 | 2 | Me | 4-CF₃-Phenyl |
| 951 | 3 | Me | 4-CF₃-Phenyl |
| 952 | 1 | CH₂Ph | 4-CF₃-Phenyl |
| 953 | 2 | CH₂Ph | 4-CF₃-Phenyl |
| 954 | 3 | CH₂Ph | 4-CF₃-Phenyl |
| 955 | 1 | COMe | 4-CF₃-Phenyl |
| 956 | 2 | COMe | 4-CF₃-Phenyl |
| 957 | 3 | COMe | 4-CF₃-Phenyl |
| 958 | 1 | CO₂Me | 4-CF₃-Phenyl |
| 959 | 2 | CO₂Me | 4-CF₃-Phenyl |
| 960 | 3 | CO₂Me | 4-CF₃-Phenyl |
| 961 | 1 | CO₂tBu | 4-CF₃-Phenyl |
| 962 | 2 | CO₂tBu | 4-CF₃-Phenyl |
| 963 | 3 | CO₂tBu | 4-CF₃-Phenyl |
| 964 | 1 | CONHMe | 4-CF₃-Phenyl |
| 965 | 2 | CONHMe | 4-CF₃-Phenyl |
| 966 | 3 | CONHMe | 4-CF₃-Phenyl |
| 967 | 1 | SO₂Me | 4-CF₃-Phenyl |
| 968 | 2 | SO₂Me | 4-CF₃-Phenyl |
| 969 | 3 | SO₂Me | 4-CF₃-Phenyl |
| 970 | 1 | SO₂NH₂ | 4-CF₃-Phenyl |
| 971 | 2 | SO₂NH₂ | 4-CF₃-Phenyl |
| 972 | 3 | SO₂NH₂ | 4-CF₃-Phenyl |
| 973 | 1 | H | 3-iPr-Phenyl |
| 974 | 2 | H | 3-iPr-Phenyl |
| 975 | 3 | H | 3-iPr-Phenyl |
| 976 | 1 | Me | 3-iPr-Phenyl |
| 977 | 2 | Me | 3-iPr-Phenyl |
| 978 | 3 | Me | 3-iPr-Phenyl |
| 979 | 1 | CH₂Ph | 3-iPr-Phenyl |
| 980 | 2 | CH₂Ph | 3-iPr-Phenyl |
| 981 | 3 | CH₂Ph | 3-iPr-Phenyl |
| 982 | 1 | COMe | 3-iPr-Phenyl |
| 983 | 2 | COMe | 3-iPr-Phenyl |
| 984 | 3 | COMe | 3-iPr-Phenyl |
| 985 | 1 | CO₂Me | 3-iPr-Phenyl |
| 986 | 2 | CO₂Me | 3-iPr-Phenyl |
| 987 | 3 | CO₂Me | 3-iPr-Phenyl |
| 988 | 1 | CO₂tBu | 3-iPr-Phenyl |
| 989 | 2 | CO₂tBu | 3-iPr-Phenyl |

TABLE 2-continued

| Entry | n | R | R³ |
|---|---|---|---|
| 990 | 3 | CO₂tBu | 3-iPr-Phenyl |
| 991 | 1 | CONHMe | 3-iPr-Phenyl |
| 992 | 2 | CONHMe | 3-iPr-Phenyl |
| 993 | 3 | CONHMe | 3-iPr-Phenyl |
| 994 | 1 | SO₂Me | 3-iPr-Phenyl |
| 995 | 2 | SO₂Me | 3-iPr-Phenyl |
| 996 | 3 | SO₂Me | 3-iPr-Phenyl |
| 997 | 1 | SO₂NH₂ | 3-iPr-Phenyl |
| 998 | 2 | SO₂NH₂ | 3-iPr-Phenyl |
| 999 | 3 | SO₂NH₂ | 3-iPr-Phenyl |
| 1000 | 1 | H | 4-NH₂-Phenyl |
| 1001 | 2 | H | 4-NH₂-Phenyl |
| 1002 | 3 | H | 4-NH₂-Phenyl |
| 1003 | 1 | Me | 4-NH₂-Phenyl |
| 1004 | 2 | Me | 4-NH₂-Phenyl |
| 1005 | 3 | Me | 4-NH₂-Phenyl |
| 1006 | 1 | CH₂Ph | 4-NH₂-Phenyl |
| 1007 | 2 | CH₂Ph | 4-NH₂-Phenyl |
| 1008 | 3 | CH₂Ph | 4-NH₂-Phenyl |
| 1009 | 1 | COMe | 4-NH₂-Phenyl |
| 1010 | 2 | COMe | 4-NH₂-Phenyl |
| 1011 | 3 | COMe | 4-NH₂-Phenyl |
| 1012 | 1 | CO₂Me | 4-NH₂-Phenyl |
| 1013 | 2 | CO₂Me | 4-NH₂-Phenyl |
| 1014 | 3 | CO₂Me | 4-NH₂-Phenyl |
| 1015 | 1 | CO₂tBu | 4-NH₂-Phenyl |
| 1016 | 2 | CO₂tBu | 4-NH₂-Phenyl |
| 1017 | 3 | CO₂tBu | 4-NH₂-Phenyl |
| 1018 | 1 | CONHMe | 4-NH₂-Phenyl |
| 1019 | 2 | CONHMe | 4-NH₂-Phenyl |
| 1020 | 3 | CONHMe | 4-NH₂-Phenyl |
| 1021 | 1 | SO₂Me | 4-NH₂-Phenyl |
| 1022 | 2 | SO₂Me | 4-NH₂-Phenyl |
| 1023 | 3 | SO₂Me | 4-NH₂-Phenyl |
| 1024 | 1 | SO₂NH₂ | 4-NH₂-Phenyl |
| 1025 | 2 | SO₂NH₂ | 4-NH₂-Phenyl |
| 1026 | 3 | SO₂NH₂ | 4-NH₂-Phenyl |
| 1027 | 1 | H | 2-NH₂-Phenyl |
| 1028 | 2 | H | 2-NH₂-Phenyl |
| 1029 | 3 | H | 2-NH₂-Phenyl |
| 1030 | 1 | Me | 2-NH₂-Phenyl |
| 1031 | 2 | Me | 2-NH₂-Phenyl |
| 1032 | 3 | Me | 2-NH₂-Phenyl |
| 1033 | 1 | CH₂Ph | 2-NH₂-Phenyl |
| 1034 | 2 | CH₂Ph | 2-NH₂-Phenyl |
| 1035 | 3 | CH₂Ph | 2-NH₂-Phenyl |
| 1036 | 1 | COMe | 2-NH₂-Phenyl |
| 1037 | 2 | COMe | 2-NH₂-Phenyl |
| 1038 | 3 | COMe | 2-NH₂-Phenyl |
| 1039 | 1 | CO₂Me | 2-NH₂-Phenyl |
| 1040 | 2 | CO₂Me | 2-NH₂-Phenyl |
| 1041 | 3 | CO₂Me | 2-NH₂-Phenyl |
| 1042 | 1 | CO₂tBu | 2-NH₂-Phenyl |
| 1043 | 2 | CO₂tBu | 2-NH₂-Phenyl |
| 1044 | 3 | CO₂tBu | 2-NH₂-Phenyl |
| 1045 | 1 | CONHMe | 2-NH₂-Phenyl |
| 1046 | 2 | CONHMe | 2-NH₂-Phenyl |
| 1047 | 3 | CONHMe | 2-NH₂-Phenyl |
| 1048 | 1 | SO₂Me | 2-NH₂-Phenyl |
| 1049 | 2 | SO₂Me | 2-NH₂-Phenyl |
| 1050 | 3 | SO₂Me | 2-NH₂-Phenyl |
| 1051 | 1 | SO₂NH₂ | 2-NH₂-Phenyl |
| 1052 | 2 | SO₂NH₂ | 2-NH₂-Phenyl |
| 1053 | 3 | SO₂NH₂ | 2-NH₂-Phenyl |
| 1054 | 1 | H | 2,6-di-Me-Phenyl |
| 1055 | 2 | H | 2,6-di-Me-Phenyl |
| 1056 | 3 | H | 2,6-di-Me-Phenyl |
| 1057 | 1 | Me | 2,6-di-Me-Phenyl |
| 1058 | 2 | Me | 2,6-di-Me-Phenyl |
| 1059 | 3 | Me | 2,6-di-Me-Phenyl |
| 1060 | 1 | CH₂Ph | 2,6-di-Me-Phenyl |
| 1061 | 2 | CH₂Ph | 2,6-di-Me-Phenyl |
| 1062 | 3 | CH₂Ph | 2,6-di-Me-Phenyl |
| 1063 | 1 | COMe | 2,6-di-Me-Phenyl |
| 1064 | 2 | COMe | 2,6-di-Me-Phenyl |
| 1065 | 3 | COMe | 2,6-di-Me-Phenyl |
| 1066 | 1 | CO₂Me | 2,6-di-Me-Phenyl |
| 1067 | 2 | CO₂Me | 2,6-di-Me-Phenyl |
| 1068 | 3 | CO₂Me | 2,6-di-Me-Phenyl |
| 1069 | 1 | CO₂tBu | 2,6-di-Me-Phenyl |
| 1070 | 2 | CO₂tBu | 2,6-di-Me-Phenyl |
| 1071 | 3 | CO₂tBu | 2,6-di-Me-Phenyl |
| 1072 | 1 | CONHMe | 2,6-di-Me-Phenyl |
| 1073 | 2 | CONHMe | 2,6-di-Me-Phenyl |
| 1074 | 3 | CONHMe | 2,6-di-Me-Phenyl |
| 1075 | 1 | SO₂Me | 2,6-di-Me-Phenyl |
| 1076 | 2 | SO₂Me | 2,6-di-Me-Phenyl |
| 1077 | 3 | SO₂Me | 2,6-di-Me-Phenyl |
| 1078 | 1 | SO₂NH₂ | 2,6-di-Me-Phenyl |
| 1079 | 2 | SO₂NH₂ | 2,6-di-Me-Phenyl |
| 1080 | 3 | SO₂NH₂ | 2,6-di-Me-Phenyl |
| 1081 | 1 | H | 2-Ph-Phenyl |
| 1082 | 2 | H | 2-Ph-Phenyl |
| 1083 | 3 | H | 2-Ph-Phenyl |
| 1084 | 1 | Me | 2-Ph-Phenyl |
| 1085 | 2 | Me | 2-Ph-Phenyl |
| 1086 | 3 | Me | 2-Ph-Phenyl |
| 1087 | 1 | CH₂Ph | 2-Ph-Phenyl |
| 1088 | 2 | CH₂Ph | 2-Ph-Phenyl |
| 1089 | 3 | CH₂Ph | 2-Ph-Phenyl |
| 1090 | 1 | COMe | 2-Ph-Phenyl |
| 1091 | 2 | COMe | 2-Ph-Phenyl |
| 1092 | 3 | COMe | 2-Ph-Phenyl |
| 1093 | 1 | CO₂Me | 2-Ph-Phenyl |
| 1094 | 2 | CO₂Me | 2-Ph-Phenyl |
| 1095 | 3 | CO₂Me | 2-Ph-Phenyl |
| 1096 | 1 | CO₂tBu | 2-Ph-Phenyl |
| 1097 | 2 | CO₂tBu | 2-Ph-Phenyl |
| 1098 | 3 | CO₂tBu | 2-Ph-Phenyl |
| 1099 | 1 | CONHMe | 2-Ph-Phenyl |
| 1100 | 2 | CONHMe | 2-Ph-Phenyl |
| 1101 | 3 | CONHMe | 2-Ph-Phenyl |
| 1102 | 1 | SO₂Me | 2-Ph-Phenyl |
| 1103 | 2 | SO₂Me | 2-Ph-Phenyl |
| 1104 | 3 | SO₂Me | 2-Ph-Phenyl |
| 1105 | 1 | SO₂NH₂ | 2-Ph-Phenyl |
| 1106 | 2 | SO₂NH₂ | 2-Ph-Phenyl |
| 1107 | 3 | SO₂NH₂ | 2-Ph-Phenyl |
| 1108 | 1 | H | 4-Ph-Phenyl |
| 1109 | 2 | H | 4-Ph-Phenyl |
| 1110 | 3 | H | 4-Ph-Phenyl |
| 1111 | 1 | Me | 4-Ph-Phenyl |
| 1112 | 2 | Me | 4-Ph-Phenyl |
| 1113 | 3 | Me | 4-Ph-Phenyl |
| 1114 | 1 | CH₂Ph | 4-Ph-Phenyl |
| 1115 | 2 | CH₂Ph | 4-Ph-Phenyl |
| 1116 | 3 | CH₂Ph | 4-Ph-Phenyl |
| 1117 | 1 | COMe | 4-Ph-Phenyl |
| 1118 | 2 | COMe | 4-Ph-Phenyl |
| 1119 | 3 | COMe | 4-Ph-Phenyl |
| 1120 | 1 | CO₂Me | 4-Ph-Phenyl |
| 1121 | 2 | CO₂Me | 4-Ph-Phenyl |
| 1122 | 3 | CO₂Me | 4-Ph-Phenyl |
| 1123 | 1 | CO₂tBu | 4-Ph-Phenyl |
| 1124 | 2 | CO₂tBu | 4-Ph-Phenyl |
| 1125 | 3 | CO₂tBu | 4-Ph-Phenyl |
| 1126 | 1 | CONHMe | 4-Ph-Phenyl |
| 1127 | 2 | CONHMe | 4-Ph-Phenyl |
| 1128 | 3 | CONHMe | 4-Ph-Phenyl |
| 1129 | 1 | SO₂Me | 4-Ph-Phenyl |
| 1130 | 2 | SO₂Me | 4-Ph-Phenyl |
| 1131 | 3 | SO₂Me | 4-Ph-Phenyl |
| 1132 | 1 | SO₂NH₂ | 4-Ph-Phenyl |
| 1133 | 2 | SO₂NH₂ | 4-Ph-Phenyl |
| 1134 | 3 | SO₂NH₂ | 4-Ph-Phenyl |
| 1135 | 1 | H | 3-morpholino-phenyl |
| 1136 | 2 | H | 3-morpholino-phenyl |
| 1137 | 3 | H | 3-morpholino-phenyl |
| 1138 | 1 | Me | 3-morpholino-phenyl |
| 1139 | 2 | Me | 3-morpholino-phenyl |
| 1140 | 3 | Me | 3-morpholino-phenyl |
| 1141 | 1 | CH₂Ph | 3-morpholino-phenyl |
| 1142 | 2 | CH₂Ph | 3-morpholino-phenyl |
| 1143 | 3 | CH₂Ph | 3-morpholino-phenyl |
| 1144 | 1 | COMe | 3-morpholino-phenyl |
| 1145 | 2 | COMe | 3-morpholino-phenyl |

TABLE 2-continued

| Entry | n | R | R³ |
|---|---|---|---|
| 1146 | 3 | COMe | 3-morpholino-phenyl |
| 1147 | 1 | CO₂Me | 3-morpholino-phenyl |
| 1148 | 2 | CO₂Me | 3-morpholino-phenyl |
| 1149 | 3 | CO₂Me | 3-morpholino-phenyl |
| 1150 | 1 | CO₂tBu | 3-morpholino-phenyl |
| 1151 | 2 | CO₂tBu | 3-morpholino-phenyl |
| 1152 | 3 | CO₂tBu | 3-morpholino-phenyl |
| 1153 | 1 | CONHMe | 3-morpholino-phenyl |
| 1154 | 2 | CONHMe | 3-morpholino-phenyl |
| 1155 | 3 | CONHMe | 3-morpholino-phenyl |
| 1156 | 1 | SO₂Me | 3-morpholino-phenyl |
| 1157 | 2 | SO₂Me | 3-morpholino-phenyl |
| 1158 | 3 | SO₂Me | 3-morpholino-phenyl |
| 1159 | 1 | SO₂NH₂ | 3-morpholino-phenyl |
| 1160 | 2 | SO₂NH₂ | 3-morpholino-phenyl |
| 1161 | 3 | SO₂NH₂ | 3-morpholino-phenyl |
| 1162 | 1 | H | 2-pyrazinyl |
| 1163 | 2 | H | 2-pyrazinyl |
| 1164 | 3 | H | 2-pyrazinyl |
| 1165 | 1 | Me | 2-pyrazinyl |
| 1166 | 2 | Me | 2-pyrazinyl |
| 1167 | 3 | Me | 2-pyrazinyl |
| 1168 | 1 | CH₂Ph | 2-pyrazinyl |
| 1169 | 2 | CH₂Ph | 2-pyrazinyl |
| 1170 | 3 | CH₂Ph | 2-pyrazinyl |
| 1171 | 1 | COMe | 2-pyrazinyl |
| 1172 | 2 | COMe | 2-pyrazinyl |
| 1173 | 3 | COMe | 2-pyrazinyl |
| 1174 | 1 | CO₂Me | 2-pyrazinyl |
| 1175 | 2 | CO₂Me | 2-pyrazinyl |
| 1176 | 3 | CO₂Me | 2-pyrazinyl |
| 1177 | 1 | CO₂tBu | 2-pyrazinyl |
| 1178 | 2 | CO₂tBu | 2-pyrazinyl |
| 1179 | 3 | CO₂tBu | 2-pyrazinyl |
| 1180 | 1 | CONHMe | 2-pyrazinyl |
| 1181 | 2 | CONHMe | 2-pyrazinyl |
| 1182 | 3 | CONHMe | 2-pyrazinyl |
| 1183 | 1 | SO₂Me | 2-pyrazinyl |
| 1184 | 2 | SO₂Me | 2-pyrazinyl |
| 1185 | 3 | SO₂Me | 2-pyrazinyl |
| 1186 | 1 | SO₂NH₂ | 2-pyrazinyl |
| 1187 | 2 | SO₂NH₂ | 2-pyrazinyl |
| 1188 | 3 | SO₂NH₂ | 2-pyrazinyl |
| 1189 | 1 | H | 5-indolyl |
| 1190 | 2 | H | 5-indolyl |
| 1191 | 3 | H | 5-indolyl |
| 1192 | 1 | Me | 5-indolyl |
| 1193 | 2 | Me | 5-indolyl |
| 1194 | 3 | Me | 5-indolyl |
| 1195 | 1 | CH₂Ph | 5-indolyl |
| 1196 | 2 | CH₂Ph | 5-indolyl |
| 1197 | 3 | CH₂Ph | 5-indolyl |
| 1198 | 1 | COMe | 5-indolyl |
| 1199 | 2 | COMe | 5-indolyl |
| 1200 | 3 | COMe | 5-indolyl |
| 1201 | 1 | CO₂Me | 5-indolyl |
| 1202 | 2 | CO₂Me | 5-indolyl |
| 1203 | 3 | CO₂Me | 5-indolyl |
| 1204 | 1 | CO₂tBu | 5-indolyl |
| 1205 | 2 | CO₂tBu | 5-indolyl |
| 1206 | 3 | CO₂tBu | 5-indolyl |
| 1207 | 1 | CONHMe | 5-indolyl |
| 1208 | 2 | CONHMe | 5-indolyl |
| 1209 | 3 | CONHMe | 5-indolyl |
| 1210 | 1 | SO₂Me | 5-indolyl |
| 1211 | 2 | SO₂Me | 5-indolyl |
| 1212 | 3 | SO₂Me | 5-indolyl |
| 1213 | 1 | SO₂NH₂ | 5-indolyl |
| 1214 | 2 | SO₂NH₂ | 5-indolyl |
| 1215 | 3 | SO₂NH₂ | 5-indolyl |
| 1216 | 1 | H | 1H-benzo[d]imidazol-4-yl |
| 1217 | 2 | H | 1H-benzo[d]imidazol-4-yl |
| 1218 | 3 | H | 1H-benzo[d]imidazol-4-yl |
| 1219 | 1 | Me | 1H-benzo[d]imidazol-4-yl |
| 1220 | 2 | Me | 1H-benzo[d]imidazol-4-yl |
| 1221 | 3 | Me | 1H-benzo[d]imidazol-4-yl |
| 1222 | 1 | CH₂Ph | 1H-benzo[d]imidazol-4-yl |
| 1223 | 2 | CH₂Ph | 1H-benzo[d]imidazol-4-yl |
| 1224 | 3 | CH₂Ph | 1H-benzo[d]imidazol-4-yl |
| 1225 | 1 | COMe | 1H-benzo[d]imidazol-4-yl |
| 1226 | 2 | COMe | 1H-benzo[d]imidazol-4-yl |
| 1227 | 3 | COMe | 1H-benzo[d]imidazol-4-yl |
| 1228 | 1 | CO₂Me | 1H-benzo[d]imidazol-4-yl |
| 1229 | 2 | CO₂Me | 1H-benzo[d]imidazol-4-yl |
| 1230 | 3 | CO₂Me | 1H-benzo[d]imidazol-4-yl |
| 1231 | 1 | CO₂tBu | 1H-benzo[d]imidazol-4-yl |
| 1232 | 2 | CO₂tBu | 1H-benzo[d]imidazol-4-yl |
| 1233 | 3 | CO₂tBu | 1H-benzo[d]imidazol-4-yl |
| 1234 | 1 | CONHMe | 1H-benzo[d]imidazol-4-yl |
| 1235 | 2 | CONHMe | 1H-benzo[d]imidazol-4-yl |
| 1236 | 3 | CONHMe | 1H-benzo[d]imidazol-4-yl |
| 1237 | 1 | SO₂Me | 1H-benzo[d]imidazol-4-yl |
| 1238 | 2 | SO₂Me | 1H-benzo[d]imidazol-4-yl |
| 1239 | 3 | SO₂Me | 1H-benzo[d]imidazol-4-yl |
| 1240 | 1 | SO₂NH₂ | 1H-benzo[d]imidazol-4-yl |
| 1241 | 2 | SO₂NH₂ | 1H-benzo[d]imidazol-4-yl |
| 1242 | 3 | SO₂NH₂ | 1H-benzo[d]imidazol-4-yl |

Exemplary embodiments include compounds having the formula (XIX)

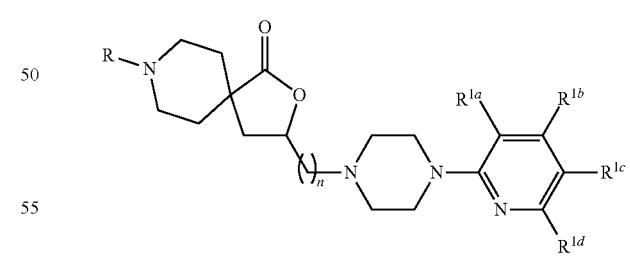

(XIX)

or a pharmaceutically acceptable salt form thereof defined herein below in Table 3.

TABLE 3

| Entry | n | R | R$^{1a}$ | R$^{1b}$ | R$^{1c}$ | R$^{1d}$ |
|---|---|---|---|---|---|---|
| 1 | 1 | H | H | H | H | H |
| 2 | 2 | H | H | H | H | H |

TABLE 3-continued

| Entry | n | R | $R^{1a}$ | $R^{1b}$ | $R^{1c}$ | $R^{1d}$ |
|---|---|---|---|---|---|---|
| 3 | 3 | H | H | H | H | H |
| 4 | 1 | Me | H | H | H | H |
| 5 | 2 | Me | H | H | H | H |
| 6 | 3 | Me | H | H | H | H |
| 7 | 1 | $CH_2Ph$ | H | H | H | H |
| 8 | 2 | $CH_2Ph$ | H | H | H | H |
| 9 | 3 | $CH_2Ph$ | H | H | H | H |
| 10 | 1 | COMe | H | H | H | H |
| 11 | 2 | COMe | H | H | H | H |
| 12 | 3 | COMe | H | H | H | H |
| 13 | 1 | $CO_2Me$ | H | H | H | H |
| 14 | 2 | $CO_2Me$ | H | H | H | H |
| 15 | 3 | $CO_2Me$ | H | H | H | H |
| 16 | 1 | $CO_2tBu$ | H | H | H | H |
| 17 | 2 | $CO_2tBu$ | H | H | H | H |
| 18 | 3 | $CO_2tBu$ | H | H | H | H |
| 19 | 1 | CONHMe | H | H | H | H |
| 20 | 2 | CONHMe | H | H | H | H |
| 21 | 3 | CONHMe | H | H | H | H |
| 22 | 1 | $SO_2Me$ | H | H | H | H |
| 23 | 2 | $SO_2Me$ | H | H | H | H |
| 24 | 3 | $SO_2Me$ | H | H | H | H |
| 25 | 1 | $SO_2NH_2$ | H | H | H | H |
| 26 | 2 | $SO_2NH_2$ | H | H | H | H |
| 27 | 3 | $SO_2NH_2$ | H | H | H | H |
| 28 | 1 | H | H | H | OH | H |
| 29 | 2 | H | H | H | OH | H |
| 30 | 3 | H | H | H | OH | H |
| 31 | 1 | Me | H | H | OH | H |
| 32 | 2 | Me | H | H | OH | H |
| 33 | 3 | Me | H | H | OH | H |
| 34 | 1 | $CH_2Ph$ | H | H | OH | H |
| 35 | 2 | $CH_2Ph$ | H | H | OH | H |
| 36 | 3 | $CH_2Ph$ | H | H | OH | H |
| 37 | 1 | COMe | H | H | OH | H |
| 38 | 2 | COMe | H | H | OH | H |
| 39 | 3 | COMe | H | H | OH | H |
| 40 | 1 | $CO_2Me$ | H | H | OH | H |
| 41 | 2 | $CO_2Me$ | H | H | OH | H |
| 42 | 3 | $CO_2Me$ | H | H | OH | H |
| 43 | 1 | $CO_2tBu$ | H | H | OH | H |
| 44 | 2 | $CO_2tBu$ | H | H | OH | H |
| 45 | 3 | $CO_2tBu$ | H | H | OH | H |
| 46 | 1 | CONHMe | H | H | OH | H |
| 47 | 2 | CONHMe | H | H | OH | H |
| 48 | 3 | CONHMe | H | H | OH | H |
| 49 | 1 | $SO_2Me$ | H | H | OH | H |
| 50 | 2 | $SO_2Me$ | H | H | OH | H |
| 51 | 3 | $SO_2Me$ | H | H | OH | H |
| 52 | 1 | $SO_2NH_2$ | H | H | OH | H |
| 53 | 2 | $SO_2NH_2$ | H | H | OH | H |
| 54 | 3 | $SO_2NH_2$ | H | H | OH | H |
| 55 | 1 | H | H | H | OMe | H |
| 56 | 2 | H | H | H | OMe | H |
| 57 | 3 | H | H | H | OMe | H |
| 58 | 1 | Me | H | H | OMe | H |
| 59 | 2 | Me | H | H | OMe | H |
| 60 | 3 | Me | H | H | OMe | H |
| 61 | 1 | $CH_2Ph$ | H | H | OMe | H |
| 62 | 2 | $CH_2Ph$ | H | H | OMe | H |
| 63 | 3 | $CH_2Ph$ | H | H | OMe | H |
| 64 | 1 | COMe | H | H | OMe | H |
| 65 | 2 | COMe | H | H | OMe | H |
| 66 | 3 | COMe | H | H | OMe | H |
| 67 | 1 | $CO_2Me$ | H | H | OMe | H |
| 68 | 2 | $CO_2Me$ | H | H | OMe | H |
| 69 | 3 | $CO_2Me$ | H | H | OMe | H |
| 70 | 1 | $CO_2tBu$ | H | H | OMe | H |
| 71 | 2 | $CO_2tBu$ | H | H | OMe | H |
| 72 | 3 | $CO_2tBu$ | H | H | OMe | H |
| 73 | 1 | CONHMe | H | H | OMe | H |
| 74 | 2 | CONHMe | H | H | OMe | H |
| 75 | 3 | CONHMe | H | H | OMe | H |
| 76 | 1 | $SO_2Me$ | H | H | OMe | H |
| 77 | 2 | $SO_2Me$ | H | H | OMe | H |
| 78 | 3 | $SO_2Me$ | H | H | OMe | H |
| 79 | 1 | $SO_2NH_2$ | H | H | OMe | H |
| 80 | 2 | $SO_2NH_2$ | H | H | OMe | H |
| 81 | 3 | $SO_2NH_2$ | H | H | OMe | H |
| 82 | 1 | H | H | H | Me | H |
| 83 | 2 | H | H | H | Me | H |
| 84 | 3 | H | H | H | Me | H |
| 85 | 1 | Me | H | H | Me | H |
| 86 | 2 | Me | H | H | Me | H |
| 87 | 3 | Me | H | H | Me | H |
| 88 | 1 | $CH_2Ph$ | H | H | Me | H |
| 89 | 2 | $CH_2Ph$ | H | H | Me | H |
| 90 | 3 | $CH_2Ph$ | H | H | Me | H |
| 91 | 1 | COMe | H | H | Me | H |
| 92 | 2 | COMe | H | H | Me | H |
| 93 | 3 | COMe | H | H | Me | H |
| 94 | 1 | $CO_2Me$ | H | H | Me | H |
| 95 | 2 | $CO_2Me$ | H | H | Me | H |
| 96 | 3 | $CO_2Me$ | H | H | Me | H |
| 97 | 1 | $CO_2tBu$ | H | H | Me | H |
| 98 | 2 | $CO_2tBu$ | H | H | Me | H |
| 99 | 3 | $CO_2tBu$ | H | H | Me | H |
| 100 | 1 | CONHMe | H | H | Me | H |
| 101 | 2 | CONHMe | H | H | Me | H |
| 102 | 3 | CONHMe | H | H | Me | H |
| 103 | 1 | $SO_2Me$ | H | H | Me | H |
| 104 | 2 | $SO_2Me$ | H | H | Me | H |
| 105 | 3 | $SO_2Me$ | H | H | Me | H |
| 106 | 1 | $SO_2NH_2$ | H | H | Me | H |
| 107 | 2 | $SO_2NH_2$ | H | H | Me | H |
| 108 | 3 | $SO_2NH_2$ | H | H | Me | H |
| 109 | 1 | H | H | H | $CF_3$ | H |
| 110 | 2 | H | H | H | $CF_3$ | H |
| 111 | 3 | H | H | H | $CF_3$ | H |
| 112 | 1 | Me | H | H | $CF_3$ | H |
| 113 | 2 | Me | H | H | $CF_3$ | H |
| 114 | 3 | Me | H | H | $CF_3$ | H |
| 115 | 1 | $CH_2Ph$ | H | H | $CF_3$ | H |
| 116 | 2 | $CH_2Ph$ | H | H | $CF_3$ | H |
| 117 | 3 | $CH_2Ph$ | H | H | $CF_3$ | H |
| 118 | 1 | COMe | H | H | $CF_3$ | H |
| 119 | 2 | COMe | H | H | $CF_3$ | H |
| 120 | 3 | COMe | H | H | $CF_3$ | H |
| 121 | 1 | $CO_2Me$ | H | H | $CF_3$ | H |
| 122 | 2 | $CO_2Me$ | H | H | $CF_3$ | H |
| 123 | 3 | $CO_2Me$ | H | H | $CF_3$ | H |
| 124 | 1 | $CO_2tBu$ | H | H | $CF_3$ | H |
| 125 | 2 | $CO_2tBu$ | H | H | $CF_3$ | H |
| 126 | 3 | $CO_2tBu$ | H | H | $CF_3$ | H |
| 127 | 1 | CONHMe | H | H | $CF_3$ | H |
| 128 | 2 | CONHMe | H | H | $CF_3$ | H |
| 129 | 3 | CONHMe | H | H | $CF_3$ | H |
| 130 | 1 | $SO_2Me$ | H | H | $CF_3$ | H |
| 131 | 2 | $SO_2Me$ | H | H | $CF_3$ | H |
| 132 | 3 | $SO_2Me$ | H | H | $CF_3$ | H |
| 133 | 1 | $SO_2NH_2$ | H | H | $CF_3$ | H |
| 134 | 2 | $SO_2NH_2$ | H | H | $CF_3$ | H |
| 135 | 3 | $SO_2NH_2$ | H | H | $CF_3$ | H |
| 136 | 1 | H | H | H | F | H |
| 137 | 2 | H | H | H | F | H |
| 138 | 3 | H | H | H | F | H |
| 139 | 1 | Me | H | H | F | H |
| 140 | 2 | Me | H | H | F | H |
| 141 | 3 | Me | H | H | F | H |
| 142 | 1 | $CH_2Ph$ | H | H | F | H |
| 143 | 2 | $CH_2Ph$ | H | H | F | H |
| 144 | 3 | $CH_2Ph$ | H | H | F | H |
| 145 | 1 | COMe | H | H | F | H |
| 146 | 2 | COMe | H | H | F | H |
| 147 | 3 | COMe | H | H | F | H |
| 148 | 1 | $CO_2Me$ | H | H | F | H |
| 149 | 2 | $CO_2Me$ | H | H | F | H |
| 150 | 3 | $CO_2Me$ | H | H | F | H |
| 151 | 1 | $CO_2tBu$ | H | H | F | H |
| 152 | 2 | $CO_2tBu$ | H | H | F | H |
| 153 | 3 | $CO_2tBu$ | H | H | F | H |
| 154 | 1 | CONHMe | H | H | F | H |
| 155 | 2 | CONHMe | H | H | F | H |
| 156 | 3 | CONHMe | H | H | F | H |
| 157 | 1 | $SO_2Me$ | H | H | F | H |
| 158 | 2 | $SO_2Me$ | H | H | F | H |

TABLE 3-continued

| Entry | n | R | $R^{1a}$ | $R^{1b}$ | $R^{1c}$ | $R^{1d}$ |
|---|---|---|---|---|---|---|
| 159 | 3 | $SO_2Me$ | H | H | F | H |
| 160 | 1 | $SO_2NH_2$ | H | H | F | H |
| 161 | 2 | $SO_2NH_2$ | H | H | F | H |
| 162 | 3 | $SO_2NH_2$ | H | H | F | H |
| 163 | 1 | H | H | H | Cl | H |
| 164 | 2 | H | H | H | Cl | H |
| 165 | 3 | H | H | H | Cl | H |
| 166 | 1 | Me | H | H | Cl | H |
| 167 | 2 | Me | H | H | Cl | H |
| 168 | 3 | Me | H | H | Cl | H |
| 169 | 1 | $CH_2Ph$ | H | H | Cl | H |
| 170 | 2 | $CH_2Ph$ | H | H | Cl | H |
| 171 | 3 | $CH_2Ph$ | H | H | Cl | H |
| 172 | 1 | COMe | H | H | Cl | H |
| 173 | 2 | COMe | H | H | Cl | H |
| 174 | 3 | COMe | H | H | Cl | H |
| 175 | 1 | $CO_2Me$ | H | H | Cl | H |
| 176 | 2 | $CO_2Me$ | H | H | Cl | H |
| 177 | 3 | $CO_2Me$ | H | H | Cl | H |
| 178 | 1 | $CO_2tBu$ | H | H | Cl | H |
| 179 | 2 | $CO_2tBu$ | H | H | Cl | H |
| 180 | 3 | $CO_2tBu$ | H | H | Cl | H |
| 181 | 1 | CONHMe | H | H | Cl | H |
| 182 | 2 | CONHMe | H | H | Cl | H |
| 183 | 3 | CONHMe | H | H | Cl | H |
| 184 | 1 | $SO_2Me$ | H | H | Cl | H |
| 185 | 2 | $SO_2Me$ | H | H | Cl | H |
| 186 | 3 | $SO_2Me$ | H | H | Cl | H |
| 187 | 1 | $SO_2NH_2$ | H | H | Cl | H |
| 188 | 2 | $SO_2NH_2$ | H | H | Cl | H |
| 189 | 3 | $SO_2NH_2$ | H | H | Cl | H |
| 190 | 1 | H | H | H | CN | H |
| 191 | 2 | H | H | H | CN | H |
| 192 | 3 | H | H | H | CN | H |
| 193 | 1 | Me | H | H | CN | H |
| 194 | 2 | Me | H | H | CN | H |
| 195 | 3 | Me | H | H | CN | H |
| 196 | 1 | $CH_2Ph$ | H | H | CN | H |
| 197 | 2 | $CH_2Ph$ | H | H | CN | H |
| 198 | 3 | $CH_2Ph$ | H | H | CN | H |
| 199 | 1 | COMe | H | H | CN | H |
| 200 | 2 | COMe | H | H | CN | H |
| 201 | 3 | COMe | H | H | CN | H |
| 202 | 1 | $CO_2Me$ | H | H | CN | H |
| 203 | 2 | $CO_2Me$ | H | H | CN | H |
| 204 | 3 | $CO_2Me$ | H | H | CN | H |
| 205 | 1 | $CO_2tBu$ | H | H | CN | H |
| 206 | 2 | $CO_2tBu$ | H | H | CN | H |
| 207 | 3 | $CO_2tBu$ | H | H | CN | H |
| 208 | 1 | CONHMe | H | H | CN | H |
| 209 | 2 | CONHMe | H | H | CN | H |
| 210 | 3 | CONHMe | H | H | CN | H |
| 211 | 1 | $SO_2Me$ | H | H | CN | H |
| 212 | 2 | $SO_2Me$ | H | H | CN | H |
| 213 | 3 | $SO_2Me$ | H | H | CN | H |
| 214 | 1 | $SO_2NH_2$ | H | H | CN | H |
| 215 | 2 | $SO_2NH_2$ | H | H | CN | H |
| 216 | 3 | $SO_2NH_2$ | H | H | CN | H |
| 217 | 1 | H | H | OH | H | H |
| 218 | 2 | H | H | OH | H | H |
| 219 | 3 | H | H | OH | H | H |
| 220 | 1 | Me | H | OH | H | H |
| 221 | 2 | Me | H | OH | H | H |
| 222 | 3 | Me | H | OH | H | H |
| 223 | 1 | $CH_2Ph$ | H | OH | H | H |
| 224 | 2 | $CH_2Ph$ | H | OH | H | H |
| 225 | 3 | $CH_2Ph$ | H | OH | H | H |
| 226 | 1 | COMe | H | OH | H | H |
| 227 | 2 | COMe | H | OH | H | H |
| 228 | 3 | COMe | H | OH | H | H |
| 229 | 1 | $CO_2Me$ | H | OH | H | H |
| 230 | 2 | $CO_2Me$ | H | OH | H | H |
| 231 | 3 | $CO_2Me$ | H | OH | H | H |
| 232 | 1 | $CO_2tBu$ | H | OH | H | H |
| 233 | 2 | $CO_2tBu$ | H | OH | H | H |
| 234 | 3 | $CO_2tBu$ | H | OH | H | H |
| 235 | 1 | CONHMe | H | OH | H | H |
| 236 | 2 | CONHMe | H | OH | H | H |
| 237 | 3 | CONHMe | H | OH | H | H |
| 238 | 1 | $SO_2Me$ | H | OH | H | H |
| 239 | 2 | $SO_2Me$ | H | OH | H | H |
| 240 | 3 | $SO_2Me$ | H | OH | H | H |
| 241 | 1 | $SO_2NH_2$ | H | OH | H | H |
| 242 | 2 | $SO_2NH_2$ | H | OH | H | H |
| 243 | 3 | $SO_2NH_2$ | H | OH | H | H |
| 244 | 1 | H | H | OMe | H | H |
| 245 | 2 | H | H | OMe | H | H |
| 246 | 3 | H | H | OMe | H | H |
| 247 | 1 | Me | H | OMe | H | H |
| 248 | 2 | Me | H | OMe | H | H |
| 249 | 3 | Me | H | OMe | H | H |
| 250 | 1 | $CH_2Ph$ | H | OMe | H | H |
| 251 | 2 | $CH_2Ph$ | H | OMe | H | H |
| 252 | 3 | $CH_2Ph$ | H | OMe | H | H |
| 253 | 1 | COMe | H | OMe | H | H |
| 254 | 2 | COMe | H | OMe | H | H |
| 255 | 3 | COMe | H | OMe | H | H |
| 256 | 1 | $CO_2Me$ | H | OMe | H | H |
| 257 | 2 | $CO_2Me$ | H | OMe | H | H |
| 258 | 3 | $CO_2Me$ | H | OMe | H | H |
| 259 | 1 | $CO_2tBu$ | H | OMe | H | H |
| 260 | 2 | $CO_2tBu$ | H | OMe | H | H |
| 261 | 3 | $CO_2tBu$ | H | OMe | H | H |
| 262 | 1 | CONHMe | H | OMe | H | H |
| 263 | 2 | CONHMe | H | OMe | H | H |
| 264 | 3 | CONHMe | H | OMe | H | H |
| 265 | 1 | $SO_2Me$ | H | OMe | H | H |
| 266 | 2 | $SO_2Me$ | H | OMe | H | H |
| 267 | 3 | $SO_2Me$ | H | OMe | H | H |
| 268 | 1 | $SO_2NH_2$ | H | OMe | H | H |
| 269 | 2 | $SO_2NH_2$ | H | OMe | H | H |
| 270 | 3 | $SO_2NH_2$ | H | OMe | H | H |
| 271 | 1 | H | H | Me | H | H |
| 272 | 2 | H | H | Me | H | H |
| 273 | 3 | H | H | Me | H | H |
| 274 | 1 | Me | H | Me | H | H |
| 275 | 2 | Me | H | Me | H | H |
| 276 | 3 | Me | H | Me | H | H |
| 277 | 1 | $CH_2Ph$ | H | Me | H | H |
| 278 | 2 | $CH_2Ph$ | H | Me | H | H |
| 279 | 3 | $CH_2Ph$ | H | Me | H | H |
| 280 | 1 | COMe | H | Me | H | H |
| 281 | 2 | COMe | H | Me | H | H |
| 282 | 3 | COMe | H | Me | H | H |
| 283 | 1 | $CO_2Me$ | H | Me | H | H |
| 284 | 2 | $CO_2Me$ | H | Me | H | H |
| 285 | 3 | $CO_2Me$ | H | Me | H | H |
| 286 | 1 | $CO_2tBu$ | H | Me | H | H |
| 287 | 2 | $CO_2tBu$ | H | Me | H | H |
| 288 | 3 | $CO_2tBu$ | H | Me | H | H |
| 289 | 1 | CONHMe | H | Me | H | H |
| 290 | 2 | CONHMe | H | Me | H | H |
| 291 | 3 | CONHMe | H | Me | H | H |
| 292 | 1 | $SO_2Me$ | H | Me | H | H |
| 293 | 2 | $SO_2Me$ | H | Me | H | H |
| 294 | 3 | $SO_2Me$ | H | Me | H | H |
| 295 | 1 | $SO_2NH_2$ | H | Me | H | H |
| 296 | 2 | $SO_2NH_2$ | H | Me | H | H |
| 297 | 3 | $SO_2NH_2$ | H | Me | H | H |
| 298 | 1 | H | H | $CF_3$ | H | H |
| 299 | 2 | H | H | $CF_3$ | H | H |
| 300 | 3 | H | H | $CF_3$ | H | H |
| 301 | 1 | Me | H | $CF_3$ | H | H |
| 302 | 2 | Me | H | $CF_3$ | H | H |
| 303 | 3 | Me | H | $CF_3$ | H | H |
| 304 | 1 | $CH_2Ph$ | H | $CF_3$ | H | H |
| 305 | 2 | $CH_2Ph$ | H | $CF_3$ | H | H |
| 306 | 3 | $CH_2Ph$ | H | $CF_3$ | H | H |
| 307 | 1 | COMe | H | $CF_3$ | H | H |
| 308 | 2 | COMe | H | $CF_3$ | H | H |
| 309 | 3 | COMe | H | $CF_3$ | H | H |
| 310 | 1 | $CO_2Me$ | H | $CF_3$ | H | H |
| 311 | 2 | $CO_2Me$ | H | $CF_3$ | H | H |
| 312 | 3 | $CO_2Me$ | H | $CF_3$ | H | H |
| 313 | 1 | $CO_2tBu$ | H | $CF_3$ | H | H |
| 314 | 2 | $CO_2tBu$ | H | $CF_3$ | H | H |

TABLE 3-continued

| Entry | n | R | R1a | R1b | R1c | R1d |
|---|---|---|---|---|---|---|
| 315 | 3 | CO2tBu | H | CF3 | H | H |
| 316 | 1 | CONHMe | H | CF3 | H | H |
| 317 | 2 | CONHMe | H | CF3 | H | H |
| 318 | 3 | CONHMe | H | CF3 | H | H |
| 319 | 1 | SO2Me | H | CF3 | H | H |
| 320 | 2 | SO2Me | H | CF3 | H | H |
| 321 | 3 | SO2Me | H | CF3 | H | H |
| 322 | 1 | SO2NH2 | H | CF3 | H | H |
| 323 | 2 | SO2NH2 | H | CF3 | H | H |
| 324 | 3 | SO2NH2 | H | CF3 | H | H |
| 325 | 1 | H | H | F | H | H |
| 326 | 2 | H | H | F | H | H |
| 327 | 3 | H | H | F | H | H |
| 328 | 1 | Me | H | F | H | H |
| 329 | 2 | Me | H | F | H | H |
| 330 | 3 | Me | H | F | H | H |
| 331 | 1 | CH2Ph | H | F | H | H |
| 332 | 2 | CH2Ph | H | F | H | H |
| 333 | 3 | CH2Ph | H | F | H | H |
| 334 | 1 | COMe | H | F | H | H |
| 335 | 2 | COMe | H | F | H | H |
| 336 | 3 | COMe | H | F | H | H |
| 337 | 1 | CO2Me | H | F | H | H |
| 338 | 2 | CO2Me | H | F | H | H |
| 339 | 3 | CO2Me | H | F | H | H |
| 340 | 1 | CO2tBu | H | F | H | H |
| 341 | 2 | CO2tBu | H | F | H | H |
| 342 | 3 | CO2tBu | H | F | H | H |
| 343 | 1 | CONHMe | H | F | H | H |
| 344 | 2 | CONHMe | H | F | H | H |
| 345 | 3 | CONHMe | H | F | H | H |
| 346 | 1 | SO2Me | H | F | H | H |
| 347 | 2 | SO2Me | H | F | H | H |
| 348 | 3 | SO2Me | H | F | H | H |
| 349 | 1 | SO2NH2 | H | F | H | H |
| 350 | 2 | SO2NH2 | H | F | H | H |
| 351 | 3 | SO2NH2 | H | F | H | H |
| 352 | 1 | H | H | Cl | H | H |
| 353 | 2 | H | H | Cl | H | H |
| 354 | 3 | H | H | Cl | H | H |
| 355 | 1 | Me | H | Cl | H | H |
| 356 | 2 | Me | H | Cl | H | H |
| 357 | 3 | Me | H | Cl | H | H |
| 358 | 1 | CH2Ph | H | Cl | H | H |
| 359 | 2 | CH2Ph | H | Cl | H | H |
| 360 | 3 | CH2Ph | H | Cl | H | H |
| 361 | 1 | COMe | H | Cl | H | H |
| 362 | 2 | COMe | H | Cl | H | H |
| 363 | 3 | COMe | H | Cl | H | H |
| 364 | 1 | CO2Me | H | Cl | H | H |
| 365 | 2 | CO2Me | H | Cl | H | H |
| 366 | 3 | CO2Me | H | Cl | H | H |
| 367 | 1 | CO2tBu | H | Cl | H | H |
| 368 | 2 | CO2tBu | H | Cl | H | H |
| 369 | 3 | CO2tBu | H | Cl | H | H |
| 370 | 1 | CONHMe | H | Cl | H | H |
| 371 | 2 | CONHMe | H | Cl | H | H |
| 372 | 3 | CONHMe | H | Cl | H | H |
| 373 | 1 | SO2Me | H | Cl | H | H |
| 374 | 2 | SO2Me | H | Cl | H | H |
| 375 | 3 | SO2Me | H | Cl | H | H |
| 376 | 1 | SO2NH2 | H | Cl | H | H |
| 377 | 2 | SO2NH2 | H | Cl | H | H |
| 378 | 3 | SO2NH2 | H | Cl | H | H |
| 379 | 1 | H | H | CN | H | H |
| 380 | 2 | H | H | CN | H | H |
| 381 | 3 | H | H | CN | H | H |
| 382 | 1 | Me | H | CN | H | H |
| 383 | 2 | Me | H | CN | H | H |
| 384 | 3 | Me | H | CN | H | H |
| 385 | 1 | CH2Ph | H | CN | H | H |
| 386 | 2 | CH2Ph | H | CN | H | H |
| 387 | 3 | CH2Ph | H | CN | H | H |
| 388 | 1 | COMe | H | CN | H | H |
| 389 | 2 | COMe | H | CN | H | H |
| 390 | 3 | COMe | H | CN | H | H |
| 391 | 1 | CO2Me | H | CN | H | H |
| 392 | 2 | CO2Me | H | CN | H | H |
| 393 | 3 | CO2Me | H | CN | H | H |
| 394 | 1 | CO2tBu | H | CN | H | H |
| 395 | 2 | CO2tBu | H | CN | H | H |
| 396 | 3 | CO2tBu | H | CN | H | H |
| 397 | 1 | CONHMe | H | CN | H | H |
| 398 | 2 | CONHMe | H | CN | H | H |
| 399 | 3 | CONHMe | H | CN | H | H |
| 400 | 1 | SO2Me | H | CN | H | H |
| 401 | 2 | SO2Me | H | CN | H | H |
| 402 | 3 | SO2Me | H | CN | H | H |
| 403 | 1 | SO2NH2 | H | CN | H | H |
| 404 | 2 | SO2NH2 | H | CN | H | H |
| 405 | 3 | SO2NH2 | H | CN | H | H |

Exemplary embodiments include compounds having the formula (XX)

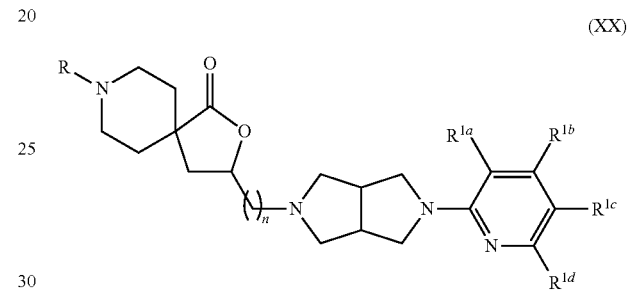

(XX)

or a pharmaceutically acceptable salt form thereof defined herein below in Table 4.

TABLE 4

| Entry | n | R | R1a | R1b | R1c | R1d |
|---|---|---|---|---|---|---|
| 1 | 1 | H | H | H | H | H |
| 2 | 2 | H | H | H | H | H |
| 3 | 3 | H | H | H | H | H |
| 4 | 1 | Me | H | H | H | H |
| 5 | 2 | Me | H | H | H | H |
| 6 | 3 | Me | H | H | H | H |
| 7 | 1 | CH2Ph | H | H | H | H |
| 8 | 2 | CH2Ph | H | H | H | H |
| 9 | 3 | CH2Ph | H | H | H | H |
| 10 | 1 | COMe | H | H | H | H |
| 11 | 2 | COMe | H | H | H | H |
| 12 | 3 | COMe | H | H | H | H |
| 13 | 1 | CO2Me | H | H | H | H |
| 14 | 2 | CO2Me | H | H | H | H |
| 15 | 3 | CO2Me | H | H | H | H |
| 16 | 1 | CO2tBu | H | H | H | H |
| 17 | 2 | CO2tBu | H | H | H | H |
| 18 | 3 | CO2tBu | H | H | H | H |
| 19 | 1 | CONHMe | H | H | H | H |
| 20 | 2 | CONHMe | H | H | H | H |
| 21 | 3 | CONHMe | H | H | H | H |
| 22 | 1 | SO2Me | H | H | H | H |
| 23 | 2 | SO2Me | H | H | H | H |
| 24 | 3 | SO2Me | H | H | H | H |
| 25 | 1 | SO2NH2 | H | H | H | H |
| 26 | 2 | SO2NH2 | H | H | H | H |
| 27 | 3 | SO2NH2 | H | H | H | H |
| 28 | 1 | H | H | H | OH | H |
| 29 | 2 | H | H | H | OH | H |
| 30 | 3 | H | H | H | OH | H |
| 31 | 1 | Me | H | H | OH | H |
| 32 | 2 | Me | H | H | OH | H |
| 33 | 3 | Me | H | H | OH | H |
| 34 | 1 | CH2Ph | H | H | OH | H |
| 35 | 2 | CH2Ph | H | H | OH | H |

TABLE 4-continued

| Entry | n | R | $R^{1a}$ | $R^{1b}$ | $R^{1c}$ | $R^{1d}$ |
|---|---|---|---|---|---|---|
| 36 | 3 | $CH_2Ph$ | H | H | OH | H |
| 37 | 1 | COMe | H | H | OH | H |
| 38 | 2 | COMe | H | H | OH | H |
| 39 | 3 | COMe | H | H | OH | H |
| 40 | 1 | $CO_2Me$ | H | H | OH | H |
| 41 | 2 | $CO_2Me$ | H | H | OH | H |
| 42 | 3 | $CO_2Me$ | H | H | OH | H |
| 43 | 1 | $CO_2tBu$ | H | H | OH | H |
| 44 | 2 | $CO_2tBu$ | H | H | OH | H |
| 45 | 3 | $CO_2tBu$ | H | H | OH | H |
| 46 | 1 | CONHMe | H | H | OH | H |
| 47 | 2 | CONHMe | H | H | OH | H |
| 48 | 3 | CONHMe | H | H | OH | H |
| 49 | 1 | $SO_2Me$ | H | H | OH | H |
| 50 | 2 | $SO_2Me$ | H | H | OH | H |
| 51 | 3 | $SO_2Me$ | H | H | OH | H |
| 52 | 1 | $SO_2NH_2$ | H | H | OH | H |
| 53 | 2 | $SO_2NH_2$ | H | H | OH | H |
| 54 | 3 | $SO_2NH_2$ | H | H | OH | H |
| 55 | 1 | H | H | H | OMe | H |
| 56 | 2 | H | H | H | OMe | H |
| 57 | 3 | H | H | H | OMe | H |
| 58 | 1 | Me | H | H | OMe | H |
| 59 | 2 | Me | H | H | OMe | H |
| 60 | 3 | Me | H | H | OMe | H |
| 61 | 1 | $CH_2Ph$ | H | H | OMe | H |
| 62 | 2 | $CH_2Ph$ | H | H | OMe | H |
| 63 | 3 | $CH_2Ph$ | H | H | OMe | H |
| 64 | 1 | COMe | H | H | OMe | H |
| 65 | 2 | COMe | H | H | OMe | H |
| 66 | 3 | COMe | H | H | OMe | H |
| 67 | 1 | $CO_2Me$ | H | H | OMe | H |
| 68 | 2 | $CO_2Me$ | H | H | OMe | H |
| 69 | 3 | $CO_2Me$ | H | H | OMe | H |
| 70 | 1 | $CO_2tBu$ | H | H | OMe | H |
| 71 | 2 | $CO_2tBu$ | H | H | OMe | H |
| 72 | 3 | $CO_2tBu$ | H | H | OMe | H |
| 73 | 1 | CONHMe | H | H | OMe | H |
| 74 | 2 | CONHMe | H | H | OMe | H |
| 75 | 3 | CONHMe | H | H | OMe | H |
| 76 | 1 | $SO_2Me$ | H | H | OMe | H |
| 77 | 2 | $SO_2Me$ | H | H | OMe | H |
| 78 | 3 | $SO_2Me$ | H | H | OMe | H |
| 79 | 1 | $SO_2NH_2$ | H | H | OMe | H |
| 80 | 2 | $SO_2NH_2$ | H | H | OMe | H |
| 81 | 3 | $SO_2NH_2$ | H | H | OMe | H |
| 82 | 1 | H | H | H | Me | H |
| 83 | 2 | H | H | H | Me | H |
| 84 | 3 | H | H | H | Me | H |
| 85 | 1 | Me | H | H | Me | H |
| 86 | 2 | Me | H | H | Me | H |
| 87 | 3 | Me | H | H | Me | H |
| 88 | 1 | $CH_2Ph$ | H | H | Me | H |
| 89 | 2 | $CH_2Ph$ | H | H | Me | H |
| 90 | 3 | $CH_2Ph$ | H | H | Me | H |
| 91 | 1 | COMe | H | H | Me | H |
| 92 | 2 | COMe | H | H | Me | H |
| 93 | 3 | COMe | H | H | Me | H |
| 94 | 1 | $CO_2Me$ | H | H | Me | H |
| 95 | 2 | $CO_2Me$ | H | H | Me | H |
| 96 | 3 | $CO_2Me$ | H | H | Me | H |
| 97 | 1 | $CO_2tBu$ | H | H | Me | H |
| 98 | 2 | $CO_2tBu$ | H | H | Me | H |
| 99 | 3 | $CO_2tBu$ | H | H | Me | H |
| 100 | 1 | CONHMe | H | H | Me | H |
| 101 | 2 | CONHMe | H | H | Me | H |
| 102 | 3 | CONHMe | H | H | Me | H |
| 103 | 1 | $SO_2Me$ | H | H | Me | H |
| 104 | 2 | $SO_2Me$ | H | H | Me | H |
| 105 | 3 | $SO_2Me$ | H | H | Me | H |
| 106 | 1 | $SO_2NH_2$ | H | H | Me | H |
| 107 | 2 | $SO_2NH_2$ | H | H | Me | H |
| 108 | 3 | $SO_2NH_2$ | H | H | Me | H |
| 109 | 1 | H | H | H | $CF_3$ | H |
| 110 | 2 | H | H | H | $CF_3$ | H |
| 111 | 3 | H | H | H | $CF_3$ | H |
| 112 | 1 | Me | H | H | $CF_3$ | H |
| 113 | 2 | Me | H | H | $CF_3$ | H |
| 114 | 3 | Me | H | H | $CF_3$ | H |
| 115 | 1 | $CH_2Ph$ | H | H | $CF_3$ | H |
| 116 | 2 | $CH_2Ph$ | H | H | $CF_3$ | H |
| 117 | 3 | $CH_2Ph$ | H | H | $CF_3$ | H |
| 118 | 1 | COMe | H | H | $CF_3$ | H |
| 119 | 2 | COMe | H | H | $CF_3$ | H |
| 120 | 3 | COMe | H | H | $CF_3$ | H |
| 121 | 1 | $CO_2Me$ | H | H | $CF_3$ | H |
| 122 | 2 | $CO_2Me$ | H | H | $CF_3$ | H |
| 123 | 3 | $CO_2Me$ | H | H | $CF_3$ | H |
| 124 | 1 | $CO_2tBu$ | H | H | $CF_3$ | H |
| 125 | 2 | $CO_2tBu$ | H | H | $CF_3$ | H |
| 126 | 3 | $CO_2tBu$ | H | H | $CF_3$ | H |
| 127 | 1 | CONHMe | H | H | $CF_3$ | H |
| 128 | 2 | CONHMe | H | H | $CF_3$ | H |
| 129 | 3 | CONHMe | H | H | $CF_3$ | H |
| 130 | 1 | $SO_2Me$ | H | H | $CF_3$ | H |
| 131 | 2 | $SO_2Me$ | H | H | $CF_3$ | H |
| 132 | 3 | $SO_2Me$ | H | H | $CF_3$ | H |
| 133 | 1 | $SO_2NH_2$ | H | H | $CF_3$ | H |
| 134 | 2 | $SO_2NH_2$ | H | H | $CF_3$ | H |
| 135 | 3 | $SO_2NH_2$ | H | H | $CF_3$ | H |
| 136 | 1 | H | H | H | F | H |
| 137 | 2 | H | H | H | F | H |
| 138 | 3 | H | H | H | F | H |
| 139 | 1 | Me | H | H | F | H |
| 140 | 2 | Me | H | H | F | H |
| 141 | 3 | Me | H | H | F | H |
| 142 | 1 | $CH_2Ph$ | H | H | F | H |
| 143 | 2 | $CH_2Ph$ | H | H | F | H |
| 144 | 3 | $CH_2Ph$ | H | H | F | H |
| 145 | 1 | COMe | H | H | F | H |
| 146 | 2 | COMe | H | H | F | H |
| 147 | 3 | COMe | H | H | F | H |
| 148 | 1 | $CO_2Me$ | H | H | F | H |
| 149 | 2 | $CO_2Me$ | H | H | F | H |
| 150 | 3 | $CO_2Me$ | H | H | F | H |
| 151 | 1 | $CO_2tBu$ | H | H | F | H |
| 152 | 2 | $CO_2tBu$ | H | H | F | H |
| 153 | 3 | $CO_2tBu$ | H | H | F | H |
| 154 | 1 | CONHMe | H | H | F | H |
| 155 | 2 | CONHMe | H | H | F | H |
| 156 | 3 | CONHMe | H | H | F | H |
| 157 | 1 | $SO_2Me$ | H | H | F | H |
| 158 | 2 | $SO_2Me$ | H | H | F | H |
| 159 | 3 | $SO_2Me$ | H | H | F | H |
| 160 | 1 | $SO_2NH_2$ | H | H | F | H |
| 161 | 2 | $SO_2NH_2$ | H | H | F | H |
| 162 | 3 | $SO_2NH_2$ | H | H | F | H |
| 163 | 1 | H | H | H | Cl | H |
| 164 | 2 | H | H | H | Cl | H |
| 165 | 3 | H | H | H | Cl | H |
| 166 | 1 | Me | H | H | Cl | H |
| 167 | 2 | Me | H | H | Cl | H |
| 168 | 3 | Me | H | H | Cl | H |
| 169 | 1 | $CH_2Ph$ | H | H | Cl | H |
| 170 | 2 | $CH_2Ph$ | H | H | Cl | H |
| 171 | 3 | $CH_2Ph$ | H | H | Cl | H |
| 172 | 1 | COMe | H | H | Cl | H |
| 173 | 2 | COMe | H | H | Cl | H |
| 174 | 3 | COMe | H | H | Cl | H |
| 175 | 1 | $CO_2Me$ | H | H | Cl | H |
| 176 | 2 | $CO_2Me$ | H | H | Cl | H |
| 177 | 3 | $CO_2Me$ | H | H | Cl | H |
| 178 | 1 | $CO_2tBu$ | H | H | Cl | H |
| 179 | 2 | $CO_2tBu$ | H | H | Cl | H |
| 180 | 3 | $CO_2tBu$ | H | H | Cl | H |
| 181 | 1 | CONHMe | H | H | Cl | H |
| 182 | 2 | CONHMe | H | H | Cl | H |
| 183 | 3 | CONHMe | H | H | Cl | H |
| 184 | 1 | $SO_2Me$ | H | H | Cl | H |
| 185 | 2 | $SO_2Me$ | H | H | Cl | H |
| 186 | 3 | $SO_2Me$ | H | H | Cl | H |
| 187 | 1 | $SO_2NH_2$ | H | H | Cl | H |
| 188 | 2 | $SO_2NH_2$ | H | H | Cl | H |
| 189 | 3 | $SO_2NH_2$ | H | H | Cl | H |
| 190 | 1 | H | H | H | CN | H |
| 191 | 2 | H | H | H | CN | H |

TABLE 4-continued

| Entry | n | R | $R^{1a}$ | $R^{1b}$ | $R^{1c}$ | $R^{1d}$ |
|---|---|---|---|---|---|---|
| 192 | 3 | H | H | H | CN | H |
| 193 | 1 | Me | H | H | CN | H |
| 194 | 2 | Me | H | H | CN | H |
| 195 | 3 | Me | H | H | CN | H |
| 196 | 1 | CH$_2$Ph | H | H | CN | H |
| 197 | 2 | CH$_2$Ph | H | H | CN | H |
| 198 | 3 | CH$_2$Ph | H | H | CN | H |
| 199 | 1 | COMe | H | H | CN | H |
| 200 | 2 | COMe | H | H | CN | H |
| 201 | 3 | COMe | H | H | CN | H |
| 202 | 1 | CO$_2$Me | H | H | CN | H |
| 203 | 2 | CO$_2$Me | H | H | CN | H |
| 204 | 3 | CO$_2$Me | H | H | CN | H |
| 205 | 1 | CO$_2$tBu | H | H | CN | H |
| 206 | 2 | CO$_2$tBu | H | H | CN | H |
| 207 | 3 | CO$_2$tBu | H | H | CN | H |
| 208 | 1 | CONHMe | H | H | CN | H |
| 209 | 2 | CONHMe | H | H | CN | H |
| 210 | 3 | CONHMe | H | H | CN | H |
| 211 | 1 | SO$_2$Me | H | H | CN | H |
| 212 | 2 | SO$_2$Me | H | H | CN | H |
| 213 | 3 | SO$_2$Me | H | H | CN | H |
| 214 | 1 | SO$_2$NH$_2$ | H | H | CN | H |
| 215 | 2 | SO$_2$NH$_2$ | H | H | CN | H |
| 216 | 3 | SO$_2$NH$_2$ | H | H | CN | H |
| 217 | 1 | H | H | OH | H | H |
| 218 | 2 | H | H | OH | H | H |
| 219 | 3 | H | H | OH | H | H |
| 220 | 1 | Me | H | OH | H | H |
| 221 | 2 | Me | H | OH | H | H |
| 222 | 3 | Me | H | OH | H | H |
| 223 | 1 | CH$_2$Ph | H | OH | H | H |
| 224 | 2 | CH$_2$Ph | H | OH | H | H |
| 225 | 3 | CH$_2$Ph | H | OH | H | H |
| 226 | 1 | COMe | H | OH | H | H |
| 227 | 2 | COMe | H | OH | H | H |
| 228 | 3 | COMe | H | OH | H | H |
| 229 | 1 | CO$_2$Me | H | OH | H | H |
| 230 | 2 | CO$_2$Me | H | OH | H | H |
| 231 | 3 | CO$_2$Me | H | OH | H | H |
| 232 | 1 | CO$_2$tBu | H | OH | H | H |
| 233 | 2 | CO$_2$tBu | H | OH | H | H |
| 234 | 3 | CO$_2$tBu | H | OH | H | H |
| 235 | 1 | CONHMe | H | OH | H | H |
| 236 | 2 | CONHMe | H | OH | H | H |
| 237 | 3 | CONHMe | H | OH | H | H |
| 238 | 1 | SO$_2$Me | H | OH | H | H |
| 239 | 2 | SO$_2$Me | H | OH | H | H |
| 240 | 3 | SO$_2$Me | H | OH | H | H |
| 241 | 1 | SO$_2$NH$_2$ | H | OH | H | H |
| 242 | 2 | SO$_2$NH$_2$ | H | OH | H | H |
| 243 | 3 | SO$_2$NH$_2$ | H | OH | H | H |
| 244 | 1 | H | H | OMe | H | H |
| 245 | 2 | H | H | OMe | H | H |
| 246 | 3 | H | H | OMe | H | H |
| 247 | 1 | Me | H | OMe | H | H |
| 248 | 2 | Me | H | OMe | H | H |
| 249 | 3 | Me | H | OMe | H | H |
| 250 | 1 | CH$_2$Ph | H | OMe | H | H |
| 251 | 2 | CH$_2$Ph | H | OMe | H | H |
| 252 | 3 | CH$_2$Ph | H | OMe | H | H |
| 253 | 1 | COMe | H | OMe | H | H |
| 254 | 2 | COMe | H | OMe | H | H |
| 255 | 3 | COMe | H | OMe | H | H |
| 256 | 1 | CO$_2$Me | H | OMe | H | H |
| 257 | 2 | CO$_2$Me | H | OMe | H | H |
| 258 | 3 | CO$_2$Me | H | OMe | H | H |
| 259 | 1 | CO$_2$tBu | H | OMe | H | H |
| 260 | 2 | CO$_2$tBu | H | OMe | H | H |
| 261 | 3 | CO$_2$tBu | H | OMe | H | H |
| 262 | 1 | CONHMe | H | OMe | H | H |
| 263 | 2 | CONHMe | H | OMe | H | H |
| 264 | 3 | CONHMe | H | OMe | H | H |
| 265 | 1 | SO$_2$Me | H | OMe | H | H |
| 266 | 2 | SO$_2$Me | H | OMe | H | H |
| 267 | 3 | SO$_2$Me | H | OMe | H | H |
| 268 | 1 | SO$_2$NH$_2$ | H | OMe | H | H |
| 269 | 2 | SO$_2$NH$_2$ | H | OMe | H | H |
| 270 | 3 | SO$_2$NH$_2$ | H | OMe | H | H |
| 271 | 1 | H | H | Me | H | H |
| 272 | 2 | H | H | Me | H | H |
| 273 | 3 | H | H | Me | H | H |
| 274 | 1 | Me | H | Me | H | H |
| 275 | 2 | Me | H | Me | H | H |
| 276 | 3 | Me | H | Me | H | H |
| 277 | 1 | CH$_2$Ph | H | Me | H | H |
| 278 | 2 | CH$_2$Ph | H | Me | H | H |
| 279 | 3 | CH$_2$Ph | H | Me | H | H |
| 280 | 1 | COMe | H | Me | H | H |
| 281 | 2 | COMe | H | Me | H | H |
| 282 | 3 | COMe | H | Me | H | H |
| 283 | 1 | CO$_2$Me | H | Me | H | H |
| 284 | 2 | CO$_2$Me | H | Me | H | H |
| 285 | 3 | CO$_2$Me | H | Me | H | H |
| 286 | 1 | CO$_2$tBu | H | Me | H | H |
| 287 | 2 | CO$_2$tBu | H | Me | H | H |
| 288 | 3 | CO$_2$tBu | H | Me | H | H |
| 289 | 1 | CONHMe | H | Me | H | H |
| 290 | 2 | CONHMe | H | Me | H | H |
| 291 | 3 | CONHMe | H | Me | H | H |
| 292 | 1 | SO$_2$Me | H | Me | H | H |
| 293 | 2 | SO$_2$Me | H | Me | H | H |
| 294 | 3 | SO$_2$Me | H | Me | H | H |
| 295 | 1 | SO$_2$NH$_2$ | H | Me | H | H |
| 296 | 2 | SO$_2$NH$_2$ | H | Me | H | H |
| 297 | 3 | SO$_2$NH$_2$ | H | Me | H | H |
| 298 | 1 | H | H | CF$_3$ | H | H |
| 299 | 2 | H | H | CF$_3$ | H | H |
| 300 | 3 | H | H | CF$_3$ | H | H |
| 301 | 1 | Me | H | CF$_3$ | H | H |
| 302 | 2 | Me | H | CF$_3$ | H | H |
| 303 | 3 | Me | H | CF$_3$ | H | H |
| 304 | 1 | CH$_2$Ph | H | CF$_3$ | H | H |
| 305 | 2 | CH$_2$Ph | H | CF$_3$ | H | H |
| 306 | 3 | CH$_2$Ph | H | CF$_3$ | H | H |
| 307 | 1 | COMe | H | CF$_3$ | H | H |
| 308 | 2 | COMe | H | CF$_3$ | H | H |
| 309 | 3 | COMe | H | CF$_3$ | H | H |
| 310 | 1 | CO$_2$Me | H | CF$_3$ | H | H |
| 311 | 2 | CO$_2$Me | H | CF$_3$ | H | H |
| 312 | 3 | CO$_2$Me | H | CF$_3$ | H | H |
| 313 | 1 | CO$_2$tBu | H | CF$_3$ | H | H |
| 314 | 2 | CO$_2$tBu | H | CF$_3$ | H | H |
| 315 | 3 | CO$_2$tBu | H | CF$_3$ | H | H |
| 316 | 1 | CONHMe | H | CF$_3$ | H | H |
| 317 | 2 | CONHMe | H | CF$_3$ | H | H |
| 318 | 3 | CONHMe | H | CF$_3$ | H | H |
| 319 | 1 | SO$_2$Me | H | CF$_3$ | H | H |
| 320 | 2 | SO$_2$Me | H | CF$_3$ | H | H |
| 321 | 3 | SO$_2$Me | H | CF$_3$ | H | H |
| 322 | 1 | SO$_2$NH$_2$ | H | CF$_3$ | H | H |
| 323 | 2 | SO$_2$NH$_2$ | H | CF$_3$ | H | H |
| 324 | 3 | SO$_2$NH$_2$ | H | CF$_3$ | H | H |
| 325 | 1 | H | H | F | H | H |
| 326 | 2 | H | H | F | H | H |
| 327 | 3 | H | H | F | H | H |
| 328 | 1 | Me | H | F | H | H |
| 329 | 2 | Me | H | F | H | H |
| 330 | 3 | Me | H | F | H | H |
| 331 | 1 | CH$_2$Ph | H | F | H | H |
| 332 | 2 | CH$_2$Ph | H | F | H | H |
| 333 | 3 | CH$_2$Ph | H | F | H | H |
| 334 | 1 | COMe | H | F | H | H |
| 335 | 2 | COMe | H | F | H | H |
| 336 | 3 | COMe | H | F | H | H |
| 337 | 1 | CO$_2$Me | H | F | H | H |
| 338 | 2 | CO$_2$Me | H | F | H | H |
| 339 | 3 | CO$_2$Me | H | F | H | H |
| 340 | 1 | CO$_2$tBu | H | F | H | H |
| 341 | 2 | CO$_2$tBu | H | F | H | H |
| 342 | 3 | CO$_2$tBu | H | F | H | H |
| 343 | 1 | CONHMe | H | F | H | H |
| 344 | 2 | CONHMe | H | F | H | H |
| 345 | 3 | CONHMe | H | F | H | H |
| 346 | 1 | SO$_2$Me | H | F | H | H |
| 347 | 2 | SO$_2$Me | H | F | H | H |

TABLE 4-continued

| Entry | n | R | $R^{1a}$ | $R^{1b}$ | $R^{1c}$ | $R^{1d}$ |
|---|---|---|---|---|---|---|
| 348 | 3 | SO$_2$Me | H | F | H | H |
| 349 | 1 | SO$_2$NH$_2$ | H | F | H | H |
| 350 | 2 | SO$_2$NH$_2$ | H | F | H | H |
| 351 | 3 | SO$_2$NH$_2$ | H | F | H | H |
| 352 | 1 | H | H | Cl | H | H |
| 353 | 2 | H | H | Cl | H | H |
| 354 | 3 | H | H | Cl | H | H |
| 355 | 1 | Me | H | Cl | H | H |
| 356 | 2 | Me | H | Cl | H | H |
| 357 | 3 | Me | H | Cl | H | H |
| 358 | 1 | CH$_2$Ph | H | Cl | H | H |
| 359 | 2 | CH$_2$Ph | H | Cl | H | H |
| 360 | 3 | CH$_2$Ph | H | Cl | H | H |
| 361 | 1 | COMe | H | Cl | H | H |
| 362 | 2 | COMe | H | Cl | H | H |
| 363 | 3 | COMe | H | Cl | H | H |
| 364 | 1 | CO$_2$Me | H | Cl | H | H |
| 365 | 2 | CO$_2$Me | H | Cl | H | H |
| 366 | 3 | CO$_2$Me | H | Cl | H | H |
| 367 | 1 | CO$_2$tBu | H | Cl | H | H |
| 368 | 2 | CO$_2$tBu | H | Cl | H | H |
| 369 | 3 | CO$_2$tBu | H | Cl | H | H |
| 370 | 1 | CONHMe | H | Cl | H | H |
| 371 | 2 | CONHMe | H | Cl | H | H |
| 372 | 3 | CONHMe | H | Cl | H | H |
| 373 | 1 | SO$_2$Me | H | Cl | H | H |
| 374 | 2 | SO$_2$Me | H | Cl | H | H |
| 375 | 3 | SO$_2$Me | H | Cl | H | H |
| 376 | 1 | SO$_2$NH$_2$ | H | Cl | H | H |
| 377 | 2 | SO$_2$NH$_2$ | H | Cl | H | H |
| 378 | 3 | SO$_2$NH$_2$ | H | Cl | H | H |
| 379 | 1 | H | H | CN | H | H |
| 380 | 2 | H | H | CN | H | H |
| 381 | 3 | H | H | CN | H | H |
| 382 | 1 | Me | H | CN | H | H |
| 383 | 2 | Me | H | CN | H | H |
| 384 | 3 | Me | H | CN | H | H |
| 385 | 1 | CH$_2$Ph | H | CN | H | H |
| 386 | 2 | CH$_2$Ph | H | CN | H | H |
| 387 | 3 | CH$_2$Ph | H | CN | H | H |
| 388 | 1 | COMe | H | CN | H | H |
| 389 | 2 | COMe | H | CN | H | H |
| 390 | 3 | COMe | H | CN | H | H |
| 391 | 1 | CO$_2$Me | H | CN | H | H |
| 392 | 2 | CO$_2$Me | H | CN | H | H |
| 393 | 3 | CO$_2$Me | H | CN | H | H |
| 394 | 1 | CO$_2$tBu | H | CN | H | H |
| 395 | 2 | CO$_2$tBu | H | CN | H | H |
| 396 | 3 | CO$_2$tBu | H | CN | H | H |
| 397 | 1 | CONHMe | H | CN | H | H |
| 398 | 2 | CONHMe | H | CN | H | H |
| 399 | 3 | CONHMe | H | CN | H | H |
| 400 | 1 | SO$_2$Me | H | CN | H | H |
| 401 | 2 | SO$_2$Me | H | CN | H | H |
| 402 | 3 | SO$_2$Me | H | CN | H | H |
| 403 | 1 | SO$_2$NH$_2$ | H | CN | H | H |
| 404 | 2 | SO$_2$NH$_2$ | H | CN | H | H |
| 405 | 3 | SO$_2$NH$_2$ | H | CN | H | H |

Exemplary embodiments include compounds having the formula (XXI)

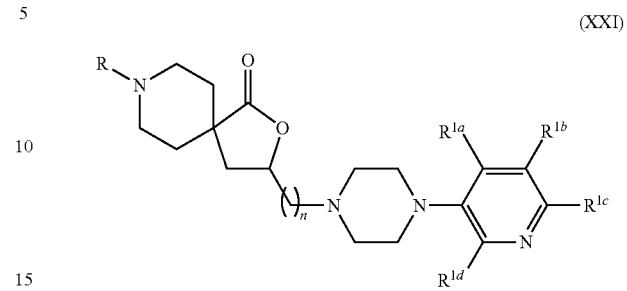

(XXI)

or a pharmaceutically acceptable salt form thereof defined herein below in Table 5.

TABLE 5

| Entry | n | R | $R^{1a}$ | $R^{1b}$ | $R^{1c}$ | $R^{1d}$ |
|---|---|---|---|---|---|---|
| 1 | 1 | H | H | H | H | H |
| 2 | 2 | H | H | H | H | H |
| 3 | 3 | H | H | H | H | H |
| 4 | 1 | Me | H | H | H | H |
| 5 | 2 | Me | H | H | H | H |
| 6 | 3 | Me | H | H | H | H |
| 7 | 1 | CH$_2$Ph | H | H | H | H |
| 8 | 2 | CH$_2$Ph | H | H | H | H |
| 9 | 3 | CH$_2$Ph | H | H | H | H |
| 10 | 1 | COMe | H | H | H | H |
| 11 | 2 | COMe | H | H | H | H |
| 12 | 3 | COMe | H | H | H | H |
| 13 | 1 | CO$_2$Me | H | H | H | H |
| 14 | 2 | CO$_2$Me | H | H | H | H |
| 15 | 3 | CO$_2$Me | H | H | H | H |
| 16 | 1 | CO$_2$tBu | H | H | H | H |
| 17 | 2 | CO$_2$tBu | H | H | H | H |
| 18 | 3 | CO$_2$tBu | H | H | H | H |
| 19 | 1 | CONHMe | H | H | H | H |
| 20 | 2 | CONHMe | H | H | H | H |
| 21 | 3 | CONHMe | H | H | H | H |
| 22 | 1 | SO$_2$Me | H | H | H | H |
| 23 | 2 | SO$_2$Me | H | H | H | H |
| 24 | 3 | SO$_2$Me | H | H | H | H |
| 25 | 1 | SO$_2$NH$_2$ | H | H | H | H |
| 26 | 2 | SO$_2$NH$_2$ | H | H | H | H |
| 27 | 3 | SO$_2$NH$_2$ | H | H | H | H |

Exemplary embodiments include compounds having the formula (XXII)

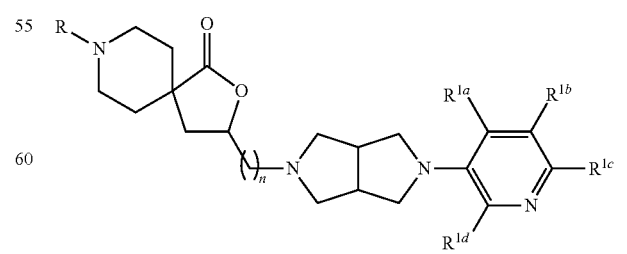

(XXII)

or a pharmaceutically acceptable salt form thereof defined herein below in Table 6.

TABLE 6

| Entry | n | R | $R^{1a}$ | $R^{1b}$ | $R^{1c}$ | $R^{1d}$ |
|---|---|---|---|---|---|---|
| 1 | 1 | H | H | H | H | H |
| 2 | 2 | H | H | H | H | H |
| 3 | 3 | H | H | H | H | H |
| 4 | 1 | Me | H | H | H | H |
| 5 | 2 | Me | H | H | H | H |
| 6 | 3 | Me | H | H | H | H |
| 7 | 1 | $CH_2Ph$ | H | H | H | H |
| 8 | 2 | $CH_2Ph$ | H | H | H | H |
| 9 | 3 | $CH_2Ph$ | H | H | H | H |
| 10 | 1 | COMe | H | H | H | H |
| 11 | 2 | COMe | H | H | H | H |
| 12 | 3 | COMe | H | H | H | H |
| 13 | 1 | $CO_2Me$ | H | H | H | H |
| 14 | 2 | $CO_2Me$ | H | H | H | H |
| 15 | 3 | $CO_2Me$ | H | H | H | H |
| 16 | 1 | $CO_2tBu$ | H | H | H | H |
| 17 | 2 | $CO_2tBu$ | H | H | H | H |
| 18 | 3 | $CO_2tBu$ | H | H | H | H |
| 19 | 1 | CONHMe | H | H | H | H |
| 20 | 2 | CONHMe | H | H | H | H |
| 21 | 3 | CONHMe | H | H | H | H |
| 22 | 1 | $SO_2Me$ | H | H | H | H |
| 23 | 2 | $SO_2Me$ | H | H | H | H |
| 24 | 3 | $SO_2Me$ | H | H | H | H |
| 25 | 1 | $SO_2NH_2$ | H | H | H | H |
| 26 | 2 | $SO_2NH_2$ | H | H | H | H |
| 27 | 3 | $SO_2NH_2$ | H | H | H | H |

Exemplary embodiments include compounds having the formula (XXIII)

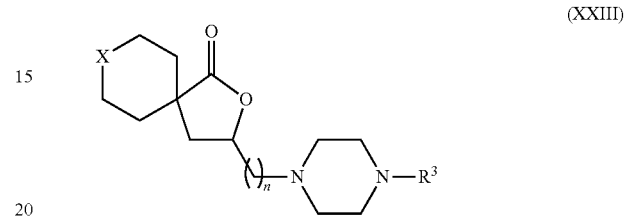

(XXIII)

or a pharmaceutically acceptable salt form thereof defined herein below in Table 7.

TABLE 7

| Entry | n | X | $R^3$ |
|---|---|---|---|
| 1 | 1 | O | Phenyl |
| 2 | 2 | O | Phenyl |
| 3 | 3 | O | Phenyl |
| 4 | 1 | S | Phenyl |
| 5 | 2 | S | Phenyl |
| 6 | 3 | S | Phenyl |
| 7 | 1 | SO | Phenyl |
| 8 | 2 | SO | Phenyl |
| 9 | 3 | SO | Phenyl |
| 10 | 1 | $SO_2$ | Phenyl |
| 11 | 2 | $SO_2$ | Phenyl |
| 12 | 3 | $SO_2$ | Phenyl |
| 13 | 1 | O | 3-OH-Phenyl |
| 14 | 2 | O | 3-OH-Phenyl |
| 15 | 3 | O | 3-OH-Phenyl |
| 16 | 1 | S | 3-OH-Phenyl |
| 17 | 2 | S | 3-OH-Phenyl |
| 18 | 3 | S | 3-OH-Phenyl |
| 19 | 1 | SO | 3-OH-Phenyl |
| 20 | 2 | SO | 3-OH-Phenyl |
| 21 | 3 | SO | 3-OH-Phenyl |
| 22 | 1 | $SO_2$ | 3-OH-Phenyl |
| 23 | 2 | $SO_2$ | 3-OH-Phenyl |
| 24 | 3 | $SO_2$ | 3-OH-Phenyl |
| 25 | 1 | O | 4-$NO_2$-Phenyl |
| 26 | 2 | O | 4-$NO_2$-Phenyl |
| 27 | 3 | O | 4-$NO_2$-Phenyl |
| 28 | 1 | S | 4-$NO_2$-Phenyl |
| 29 | 2 | S | 4-$NO_2$-Phenyl |
| 30 | 3 | S | 4-$NO_2$-Phenyl |
| 31 | 1 | SO | 4-$NO_2$-Phenyl |
| 32 | 2 | SO | 4-$NO_2$-Phenyl |
| 33 | 3 | SO | 4-$NO_2$-Phenyl |
| 34 | 1 | $SO_2$ | 4-$NO_2$-Phenyl |
| 35 | 2 | $SO_2$ | 4-$NO_2$-Phenyl |
| 36 | 3 | $SO_2$ | 4-$NO_2$-Phenyl |
| 37 | 1 | O | 3-OMe-Phenyl |
| 38 | 2 | O | 3-OMe-Phenyl |
| 39 | 3 | O | 3-OMe-Phenyl |
| 40 | 1 | S | 3-OMe-Phenyl |
| 41 | 2 | S | 3-OMe-Phenyl |
| 42 | 3 | S | 3-OMe-Phenyl |
| 43 | 1 | SO | 3-OMe-Phenyl |
| 44 | 2 | SO | 3-OMe-Phenyl |
| 45 | 3 | SO | 3-OMe-Phenyl |
| 46 | 1 | $SO_2$ | 3-OMe-Phenyl |
| 47 | 2 | $SO_2$ | 3-OMe-Phenyl |
| 277 | 1 | O | 4-OH-Phenyl |
| 278 | 2 | O | 4-OH-Phenyl |
| 279 | 3 | O | 4-OH-Phenyl |
| 280 | 1 | S | 4-OH-Phenyl |
| 281 | 2 | S | 4-OH-Phenyl |
| 282 | 3 | S | 4-OH-Phenyl |
| 283 | 1 | SO | 4-OH-Phenyl |
| 284 | 2 | SO | 4-OH-Phenyl |
| 285 | 3 | SO | 4-OH-Phenyl |
| 286 | 1 | $SO_2$ | 4-OH-Phenyl |
| 287 | 2 | $SO_2$ | 4-OH-Phenyl |
| 288 | 3 | $SO_2$ | 4-OH-Phenyl |
| 289 | 1 | O | 2-OH-Phenyl |
| 290 | 2 | O | 2-OH-Phenyl |
| 291 | 3 | O | 2-OH-Phenyl |
| 292 | 1 | S | 2-OH-Phenyl |
| 293 | 2 | S | 2-OH-Phenyl |
| 294 | 3 | S | 2-OH-Phenyl |
| 295 | 1 | SO | 2-OH-Phenyl |
| 296 | 2 | SO | 2-OH-Phenyl |
| 297 | 3 | SO | 2-OH-Phenyl |
| 298 | 1 | $SO_2$ | 2-OH-Phenyl |
| 299 | 2 | $SO_2$ | 2-OH-Phenyl |
| 300 | 3 | $SO_2$ | 2-OH-Phenyl |
| 301 | 1 | O | 4-OMe-Phenyl |
| 302 | 2 | O | 4-OMe-Phenyl |
| 303 | 3 | O | 4-OMe-Phenyl |
| 304 | 1 | S | 4-OMe-Phenyl |
| 305 | 2 | S | 4-OMe-Phenyl |
| 306 | 3 | S | 4-OMe-Phenyl |
| 307 | 1 | SO | 4-OMe-Phenyl |
| 308 | 2 | SO | 4-OMe-Phenyl |
| 309 | 3 | SO | 4-OMe-Phenyl |
| 310 | 1 | $SO_2$ | 4-OMe-Phenyl |
| 311 | 2 | $SO_2$ | 4-OMe-Phenyl |
| 312 | 3 | $SO_2$ | 4-OMe-Phenyl |
| 313 | 1 | O | 2-OMe-Phenyl |
| 314 | 2 | O | 2-OMe-Phenyl |
| 315 | 3 | O | 2-OMe-Phenyl |
| 316 | 1 | S | 2-OMe-Phenyl |
| 317 | 2 | S | 2-OMe-Phenyl |
| 318 | 3 | S | 2-OMe-Phenyl |
| 319 | 1 | SO | 2-OMe-Phenyl |
| 320 | 2 | SO | 2-OMe-Phenyl |
| 321 | 3 | SO | 2-OMe-Phenyl |
| 322 | 1 | $SO_2$ | 2-OMe-Phenyl |
| 323 | 2 | $SO_2$ | 2-OMe-Phenyl |

TABLE 7-continued

| Entry | n | X | R³ | Entry | n | R | R³ |
|---|---|---|---|---|---|---|---|
| 48 | 3 | SO₂ | 3-OMe-Phenyl | 324 | 3 | SO₂ | 2-OMe-Phenyl |
| 49 | 1 | O | 4-CN-Phenyl | 325 | 1 | O | 3-CN-Phenyl |
| 50 | 2 | O | 4-CN-Phenyl | 326 | 2 | O | 3-CN-Phenyl |
| 51 | 3 | O | 4-CN-Phenyl | 327 | 3 | O | 3-CN-Phenyl |
| 52 | 1 | S | 4-CN-Phenyl | 328 | 1 | S | 3-CN-Phenyl |
| 53 | 2 | S | 4-CN-Phenyl | 329 | 2 | S | 3-CN-Phenyl |
| 54 | 3 | S | 4-CN-Phenyl | 330 | 3 | S | 3-CN-Phenyl |
| 55 | 1 | SO | 4-CN-Phenyl | 331 | 1 | SO | 3-CN-Phenyl |
| 56 | 2 | SO | 4-CN-Phenyl | 332 | 2 | SO | 3-CN-Phenyl |
| 57 | 3 | SO | 4-CN-Phenyl | 333 | 3 | SO | 3-CN-Phenyl |
| 58 | 1 | SO₂ | 4-CN-Phenyl | 334 | 1 | SO₂ | 3-CN-Phenyl |
| 59 | 2 | SO₂ | 4-CN-Phenyl | 335 | 2 | SO₂ | 3-CN-Phenyl |
| 60 | 3 | SO₂ | 4-CN-Phenyl | 336 | 3 | SO₂ | 3-CN-Phenyl |
| 61 | 1 | O | 2-CN-Phenyl | 337 | 1 | O | 2-Me-Phenyl |
| 62 | 2 | O | 2-CN-Phenyl | 338 | 2 | O | 2-Me-Phenyl |
| 63 | 3 | O | 2-CN-Phenyl | 339 | 3 | O | 2-Me-Phenyl |
| 64 | 1 | S | 2-CN-Phenyl | 340 | 1 | S | 2-Me-Phenyl |
| 65 | 2 | S | 2-CN-Phenyl | 341 | 2 | S | 2-Me-Phenyl |
| 66 | 3 | S | 2-CN-Phenyl | 342 | 3 | S | 2-Me-Phenyl |
| 67 | 1 | SO | 2-CN-Phenyl | 343 | 1 | SO | 2-Me-Phenyl |
| 68 | 2 | SO | 2-CN-Phenyl | 344 | 2 | SO | 2-Me-Phenyl |
| 69 | 3 | SO | 2-CN-Phenyl | 345 | 3 | SO | 2-Me-Phenyl |
| 70 | 1 | SO₂ | 2-CN-Phenyl | 346 | 1 | SO₂ | 2-Me-Phenyl |
| 71 | 2 | SO₂ | 2-CN-Phenyl | 347 | 2 | SO₂ | 2-Me-Phenyl |
| 72 | 3 | SO₂ | 2-CN-Phenyl | 348 | 3 | SO₂ | 2-Me-Phenyl |
| 73 | 1 | O | 3-Me-Phenyl | 349 | 1 | O | 4-Me-Phenyl |
| 74 | 2 | O | 3-Me-Phenyl | 350 | 2 | O | 4-Me-Phenyl |
| 75 | 3 | O | 3-Me-Phenyl | 351 | 3 | O | 4-Me-Phenyl |
| 76 | 1 | S | 3-Me-Phenyl | 352 | 1 | S | 4-Me-Phenyl |
| 77 | 2 | S | 3-Me-Phenyl | 353 | 2 | S | 4-Me-Phenyl |
| 78 | 3 | S | 3-Me-Phenyl | 354 | 3 | S | 4-Me-Phenyl |
| 79 | 1 | SO | 3-Me-Phenyl | 355 | 1 | SO | 4-Me-Phenyl |
| 80 | 2 | SO | 3-Me-Phenyl | 356 | 2 | SO | 4-Me-Phenyl |
| 81 | 3 | SO | 3-Me-Phenyl | 357 | 3 | SO | 4-Me-Phenyl |
| 82 | 1 | SO₂ | 3-Me-Phenyl | 358 | 1 | SO₂ | 4-Me-Phenyl |
| 83 | 2 | SO₂ | 3-Me-Phenyl | 359 | 2 | SO₂ | 4-Me-Phenyl |
| 84 | 3 | SO₂ | 3-Me-Phenyl | 360 | 3 | SO₂ | 4-Me-Phenyl |
| 85 | 1 | O | 2-F-Phenyl | 361 | 1 | O | 3-F-Phenyl |
| 86 | 2 | O | 2-F-Phenyl | 362 | 2 | O | 3-F-Phenyl |
| 87 | 3 | O | 2-F-Phenyl | 363 | 3 | O | 3-F-Phenyl |
| 88 | 1 | S | 2-F-Phenyl | 364 | 1 | S | 3-F-Phenyl |
| 89 | 2 | S | 2-F-Phenyl | 365 | 2 | S | 3-F-Phenyl |
| 90 | 3 | S | 2-F-Phenyl | 366 | 3 | S | 3-F-Phenyl |
| 91 | 1 | SO | 2-F-Phenyl | 367 | 1 | SO | 3-F-Phenyl |
| 92 | 2 | SO | 2-F-Phenyl | 368 | 2 | SO | 3-F-Phenyl |
| 93 | 3 | SO | 2-F-Phenyl | 369 | 3 | SO | 3-F-Phenyl |
| 94 | 1 | SO₂ | 2-F-Phenyl | 370 | 1 | SO₂ | 3-F-Phenyl |
| 95 | 2 | SO₂ | 2-F-Phenyl | 371 | 2 | SO₂ | 3-F-Phenyl |
| 96 | 3 | SO₂ | 2-F-Phenyl | 372 | 3 | SO₂ | 3-F-Phenyl |
| 97 | 1 | O | 4-F-Phenyl | 373 | 1 | O | 2-Cl-Phenyl |
| 98 | 2 | O | 4-F-Phenyl | 374 | 2 | O | 2-Cl-Phenyl |
| 99 | 3 | O | 4-F-Phenyl | 375 | 3 | O | 2-Cl-Phenyl |
| 100 | 1 | S | 4-F-Phenyl | 376 | 1 | S | 2-Cl-Phenyl |
| 101 | 2 | S | 4-F-Phenyl | 377 | 2 | S | 2-Cl-Phenyl |
| 102 | 3 | S | 4-F-Phenyl | 378 | 3 | S | 2-Cl-Phenyl |
| 103 | 1 | SO | 4-F-Phenyl | 379 | 1 | SO | 2-Cl-Phenyl |
| 104 | 2 | SO | 4-F-Phenyl | 380 | 2 | SO | 2-Cl-Phenyl |
| 105 | 3 | SO | 4-F-Phenyl | 381 | 3 | SO | 2-Cl-Phenyl |
| 106 | 1 | SO₂ | 4-F-Phenyl | 382 | 1 | SO₂ | 2-Cl-Phenyl |
| 107 | 2 | SO₂ | 4-F-Phenyl | 383 | 2 | SO₂ | 2-Cl-Phenyl |
| 108 | 3 | SO₂ | 4-F-Phenyl | 384 | 3 | SO₂ | 2-Cl-Phenyl |
| 109 | 1 | O | 3-Cl-Phenyl | 385 | 1 | O | 4-Cl-Phenyl |
| 110 | 2 | O | 3-Cl-Phenyl | 386 | 2 | O | 4-Cl-Phenyl |
| 111 | 3 | O | 3-Cl-Phenyl | 387 | 3 | O | 4-Cl-Phenyl |
| 112 | 1 | S | 3-Cl-Phenyl | 388 | 1 | S | 4-Cl-Phenyl |
| 113 | 2 | S | 3-Cl-Phenyl | 389 | 2 | S | 4-Cl-Phenyl |
| 114 | 3 | S | 3-Cl-Phenyl | 390 | 3 | S | 4-Cl-Phenyl |
| 115 | 1 | SO | 3-Cl-Phenyl | 391 | 1 | SO | 4-Cl-Phenyl |
| 116 | 2 | SO | 3-Cl-Phenyl | 392 | 2 | SO | 4-Cl-Phenyl |
| 117 | 3 | SO | 3-Cl-Phenyl | 393 | 3 | SO | 4-Cl-Phenyl |
| 118 | 1 | SO₂ | 3-Cl-Phenyl | 394 | 1 | SO₂ | 4-Cl-Phenyl |
| 119 | 2 | SO₂ | 3-Cl-Phenyl | 395 | 2 | SO₂ | 4-Cl-Phenyl |
| 120 | 3 | SO₂ | 3-Cl-Phenyl | 396 | 3 | SO₂ | 4-Cl-Phenyl |
| 121 | 1 | O | 2-Br-Phenyl | 397 | 1 | O | 3-Br-Phenyl |
| 122 | 2 | O | 2-Br-Phenyl | 398 | 2 | O | 3-Br-Phenyl |
| 123 | 3 | O | 2-Br-Phenyl | 399 | 3 | O | 3-Br-Phenyl |
| 124 | 1 | S | 2-Br-Phenyl | 400 | 1 | S | 3-Br-Phenyl |
| 125 | 2 | S | 2-Br-Phenyl | 401 | 2 | S | 3-Br-Phenyl |

TABLE 7-continued

| Entry | n | X | R³ | Entry | n | R | R³ |
|---|---|---|---|---|---|---|---|
| 126 | 3 | S | 2-Br-Phenyl | 402 | 3 | S | 3-Br-Phenyl |
| 127 | 1 | SO | 2-Br-Phenyl | 403 | 1 | SO | 3-Br-Phenyl |
| 128 | 2 | SO | 2-Br-Phenyl | 404 | 2 | SO | 3-Br-Phenyl |
| 129 | 3 | SO | 2-Br-Phenyl | 405 | 3 | SO | 3-Br-Phenyl |
| 130 | 1 | SO$_2$ | 2-Br-Phenyl | 406 | 1 | SO$_2$ | 3-Br-Phenyl |
| 131 | 2 | SO$_2$ | 2-Br-Phenyl | 407 | 2 | SO$_2$ | 3-Br-Phenyl |
| 132 | 3 | SO$_2$ | 2-Br-Phenyl | 408 | 3 | SO$_2$ | 3-Br-Phenyl |
| 133 | 1 | O | 4-Br-Phenyl | 409 | 1 | O | 2-CF$_3$-Phenyl |
| 134 | 2 | O | 4-Br-Phenyl | 410 | 2 | O | 2-CF$_3$-Phenyl |
| 135 | 3 | O | 4-Br-Phenyl | 411 | 3 | O | 2-CF$_3$-Phenyl |
| 136 | 1 | S | 4-Br-Phenyl | 412 | 1 | S | 2-CF$_3$-Phenyl |
| 137 | 2 | S | 4-Br-Phenyl | 413 | 2 | S | 2-CF$_3$-Phenyl |
| 138 | 3 | S | 4-Br-Phenyl | 414 | 3 | S | 2-CF$_3$-Phenyl |
| 139 | 1 | SO | 4-Br-Phenyl | 415 | 1 | SO | 2-CF$_3$-Phenyl |
| 140 | 2 | SO | 4-Br-Phenyl | 416 | 2 | SO | 2-CF$_3$-Phenyl |
| 141 | 3 | SO | 4-Br-Phenyl | 417 | 3 | SO | 2-CF$_3$-Phenyl |
| 142 | 1 | SO$_2$ | 4-Br-Phenyl | 418 | 1 | SO$_2$ | 2-CF$_3$-Phenyl |
| 143 | 2 | SO$_2$ | 4-Br-Phenyl | 419 | 2 | SO$_2$ | 2-CF$_3$-Phenyl |
| 144 | 3 | SO$_2$ | 4-Br-Phenyl | 420 | 3 | SO$_2$ | 2-CF$_3$-Phenyl |
| 145 | 1 | O | 3-CF$_3$-Phenyl | 421 | 1 | O | 4-CF$_3$-Phenyl |
| 146 | 2 | O | 3-CF$_3$-Phenyl | 422 | 2 | O | 4-CF$_3$-Phenyl |
| 147 | 3 | O | 3-CF$_3$-Phenyl | 423 | 3 | O | 4-CF$_3$-Phenyl |
| 148 | 1 | S | 3-CF$_3$-Phenyl | 424 | 1 | S | 4-CF$_3$-Phenyl |
| 149 | 2 | S | 3-CF$_3$-Phenyl | 425 | 2 | S | 4-CF$_3$-Phenyl |
| 150 | 3 | S | 3-CF$_3$-Phenyl | 426 | 3 | S | 4-CF$_3$-Phenyl |
| 151 | 1 | SO | 3-CF$_3$-Phenyl | 427 | 1 | SO | 4-CF$_3$-Phenyl |
| 152 | 2 | SO | 3-CF$_3$-Phenyl | 428 | 2 | SO | 4-CF$_3$-Phenyl |
| 153 | 3 | SO | 3-CF$_3$-Phenyl | 429 | 3 | SO | 4-CF$_3$-Phenyl |
| 154 | 1 | SO$_2$ | 3-CF$_3$-Phenyl | 430 | 1 | SO$_2$ | 4-CF$_3$-Phenyl |
| 155 | 2 | SO$_2$ | 3-CF$_3$-Phenyl | 431 | 2 | SO$_2$ | 4-CF$_3$-Phenyl |
| 156 | 3 | SO$_2$ | 3-CF$_3$-Phenyl | 432 | 3 | SO$_2$ | 4-CF$_3$-Phenyl |
| 157 | 1 | O | 2-iPr-Phenyl | 433 | 1 | O | 3-iPr-Phenyl |
| 158 | 2 | O | 2-iPr-Phenyl | 434 | 2 | O | 3-iPr-Phenyl |
| 159 | 3 | O | 2-iPr-Phenyl | 435 | 3 | O | 3-iPr-Phenyl |
| 160 | 1 | S | 2-iPr-Phenyl | 436 | 1 | S | 3-iPr-Phenyl |
| 161 | 2 | S | 2-iPr-Phenyl | 437 | 2 | S | 3-iPr-Phenyl |
| 162 | 3 | S | 2-iPr-Phenyl | 438 | 3 | S | 3-iPr-Phenyl |
| 163 | 1 | SO | 2-iPr-Phenyl | 439 | 1 | SO | 3-iPr-Phenyl |
| 164 | 2 | SO | 2-iPr-Phenyl | 440 | 2 | SO | 3-iPr-Phenyl |
| 165 | 3 | SO | 2-iPr-Phenyl | 441 | 3 | SO | 3-iPr-Phenyl |
| 166 | 1 | SO$_2$ | 2-iPr-Phenyl | 442 | 1 | SO$_2$ | 3-iPr-Phenyl |
| 167 | 2 | SO$_2$ | 2-iPr-Phenyl | 443 | 2 | SO$_2$ | 3-iPr-Phenyl |
| 168 | 3 | SO$_2$ | 2-iPr-Phenyl | 444 | 3 | SO$_2$ | 3-iPr-Phenyl |
| 169 | 1 | O | 4-iPr-Phenyl | 445 | 1 | O | 4-NH$_2$-Phenyl |
| 170 | 2 | O | 4-iPr-Phenyl | 446 | 2 | O | 4-NH$_2$-Phenyl |
| 171 | 3 | O | 4-iPr-Phenyl | 447 | 3 | O | 4-NH$_2$-Phenyl |
| 172 | 1 | S | 4-iPr-Phenyl | 448 | 1 | S | 4-NH$_2$-Phenyl |
| 173 | 2 | S | 4-iPr-Phenyl | 449 | 2 | S | 4-NH$_2$-Phenyl |
| 174 | 3 | S | 4-iPr-Phenyl | 450 | 3 | S | 4-NH$_2$-Phenyl |
| 175 | 1 | SO | 4-iPr-Phenyl | 451 | 1 | SO | 4-NH$_2$-Phenyl |
| 176 | 2 | SO | 4-iPr-Phenyl | 452 | 2 | SO | 4-NH$_2$-Phenyl |
| 177 | 3 | SO | 4-iPr-Phenyl | 453 | 3 | SO | 4-NH$_2$-Phenyl |
| 178 | 1 | SO$_2$ | 4-iPr-Phenyl | 454 | 1 | SO$_2$ | 4-NH$_2$-Phenyl |
| 179 | 2 | SO$_2$ | 4-iPr-Phenyl | 455 | 2 | SO$_2$ | 4-NH$_2$-Phenyl |
| 180 | 3 | SO$_2$ | 4-iPr-Phenyl | 456 | 3 | SO$_2$ | 4-NH$_2$-Phenyl |
| 181 | 1 | O | 3-NH$_2$-Phenyl | 457 | 1 | O | 2-NH$_2$-Phenyl |
| 182 | 2 | O | 3-NH$_2$-Phenyl | 458 | 2 | O | 2-NH$_2$-Phenyl |
| 183 | 3 | O | 3-NH$_2$-Phenyl | 459 | 3 | O | 2-NH$_2$-Phenyl |
| 184 | 1 | S | 3-NH$_2$-Phenyl | 460 | 1 | S | 2-NH$_2$-Phenyl |
| 185 | 2 | S | 3-NH$_2$-Phenyl | 461 | 2 | S | 2-NH$_2$-Phenyl |
| 186 | 3 | S | 3-NH$_2$-Phenyl | 462 | 3 | S | 2-NH$_2$-Phenyl |
| 187 | 1 | SO | 3-NH$_2$-Phenyl | 463 | 1 | SO | 2-NH$_2$-Phenyl |
| 188 | 2 | SO | 3-NH$_2$-Phenyl | 464 | 2 | SO | 2-NH$_2$-Phenyl |
| 189 | 3 | SO | 3-NH$_2$-Phenyl | 465 | 3 | SO | 2-NH$_2$-Phenyl |
| 190 | 1 | SO$_2$ | 3-NH$_2$-Phenyl | 466 | 1 | SO$_2$ | 2-NH$_2$-Phenyl |
| 191 | 2 | SO$_2$ | 3-NH$_2$-Phenyl | 467 | 2 | SO$_2$ | 2-NH$_2$-Phenyl |
| 192 | 3 | SO$_2$ | 3-NH$_2$-Phenyl | 468 | 3 | SO$_2$ | 2-NH$_2$-Phenyl |
| 193 | 1 | O | 2,4-di-Me-Phenyl | 469 | 1 | O | 2,6-di-Me-Phenyl |
| 194 | 2 | O | 2,4-di-Me-Phenyl | 470 | 2 | O | 2,6-di-Me-Phenyl |
| 195 | 3 | O | 2,4-di-Me-Phenyl | 471 | 3 | O | 2,6-di-Me-Phenyl |
| 196 | 1 | S | 2,4-di-Me-Phenyl | 472 | 1 | S | 2,6-di-Me-Phenyl |
| 197 | 2 | S | 2,4-di-Me-Phenyl | 473 | 2 | S | 2,6-di-Me-Phenyl |
| 198 | 3 | S | 2,4-di-Me-Phenyl | 474 | 3 | S | 2,6-di-Me-Phenyl |
| 199 | 1 | SO | 2,4-di-Me-Phenyl | 475 | 1 | SO | 2,6-di-Me-Phenyl |
| 200 | 2 | SO | 2,4-di-Me-Phenyl | 476 | 2 | SO | 2,6-di-Me-Phenyl |
| 201 | 3 | SO | 2,4-di-Me-Phenyl | 477 | 3 | SO | 2,6-di-Me-Phenyl |
| 202 | 1 | SO$_2$ | 2,4-di-Me-Phenyl | 478 | 1 | SO$_2$ | 2,6-di-Me-Phenyl |
| 203 | 2 | SO$_2$ | 2,4-di-Me-Phenyl | 479 | 2 | SO$_2$ | 2,6-di-Me-Phenyl |

TABLE 7-continued

| Entry | n | X | R³ | Entry | n | R | R³ |
|---|---|---|---|---|---|---|---|
| 204 | 3 | SO₂ | 2,4-di-Me-Phenyl | 480 | 3 | SO₂ | 2,6-di-Me-Phenyl |
| 205 | 1 | O | 2,6-di-iPr-Phenyl | 481 | 1 | O | 2-Ph-Phenyl |
| 206 | 2 | O | 2,6-di-iPr-Phenyl | 482 | 2 | O | 2-Ph-Phenyl |
| 207 | 3 | O | 2,6-di-iPr-Phenyl | 483 | 3 | O | 2-Ph-Phenyl |
| 208 | 1 | S | 2,6-di-iPr-Phenyl | 484 | 1 | S | 2-Ph-Phenyl |
| 209 | 2 | S | 2,6-di-iPr-Phenyl | 485 | 2 | S | 2-Ph-Phenyl |
| 210 | 3 | S | 2,6-di-iPr-Phenyl | 486 | 3 | S | 2-Ph-Phenyl |
| 211 | 1 | SO | 2,6-di-iPr-Phenyl | 487 | 1 | SO | 2-Ph-Phenyl |
| 212 | 2 | SO | 2,6-di-iPr-Phenyl | 488 | 2 | SO | 2-Ph-Phenyl |
| 213 | 3 | SO | 2,6-di-iPr-Phenyl | 489 | 3 | SO | 2-Ph-Phenyl |
| 214 | 1 | SO₂ | 2,6-di-iPr-Phenyl | 490 | 1 | SO₂ | 2-Ph-Phenyl |
| 215 | 2 | SO₂ | 2,6-di-iPr-Phenyl | 491 | 2 | SO₂ | 2-Ph-Phenyl |
| 216 | 3 | SO₂ | 2,6-di-iPr-Phenyl | 492 | 3 | SO₂ | 2-Ph-Phenyl |
| 217 | 1 | O | 3-Ph-Phenyl | 493 | 1 | O | 4-Ph-Phenyl |
| 218 | 2 | O | 3-Ph-Phenyl | 494 | 2 | O | 4-Ph-Phenyl |
| 219 | 3 | O | 3-Ph-Phenyl | 495 | 3 | O | 4-Ph-Phenyl |
| 220 | 1 | S | 3-Ph-Phenyl | 496 | 1 | S | 4-Ph-Phenyl |
| 221 | 2 | S | 3-Ph-Phenyl | 497 | 2 | S | 4-Ph-Phenyl |
| 222 | 3 | S | 3-Ph-Phenyl | 498 | 3 | S | 4-Ph-Phenyl |
| 223 | 1 | SO | 3-Ph-Phenyl | 499 | 1 | SO | 4-Ph-Phenyl |
| 224 | 2 | SO | 3-Ph-Phenyl | 500 | 2 | SO | 4-Ph-Phenyl |
| 225 | 3 | SO | 3-Ph-Phenyl | 501 | 3 | SO | 4-Ph-Phenyl |
| 226 | 1 | SO₂ | 3-Ph-Phenyl | 502 | 1 | SO₂ | 4-Ph-Phenyl |
| 227 | 2 | SO₂ | 3-Ph-Phenyl | 503 | 2 | SO₂ | 4-Ph-Phenyl |
| 228 | 3 | SO₂ | 3-Ph-Phenyl | 504 | 3 | SO₂ | 4-Ph-Phenyl |
| 229 | 1 | O | 2-morpholino-phenyl | 505 | 1 | O | 3-morpholino-phenyl |
| 230 | 2 | O | 2-morpholino-phenyl | 506 | 2 | O | 3-morpholino-phenyl |
| 231 | 3 | O | 2-morpholino-phenyl | 507 | 3 | O | 3-morpholino-phenyl |
| 232 | 1 | S | 2-morpholino-phenyl | 508 | 1 | S | 3-morpholino-phenyl |
| 233 | 2 | S | 2-morpholino-phenyl | 509 | 2 | S | 3-morpholino-phenyl |
| 234 | 3 | S | 2-morpholino-phenyl | 510 | 3 | S | 3-morpholino-phenyl |
| 235 | 1 | SO | 2-morpholino-phenyl | 511 | 1 | SO | 3-morpholino-phenyl |
| 236 | 2 | SO | 2-morpholino-phenyl | 512 | 2 | SO | 3-morpholino-phenyl |
| 237 | 3 | SO | 2-morpholino-phenyl | 513 | 3 | SO | 3-morpholino-phenyl |
| 238 | 1 | SO₂ | 2-morpholino-phenyl | 514 | 1 | SO₂ | 3-morpholino-phenyl |
| 239 | 2 | SO₂ | 2-morpholino-phenyl | 515 | 2 | SO₂ | 3-morpholino-phenyl |
| 240 | 3 | SO₂ | 2-morpholino-phenyl | 516 | 3 | SO₂ | 3-morpholino-phenyl |
| 241 | 1 | O | 4-morpholino-phenyl | 517 | 1 | O | 2-pyrazinyl |
| 242 | 2 | O | 4-morpholino-phenyl | 518 | 2 | O | 2-pyrazinyl |
| 243 | 3 | O | 4-morpholino-phenyl | 519 | 3 | O | 2-pyrazinyl |
| 244 | 1 | S | 4-morpholino-phenyl | 520 | 1 | S | 2-pyrazinyl |
| 245 | 2 | S | 4-morpholino-phenyl | 521 | 2 | S | 2-pyrazinyl |
| 246 | 3 | S | 4-morpholino-phenyl | 522 | 3 | S | 2-pyrazinyl |
| 247 | 1 | SO | 4-morpholino-phenyl | 523 | 1 | SO | 2-pyrazinyl |
| 248 | 2 | SO | 4-morpholino-phenyl | 524 | 2 | SO | 2-pyrazinyl |
| 249 | 3 | SO | 4-morpholino-phenyl | 525 | 3 | SO | 2-pyrazinyl |
| 250 | 1 | SO₂ | 4-morpholino-phenyl | 526 | 1 | SO₂ | 2-pyrazinyl |
| 251 | 2 | SO₂ | 4-morpholino-phenyl | 527 | 2 | SO₂ | 2-pyrazinyl |
| 252 | 3 | SO₂ | 4-morpholino-phenyl | 528 | 3 | SO₂ | 2-pyrazinyl |
| 253 | 1 | O | 2-pyrimidinyl | 529 | 1 | O | 5-indolyl |
| 254 | 2 | O | 2-pyrimidinyl | 530 | 2 | O | 5-indolyl |
| 255 | 3 | O | 2-pyrimidinyl | 531 | 3 | O | 5-indolyl |
| 256 | 1 | S | 2-pyrimidinyl | 532 | 1 | S | 5-indolyl |
| 257 | 2 | S | 2-pyrimidinyl | 533 | 2 | S | 5-indolyl |
| 258 | 3 | S | 2-pyrimidinyl | 534 | 3 | S | 5-indolyl |
| 259 | 1 | SO | 2-pyrimidinyl | 535 | 1 | SO | 5-indolyl |
| 260 | 2 | SO | 2-pyrimidinyl | 536 | 2 | SO | 5-indolyl |
| 261 | 3 | SO | 2-pyrimidinyl | 537 | 3 | SO | 5-indolyl |
| 262 | 1 | SO₂ | 2-pyrimidinyl | 538 | 1 | SO₂ | 5-indolyl |
| 263 | 2 | SO₂ | 2-pyrimidinyl | 539 | 2 | SO₂ | 5-indolyl |
| 264 | 3 | SO₂ | 2-pyrimidinyl | 540 | 3 | SO₂ | 5-indolyl |
| 265 | 1 | O | 2-methyl-1H-benzo[d]imidazol-4-yl | 541 | 1 | O | 1H-benzo[d]imidazol-4-yl |
| 266 | 2 | O | 2-methyl-1H-benzo[d]imidazol-4-yl | 542 | 2 | O | 1H-benzo[d]imidazol-4-yl |
| 267 | 3 | O | 2-methyl-1H-benzo[d]imidazol-4-yl | 543 | 3 | O | 1H-benzo[d]imidazol-4-yl |
| 268 | 1 | S | 2-methyl-1H-benzo[d]imidazol-4-yl | 544 | 1 | S | 1H-benzo[d]imidazol-4-yl |
| 269 | 2 | S | 2-methyl-1H-benzo[d]imidazol-4-yl | 545 | 2 | S | 1H-benzo[d]imidazol-4-yl |
| 270 | 3 | S | 2-methyl-1H-benzo[d]imidazol-4-yl | 546 | 3 | S | 1H-benzo[d]imidazol-4-yl |
| 271 | 1 | SO | 2-methyl-1H-benzo[d]imidazol-4-yl | 547 | 1 | SO | 1H-benzo[d]imidazol-4-yl |
| 272 | 2 | SO | 2-methyl-1H-benzo[d]imidazol-4-yl | 548 | 2 | SO | 1H-benzo[d]imidazol-4-yl |

TABLE 7-continued

| Entry | n | X | R³ | Entry | n | R | R³ |
|---|---|---|---|---|---|---|---|
| 273 | 3 | SO | 2-methyl-1H-benzo[d]imidazol-4-yl | 549 | 3 | SO | 1H-benzo[d]imidazol-4-yl |
| 274 | 1 | SO₂ | 2-methyl-1H-benzo[d]imidazol-4-yl | 550 | 1 | SO₂ | 1H-benzo[d]imidazol-4-yl |
| 275 | 2 | SO₂ | 2-methyl-1H-benzo[d]imidazol-4-yl | 551 | 2 | SO₂ | 1H-benzo[d]imidazol-4-yl |
| 276 | 3 | SO₂ | 2-methyl-1H-benzo[d]imidazol-4-yl | 552 | 3 | SO₂ | 1H-benzo[d]imidazol-4-yl |

Exemplary embodiments include compounds having the formula (XXIV)

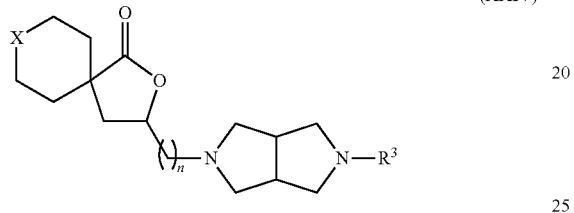

(XXIV)

or a pharmaceutically acceptably salt form thereof defined herein below in Table 8.

TABLE 8

| Entry | n | X | R³ | Entry | n | R | R³ |
|---|---|---|---|---|---|---|---|
| 1 | 1 | O | Phenyl | 277 | 1 | O | 4-OH-Phenyl |
| 2 | 2 | O | Phenyl | 278 | 2 | O | 4-OH-Phenyl |
| 3 | 3 | O | Phenyl | 279 | 3 | O | 4-OH-Phenyl |
| 4 | 1 | S | Phenyl | 280 | 1 | S | 4-OH-Phenyl |
| 5 | 2 | S | Phenyl | 281 | 2 | S | 4-OH-Phenyl |
| 6 | 3 | S | Phenyl | 282 | 3 | S | 4-OH-Phenyl |
| 7 | 1 | SO | Phenyl | 283 | 1 | SO | 4-OH-Phenyl |
| 8 | 2 | SO | Phenyl | 284 | 2 | SO | 4-OH-Phenyl |
| 9 | 3 | SO | Phenyl | 285 | 3 | SO | 4-OH-Phenyl |
| 10 | 1 | SO₂ | Phenyl | 286 | 1 | SO₂ | 4-OH-Phenyl |
| 11 | 2 | SO₂ | Phenyl | 287 | 2 | SO₂ | 4-OH-Phenyl |
| 12 | 3 | SO₂ | Phenyl | 288 | 3 | SO₂ | 4-OH-Phenyl |
| 13 | 1 | O | 3-OH-Phenyl | 289 | 1 | O | 2-OH-Phenyl |
| 14 | 2 | O | 3-OH-Phenyl | 290 | 2 | O | 2-OH-Phenyl |
| 15 | 3 | O | 3-OH-Phenyl | 291 | 3 | O | 2-OH-Phenyl |
| 16 | 1 | S | 3-OH-Phenyl | 292 | 1 | S | 2-OH-Phenyl |
| 17 | 2 | S | 3-OH-Phenyl | 293 | 2 | S | 2-OH-Phenyl |
| 18 | 3 | S | 3-OH-Phenyl | 294 | 3 | S | 2-OH-Phenyl |
| 19 | 1 | SO | 3-OH-Phenyl | 295 | 1 | SO | 2-OH-Phenyl |
| 20 | 2 | SO | 3-OH-Phenyl | 296 | 2 | SO | 2-OH-Phenyl |
| 21 | 3 | SO | 3-OH-Phenyl | 297 | 3 | SO | 2-OH-Phenyl |
| 22 | 1 | SO₂ | 3-OH-Phenyl | 298 | 1 | SO₂ | 2-OH-Phenyl |
| 23 | 2 | SO₂ | 3-OH-Phenyl | 299 | 2 | SO₂ | 2-OH-Phenyl |
| 24 | 3 | SO₂ | 3-OH-Phenyl | 300 | 3 | SO₂ | 2-OH-Phenyl |
| 25 | 1 | O | 4-NO₂-Phenyl | 301 | 1 | O | 4-OMe-Phenyl |
| 26 | 2 | O | 4-NO₂-Phenyl | 302 | 2 | O | 4-OMe-Phenyl |
| 27 | 3 | O | 4-NO₂-Phenyl | 303 | 3 | O | 4-OMe-Phenyl |
| 28 | 1 | S | 4-NO₂-Phenyl | 304 | 1 | S | 4-OMe-Phenyl |
| 29 | 2 | S | 4-NO₂-Phenyl | 305 | 2 | S | 4-OMe-Phenyl |
| 30 | 3 | S | 4-NO₂-Phenyl | 306 | 3 | S | 4-OMe-Phenyl |
| 31 | 1 | SO | 4-NO₂-Phenyl | 307 | 1 | SO | 4-OMe-Phenyl |
| 32 | 2 | SO | 4-NO₂-Phenyl | 308 | 2 | SO | 4-OMe-Phenyl |
| 33 | 3 | SO | 4-NO₂-Phenyl | 309 | 3 | SO | 4-OMe-Phenyl |
| 34 | 1 | SO₂ | 4-NO₂-Phenyl | 310 | 1 | SO₂ | 4-OMe-Phenyl |
| 35 | 2 | SO₂ | 4-NO₂-Phenyl | 311 | 2 | SO₂ | 4-OMe-Phenyl |
| 36 | 3 | SO₂ | 4-NO₂-Phenyl | 312 | 3 | SO₂ | 4-OMe-Phenyl |
| 37 | 1 | O | 3-OMe-Phenyl | 313 | 1 | O | 2-OMe-Phenyl |
| 38 | 2 | O | 3-OMe-Phenyl | 314 | 2 | O | 2-OMe-Phenyl |
| 39 | 3 | O | 3-OMe-Phenyl | 315 | 3 | O | 2-OMe-Phenyl |
| 40 | 1 | S | 3-OMe-Phenyl | 316 | 1 | S | 2-OMe-Phenyl |
| 41 | 2 | S | 3-OMe-Phenyl | 317 | 2 | S | 2-OMe-Phenyl |
| 42 | 3 | S | 3-OMe-Phenyl | 318 | 3 | S | 2-OMe-Phenyl |
| 43 | 1 | SO | 3-OMe-Phenyl | 319 | 1 | SO | 2-OMe-Phenyl |

TABLE 8-continued

| Entry | n | X | R³ | Entry | n | R | R³ |
|---|---|---|---|---|---|---|---|
| 44 | 2 | SO | 3-OMe-Phenyl | 320 | 2 | SO | 2-OMe-Phenyl |
| 45 | 3 | SO | 3-OMe-Phenyl | 321 | 3 | SO | 2-OMe-Phenyl |
| 46 | 1 | SO₂ | 3-OMe-Phenyl | 322 | 1 | SO₂ | 2-OMe-Phenyl |
| 47 | 2 | SO₂ | 3-OMe-Phenyl | 323 | 2 | SO₂ | 2-OMe-Phenyl |
| 48 | 3 | SO₂ | 3-OMe-Phenyl | 324 | 3 | SO₂ | 2-OMe-Phenyl |
| 49 | 1 | O | 4-CN-Phenyl | 325 | 1 | O | 3-CN-Phenyl |
| 50 | 2 | O | 4-CN-Phenyl | 326 | 2 | O | 3-CN-Phenyl |
| 51 | 3 | O | 4-CN-Phenyl | 327 | 3 | O | 3-CN-Phenyl |
| 52 | 1 | S | 4-CN-Phenyl | 328 | 1 | S | 3-CN-Phenyl |
| 53 | 2 | S | 4-CN-Phenyl | 329 | 2 | S | 3-CN-Phenyl |
| 54 | 3 | S | 4-CN-Phenyl | 330 | 3 | S | 3-CN-Phenyl |
| 55 | 1 | SO | 4-CN-Phenyl | 331 | 1 | SO | 3-CN-Phenyl |
| 56 | 2 | SO | 4-CN-Phenyl | 332 | 2 | SO | 3-CN-Phenyl |
| 57 | 3 | SO | 4-CN-Phenyl | 333 | 3 | SO | 3-CN-Phenyl |
| 58 | 1 | SO₂ | 4-CN-Phenyl | 334 | 1 | SO₂ | 3-CN-Phenyl |
| 59 | 2 | SO₂ | 4-CN-Phenyl | 335 | 2 | SO₂ | 3-CN-Phenyl |
| 60 | 3 | SO₂ | 4-CN-Phenyl | 336 | 3 | SO₂ | 3-CN-Phenyl |
| 61 | 1 | O | 2-CN-Phenyl | 337 | 1 | O | 2-Me-Phenyl |
| 62 | 2 | O | 2-CN-Phenyl | 338 | 2 | O | 2-Me-Phenyl |
| 63 | 3 | O | 2-CN-Phenyl | 339 | 3 | O | 2-Me-Phenyl |
| 64 | 1 | S | 2-CN-Phenyl | 340 | 1 | S | 2-Me-Phenyl |
| 65 | 2 | S | 2-CN-Phenyl | 341 | 2 | S | 2-Me-Phenyl |
| 66 | 3 | S | 2-CN-Phenyl | 342 | 3 | S | 2-Me-Phenyl |
| 67 | 1 | SO | 2-CN-Phenyl | 343 | 1 | SO | 2-Me-Phenyl |
| 68 | 2 | SO | 2-CN-Phenyl | 344 | 2 | SO | 2-Me-Phenyl |
| 69 | 3 | SO | 2-CN-Phenyl | 345 | 3 | SO | 2-Me-Phenyl |
| 70 | 1 | SO₂ | 2-CN-Phenyl | 346 | 1 | SO₂ | 2-Me-Phenyl |
| 71 | 2 | SO₂ | 2-CN-Phenyl | 347 | 2 | SO₂ | 2-Me-Phenyl |
| 72 | 3 | SO₂ | 2-CN-Phenyl | 348 | 3 | SO₂ | 2-Me-Phenyl |
| 73 | 1 | O | 3-Me-Phenyl | 349 | 1 | O | 4-Me-Phenyl |
| 74 | 2 | O | 3-Me-Phenyl | 350 | 2 | O | 4-Me-Phenyl |
| 75 | 3 | O | 3-Me-Phenyl | 351 | 3 | O | 4-Me-Phenyl |
| 76 | 1 | S | 3-Me-Phenyl | 352 | 1 | S | 4-Me-Phenyl |
| 77 | 2 | S | 3-Me-Phenyl | 353 | 2 | S | 4-Me-Phenyl |
| 78 | 3 | S | 3-Me-Phenyl | 354 | 3 | S | 4-Me-Phenyl |
| 79 | 1 | SO | 3-Me-Phenyl | 355 | 1 | SO | 4-Me-Phenyl |
| 80 | 2 | SO | 3-Me-Phenyl | 356 | 2 | SO | 4-Me-Phenyl |
| 81 | 3 | SO | 3-Me-Phenyl | 357 | 3 | SO | 4-Me-Phenyl |
| 82 | 1 | SO₂ | 3-Me-Phenyl | 358 | 1 | SO₂ | 4-Me-Phenyl |
| 83 | 2 | SO₂ | 3-Me-Phenyl | 359 | 2 | SO₂ | 4-Me-Phenyl |
| 84 | 3 | SO₂ | 3-Me-Phenyl | 360 | 3 | SO₂ | 4-Me-Phenyl |
| 85 | 1 | O | 2-F-Phenyl | 361 | 1 | O | 3-F-Phenyl |
| 86 | 2 | O | 2-F-Phenyl | 362 | 2 | O | 3-F-Phenyl |
| 87 | 3 | O | 2-F-Phenyl | 363 | 3 | O | 3-F-Phenyl |
| 88 | 1 | S | 2-F-Phenyl | 364 | 1 | S | 3-F-Phenyl |
| 89 | 2 | S | 2-F-Phenyl | 365 | 2 | S | 3-F-Phenyl |
| 90 | 3 | S | 2-F-Phenyl | 366 | 3 | S | 3-F-Phenyl |
| 91 | 1 | SO | 2-F-Phenyl | 367 | 1 | SO | 3-F-Phenyl |
| 92 | 2 | SO | 2-F-Phenyl | 368 | 2 | SO | 3-F-Phenyl |
| 93 | 3 | SO | 2-F-Phenyl | 369 | 3 | SO | 3-F-Phenyl |
| 94 | 1 | SO₂ | 2-F-Phenyl | 370 | 1 | SO₂ | 3-F-Phenyl |
| 95 | 2 | SO₂ | 2-F-Phenyl | 371 | 2 | SO₂ | 3-F-Phenyl |
| 96 | 3 | SO₂ | 2-F-Phenyl | 372 | 3 | SO₂ | 3-F-Phenyl |
| 97 | 1 | O | 4-F-Phenyl | 373 | 1 | O | 2-Cl-Phenyl |
| 98 | 2 | O | 4-F-Phenyl | 374 | 2 | O | 2-Cl-Phenyl |
| 99 | 3 | O | 4-F-Phenyl | 375 | 3 | O | 2-Cl-Phenyl |
| 100 | 1 | S | 4-F-Phenyl | 376 | 1 | S | 2-Cl-Phenyl |
| 101 | 2 | S | 4-F-Phenyl | 377 | 2 | S | 2-Cl-Phenyl |
| 102 | 3 | S | 4-F-Phenyl | 378 | 3 | S | 2-Cl-Phenyl |
| 103 | 1 | SO | 4-F-Phenyl | 379 | 1 | SO | 2-Cl-Phenyl |
| 104 | 2 | SO | 4-F-Phenyl | 380 | 2 | SO | 2-Cl-Phenyl |
| 105 | 3 | SO | 4-F-Phenyl | 381 | 3 | SO | 2-Cl-Phenyl |
| 106 | 1 | SO₂ | 4-F-Phenyl | 382 | 1 | SO₂ | 2-Cl-Phenyl |
| 107 | 2 | SO₂ | 4-F-Phenyl | 383 | 2 | SO₂ | 2-Cl-Phenyl |
| 108 | 3 | SO₂ | 4-F-Phenyl | 384 | 3 | SO₂ | 2-Cl-Phenyl |
| 109 | 1 | O | 3-Cl-Phenyl | 385 | 1 | O | 4-Cl-Phenyl |
| 110 | 2 | O | 3-Cl-Phenyl | 386 | 2 | O | 4-Cl-Phenyl |
| 111 | 3 | O | 3-Cl-Phenyl | 387 | 3 | O | 4-Cl-Phenyl |
| 112 | 1 | S | 3-Cl-Phenyl | 388 | 1 | S | 4-Cl-Phenyl |
| 113 | 2 | S | 3-Cl-Phenyl | 389 | 2 | S | 4-Cl-Phenyl |
| 114 | 3 | S | 3-Cl-Phenyl | 390 | 3 | S | 4-Cl-Phenyl |
| 115 | 1 | SO | 3-Cl-Phenyl | 391 | 1 | SO | 4-Cl-Phenyl |
| 116 | 2 | SO | 3-Cl-Phenyl | 392 | 2 | SO | 4-Cl-Phenyl |
| 117 | 3 | SO | 3-Cl-Phenyl | 393 | 3 | SO | 4-Cl-Phenyl |
| 118 | 1 | SO₂ | 3-Cl-Phenyl | 394 | 1 | SO₂ | 4-Cl-Phenyl |
| 119 | 2 | SO₂ | 3-Cl-Phenyl | 395 | 2 | SO₂ | 4-Cl-Phenyl |
| 120 | 3 | SO₂ | 3-Cl-Phenyl | 396 | 3 | SO₂ | 4-Cl-Phenyl |
| 121 | 1 | O | 2-Br-Phenyl | 397 | 1 | O | 3-Br-Phenyl |

TABLE 8-continued

| Entry | n | X | R³ | Entry | n | R | R³ |
|---|---|---|---|---|---|---|---|
| 122 | 2 | O | 2-Br-Phenyl | 398 | 2 | O | 3-Br-Phenyl |
| 123 | 3 | O | 2-Br-Phenyl | 399 | 3 | O | 3-Br-Phenyl |
| 124 | 1 | S | 2-Br-Phenyl | 400 | 1 | S | 3-Br-Phenyl |
| 125 | 2 | S | 2-Br-Phenyl | 401 | 2 | S | 3-Br-Phenyl |
| 126 | 3 | S | 2-Br-Phenyl | 402 | 3 | S | 3-Br-Phenyl |
| 127 | 1 | SO | 2-Br-Phenyl | 403 | 1 | SO | 3-Br-Phenyl |
| 128 | 2 | SO | 2-Br-Phenyl | 404 | 2 | SO | 3-Br-Phenyl |
| 129 | 3 | SO | 2-Br-Phenyl | 405 | 3 | SO | 3-Br-Phenyl |
| 130 | 1 | $SO_2$ | 2-Br-Phenyl | 406 | 1 | $SO_2$ | 3-Br-Phenyl |
| 131 | 2 | $SO_2$ | 2-Br-Phenyl | 407 | 2 | $SO_2$ | 3-Br-Phenyl |
| 132 | 3 | $SO_2$ | 2-Br-Phenyl | 408 | 3 | $SO_2$ | 3-Br-Phenyl |
| 133 | 1 | O | 4-Br-Phenyl | 409 | 1 | O | 2-$CF_3$-Phenyl |
| 134 | 2 | O | 4-Br-Phenyl | 410 | 2 | O | 2-$CF_3$-Phenyl |
| 135 | 3 | O | 4-Br-Phenyl | 411 | 3 | O | 2-$CF_3$-Phenyl |
| 136 | 1 | S | 4-Br-Phenyl | 412 | 1 | S | 2-$CF_3$-Phenyl |
| 137 | 2 | S | 4-Br-Phenyl | 413 | 2 | S | 2-$CF_3$-Phenyl |
| 138 | 3 | S | 4-Br-Phenyl | 414 | 3 | S | 2-$CF_3$-Phenyl |
| 139 | 1 | SO | 4-Br-Phenyl | 415 | 1 | SO | 2-$CF_3$-Phenyl |
| 140 | 2 | SO | 4-Br-Phenyl | 416 | 2 | SO | 2-$CF_3$-Phenyl |
| 141 | 3 | SO | 4-Br-Phenyl | 417 | 3 | SO | 2-$CF_3$-Phenyl |
| 142 | 1 | $SO_2$ | 4-Br-Phenyl | 418 | 1 | $SO_2$ | 2-$CF_3$-Phenyl |
| 143 | 2 | $SO_2$ | 4-Br-Phenyl | 419 | 2 | $SO_2$ | 2-$CF_3$-Phenyl |
| 144 | 3 | $SO_2$ | 4-Br-Phenyl | 420 | 3 | $SO_2$ | 2-$CF_3$-Phenyl |
| 145 | 1 | O | 3-$CF_3$-Phenyl | 421 | 1 | O | 4-$CF_3$-Phenyl |
| 146 | 2 | O | 3-$CF_3$-Phenyl | 422 | 2 | O | 4-$CF_3$-Phenyl |
| 147 | 3 | O | 3-$CF_3$-Phenyl | 423 | 3 | O | 4-$CF_3$-Phenyl |
| 148 | 1 | S | 3-$CF_3$-Phenyl | 424 | 1 | S | 4-$CF_3$-Phenyl |
| 149 | 2 | S | 3-$CF_3$-Phenyl | 425 | 2 | S | 4-$CF_3$-Phenyl |
| 150 | 3 | S | 3-$CF_3$-Phenyl | 426 | 3 | S | 4-$CF_3$-Phenyl |
| 151 | 1 | SO | 3-$CF_3$-Phenyl | 427 | 1 | SO | 4-$CF_3$-Phenyl |
| 152 | 2 | SO | 3-$CF_3$-Phenyl | 428 | 2 | SO | 4-$CF_3$-Phenyl |
| 153 | 3 | SO | 3-$CF_3$-Phenyl | 429 | 3 | SO | 4-$CF_3$-Phenyl |
| 154 | 1 | $SO_2$ | 3-$CF_3$-Phenyl | 430 | 1 | $SO_2$ | 4-$CF_3$-Phenyl |
| 155 | 2 | $SO_2$ | 3-$CF_3$-Phenyl | 431 | 2 | $SO_2$ | 4-$CF_3$-Phenyl |
| 156 | 3 | $SO_2$ | 3-$CF_3$-Phenyl | 432 | 3 | $SO_2$ | 4-$CF_3$-Phenyl |
| 157 | 1 | O | 2-iPr-Phenyl | 433 | 1 | O | 3-iPr-Phenyl |
| 158 | 2 | O | 2-iPr-Phenyl | 434 | 2 | O | 3-iPr-Phenyl |
| 159 | 3 | O | 2-iPr-Phenyl | 435 | 3 | O | 3-iPr-Phenyl |
| 160 | 1 | S | 2-iPr-Phenyl | 436 | 1 | S | 3-iPr-Phenyl |
| 161 | 2 | S | 2-iPr-Phenyl | 437 | 2 | S | 3-iPr-Phenyl |
| 162 | 3 | S | 2-iPr-Phenyl | 438 | 3 | S | 3-iPr-Phenyl |
| 163 | 1 | SO | 2-iPr-Phenyl | 439 | 1 | SO | 3-iPr-Phenyl |
| 164 | 2 | SO | 2-iPr-Phenyl | 440 | 2 | SO | 3-iPr-Phenyl |
| 165 | 3 | SO | 2-iPr-Phenyl | 441 | 3 | SO | 3-iPr-Phenyl |
| 166 | 1 | $SO_2$ | 2-iPr-Phenyl | 442 | 1 | $SO_2$ | 3-iPr-Phenyl |
| 167 | 2 | $SO_2$ | 2-iPr-Phenyl | 443 | 2 | $SO_2$ | 3-iPr-Phenyl |
| 168 | 3 | $SO_2$ | 2-iPr-Phenyl | 444 | 3 | $SO_2$ | 3-iPr-Phenyl |
| 169 | 1 | O | 4-iPr-Phenyl | 445 | 1 | O | 4-$NH_2$-Phenyl |
| 170 | 2 | O | 4-iPr-Phenyl | 446 | 2 | O | 4-$NH_2$-Phenyl |
| 171 | 3 | O | 4-iPr-Phenyl | 447 | 3 | O | 4-$NH_2$-Phenyl |
| 172 | 1 | S | 4-iPr-Phenyl | 448 | 1 | S | 4-$NH_2$-Phenyl |
| 173 | 2 | S | 4-iPr-Phenyl | 449 | 2 | S | 4-$NH_2$-Phenyl |
| 174 | 3 | S | 4-iPr-Phenyl | 450 | 3 | S | 4-$NH_2$-Phenyl |
| 175 | 1 | SO | 4-iPr-Phenyl | 451 | 1 | SO | 4-$NH_2$-Phenyl |
| 176 | 2 | SO | 4-iPr-Phenyl | 452 | 2 | SO | 4-$NH_2$-Phenyl |
| 177 | 3 | SO | 4-iPr-Phenyl | 453 | 3 | SO | 4-$NH_2$-Phenyl |
| 178 | 1 | $SO_2$ | 4-iPr-Phenyl | 454 | 1 | $SO_2$ | 4-$NH_2$-Phenyl |
| 179 | 2 | $SO_2$ | 4-iPr-Phenyl | 455 | 2 | $SO_2$ | 4-$NH_2$-Phenyl |
| 180 | 3 | $SO_2$ | 4-iPr-Phenyl | 456 | 3 | $SO_2$ | 4-$NH_2$-Phenyl |
| 181 | 1 | O | 3-$NH_2$-Phenyl | 457 | 1 | O | 2-$NH_2$-Phenyl |
| 182 | 2 | O | 3-$NH_2$-Phenyl | 458 | 2 | O | 2-$NH_2$-Phenyl |
| 183 | 3 | O | 3-$NH_2$-Phenyl | 459 | 3 | O | 2-$NH_2$-Phenyl |
| 184 | 1 | S | 3-$NH_2$-Phenyl | 460 | 1 | S | 2-$NH_2$-Phenyl |
| 185 | 2 | S | 3-$NH_2$-Phenyl | 461 | 2 | S | 2-$NH_2$-Phenyl |
| 186 | 3 | S | 3-$NH_2$-Phenyl | 462 | 3 | S | 2-$NH_2$-Phenyl |
| 187 | 1 | SO | 3-$NH_2$-Phenyl | 463 | 1 | SO | 2-$NH_2$-Phenyl |
| 188 | 2 | SO | 3-$NH_2$-Phenyl | 464 | 2 | SO | 2-$NH_2$-Phenyl |
| 189 | 3 | SO | 3-$NH_2$-Phenyl | 465 | 3 | SO | 2-$NH_2$-Phenyl |
| 190 | 1 | $SO_2$ | 3-$NH_2$-Phenyl | 466 | 1 | $SO_2$ | 2-$NH_2$-Phenyl |
| 191 | 2 | $SO_2$ | 3-$NH_2$-Phenyl | 467 | 2 | $SO_2$ | 2-$NH_2$-Phenyl |
| 192 | 3 | $SO_2$ | 3-$NH_2$-Phenyl | 468 | 3 | $SO_2$ | 2-$NH_2$-Phenyl |
| 193 | 1 | O | 2,4-di-Me-Phenyl | 469 | 1 | O | 2,6-di-Me-Phenyl |
| 194 | 2 | O | 2,4-di-Me-Phenyl | 470 | 2 | O | 2,6-di-Me-Phenyl |
| 195 | 3 | O | 2,4-di-Me-Phenyl | 471 | 3 | O | 2,6-di-Me-Phenyl |
| 196 | 1 | S | 2,4-di-Me-Phenyl | 472 | 1 | S | 2,6-di-Me-Phenyl |
| 197 | 2 | S | 2,4-di-Me-Phenyl | 473 | 2 | S | 2,6-di-Me-Phenyl |
| 198 | 3 | S | 2,4-di-Me-Phenyl | 474 | 3 | S | 2,6-di-Me-Phenyl |
| 199 | 1 | SO | 2,4-di-Me-Phenyl | 475 | 1 | SO | 2,6-di-Me-Phenyl |

TABLE 8-continued

| Entry | n | X | R³ | Entry | n | R | R³ |
|---|---|---|---|---|---|---|---|
| 200 | 2 | SO | 2,4-di-Me-Phenyl | 476 | 2 | SO | 2,6-di-Me-Phenyl |
| 201 | 3 | SO | 2,4-di-Me-Phenyl | 477 | 3 | SO | 2,6-di-Me-Phenyl |
| 202 | 1 | SO₂ | 2,4-di-Me-Phenyl | 478 | 1 | SO₂ | 2,6-di-Me-Phenyl |
| 203 | 2 | SO₂ | 2,4-di-Me-Phenyl | 479 | 2 | SO₂ | 2,6-di-Me-Phenyl |
| 204 | 3 | SO₂ | 2,4-di-Me-Phenyl | 480 | 3 | SO₂ | 2,6-di-Me-Phenyl |
| 205 | 1 | O | 2,6-di-iPr-Phenyl | 481 | 1 | O | 2-Ph-Phenyl |
| 206 | 2 | O | 2,6-di-iPr-Phenyl | 482 | 2 | O | 2-Ph-Phenyl |
| 207 | 3 | O | 2,6-di-iPr-Phenyl | 483 | 3 | O | 2-Ph-Phenyl |
| 208 | 1 | S | 2,6-di-iPr-Phenyl | 484 | 1 | S | 2-Ph-Phenyl |
| 209 | 2 | S | 2,6-di-iPr-Phenyl | 485 | 2 | S | 2-Ph-Phenyl |
| 210 | 3 | S | 2,6-di-iPr-Phenyl | 486 | 3 | S | 2-Ph-Phenyl |
| 211 | 1 | SO | 2,6-di-iPr-Phenyl | 487 | 1 | SO | 2-Ph-Phenyl |
| 212 | 2 | SO | 2,6-di-iPr-Phenyl | 488 | 2 | SO | 2-Ph-Phenyl |
| 213 | 3 | SO | 2,6-di-iPr-Phenyl | 489 | 3 | SO | 2-Ph-Phenyl |
| 214 | 1 | SO₂ | 2,6-di-iPr-Phenyl | 490 | 1 | SO₂ | 2-Ph-Phenyl |
| 215 | 2 | SO₂ | 2,6-di-iPr-Phenyl | 491 | 2 | SO₂ | 2-Ph-Phenyl |
| 216 | 3 | SO₂ | 2,6-di-iPr-Phenyl | 492 | 3 | SO₂ | 2-Ph-Phenyl |
| 217 | 1 | O | 3-Ph-Phenyl | 493 | 1 | O | 4-Ph-Phenyl |
| 218 | 2 | O | 3-Ph-Phenyl | 494 | 2 | O | 4-Ph-Phenyl |
| 219 | 3 | O | 3-Ph-Phenyl | 495 | 3 | O | 4-Ph-Phenyl |
| 220 | 1 | S | 3-Ph-Phenyl | 496 | 1 | S | 4-Ph-Phenyl |
| 221 | 2 | S | 3-Ph-Phenyl | 497 | 2 | S | 4-Ph-Phenyl |
| 222 | 3 | S | 3-Ph-Phenyl | 498 | 3 | S | 4-Ph-Phenyl |
| 223 | 1 | SO | 3-Ph-Phenyl | 499 | 1 | SO | 4-Ph-Phenyl |
| 224 | 2 | SO | 3-Ph-Phenyl | 500 | 2 | SO | 4-Ph-Phenyl |
| 225 | 3 | SO | 3-Ph-Phenyl | 501 | 3 | SO | 4-Ph-Phenyl |
| 226 | 1 | SO₂ | 3-Ph-Phenyl | 502 | 1 | SO₂ | 4-Ph-Phenyl |
| 227 | 2 | SO₂ | 3-Ph-Phenyl | 503 | 2 | SO₂ | 4-Ph-Phenyl |
| 228 | 3 | SO₂ | 3-Ph-Phenyl | 504 | 3 | SO₂ | 4-Ph-Phenyl |
| 229 | 1 | O | 2-morpholino-phenyl | 505 | 1 | O | 3-morpholino-phenyl |
| 230 | 2 | O | 2-morpholino-phenyl | 506 | 2 | O | 3-morpholino-phenyl |
| 231 | 3 | O | 2-morpholino-phenyl | 507 | 3 | O | 3-morpholino-phenyl |
| 232 | 1 | S | 2-morpholino-phenyl | 508 | 1 | S | 3-morpholino-phenyl |
| 233 | 2 | S | 2-morpholino-phenyl | 509 | 2 | S | 3-morpholino-phenyl |
| 234 | 3 | S | 2-morpholino-phenyl | 510 | 3 | S | 3-morpholino-phenyl |
| 235 | 1 | SO | 2-morpholino-phenyl | 511 | 1 | SO | 3-morpholino-phenyl |
| 236 | 2 | SO | 2-morpholino-phenyl | 512 | 2 | SO | 3-morpholino-phenyl |
| 237 | 3 | SO | 2-morpholino-phenyl | 513 | 3 | SO | 3-morpholino-phenyl |
| 238 | 1 | SO₂ | 2-morpholino-phenyl | 514 | 1 | SO₂ | 3-morpholino-phenyl |
| 239 | 2 | SO₂ | 2-morpholino-phenyl | 515 | 2 | SO₂ | 3-morpholino-phenyl |
| 240 | 3 | SO₂ | 2-morpholino-phenyl | 516 | 3 | SO₂ | 3-morpholino-phenyl |
| 241 | 1 | O | 4-morpholino-phenyl | 517 | 1 | O | 2-pyrazinyl |
| 242 | 2 | O | 4-morpholino-phenyl | 518 | 2 | O | 2-pyrazinyl |
| 243 | 3 | O | 4-morpholino-phenyl | 519 | 3 | O | 2-pyrazinyl |
| 244 | 1 | S | 4-morpholino-phenyl | 520 | 1 | S | 2-pyrazinyl |
| 245 | 2 | S | 4-morpholino-phenyl | 521 | 2 | S | 2-pyrazinyl |
| 246 | 3 | S | 4-morpholino-phenyl | 522 | 3 | S | 2-pyrazinyl |
| 247 | 1 | SO | 4-morpholino-phenyl | 523 | 1 | SO | 2-pyrazinyl |
| 248 | 2 | SO | 4-morpholino-phenyl | 524 | 2 | SO | 2-pyrazinyl |
| 249 | 3 | SO | 4-morpholino-phenyl | 525 | 3 | SO | 2-pyrazinyl |
| 250 | 1 | SO₂ | 4-morpholino-phenyl | 526 | 1 | SO₂ | 2-pyrazinyl |
| 251 | 2 | SO₂ | 4-morpholino-phenyl | 527 | 2 | SO₂ | 2-pyrazinyl |
| 252 | 3 | SO₂ | 4-morpholino-phenyl | 528 | 3 | SO₂ | 2-pyrazinyl |
| 253 | 1 | O | 2-pyrimidinyl | 529 | 1 | O | 5-indolyl |
| 254 | 2 | O | 2-pyrimidinyl | 530 | 2 | O | 5-indolyl |
| 255 | 3 | O | 2-pyrimidinyl | 531 | 3 | O | 5-indolyl |
| 256 | 1 | S | 2-pyrimidinyl | 532 | 1 | S | 5-indolyl |
| 257 | 2 | S | 2-pyrimidinyl | 533 | 2 | S | 5-indolyl |
| 258 | 3 | S | 2-pyrimidinyl | 534 | 3 | S | 5-indolyl |
| 259 | 1 | SO | 2-pyrimidinyl | 535 | 1 | SO | 5-indolyl |
| 260 | 2 | SO | 2-pyrimidinyl | 536 | 2 | SO | 5-indolyl |
| 261 | 3 | SO | 2-pyrimidinyl | 537 | 3 | SO | 5-indolyl |
| 262 | 1 | SO₂ | 2-pyrimidinyl | 538 | 1 | SO₂ | 5-indolyl |
| 263 | 2 | SO₂ | 2-pyrimidinyl | 539 | 2 | SO₂ | 5-indolyl |
| 264 | 3 | SO₂ | 2-pyrimidinyl | 540 | 3 | SO₂ | 5-indolyl |
| 265 | 1 | O | 2-methyl-1H-benzo[d]imidazol-4-yl | 541 | 1 | O | 1H-benzo[d]imidazol-4-yl |
| 266 | 2 | O | 2-methyl-1H-benzo[d]imidazol-4-yl | 542 | 2 | O | 1H-benzo[d]imidazol-4-yl |
| 267 | 3 | O | 2-methyl-1H-benzo[d]imidazol-4-yl | 543 | 3 | O | 1H-benzo[d]imidazol-4-yl |
| 268 | 1 | S | 2-methyl-1H-benzo[d]imidazol-4-yl | 544 | 1 | S | 1H-benzo[d]imidazol-4-yl |
| 269 | 2 | S | 2-methyl-1H-benzo[d]imidazol-4-yl | 545 | 2 | S | 1H-benzo[d]imidazol-4-yl |
| 270 | 3 | S | 2-methyl-1H-benzo[d]imidazol-4-yl | 546 | 3 | S | 1H-benzo[d]imidazol-4-yl |

TABLE 8-continued

| Entry | n | X | R³ | Entry | n | R | R³ |
|---|---|---|---|---|---|---|---|
| 271 | 1 | SO | 2-methyl-1H-benzo[d]imidazol-4-yl | 547 | 1 | SO | 1H-benzo[d]imidazol-4-yl |
| 272 | 2 | SO | 2-methyl-1H-benzo[d]imidazol-4-yl | 548 | 2 | SO | 1H-benzo[d]imidazol-4-yl |
| 273 | 3 | SO | 2-methyl-1H-benzo[d]imidazol-4-yl | 549 | 3 | SO | 1H-benzo[d]imidazol-4-yl |
| 274 | 1 | SO₂ | 2-methyl-1H-benzo[d]imidazol-4-yl | 550 | 1 | SO₂ | 1H-benzo[d]imidazol-4-yl |
| 275 | 2 | SO₂ | 2-methyl-1H-benzo[d]imidazol-4-yl | 551 | 2 | SO₂ | 1H-benzo[d]imidazol-4-yl |
| 276 | 3 | SO₂ | 2-methyl-1H-benzo[d]imidazol-4-yl | 552 | 3 | SO₂ | 1H-benzo[d]imidazol-4-yl |

Exemplary embodiments include compounds having the formula (XXV)

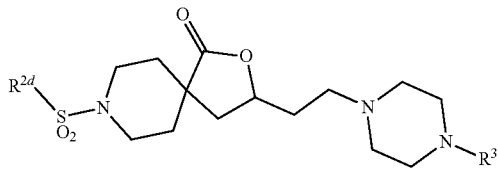

(XXV)

or a pharmaceutically acceptable salt form thereof defined heroin below in Table 9

TABLE 9

| Entry | R²ᵈ | R³ |
|---|---|---|
| 1 | ethyl | 4-CH₃-phenyl |
| 2 | n-propyl | 4-CH₃-phenyl |
| 3 | isopropyl | 4-CH₃-phenyl |
| 4 | —CH₂CH(CH₃)₂ | 4-CH₃-phenyl |
| 5 | CF₃ | 4-CH₃-phenyl |
| 6 | —CH₂CF₃ | 4-CH₃-phenyl |
| 7 | —CH₂CH₂CF₃ | 4-CH₃-phenyl |
| 8 | cyclopropyl | 4-CH₃-phenyl |
| 9 | Cyclobutyl | 4-CH₃-phenyl |
| 10 | cyclopentyl | 4-CH₃-phenyl |
| 11 | cyclohexyl | 4-CH₃-phenyl |
| 12 | 3-pyridyl | 4-CH₃-phenyl |
| 13 | 1-methyl-1H-pyrazol-4-yl | 4-CH₃-phenyl |
| 14 | 1H-imidazol-4-yl | 4-CH₃-phenyl |
| 15 | 2-furanyl | 4-CH₃-phenyl |
| 16 | ethyl | 3-CH₃-phenyl |
| 17 | n-propyl | 3-CH₃-phenyl |
| 18 | isopropyl | 3-CH₃-phenyl |
| 19 | —CH₂CH(CH₃)₂ | 3-CH₃-phenyl |
| 20 | —CF₃ | 3-CH₃-phenyl |
| 21 | —CH₂CF₃ | 3-CH₃-phenyl |
| 22 | —CH₂CH₂CF₃ | 3-CH₃-phenyl |
| 23 | cyclopropyl | 3-CH₃-phenyl |
| 24 | Cyclobutyl | 3-CH₃-phenyl |
| 25 | cyclopentyl | 3-CH₃-phenyl |
| 26 | cyclohexyl | 3-CH₃-phenyl |
| 27 | 3-pyridyl | 3-CH₃-phenyl |
| 28 | 1-methyl-1H-pyrazol-4-yl | 3-CH₃-phenyl |
| 29 | 1H-imidazol-4-yl | 3-CH₃-phenyl |
| 30 | 2-furanyl | 3-CH₃-phenyl |
| 31 | ethyl | 3-OH-Phenyl |
| 32 | n-propyl | 3-OH-Phenyl |
| 33 | isopropyl | 3-OH-Phenyl |
| 34 | —CH₂CH(CH₃)₂ | 3-OH-Phenyl |
| 35 | —CF₃ | 3-OH-Phenyl |
| 36 | —CH₂CF₃ | 3-OH-Phenyl |
| 37 | —CH₂CH₂CF₃ | 3-OH-Phenyl |
| 38 | cyclopropyl | 3-OH-Phenyl |
| 39 | Cyclobutyl | 3-OH-Phenyl |
| 40 | cyclopentyl | 3-OH-Phenyl |
| 41 | cyclohexyl | 3-OH-Phenyl |
| 42 | 3-pyridyl | 3-OH-Phenyl |
| 43 | 1-methyl-1H-pyrazol-4-yl | 3-OH-Phenyl |
| 44 | 1H-imidazol-4-yl | 3-OH-Phenyl |
| 45 | 2-furanyl | 3-OH-Phenyl |
| 46 | ethyl | 4-OMe-Phenyl |
| 47 | n-propyl | 4-OMe-Phenyl |
| 48 | isopropyl | 4-OMe-Phenyl |
| 49 | —CH₂CH(CH₃)₂ | 4-OMe-Phenyl |
| 50 | —CF₃ | 4-OMe-Phenyl |
| 51 | —CH₂CF₃ | 4-OMe-Phenyl |
| 52 | —CH₂CH₂CF₃ | 4-OMe-Phenyl |
| 53 | cyclopropyl | 4-OMe-Phenyl |
| 54 | Cyclobutyl | 4-OMe-Phenyl |
| 55 | cyclopentyl | 4-OMe-Phenyl |
| 56 | cyclohexyl | 4-OMe-Phenyl |
| 57 | 3-pyridyl | 4-OMe-Phenyl |
| 58 | 1-methyl-1H-pyrazol-4-yl | 4-OMe-Phenyl |
| 59 | 1H-imidazol-4-yl | 4-OMe-Phenyl |
| 60 | 2-furanyl | 4-OMe-Phenyl |
| 61 | ethyl | 2-OMe-Phenyl |
| 62 | n-propyl | 2-OMe-Phenyl |
| 63 | isopropyl | 2-OMe-Phenyl |
| 64 | —CH₂CH(CH₃)₂ | 2-OMe-Phenyl |
| 65 | —CF₃ | 2-OMe-Phenyl |
| 66 | —CH₂CF₃ | 2-OMe-Phenyl |
| 67 | —CH₂CH₂CF₃ | 2-OMe-Phenyl |
| 68 | cyclopropyl | 2-OMe-Phenyl |
| 69 | Cyclobutyl | 2-OMe-Phenyl |
| 70 | cyclopentyl | 2-OMe-Phenyl |
| 71 | cyclohexyl | 2-OMe-Phenyl |
| 72 | 3-pyridyl | 2-OMe-Phenyl |
| 73 | 1-methyl-1H-pyrazol-4-yl | 2-OMe-Phenyl |
| 74 | 1H-imidazol-4-yl | 2-OMe-Phenyl |
| 75 | 2-furanyl | 2-OMe-Phenyl |
| 76 | ethyl | 3-CN-Phenyl |
| 77 | n-propyl | 3-CN-Phenyl |
| 78 | isopropyl | 3-CN-Phenyl |
| 79 | —CH₂CH(CH₃)₂ | 3-CN-Phenyl |
| 80 | —CF₃ | 3-CN-Phenyl |
| 81 | —CH₂CF₃ | 3-CN-Phenyl |
| 82 | —CH₂CH₂CF₃ | 3-CN-Phenyl |
| 83 | cyclopropyl | 3-CN-Phenyl |
| 84 | Cyclobutyl | 3-CN-Phenyl |
| 85 | cyclopentyl | 3-CN-Phenyl |
| 86 | cyclohexyl | 3-CN-Phenyl |
| 87 | 3-pyridyl | 3-CN-Phenyl |
| 88 | 1-methyl-1H-pyrazol-4-yl | 3-CN-Phenyl |
| 89 | 1H-imidazol-4-yl | 3-CN-Phenyl |
| 90 | 2-furanyl | 3-CN-Phenyl |

TABLE 9-continued

| Entry | $R^{2d}$ | $R^3$ |
|---|---|---|
| 91 | ethyl | 2-F-Phenyl |
| 92 | n-propyl | 2-F-Phenyl |
| 93 | isopropyl | 2-F-Phenyl |
| 94 | —CH$_2$CH(CH$_3$)$_2$ | 2-F-Phenyl |
| 95 | —CF$_3$ | 2-F-Phenyl |
| 96 | —CH$_2$CF$_3$ | 2-F-Phenyl |
| 97 | —CH$_2$CH$_2$CF$_3$ | 2-F-Phenyl |
| 98 | cyclopropyl | 2-F-Phenyl |
| 99 | Cyclobutyl | 2-F-Phenyl |
| 100 | cyclopentyl | 2-F-Phenyl |
| 101 | cyclohexyl | 2-F-Phenyl |
| 102 | 3-pyridyl | 2-F-Phenyl |
| 103 | 1-methyl-1H-pyrazol-4-yl | 2-F-Phenyl |
| 104 | 1H-imidazol-4-yl | 2-F-Phenyl |
| 105 | 2-furanyl | 2-F-Phenyl |
| 106 | ethyl | 4-F-Phenyl |
| 107 | n-propyl | 4-F-Phenyl |
| 108 | isopropyl | 4-F-Phenyl |
| 109 | —CH$_2$CH(CH$_3$)$_2$ | 4-F-Phenyl |
| 110 | —CF$_3$ | 4-F-Phenyl |
| 111 | —CH$_2$CF$_3$ | 4-F-Phenyl |
| 112 | —CH$_2$CH$_2$CF$_3$ | 4-F-Phenyl |
| 113 | cyclopropyl | 4-F-Phenyl |
| 114 | Cyclobutyl | 4-F-Phenyl |
| 115 | cyclopentyl | 4-F-Phenyl |
| 116 | cyclohexyl | 4-F-Phenyl |
| 117 | 3-pyridyl | 4-F-Phenyl |
| 118 | 1-methyl-1H-pyrazol-4-yl | 4-F-Phenyl |
| 119 | 1H-imidazol-4-yl | 4-F-Phenyl |
| 120 | 2-furanyl | 4-F-Phenyl |
| 121 | ethyl | 3-Cl-Phenyl |
| 122 | n-propyl | 3-Cl-Phenyl |
| 123 | isopropyl | 3-Cl-Phenyl |
| 124 | —CH$_2$CH(CH$_3$)$_2$ | 3-Cl-Phenyl |
| 125 | —CF$_3$ | 3-Cl-Phenyl |
| 126 | —CH$_2$CF$_3$ | 3-Cl-Phenyl |
| 127 | —CH$_2$CH$_2$CF$_3$ | 3-Cl-Phenyl |
| 128 | cyclopropyl | 3-Cl-Phenyl |
| 129 | Cyclobutyl | 3-Cl-Phenyl |
| 130 | cyclopentyl | 3-Cl-Phenyl |
| 131 | cyclohexyl | 3-Cl-Phenyl |
| 132 | 3-pyridyl | 3-Cl-Phenyl |
| 133 | 1-methyl-1H-pyrazol-4-yl | 3-Cl-Phenyl |
| 134 | 1H-imidazol-4-yl | 3-Cl-Phenyl |
| 135 | 2-furanyl | 3-Cl-Phenyl |
| 136 | ethyl | 2-Br-Phenyl |
| 137 | n-propyl | 2-Br-Phenyl |
| 138 | isopropyl | 2-Br-Phenyl |
| 139 | —CH$_2$CH(CH$_3$)$_2$ | 2-Br-Phenyl |
| 140 | —CF$_3$ | 2-Br-Phenyl |
| 141 | —CH$_2$CF$_3$ | 2-Br-Phenyl |
| 142 | —CH$_2$CH$_2$CF$_3$ | 2-Br-Phenyl |
| 143 | cyclopropyl | 2-Br-Phenyl |
| 144 | Cyclobutyl | 2-Br-Phenyl |
| 145 | cyclopentyl | 2-Br-Phenyl |
| 146 | cyclohexyl | 2-Br-Phenyl |
| 147 | 3-pyridyl | 2-Br-Phenyl |
| 148 | 1-methyl-1H-pyrazol-4-yl | 2-Br-Phenyl |
| 149 | 1H-imidazol-4-yl | 2-Br-Phenyl |
| 150 | 2-furanyl | 2-Br-Phenyl |
| 151 | ethyl | 4-Br-Phenyl |
| 152 | n-propyl | 4-Br-Phenyl |
| 153 | isopropyl | 4-Br-Phenyl |
| 154 | —CH$_2$CH(CH$_3$)$_2$ | 4-Br-Phenyl |
| 155 | —CF$_3$ | 4-Br-Phenyl |
| 156 | —CH$_2$CF$_3$ | 4-Br-Phenyl |
| 157 | —CH$_2$CH$_2$CF$_3$ | 4-Br-Phenyl |
| 158 | cyclopropyl | 4-Br-Phenyl |
| 159 | Cyclobutyl | 4-Br-Phenyl |
| 160 | cyclopentyl | 4-Br-Phenyl |
| 161 | cyclohexyl | 4-Br-Phenyl |
| 162 | 3-pyridyl | 4-Br-Phenyl |
| 163 | 1-methyl-1H-pyrazol-4-yl | 4-Br-Phenyl |
| 164 | 1H-imidazol-4-yl | 4-Br-Phenyl |
| 165 | 2-furanyl | 4-Br-Phenyl |
| 166 | ethyl | 3-CF$_3$-Phenyl |
| 167 | n-propyl | 3-CF$_3$-Phenyl |
| 168 | isopropyl | 3-CF$_3$-Phenyl |
| 169 | —CH$_2$CH(CH$_3$)$_2$ | 3-CF$_3$-Phenyl |
| 170 | —CF$_3$ | 3-CF$_3$-Phenyl |
| 171 | —CH$_2$CF$_3$ | 3-CF$_3$-Phenyl |
| 172 | —CH$_2$CH$_2$CF$_3$ | 3-CF$_3$-Phenyl |
| 173 | cyclopropyl | 3-CF$_3$-Phenyl |
| 174 | Cyclobutyl | 3-CF$_3$-Phenyl |
| 175 | cyclopentyl | 3-CF$_3$-Phenyl |
| 176 | cyclohexyl | 3-CF$_3$-Phenyl |
| 177 | 3-pyridyl | 3-CF$_3$-Phenyl |
| 178 | 1-methyl-1H-pyrazol-4-yl | 3-CF$_3$-Phenyl |
| 179 | 1H-imidazol-4-yl | 3-CF$_3$-Phenyl |
| 180 | 2-furanyl | 3-CF$_3$-Phenyl |
| 181 | ethyl | 2-iPr-Phenyl |
| 182 | n-propyl | 2-iPr-Phenyl |
| 183 | isopropyl | 2-iPr-Phenyl |
| 184 | —CH$_2$CH(CH$_3$)$_2$ | 2-iPr-Phenyl |
| 185 | —CF$_3$ | 2-iPr-Phenyl |
| 186 | —CH$_2$CF$_3$ | 2-iPr-Phenyl |
| 187 | —CH$_2$CH$_2$CF$_3$ | 2-iPr-Phenyl |
| 188 | cyclopropyl | 2-iPr-Phenyl |
| 189 | Cyclobutyl | 2-iPr-Phenyl |
| 190 | cyclopentyl | 2-iPr-Phenyl |
| 191 | cyclohexyl | 2-iPr-Phenyl |
| 192 | 3-pyridyl | 2-iPr-Phenyl |
| 193 | 1-methyl-1H-pyrazol-4-yl | 2-iPr-Phenyl |
| 194 | 1H-imidazol-4-yl | 2-iPr-Phenyl |
| 195 | 2-furanyl | 2-iPr-Phenyl |
| 196 | ethyl | 4-iPr-Phenyl |
| 197 | n-propyl | 4-iPr-Phenyl |
| 198 | isopropyl | 4-iPr-Phenyl |
| 199 | —CH$_2$CH(CH$_3$)$_2$ | 4-iPr-Phenyl |
| 200 | —CF$_3$ | 4-iPr-Phenyl |
| 201 | —CH$_2$CF$_3$ | 4-iPr-Phenyl |
| 202 | —CH$_2$CH$_2$CF$_3$ | 4-iPr-Phenyl |
| 203 | cyclopropyl | 4-iPr-Phenyl |
| 204 | Cyclobutyl | 4-iPr-Phenyl |
| 205 | cyclopentyl | 4-iPr-Phenyl |
| 206 | cyclohexyl | 4-iPr-Phenyl |
| 207 | 3-pyridyl | 4-iPr-Phenyl |
| 208 | 1-methyl-1H-pyrazol-4-yl | 4-iPr-Phenyl |
| 209 | 1H-imidazol-4-yl | 4-iPr-Phenyl |
| 210 | 2-furanyl | 4-iPr-Phenyl |
| 211 | ethyl | 3-morpholino-phenyl |
| 212 | n-propyl | 3-morpholino-phenyl |
| 213 | isopropyl | 3-morpholino-phenyl |
| 214 | —CH$_2$CH(CH$_3$)$_2$ | 3-morpholino-phenyl |
| 215 | —CF$_3$ | 3-morpholino-phenyl |
| 216 | —CH$_2$CF$_3$ | 3-morpholino-phenyl |
| 217 | —CH$_2$CH$_2$CF$_3$ | 3-morpholino-phenyl |
| 218 | cyclopropyl | 3-morpholino-phenyl |
| 219 | Cyclobutyl | 3-morpholino-phenyl |
| 220 | cyclopentyl | 3-morpholino-phenyl |
| 221 | cyclohexyl | 3-morpholino-phenyl |
| 222 | 3-pyridyl | 3-morpholino-phenyl |
| 223 | 1-methyl-1H-pyrazol-4-yl | 3-morpholino-phenyl |
| 224 | 1H-imidazol-4-yl | 3-morpholino-phenyl |
| 225 | 2-furanyl | 3-morpholino-phenyl |
| 226 | ethyl | 4-cyano-2-morpholino-phenyl |
| 227 | n-propyl | 4-cyano-2-morpholino-phenyl |
| 228 | isopropyl | 4-cyano-2-morpholino-phenyl |
| 229 | —CH$_2$CH(CH$_3$)$_2$ | 4-cyano-2-morpholino-phenyl |
| 230 | —CF$_3$ | 4-cyano-2-morpholino-phenyl |
| 231 | —CH$_2$CF$_3$ | 4-cyano-2-morpholino-phenyl |

TABLE 9-continued

| Entry | R$^{2d}$ | R$^3$ |
|---|---|---|
| 232 | —CH$_2$CH$_2$CF$_3$ | 4-cyano-2-morpholino-phenyl |
| 233 | cyclopropyl | 4-cyano-2-morpholino-phenyl |
| 234 | Cyclobutyl | 4-cyano-2-morpholino-phenyl |
| 235 | cyclopentyl | 4-cyano-2-morpholino-phenyl |
| 236 | cyclohexyl | 4-cyano-2-morpholino-phenyl |
| 237 | 3-pyridyl | 4-cyano-2-morpholino-phenyl |
| 238 | 1-methyl-1H-pyrazol-4-yl | 4-cyano-2-morpholino-phenyl |
| 239 | 1H-imidazol-4-yl | 4-cyano-2-morpholino-phenyl |
| 240 | 2-furanyl | 4-cyano-2-morpholino-phenyl |
| 241 | ethyl | 4-hydroxy-2-morpholino-phenyl |
| 242 | n-propyl | 4-hydroxy-2-morpholino-phenyl |
| 243 | isopropyl | 4-hydroxy-2-morpholino-phenyl |
| 244 | —CH$_2$CH(CH$_3$)$_2$ | 4-hydroxy-2-morpholino-phenyl |
| 245 | —CF$_3$ | 4-hydroxy-2-morpholino-phenyl |
| 246 | —CH$_2$CF$_3$ | 4-hydroxy-2-morpholino-phenyl |
| 247 | —CH$_2$CH$_2$CF$_3$ | 4-hydroxy-2-morpholino-phenyl |
| 248 | cyclopropyl | 4-hydroxy-2-morpholino-phenyl |
| 249 | Cyclobutyl | 4-hydroxy-2-morpholino-phenyl |
| 250 | cyclopentyl | 4-hydroxy-2-morpholino-phenyl |
| 251 | cyclohexyl | 4-hydroxy-2-morpholino-phenyl |
| 252 | 3-pyridyl | 4-hydroxy-2-morpholino-phenyl |
| 253 | 1-methyl-1H-pyrazol-4-yl | 4-hydroxy-2-morpholino-phenyl |
| 254 | 1H-imidazol-4-yl | 4-hydroxy-2-morpholino-phenyl |
| 255 | 2-furanyl | 4-hydroxy-2-morpholino-phenyl |
| 256 | ethyl | 2-CH$_3$-phenyl |
| 257 | n-propyl | 2-CH$_3$-phenyl |
| 258 | isopropyl | 2-CH$_3$-phenyl |
| 259 | —CH$_2$CH(CH$_3$)$_2$ | 2-CH$_3$-phenyl |
| 260 | CF$_3$ | 2-CH$_3$-phenyl |
| 261 | —CH$_2$CF$_3$ | 2-CH$_3$-phenyl |
| 262 | —CH$_2$CH$_2$CF$_3$ | 2-CH$_3$-phenyl |
| 263 | cyclopropyl | 2-CH$_3$-phenyl |
| 264 | Cyclobutyl | 2-CH$_3$-phenyl |
| 265 | cyclopentyl | 2-CH$_3$-phenyl |
| 266 | cyclohexyl | 2-CH$_3$-phenyl |
| 267 | 3-pyridyl | 2-CH$_3$-phenyl |
| 268 | 1-methyl-1H-pyrazol-4-yl | 2-CH$_3$-phenyl |
| 269 | 1H-imidazol-4-yl | 2-CH$_3$-phenyl |
| 270 | 2-furanyl | 2-CH$_3$-phenyl |
| 271 | ethyl | 4-OH-Phenyl |
| 272 | n-propyl | 4-OH-Phenyl |
| 273 | isopropyl | 4-OH-Phenyl |
| 274 | —CH$_2$CH(CH$_3$)$_2$ | 4-OH-Phenyl |
| 275 | —CF$_3$ | 4-OH-Phenyl |
| 276 | —CH$_2$CF$_3$ | 4-OH-Phenyl |
| 277 | —CH$_2$CH$_2$CF$_3$ | 4-OH-Phenyl |
| 278 | cyclopropyl | 4-OH-Phenyl |
| 279 | Cyclobutyl | 4-OH-Phenyl |
| 280 | cyclopentyl | 4-OH-Phenyl |
| 281 | cyclohexyl | 4-OH-Phenyl |
| 282 | 3-pyridyl | 4-OH-Phenyl |
| 283 | 1-methyl-1H-pyrazol-4-yl | 4-OH-Phenyl |
| 284 | 1H-imidazol-4-yl | 4-OH-Phenyl |
| 285 | 2-furanyl | 4-OH-Phenyl |
| 286 | ethyl | 2-OH-Phenyl |
| 287 | n-propyl | 2-OH-Phenyl |
| 288 | isopropyl | 2-OH-Phenyl |
| 289 | —CH$_2$CH(CH$_3$)$_2$ | 2-OH-Phenyl |
| 290 | —CF$_3$ | 2-OH-Phenyl |
| 291 | —CH$_2$CF$_3$ | 2-OH-Phenyl |
| 292 | —CH$_2$CH$_2$CF$_3$ | 2-OH-Phenyl |
| 293 | cyclopropyl | 2-OH-Phenyl |
| 294 | Cyclobutyl | 2-OH-Phenyl |
| 295 | cyclopentyl | 2-OH-Phenyl |
| 296 | cyclohexyl | 2-OH-Phenyl |
| 297 | 3-pyridyl | 2-OH-Phenyl |
| 298 | 1-methyl-1H-pyrazol-4-yl | 2-OH-Phenyl |
| 299 | 1H-imidazol-4-yl | 2-OH-Phenyl |
| 300 | 2-furanyl | 2-OH-Phenyl |
| 301 | ethyl | 3-OMe-Phenyl |
| 302 | n-propyl | 3-OMe-Phenyl |
| 303 | isopropyl | 3-OMe-Phenyl |
| 304 | —CH$_2$CH(CH$_3$)$_2$ | 3-OMe-Phenyl |
| 305 | —CF$_3$ | 3-OMe-Phenyl |
| 306 | —CH$_2$CF$_3$ | 3-OMe-Phenyl |
| 307 | —CH$_2$CH$_2$CF$_3$ | 3-OMe-Phenyl |
| 308 | cyclopropyl | 3-OMe-Phenyl |
| 309 | Cyclobutyl | 3-OMe-Phenyl |
| 310 | cyclopentyl | 3-OMe-Phenyl |
| 311 | cyclohexyl | 3-OMe-Phenyl |
| 312 | 3-pyridyl | 3-OMe-Phenyl |
| 313 | 1-methyl-1H-pyrazol-4-yl | 3-OMe-Phenyl |
| 314 | 1H-imidazol-4-yl | 3-OMe-Phenyl |
| 315 | 2-furanyl | 3-OMe-Phenyl |
| 316 | ethyl | 4-CN-Phenyl |
| 317 | n-propyl | 4-CN-Phenyl |
| 318 | isopropyl | 4-CN-Phenyl |
| 319 | —CH$_2$CH(CH$_3$)$_2$ | 4-CN-Phenyl |
| 320 | —CF$_3$ | 4-CN-Phenyl |
| 321 | —CH$_2$CF$_3$ | 4-CN-Phenyl |
| 322 | —CH$_2$CH$_2$CF$_3$ | 4-CN-Phenyl |
| 323 | cyclopropyl | 4-CN-Phenyl |
| 324 | Cyclobutyl | 4-CN-Phenyl |
| 325 | cyclopentyl | 4-CN-Phenyl |
| 326 | cyclohexyl | 4-CN-Phenyl |
| 327 | 3-pyridyl | 4-CN-Phenyl |
| 328 | 1-methyl-1H-pyrazol-4-yl | 4-CN-Phenyl |
| 329 | 1H-imidazol-4-yl | 4-CN-Phenyl |
| 330 | 2-furanyl | 4-CN-Phenyl |
| 331 | ethyl | 2-CN-Phenyl |
| 332 | n-propyl | 2-CN-Phenyl |
| 333 | isopropyl | 2-CN-Phenyl |
| 334 | —CH$_2$CH(CH$_3$)$_2$ | 2-CN-Phenyl |
| 335 | —CF$_3$ | 2-CN-Phenyl |
| 336 | —CH$_2$CF$_3$ | 2-CN-Phenyl |
| 337 | —CH$_2$CH$_2$CF$_3$ | 2-CN-Phenyl |
| 338 | cyclopropyl | 2-CN-Phenyl |
| 339 | Cyclobutyl | 2-CN-Phenyl |
| 340 | cyclopentyl | 2-CN-Phenyl |
| 341 | cyclohexyl | 2-CN-Phenyl |
| 342 | 3-pyridyl | 2-CN-Phenyl |
| 343 | 1-methyl-1H-pyrazol-4-yl | 2-CN-Phenyl |
| 344 | 1H-imidazol-4-yl | 2-CN-Phenyl |
| 345 | 2-furanyl | 2-CN-Phenyl |
| 346 | ethyl | 3-F-Phenyl |
| 347 | n-propyl | 3-F-Phenyl |
| 348 | isopropyl | 3-F-Phenyl |
| 349 | —CH$_2$CH(CH$_3$)$_2$ | 3-F-Phenyl |
| 350 | —CF$_3$ | 3-F-Phenyl |
| 351 | —CH$_2$CF$_3$ | 3-F-Phenyl |
| 352 | —CH$_2$CH$_2$CF$_3$ | 3-F-Phenyl |
| 353 | cyclopropyl | 3-F-Phenyl |
| 354 | Cyclobutyl | 3-F-Phenyl |
| 355 | cyclopentyl | 3-F-Phenyl |
| 356 | cyclohexyl | 3-F-Phenyl |
| 357 | 3-pyridyl | 3-F-Phenyl |

TABLE 9-continued

| Entry | R²ᵈ | R³ |
|---|---|---|
| 358 | 1-methyl-1H-pyrazol-4-yl | 3-F-Phenyl |
| 359 | 1H-imidazol-4-yl | 3-F-Phenyl |
| 360 | 2-furanyl | 3-F-Phenyl |
| 361 | ethyl | 2-Cl-Phenyl |
| 362 | n-propyl | 2-Cl-Phenyl |
| 363 | isopropyl | 2-Cl-Phenyl |
| 364 | —CH$_2$CH(CH$_3$)$_2$ | 2-Cl-Phenyl |
| 365 | —CF$_3$ | 2-Cl-Phenyl |
| 366 | —CH$_2$CF$_3$ | 2-Cl-Phenyl |
| 367 | —CH$_2$CH$_2$CF$_3$ | 2-Cl-Phenyl |
| 368 | cyclopropyl | 2-Cl-Phenyl |
| 369 | Cyclobutyl | 2-Cl-Phenyl |
| 370 | cyclopentyl | 2-Cl-Phenyl |
| 371 | cyclohexyl | 2-Cl-Phenyl |
| 372 | 3-pyridyl | 2-Cl-Phenyl |
| 373 | 1-methyl-1H-pyrazol-4-yl | 2-Cl-Phenyl |
| 374 | 1H-imidazol-4-yl | 2-Cl-Phenyl |
| 375 | 2-furanyl | 2-Cl-Phenyl |
| 376 | ethyl | 4-Cl-Phenyl |
| 377 | n-propyl | 4-Cl-Phenyl |
| 378 | isopropyl | 4-Cl-Phenyl |
| 379 | —CH$_2$CH(CH$_3$)$_2$ | 4-Cl-Phenyl |
| 380 | —CF$_3$ | 4-Cl-Phenyl |
| 381 | —CH$_2$CF$_3$ | 4-Cl-Phenyl |
| 382 | —CH$_2$CH$_2$CF$_3$ | 4-Cl-Phenyl |
| 383 | cyclopropyl | 4-Cl-Phenyl |
| 384 | Cyclobutyl | 4-Cl-Phenyl |
| 385 | cyclopentyl | 4-Cl-Phenyl |
| 386 | cyclohexyl | 4-Cl-Phenyl |
| 387 | 3-pyridyl | 4-Cl-Phenyl |
| 388 | 1-methyl-1H-pyrazol-4-yl | 4-Cl-Phenyl |
| 389 | 1H-imidazol-4-yl | 4-Cl-Phenyl |
| 390 | 2-furanyl | 4-Cl-Phenyl |
| 391 | ethyl | 3-Br-Phenyl |
| 392 | n-propyl | 3-Br-Phenyl |
| 393 | isopropyl | 3-Br-Phenyl |
| 394 | —CH$_2$CH(CH$_3$)$_2$ | 3-Br-Phenyl |
| 395 | —CF$_3$ | 3-Br-Phenyl |
| 396 | —CH$_2$CF$_3$ | 3-Br-Phenyl |
| 397 | —CH$_2$CH$_2$CF$_3$ | 3-Br-Phenyl |
| 398 | cyclopropyl | 3-Br-Phenyl |
| 399 | Cyclobutyl | 3-Br-Phenyl |
| 400 | cyclopentyl | 3-Br-Phenyl |
| 401 | cyclohexyl | 3-Br-Phenyl |
| 402 | 3-pyridyl | 3-Br-Phenyl |
| 403 | 1-methyl-1H-pyrazol-4-yl | 3-Br-Phenyl |
| 404 | 1H-imidazol-4-yl | 3-Br-Phenyl |
| 405 | 2-furanyl | 3-Br-Phenyl |
| 406 | ethyl | 2-CF$_3$-Phenyl |
| 407 | n-propyl | 2-CF$_3$-Phenyl |
| 408 | isopropyl | 2-CF$_3$-Phenyl |
| 409 | —CH$_2$CH(CH$_3$)$_2$ | 2-CF$_3$-Phenyl |
| 410 | —CF$_3$ | 2-CF$_3$-Phenyl |
| 411 | —CH$_2$CF$_3$ | 2-CF$_3$-Phenyl |
| 412 | —CH$_2$CH$_2$CF$_3$ | 2-CF$_3$-Phenyl |
| 413 | cyclopropyl | 2-CF$_3$-Phenyl |
| 414 | Cyclobutyl | 2-CF$_3$-Phenyl |
| 415 | cyclopentyl | 2-CF$_3$-Phenyl |
| 416 | cyclohexyl | 2-CF$_3$-Phenyl |
| 417 | 3-pyridyl | 2-CF$_3$-Phenyl |
| 418 | 1-methyl-1H-pyrazol-4-yl | 2-CF$_3$-Phenyl |
| 419 | 1H-imidazol-4-yl | 2-CF$_3$-Phenyl |
| 420 | 2-furanyl | 2-CF$_3$-Phenyl |
| 421 | ethyl | 4-CF$_3$-Phenyl |
| 422 | n-propyl | 4-CF$_3$-Phenyl |
| 423 | isopropyl | 4-CF$_3$-Phenyl |
| 424 | —CH$_2$CH(CH$_3$)$_2$ | 4-CF$_3$-Phenyl |
| 425 | —CF$_3$ | 4-CF$_3$-Phenyl |
| 426 | —CH$_2$CF$_3$ | 4-CF$_3$-Phenyl |
| 427 | —CH$_2$CH$_2$CF$_3$ | 4-CF$_3$-Phenyl |
| 428 | cyclopropyl | 4-CF$_3$-Phenyl |
| 429 | Cyclobutyl | 4-CF$_3$-Phenyl |
| 430 | cyclopentyl | 4-CF$_3$-Phenyl |
| 431 | cyclohexyl | 4-CF$_3$-Phenyl |
| 432 | 3-pyridyl | 4-CF$_3$-Phenyl |
| 433 | 1-methyl-1H-pyrazol-4-yl | 4-CF$_3$-Phenyl |
| 434 | 1H-imidazol-4-yl | 4-CF$_3$-Phenyl |
| 435 | 2-furanyl | 4-CF$_3$-Phenyl |
| 436 | ethyl | 3-iPr-Phenyl |
| 437 | n-propyl | 3-iPr-Phenyl |
| 438 | isopropyl | 3-iPr-Phenyl |
| 439 | —CH$_2$CH(CH$_3$)$_2$ | 3-iPr-Phenyl |
| 440 | —CF$_3$ | 3-iPr-Phenyl |
| 441 | —CH$_2$CF$_3$ | 3-iPr-Phenyl |
| 442 | —CH$_2$CH$_2$CF$_3$ | 3-iPr-Phenyl |
| 443 | cyclopropyl | 3-iPr-Phenyl |
| 444 | Cyclobutyl | 3-iPr-Phenyl |
| 445 | cyclopentyl | 3-iPr-Phenyl |
| 446 | cyclohexyl | 3-iPr-Phenyl |
| 447 | 3-pyridyl | 3-iPr-Phenyl |
| 448 | 1-methyl-1H-pyrazol-4-yl | 3-iPr-Phenyl |
| 449 | 1H-imidazol-4-yl | 3-iPr-Phenyl |
| 450 | 2-furanyl | 3-iPr-Phenyl |
| 451 | ethyl | 2-morpholino-phenyl |
| 452 | n-propyl | 2-morpholino-phenyl |
| 453 | isopropyl | 2-morpholino-phenyl |
| 454 | —CH$_2$CH(CH$_3$)$_2$ | 2-morpholino-phenyl |
| 455 | —CF$_3$ | 2-morpholino-phenyl |
| 456 | —CH$_2$CF$_3$ | 2-morpholino-phenyl |
| 457 | —CH$_2$CH$_2$CF$_3$ | 2-morpholino-phenyl |
| 458 | cyclopropyl | 2-morpholino-phenyl |
| 459 | Cyclobutyl | 2-morpholino-phenyl |
| 460 | cyclopentyl | 2-morpholino-phenyl |
| 461 | cyclohexyl | 2-morpholino-phenyl |
| 462 | 3-pyridyl | 2-morpholino-phenyl |
| 463 | 1-methyl-1H-pyrazol-4-yl | 2-morpholino-phenyl |
| 464 | 1H-imidazol-4-yl | 2-morpholino-phenyl |
| 465 | 2-furanyl | 2-morpholino-phenyl |
| 466 | ethyl | 4-morpholino-phenyl |
| 467 | n-propyl | 4-morpholino-phenyl |
| 468 | isopropyl | 4-morpholino-phenyl |
| 469 | —CH$_2$CH(CH$_3$)$_2$ | 4-morpholino-phenyl |
| 470 | —CF$_3$ | 4-morpholino-phenyl |
| 471 | —CH$_2$CF$_3$ | 4-morpholino-phenyl |
| 472 | —CH$_2$CH$_2$CF$_3$ | 4-morpholino-phenyl |
| 473 | cyclopropyl | 4-morpholino-phenyl |
| 474 | Cyclobutyl | 4-morpholino-phenyl |
| 475 | cyclopentyl | 4-morpholino-phenyl |
| 476 | cyclohexyl | 4-morpholino-phenyl |
| 477 | 3-pyridyl | 4-morpholino-phenyl |
| 478 | 1-methyl-1H-pyrazol-4-yl | 4-morpholino-phenyl |

TABLE 9-continued

| Entry | $R^{2d}$ | $R^3$ |
| --- | --- | --- |
| 479 | 1H-imidazol-4-yl | 4-morpholino-phenyl |
| 480 | 2-furanyl | 4-morpholino-phenyl |
| 481 | ethyl | 4-methyl-2-morpholino-phenyl |
| 482 | n-propyl | 4-methyl-2-morpholino-phenyl |
| 483 | isopropyl | 4-methyl-2-morpholino-phenyl |
| 484 | —CH$_2$CH(CH$_3$)$_2$ | 4-methyl-2-morpholino-phenyl |
| 485 | —CF$_3$ | 4-methyl-2-morpholino-phenyl |
| 486 | —CH$_2$CF$_3$ | 4-methyl-2-morpholino-phenyl |
| 487 | —CH$_2$CH$_2$CF$_3$ | 4-methyl-2-morpholino-phenyl |
| 488 | cyclopropyl | 4-methyl-2-morpholino-phenyl |
| 489 | Cyclobutyl | 4-methyl-2-morpholino-phenyl |
| 490 | cyclopentyl | 4-methyl-2-morpholino-phenyl |
| 491 | cyclohexyl | 4-methyl-2-morpholino-phenyl |
| 492 | 3-pyridyl | 4-methyl-2-morpholino-pheny |
| 493 | 1-methyl-1H-pyrazol-4-yl | 4-methyl-2-morpholino-phenyl |
| 494 | 1H-imidazol-4-yl | 4-methyl-2-morpholino-phenyl |
| 495 | 2-furanyl | 4-methyl-2-morpholino-phenyl |

Exemplary embodiments include compounds having the formula (XXVI)

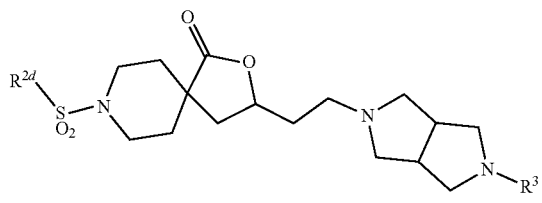

(XXVI)

or a pharmaceutically acceptable salt form thereof defined herein below in Table 10.

TABLE 10

| Entry | $R^{2d}$ | $R^3$ |
| --- | --- | --- |
| 1 | ethyl | 4-CH$_3$-phenyl |
| 2 | n-propyl | 4-CH$_3$-phenyl |
| 3 | isopropyl | 4-CH$_3$-phenyl |
| 4 | —CH$_2$CH(CH$_3$)$_2$ | 4-CH$_3$-phenyl |
| 5 | CF$_3$ | 4-CH$_3$-phenyl |
| 6 | —CH$_2$CF$_3$ | 4-CH$_3$-phenyl |
| 7 | —CH$_2$CH$_2$CF$_3$ | 4-CH$_3$-phenyl |
| 8 | cyclopropyl | 4-CH$_3$-phenyl |
| 9 | Cyclobutyl | 4-CH$_3$-phenyl |
| 10 | cyclopentyl | 4-CH$_3$-phenyl |
| 11 | cyclohexyl | 4-CH$_3$-phenyl |
| 12 | 3-pyridyl | 4-CH$_3$-phenyl |
| 13 | 1-methyl-1H-pyrazol-4-yl | 4-CH$_3$-phenyl |
| 14 | 1H-imidazol-4-yl | 4-CH$_3$-phenyl |
| 15 | 2-furanyl | 4-CH$_3$-phenyl |
| 16 | ethyl | 3-CH$_3$-phenyl |
| 17 | n-propyl | 3-CH$_3$-phenyl |
| 18 | isopropyl | 3-CH$_3$-phenyl |
| 19 | —CH$_2$CH(CH$_3$)$_2$ | 3-CH$_3$-phenyl |
| 20 | —CF$_3$ | 3-CH$_3$-phenyl |
| 21 | —CH$_2$CF$_3$ | 3-CH$_3$-phenyl |
| 22 | —CH$_2$CH$_2$CF$_3$ | 3-CH$_3$-phenyl |
| 23 | cyclopropyl | 3-CH$_3$-phenyl |
| 24 | Cyclobutyl | 3-CH$_3$-phenyl |
| 25 | cyclopentyl | 3-CH$_3$-phenyl |
| 26 | cyclohexyl | 3-CH$_3$-phenyl |
| 27 | 3-pyridyl | 3-CH$_3$-phenyl |
| 28 | 1-methyl-1H-pyrazol-4-yl | 3-CH$_3$-phenyl |
| 29 | 1H-imidazol-4-yl | 3-CH$_3$-phenyl |
| 30 | 2-furanyl | 3-CH$_3$-phenyl |
| 31 | ethyl | 3-OH-Phenyl |
| 32 | n-propyl | 3-OH-Phenyl |
| 33 | isopropyl | 3-OH-Phenyl |
| 34 | —CH$_2$CH(CH$_3$)$_2$ | 3-OH-Phenyl |
| 35 | —CF$_3$ | 3-OH-Phenyl |
| 36 | —CH$_2$CF$_3$ | 3-OH-Phenyl |
| 37 | —CH$_2$CH$_2$CF$_3$ | 3-OH-Phenyl |
| 38 | cyclopropyl | 3-OH-Phenyl |
| 39 | Cyclobutyl | 3-OH-Phenyl |
| 40 | cyclopentyl | 3-OH-Phenyl |
| 41 | cyclohexyl | 3-OH-Phenyl |
| 42 | 3-pyridyl | 3-OH-Phenyl |
| 43 | 1-methyl-1H-pyrazol-4-yl | 3-OH-Phenyl |
| 44 | 1H-imidazol-4-yl | 3-OH-Phenyl |
| 45 | 2-furanyl | 3-OH-Phenyl |
| 46 | ethyl | 4-OMe-Phenyl |
| 47 | n-propyl | 4-OMe-Phenyl |
| 48 | isopropyl | 4-OMe-Phenyl |
| 49 | —CH$_2$CH(CH$_3$)$_2$ | 4-OMe-Phenyl |
| 50 | —CF$_3$ | 4-OMe-Phenyl |
| 51 | —CH$_2$CF$_3$ | 4-OMe-Phenyl |
| 52 | —CH$_2$CH$_2$CF$_3$ | 4-OMe-Phenyl |
| 53 | cyclopropyl | 4-OMe-Phenyl |
| 54 | Cyclobutyl | 4-OMe-Phenyl |
| 55 | cyclopentyl | 4-OMe-Phenyl |
| 56 | cyclohexyl | 4-OMe-Phenyl |
| 57 | 3-pyridyl | 4-OMe-Phenyl |
| 58 | 1-methyl-1H-pyrazol-4-yl | 4-OMe-Phenyl |
| 59 | 1H-imidazol-4-yl | 4-OMe-Phenyl |
| 60 | 2-furanyl | 4-OMe-Phenyl |
| 61 | ethyl | 2-OMe-Phenyl |
| 62 | n-propyl | 2-OMe-Phenyl |
| 63 | isopropyl | 2-OMe-Phenyl |
| 64 | —CH$_2$CH(CH$_3$)$_2$ | 2-OMe-Phenyl |
| 65 | —CF$_3$ | 2-OMe-Phenyl |
| 66 | —CH$_2$CF$_3$ | 2-OMe-Phenyl |
| 67 | —CH$_2$CH$_2$CF$_3$ | 2-OMe-Phenyl |
| 68 | cyclopropyl | 2-OMe-Phenyl |
| 69 | Cyclobutyl | 2-OMe-Phenyl |
| 70 | cyclopentyl | 2-OMe-Phenyl |
| 71 | cyclohexyl | 2-OMe-Phenyl |
| 72 | 3-pyridyl | 2-OMe-Phenyl |
| 73 | 1-methyl-1H-pyrazol-4-yl | 2-OMe-Phenyl |
| 74 | 1H-imidazol-4-yl | 2-OMe-Phenyl |
| 75 | 2-furanyl | 2-OMe-Phenyl |
| 76 | ethyl | 3-CN-Phenyl |
| 77 | n-propyl | 3-CN-Phenyl |
| 78 | isopropyl | 3-CN-Phenyl |
| 79 | —CH$_2$CH(CH$_3$)$_2$ | 3-CN-Phenyl |
| 80 | —CF$_3$ | 3-CN-Phenyl |
| 81 | —CH$_2$CF$_3$ | 3-CN-Phenyl |
| 82 | —CH$_2$CH$_2$CF$_3$ | 3-CN-Phenyl |
| 83 | cyclopropyl | 3-CN-Phenyl |
| 84 | Cyclobutyl | 3-CN-Phenyl |
| 85 | cyclopentyl | 3-CN-Phenyl |
| 86 | cyclohexyl | 3-CN-Phenyl |
| 87 | 3-pyridyl | 3-CN-Phenyl |
| 88 | 1-methyl-1H-pyrazol-4-yl | 3-CN-Phenyl |
| 89 | 1H-imidazol-4-yl | 3-CN-Phenyl |

TABLE 10-continued

| Entry | R²ᵈ | R³ |
|---|---|---|
| 90 | 2-furanyl | 3-CN-Phenyl |
| 91 | ethyl | 2-F-Phenyl |
| 92 | n-propyl | 2-F-Phenyl |
| 93 | isopropyl | 2-F-Phenyl |
| 94 | —CH₂CH(CH₃)₂ | 2-F-Phenyl |
| 95 | —CF₃ | 2-F-Phenyl |
| 96 | —CH₂CF₃ | 2-F-Phenyl |
| 97 | —CH₂CH₂CF₃ | 2-F-Phenyl |
| 98 | cyclopropyl | 2-F-Phenyl |
| 99 | Cyclobutyl | 2-F-Phenyl |
| 100 | cyclopentyl | 2-F-Phenyl |
| 101 | cyclohexyl | 2-F-Phenyl |
| 102 | 3-pyridyl | 2-F-Phenyl |
| 103 | 1-methyl-1H-pyrazol-4-yl | 2-F-Phenyl |
| 104 | 1H-imidazol-4-yl | 2-F-Phenyl |
| 105 | 2-furanyl | 2-F-Phenyl |
| 106 | ethyl | 4-F-Phenyl |
| 107 | n-propyl | 4-F-Phenyl |
| 108 | isopropyl | 4-F-Phenyl |
| 109 | —CH₂CH(CH₃)₂ | 4-F-Phenyl |
| 110 | —CF₃ | 4-F-Phenyl |
| 111 | —CH₂CF₃ | 4-F-Phenyl |
| 112 | —CH₂CH₂CF₃ | 4-F-Phenyl |
| 113 | cyclopropyl | 4-F-Phenyl |
| 114 | Cyclobutyl | 4-F-Phenyl |
| 115 | cyclopentyl | 4-F-Phenyl |
| 116 | cyclohexyl | 4-F-Phenyl |
| 117 | 3-pyridyl | 4-F-Phenyl |
| 118 | 1-methyl-1H-pyrazol-4-yl | 4-F-Phenyl |
| 119 | 1H-imidazol-4-yl | 4-F-Phenyl |
| 120 | 2-furanyl | 4-F-Phenyl |
| 121 | ethyl | 3-Cl-Phenyl |
| 122 | n-propyl | 3-Cl-Phenyl |
| 123 | isopropyl | 3-Cl-Phenyl |
| 124 | —CH₂CH(CH₃)₂ | 3-Cl-Phenyl |
| 125 | —CF₃ | 3-Cl-Phenyl |
| 126 | —CH₂CF₃ | 3-Cl-Phenyl |
| 127 | —CH₂CH₂CF₃ | 3-Cl-Phenyl |
| 128 | cyclopropyl | 3-Cl-Phenyl |
| 129 | Cyclobutyl | 3-Cl-Phenyl |
| 130 | cyclopentyl | 3-Cl-Phenyl |
| 131 | cyclohexyl | 3-Cl-Phenyl |
| 132 | 3-pyridyl | 3-Cl-Phenyl |
| 133 | 1-methyl-1H-pyrazol-4-yl | 3-Cl-Phenyl |
| 134 | 1H-imidazol-4-yl | 3-Cl-Phenyl |
| 135 | 2-furanyl | 3-Cl-Phenyl |
| 136 | ethyl | 2-Br-Phenyl |
| 137 | n-propyl | 2-Br-Phenyl |
| 138 | isopropyl | 2-Br-Phenyl |
| 139 | —CH₂CH(CH₃)₂ | 2-Br-Phenyl |
| 140 | —CF₃ | 2-Br-Phenyl |
| 141 | —CH₂CF₃ | 2-Br-Phenyl |
| 142 | —CH₂CH₂CF₃ | 2-Br-Phenyl |
| 143 | cyclopropyl | 2-Br-Phenyl |
| 144 | Cyclobutyl | 2-Br-Phenyl |
| 145 | cyclopentyl | 2-Br-Phenyl |
| 146 | cyclohexyl | 2-Br-Phenyl |
| 147 | 3-pyridyl | 2-Br-Phenyl |
| 148 | 1-methyl-1H-pyrazol-4-yl | 2-Br-Phenyl |
| 149 | 1H-imidazol-4-yl | 2-Br-Phenyl |
| 150 | 2-luranyl | 2-Br-Phenyl |
| 151 | ethyl | 4-Br-Phenyl |
| 152 | n-propyl | 4-Br-Phenyl |
| 153 | isopropyl | 4-Br-Phenyl |
| 154 | —CH₂CH(CH₃)₂ | 4-Br-Phenyl |
| 155 | —CF₃ | 4-Br-Phenyl |
| 156 | —CH₂CF₃ | 4-Br-Phenyl |
| 157 | —CH₂CH₂CF₃ | 4-Br-Phenyl |
| 158 | cyclopropyl | 4-Br-Phenyl |
| 159 | Cyclobutyl | 4-Br-Phenyl |
| 160 | cyclopentyl | 4-Br-Phenyl |
| 161 | cyclohexyl | 4-Br-Phenyl |
| 162 | 3-pyridyl | 4-Br-Phenyl |
| 163 | 1-methyl-1H-pyraz.ol-4-yl | 4-Br-Phenyl |
| 164 | 1H-imidazol-4-yl | 4-Br-Phenyl |
| 165 | 2-furanyl | 4-Br-Phenyl |
| 166 | ethyl | 3-CF₃-Phenyl |
| 167 | n-propyl | 3-CF₃-Phenyl |
| 168 | isopropyl | 3-CF₃-Phenyl |
| 169 | —CH₂CH(CH₃)₂ | 3-CF₃-Phenyl |
| 170 | —CF₃ | 3-CF₃-Phenyl |
| 171 | —CH₂CF₃ | 3-CF₃-Phenyl |
| 172 | —CH₂CH₂CF₃ | 3-CF₃-Phenyl |
| 173 | cyclopropyl | 3-CF₃-Phenyl |
| 174 | Cyclobutyl | 3-CF₃-Phenyl |
| 175 | cyclopentyl | 3-CF₃-Phenyl |
| 176 | cyclohexyl | 3-CF₃-Phenyl |
| 177 | 3-pyridyl | 3-CF₃-Phenyl |
| 178 | 1-methyl-1H-pyrazol-4-yl | 3-CF₃-Phenyl |
| 179 | 1H-imidazol-4-yl | 3-CF₃-Phenyl |
| 180 | 2-furanyl | 3-CF₃-Phenyl |
| 181 | ethyl | 2-iPr-Phenyl |
| 182 | n-propyl | 2-iPr-Phenyl |
| 183 | isopropyl | 2-iPr-Phenyl |
| 184 | —CH₂CH(CH₃)₂ | 2-iPr-Phenyl |
| 185 | —CF₃ | 2-iPr-Phenyl |
| 186 | —CH₂CF₃ | 2-iPr-Phenyl |
| 187 | —CH₂CH₂CF₃ | 2-iPr-Phenyl |
| 188 | cyclopropyl | 2-iPr-Phenyl |
| 189 | Cyclobutyl | 2-iPr-Phenyl |
| 190 | cyclopentyl | 2-iPr-Phenyl |
| 191 | cyclohexyl | 2-iPr-Phenyl |
| 192 | 3-pyridyl | 2-iPr-Phenyl |
| 193 | 1-methyl-1H-pyrazol-4-yl | 2-iPr-Phenyl |
| 194 | 1H-imidazol-4-yl | 2-iPr-Phenyl |
| 195 | 2-furanyl | 2-iPr-Phenyl |
| 196 | ethyl | 4-iPr-Phenyl |
| 197 | n-propyl | 4-iPr-Phenyl |
| 198 | isopropyl | 4-iPr-Phenyl |
| 199 | —CH₂CH(CH₃)₂ | 4-iPr-Phenyl |
| 200 | —CF₃ | 4-iPr-Phenyl |
| 201 | —CH₂CF₃ | 4-iPr-Phenyl |
| 202 | —CH₂CH₂CF₃ | 4-iPr-Phenyl |
| 203 | cyclopropyl | 4-iPr-Phenyl |
| 204 | Cyclobutyl | 4-iPr-Phenyl |
| 205 | cyclopentyl | 4-iPr-Phenyl |
| 206 | cyclohexyl | 4-iPr-Phenyl |
| 207 | 3-pyridyl | 4-iPr-Phenyl |
| 208 | 1-methyl-1H-pyrazol-4-yl | 4-iPr-Phenyl |
| 209 | 1H-imidazol-4-yl | 4-iPr-Phenyl |
| 210 | 2-furanyl | 4-iPr-Phenyl |
| 211 | ethyl | 3-morpholino-phenyl |
| 212 | n-propyl | 3-morpholino-phenyl |
| 213 | isopropyl | 3-morpholino-phenyl |
| 214 | —CH₂CH(CH₃)₂ | 3-morpholino-phenyl |
| 215 | —CF₃ | 3-morpholino-phenyl |
| 216 | —CH₂CF₃ | 3-morpholino-phenyl |
| 217 | —CH₂CH₂CF₃ | 3-morpholino-phenyl |
| 218 | cyclopropyl | 3-morpholino-phenyl |
| 219 | Cyclobutyl | 3-morpholino-phenyl |
| 220 | cyclopentyl | 3-morpholino-phenyl |
| 221 | cyclohexyl | 3-morpholino-phenyl |
| 222 | 3-pyridyl | 3-morpholino-phenyl |
| 223 | 1-methyl-1H-pyrazol-4-yl | 3-morpholino-phenyl |

TABLE 10-continued

| Entry | R²ᵈ | R³ |
|---|---|---|
| 224 | 1H-imidazol-4-yl | 3-morpholino-phenyl |
| 225 | 2-furanyl | 3-morpholino-phenyl |
| 226 | ethyl | 4-cyano-2-morpholino-phenyl |
| 227 | n-propyl | 4-cyano-2-morpholino-phenyl |
| 228 | isopropyl | 4-cyano-2-morpholino-phenyl |
| 229 | —CH₂CH(CH₃)₂ | 4-cyano-2-morpholino-phenyl |
| 230 | —CF₃ | 4-cyano-2-morpholino-phenyl |
| 231 | —CH₂CF₃ | 4-cyano-2-morpholino-phenyl |
| 232 | —CH₂CH₂CF₃ | 4-cyano-2-morpholino-phenyl |
| 233 | cyclopropyl | 4-cyano-2-morpholino-phenyl |
| 234 | Cyclobutyl | 4-cyano-2-morpholino-phenyl |
| 235 | cyclopentyl | 4-cyano-2-morpholino-phenyl |
| 236 | cyclohexyl | 4-cyano-2-morpholino-phenyl |
| 237 | 3-pyridyl | 4-cyano-2-morpholino-phenyl |
| 238 | 1-methyl-1H-pyrazol-4-yl | 4-cyano-2-morpholino-phenyl |
| 239 | 1H-imidazol-4-yl | 4-cyano-2-morpholino-phenyl |
| 240 | 2-furanyl | 4-cyano-2-morpholino-phenyl |
| 241 | ethyl | 4-hydroxy-2-morpholino-phenyl |
| 242 | n-propyl | 4-hydroxy-2-morpholino-phenyl |
| 243 | isopropyl | 4-hydroxy-2-morpholino-phenyl |
| 244 | —CH₂CH(CH₃)₂ | 4-hydroxy-2-morpholino-phenyl |
| 245 | —CF₃ | 4-hydroxy-2-morpholino-phenyl |
| 246 | —CH₂CF₃ | 4-hydroxy-2-morpholino-phenyl |
| 247 | —CH₂CH₂CF₃ | 4-hydroxy-2-morpholino-phenyl |
| 248 | cyclopropyl | 4-hydroxy-2-morpholino-phenyl |
| 249 | Cyclobutyl | 4-hydroxy-2-morpholino-phenyl |
| 250 | cyclopentyl | 4-hydroxy-2-morpholino-phenyl |
| 251 | cyclohexyl | 4-hydroxy-2-morpholino-phenyl |
| 252 | 3-pyridyl | 4-hydroxy-2-morpholino-phenyl |
| 253 | 1-methyl-1H-pyrazol-4-yl | 4-hydroxy-2-morpholino-phenyl |
| 254 | 1H-imidazol-4-yl | 4-hydroxy-2-morpholino-phenyl |
| 255 | 2-furanyl | 4-hydroxy-2-morpholino-phenyl |
| 256 | ethyl | 2-CH₃-phenyl |
| 257 | n-propyl | 2-CH₃-phenyl |
| 258 | isopropyl | 2-CH₃-phenyl |
| 259 | —CH₂CH(CH₃)₂ | 2-CH₃-phenyl |
| 260 | CF₃ | 2-CH₃-phenyl |
| 261 | —CH₂CF₃ | 2-CH₃-phenyl |
| 262 | —CH₂CH₂CF₃ | 2-CH₃-phenyl |
| 263 | cyclopropyl | 2-CH₃-phenyl |
| 264 | Cyclobutyl | 2-CH₃-phenyl |
| 265 | cyclopentyl | 2-CH₃-phenyl |
| 266 | cyclohexyl | 2-CH₃-phenyl |
| 267 | 3-pyridyl | 2-CH₃-phenyl |
| 268 | 1-methyl-1H-pyrazol-4-yl | 2-CH₃-phenyl |
| 269 | 1H-imidazol-4-yl | 2-CH₃-phenyl |
| 270 | 2-furanyl | 2-CH₃-phenyl |
| 271 | ethyl | 4-OH-Phenyl |
| 272 | n-propyl | 4-OH-Phenyl |
| 273 | isopropyl | 4-OH-Phenyl |
| 274 | —CH₂CH(CH₃)₂ | 4-OH-Phenyl |
| 275 | —CF₃ | 4-OH-Phenyl |
| 276 | —CH₂CF₃ | 4-OH-Phenyl |
| 277 | —CH₂CH₂CF₃ | 4-OH-Phenyl |
| 278 | cyclopropyl | 4-OH-Phenyl |
| 279 | Cyclobutyl | 4-OH-Phenyl |
| 280 | cyclopentyl | 4-OH-Phenyl |
| 281 | cyclohexyl | 4-OH-Phenyl |
| 282 | 3-pyridyl | 4-OH-Phenyl |
| 283 | 1-methyl-1H-pyrazol-4-yl | 4-OH-Phenyl |
| 284 | 1H-imidazol-4-yl | 4-OH-Phenyl |
| 285 | 2-furanyl | 4-OH-Phenyl |
| 286 | ethyl | 2-OH-Phenyl |
| 287 | n-propyl | 2-OH-Phenyl |
| 288 | isopropyl | 2-OH-Phenyl |
| 289 | —CH₂CH(CH₃)₂ | 2-OH-Phenyl |
| 290 | —CF₃ | 2-OH-Phenyl |
| 291 | —CH₂CF₃ | 2-OH-Phenyl |
| 292 | —CH₂CH₂CF₃ | 2-OH-Phenyl |
| 293 | cyclopropyl | 2-OH-Phenyl |
| 294 | Cyclobutyl | 2-OH-Phenyl |
| 295 | cyclopentyl | 2-OH-Phenyl |
| 296 | cyclohexyl | 2-OH-Phenyl |
| 297 | 3-pyridyl | 2-OH-Phenyl |
| 298 | 1-methyl-1H-pyrazol-4-yl | 2-OH-Phenyl |
| 299 | 1H-imidazol-4-yl | 2-OH-Phenyl |
| 300 | 2-furanyl | 2-OH-Phenyl |
| 301 | ethyl | 3-OMe-Phenyl |
| 302 | n-propyl | 3-OMe-Phenyl |
| 303 | isopropyl | 3-OMe-Phenyl |
| 304 | —CH₂CH(CH₃)₂ | 3-OMe-Phenyl |
| 305 | —CF₃ | 3-OMe-Phenyl |
| 306 | —CH₂CF₃ | 3-OMe-Phenyl |
| 307 | —CH₂CH₂CF₃ | 3-OMe-Phenyl |
| 308 | cyclopropyl | 3-OMe-Phenyl |
| 309 | Cyclobutyl | 3-OMe-Phenyl |
| 310 | cyclopentyl | 3-OMe-Phenyl |
| 311 | cyclohexyl | 3-OMe-Phenyl |
| 312 | 3-pyridyl | 3-OMe-Phenyl |
| 313 | 1-methyl-1H-pyrazol-4-yl | 3-OMe-Phenyl |
| 314 | 1H-imidazol-4-yl | 3-OMe-Phenyl |
| 315 | 2-furanyl | 3-OMe-Phenyl |
| 316 | ethyl | 4-CN-Phenyl |
| 317 | n-propyl | 4-CN-Phenyl |
| 318 | isopropyl | 4-CN-Phenyl |
| 319 | —CH₂CH(CH₃)₂ | 4-CN-Phenyl |
| 320 | —CF₃ | 4-CN-Phenyl |
| 321 | —CH₂CF₃ | 4-CN-Phenyl |
| 322 | —CH₂CH₂CF₃ | 4-CN-Phenyl |
| 323 | cyclopropyl | 4-CN-Phenyl |
| 324 | Cyclobutyl | 4-CN-Phenyl |
| 325 | cyclopentyl | 4-CN-Phenyl |
| 326 | cyclohexyl | 4-CN-Phenyl |
| 327 | 3-pyridyl | 4-CN-Phenyl |
| 328 | 1-methyl-1H-pyrazol-4-yl | 4-CN-Phenyl |
| 329 | 1H-imidazol-4-yl | 4-CN-Phenyl |
| 330 | 2-furanyl | 4-CN-Phenyl |
| 331 | ethyl | 2-CN-Phenyl |
| 332 | n-propyl | 2-CN-Phenyl |
| 333 | isopropyl | 2-CN-Phenyl |
| 334 | —CH₂CH(CH₃)₂ | 2-CN-Phenyl |
| 335 | —CF₃ | 2-CN-Phenyl |
| 336 | —CH₂CF₃ | 2-CN-Phenyl |
| 337 | —CH₂CH₂CF₃ | 2-CN-Phenyl |
| 338 | cyclopropyl | 2-CN-Phenyl |
| 339 | Cyclobutyl | 2-CN-Phenyl |
| 340 | cyclopentyl | 2-CN-Phenyl |
| 341 | cyclohexyl | 2-CN-Phenyl |
| 342 | 3-pyridyl | 2-CN-Phenyl |

TABLE 10-continued

| Entry | R$^{2d}$ | R$^3$ |
|---|---|---|
| 343 | 1-methyl-1H-pyrazol-4-yl | 2-CN-Phenyl |
| 344 | 1H-imidazol-4-yl | 2-CN-Phenyl |
| 345 | 2-furanyl | 2-CN-Phenyl |
| 346 | ethyl | 3-F-Phenyl |
| 347 | n-propyl | 3-F-Phenyl |
| 348 | isopropyl | 3-F-Phenyl |
| 349 | —CH$_2$CH(CH$_3$)$_2$ | 3-F-Phenyl |
| 350 | —CF$_3$ | 3-F-Phenyl |
| 351 | —CH$_2$CF$_3$ | 3-F-Phenyl |
| 352 | —CH$_2$CH$_2$CF$_3$ | 3-F-Phenyl |
| 353 | cyclopropyl | 3-F-Phenyl |
| 354 | Cyclobutyl | 3-F-Phenyl |
| 355 | cyclopentyl | 3-F-Phenyl |
| 356 | cyclohexyl | 3-F-Phenyl |
| 357 | 3-pyridyl | 3-F-Phenyl |
| 358 | 1-methyl-1H-pyrazol-4-yl | 3-F-Phenyl |
| 359 | 1H-imidazol-4-yl | 3-F-Phenyl |
| 360 | 2-furanyl | 3-F-Phenyl |
| 361 | ethyl | 2-Cl-Phenyl |
| 362 | n-propyl | 2-Cl-Phenyl |
| 363 | isopropyl | 2-Cl-Phenyl |
| 364 | —CH$_2$CH(CH$_3$)$_2$ | 2-Cl-Phenyl |
| 365 | —CF$_3$ | 2-Cl-Phenyl |
| 366 | —CH$_2$CF$_3$ | 2-Cl-Phenyl |
| 367 | —CH$_2$CH$_2$CF$_3$ | 2-Cl-Phenyl |
| 368 | cyclopropyl | 2-Cl-Phenyl |
| 369 | Cyclobutyl | 2-Cl-Phenyl |
| 370 | cyclopentyl | 2-Cl-Phenyl |
| 371 | cyclohexyl | 2-Cl-Phenyl |
| 372 | 3-pyridyl | 2-Cl-Phenyl |
| 373 | 1-methyl-1H-pyrazol-4-yl | 2-Cl-Phenyl |
| 374 | 1H-imidazol-4-yl | 2-Cl-Phenyl |
| 375 | 2-furanyl | 2-Cl-Phenyl |
| 376 | ethyl | 4-Cl-Phenyl |
| 377 | n-propyl | 4-Cl-Phenyl |
| 378 | isopropyl | 4-Cl-Phenyl |
| 379 | —CH$_2$CH(CH$_3$)$_2$ | 4-Cl-Phenyl |
| 380 | —CF$_3$ | 4-Cl-Phenyl |
| 381 | —CH$_2$CF$_3$ | 4-Cl-Phenyl |
| 382 | —CH$_2$CH$_2$CF$_3$ | 4-Cl-Phenyl |
| 383 | cyclopropyl | 4-Cl-Phenyl |
| 384 | Cyclobutyl | 4-Cl-Phenyl |
| 385 | cyclopentyl | 4-Cl-Phenyl |
| 386 | cyclohexyl | 4-Cl-Phenyl |
| 387 | 3-pyridyl | 4-Cl-Phenyl |
| 388 | 1-methyl-1H-pyrazol-4-yl | 4-Cl-Phenyl |
| 389 | 1H-imidazol-4-yl | 4-Cl-Phenyl |
| 390 | 2-furanyl | 4-Cl-Phenyl |
| 391 | ethyl | 3-Br-Phenyl |
| 392 | n-propyl | 3-Br-Phenyl |
| 393 | isopropyl | 3-Br-Phenyl |
| 394 | —CH$_2$CH(CH$_3$)$_2$ | 3-Br-Phenyl |
| 395 | —CF$_3$ | 3-Br-Phenyl |
| 396 | —CH$_2$CF$_3$ | 3-Br-Phenyl |
| 397 | —CH$_2$CH$_2$CF$_3$ | 3-Br-Phenyl |
| 398 | cyclopropyl | 3-Br-Phenyl |
| 399 | Cyclobutyl | 3-Br-Phenyl |
| 400 | cyclopentyl | 3-Br-Phenyl |
| 401 | cyclohexyl | 3-Br-Phenyl |
| 402 | 3-pyridyl | 3-Br-Phenyl |
| 403 | 1-methyl-1H-pyrazol-4-yl | 3-Br-Phenyl |
| 404 | 1H-imidazol-4-yl | 3-Br-Phenyl |
| 405 | 2-furanyl | 3-Br-Phenyl |
| 406 | ethyl | 2-CF$_3$-Phenyl |
| 407 | n-propyl | 2-CF$_3$-Phenyl |
| 408 | isopropyl | 2-CF$_3$-Phenyl |
| 409 | —CH$_2$CH(CH$_3$)$_2$ | 2-CF$_3$-Phenyl |
| 410 | —CF$_3$ | 2-CF$_3$-Phenyl |
| 411 | —CH$_2$CF$_3$ | 2-CF$_3$-Phenyl |
| 412 | —CH$_2$CH$_2$CF$_3$ | 2-CF$_3$-Phenyl |
| 413 | cyclopropyl | 2-CF$_3$-Phenyl |
| 414 | Cyclobutyl | 2-CF$_3$-Phenyl |
| 415 | cyclopentyl | 2-CF$_3$-Phenyl |
| 416 | cyclohexyl | 2-CF$_3$-Phenyl |
| 417 | 3-pyridyl | 2-CF$_3$-Phenyl |
| 418 | 1-methyl-1H-pyrazol-4-yl | 2-CF$_3$-Phenyl |
| 419 | 1H-imidazol-4-yl | 2-CF$_3$-Phenyl |
| 420 | 2-furanyl | 2-CF$_3$-Phenyl |
| 421 | ethyl | 4-CF$_3$-Phenyl |
| 422 | n-propyl | 4-CF$_3$-Phenyl |
| 423 | isopropyl | 4-CF$_3$-Phenyl |
| 424 | —CH$_2$CH(CH$_3$)$_2$ | 4-CF$_3$-Phenyl |
| 425 | —CF$_3$ | 4-CF$_3$-Phenyl |
| 426 | —CH$_2$CF$_3$ | 4-CF$_3$-Phenyl |
| 427 | —CH$_2$CH$_2$CF$_3$ | 4-CF$_3$-Phenyl |
| 428 | cyclopropyl | 4-CF$_3$-Phenyl |
| 429 | Cyclobutyl | 4-CF$_3$-Phenyl |
| 430 | cyclopentyl | 4-CF$_3$-Phenyl |
| 431 | cyclohexyl | 4-CF$_3$-Phenyl |
| 432 | 3-pyridyl | 4-CF$_3$-Phenyl |
| 433 | 1-methyl-1H-pyrazol-4-yl | 4-CF$_3$-Phenyl |
| 434 | 1H-imidazol-4-yl | 4-CF$_3$-Phenyl |
| 435 | 2-furanyl | 4-CF$_3$-Phenyl |
| 436 | ethyl | 3-iPr-Phenyl |
| 437 | n-propyl | 3-iPr-Phenyl |
| 438 | isopropyl | 3-iPr-Phenyl |
| 439 | —CH$_2$CH(CH$_3$)$_2$ | 3-iPr-Phenyl |
| 440 | —CF$_3$ | 3-iPr-Phenyl |
| 441 | —CH$_2$CF$_3$ | 3-iPr-Phenyl |
| 442 | —CH$_2$CH$_2$CF$_3$ | 3-iPr-Phenyl |
| 443 | cyclopropyl | 3-iPr-Phenyl |
| 444 | Cyclobutyl | 3-iPr-Phenyl |
| 445 | cyclopentyl | 3-iPr-Phenyl |
| 446 | cyclohexyl | 3-iPr-Phenyl |
| 447 | 3-pyridyl | 3-iPr-Phenyl |
| 448 | 1-methyl-1H-pyrazol-4-yl | 3-iPr-Phenyl |
| 449 | 1H-imidazol-4-yl | 3-iPr-Phenyl |
| 450 | 2-furanyl | 3-iPr-Phenyl |
| 451 | ethyl | 2-morpholino-phenyl |
| 452 | n-propyl | 2-morpholino-phenyl |
| 453 | isopropyl | 2-morpholino-phenyl |
| 454 | —CH$_2$CH(CH$_3$)$_2$ | 2-morpholino-phenyl |
| 455 | —CF$_3$ | 2-morpholino-phenyl |
| 456 | —CH$_2$CF$_3$ | 2-morpholino-phenyl |
| 457 | —CH$_2$CH$_2$CF$_3$ | 2-morpholino-phenyl |
| 458 | cyclopropyl | 2-morpholino-phenyl |
| 459 | Cyclobutyl | 2-morpholino-phenyl |
| 460 | cyclopentyl | 2-morpholino-phenyl |
| 461 | cyclohexyl | 2-morpholino-phenyl |
| 462 | 3-pyridyl | 2-morpholino-phenyl |
| 463 | 1-methyl-1H-pyrazol-4-yl | 2-morpholino-phenyl |
| 464 | 1H-imidazol-4-yl | 2-morpholino-phenyl |
| 465 | 2-furanyl | 2-morpholino-phenyl |
| 466 | ethyl | 4-morpholino-phenyl |
| 467 | n-propyl | 4-morpholino-phenyl |
| 468 | isopropyl | 4-morpholino-phenyl |
| 469 | —CH$_2$CH(CH$_3$)$_2$ | 4-morpholino-phenyl |
| 470 | —CF$_3$ | 4-morpholino-phenyl |

TABLE 10-continued

| Entry | R$^{2d}$ | R$^3$ |
|---|---|---|
| 471 | —CH$_2$CF$_3$ | 4-morpholino-phenyl |
| 472 | —CH$_2$CH$_2$CF$_3$ | 4-morpholino-phenyl |
| 473 | cyclopropyl | 4-morpholino-phenyl |
| 474 | Cyclobutyl | 4-morpholino-phenyl |
| 475 | cyclopentyl | 4-morpholino-phenyl |
| 476 | cyclohexyl | 4-morpholino-phenyl |
| 477 | 3-pyridyl | 4-morpholino-phenyl |
| 478 | 1-methyl-1H-pyrazol-4-yl | 4-morpholino-phenyl |
| 479 | 1H-imidazol-4-yl | 4-morpholino-phenyl |
| 480 | 2-furanyl | 4-morpholino-phenyl |
| 481 | ethyl | 4-methyl-2-morpholino-phenyl |
| 482 | n-propyl | 4-methyl-2-morpholino-phenyl |
| 483 | isopropyl | 4-methyl-2-morpholino-phenyl |
| 484 | —CH$_2$CH(CH$_3$)$_2$ | 4-methyl-2-morpholino-phenyl |
| 485 | —CF$_3$ | 4-methyl-2-morpholino-phenyl |
| 486 | —CH$_2$CF$_3$ | 4-methyl-2-morpholino-phenyl |
| 487 | —CH$_2$CH$_2$CF$_3$ | 4-methyl-2-morpholino-phenyl |
| 488 | cyclopropyl | 4-methyl-2-morpholino-phenyl |
| 489 | Cyclobutyl | 4-methyl-2-morpholino-phenyl |
| 490 | cyclopentyl | 4-melhyl-2-morpholino-phenyl |
| 491 | cyclohexyl | 4-methyl-2-morpholino-phenyl |
| 492 | 3-pyridyl | 4-methyl-2-morpholino-phenyl |
| 493 | 1-methyl-1H-pyrazol-4-yl | 4-methyl-2-morpholino-phenyl |
| 494 | 1H-imidazol-4-yl | 4-methyl-2-morpholino-phenyl |
| 495 | 2-furanyl | 4-methyl-2-morpholino-phenyl |

For the purposes of demonstrating the manner in which the compounds of the present invention are named and referred to herein, the compound having the formula:

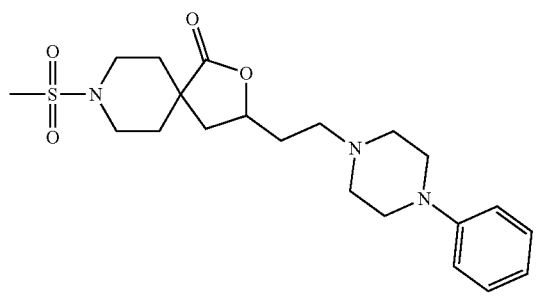 [SMILES: CS(=O)(=O)N1CCC2(CC1)CC(CCN1CCN(c3ccccc3)CC1)OC2=O]

has the chemical name 8-(methylsulfonyl)-3-(2-(4-phenylpiperazin-1-yl)ethyl)-2-oxa-8-azaspiro[4.5]decan-1-one.

For the purposes of demonstrating the manner in which the compounds of the present invention are named and referred to herein, the compound having the formula:

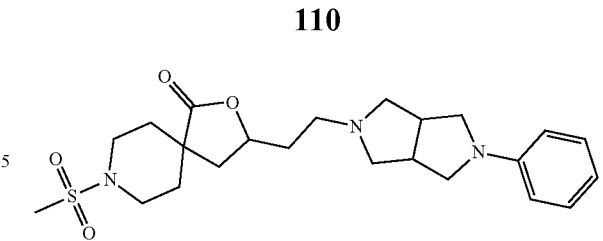

has the chemical name 8-(methylsulfonyl)-3-(2-(5-phenyl-hexahydropyrrolo[3,4-c]pyrrol-2(1H)-yl)ethyl)-2-oxa-8-azaspiro[4.5]decan-1-one.

For the purposes of the present invention, a compound depicted by the racemic formula, for example:

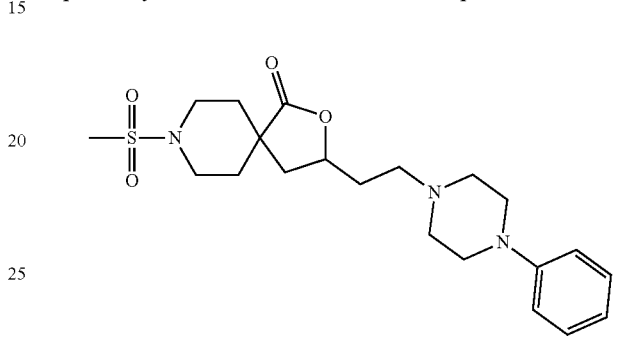

will stand equally well for either of the two enantiomers having the formula:

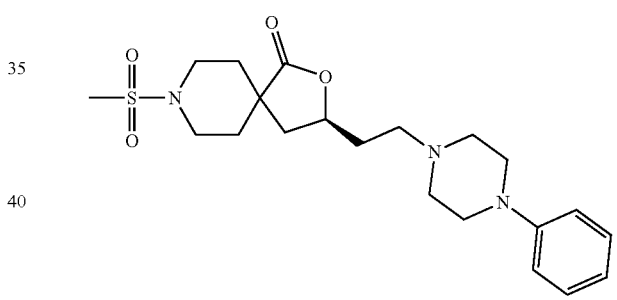

or the formula:

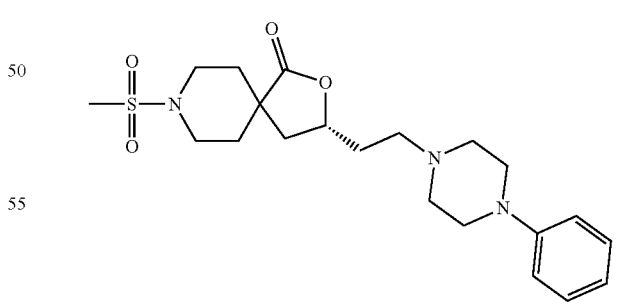

or mixtures thereof, or in the case where a second chiral center is present, all diastereomers.

In all of the embodiments provided herein, examples of suitable optional substituents are not intended to limit the scope of the claimed invention. The compounds of the invention may contain any of the substituents, or combinations of substituents, provided herein.

111

Process for Preparing the 5-Hydroxytryptamine Receptor 7 Activity Modulators of the Invention The present invention further relates to a process for preparing the 5-hydroxytryptamine receptor 7 activity modulators of the present invention.

Compounds of the present teachings can be prepared in accordance with the procedures outlined herein, from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions can vary with the particular reactants or solvent used, but such conditions can be determined by one skilled in the art by routine optimization procedures. Those skilled in the art of organic synthesis will recognize that the nature and order of the synthetic steps presented can be varied for the purpose of optimizing the formation of the compounds described herein.

The processes described herein can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatography such as high pressure liquid chromatograpy (HPLC), gas chromatography (GC), gel-permeation chromatography (GPC), or thin layer chromatography (TLC).

Preparation of the compounds can involve protection and deprotection of various chemical groups. The need for protection and deprotection and the selection of appropriate protecting groups can be readily determined by one skilled in the art. The chemistry of protecting groups can be found, for example, in Greene et al., *Protective Groups in Organic Synthesis,* 2d. Ed. (Wiley & Sons, 1991), the entire disclosure of which is incorporated by reference herein for all purposes.

The reactions or the processes described herein can be carried out in suitable solvents which can be readily selected by one skilled in the art of organic synthesis. Suitable solvents typically are substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

The compounds of these teachings can be prepared by methods known in the art of organic chemistry. The reagents used in the preparation of the compounds of these teachings can be either commercially obtained or can be prepared by standard procedures described in the literature. For example, compounds of the present invention can be prepared according to the method illustrated in the General Synthetic Schemes:

General Synthetic Schemes for Preparation of Compounds

The reagents used in the preparation of the compounds of this invention can be either commercially obtained or can be prepared by standard procedures described in the literature.

112

In accordance with this invention, compounds in the genus may be produced by one of the following reaction schemes.

Compounds of the disclosure may be prepared according to the process outlined in Scheme 1-x.

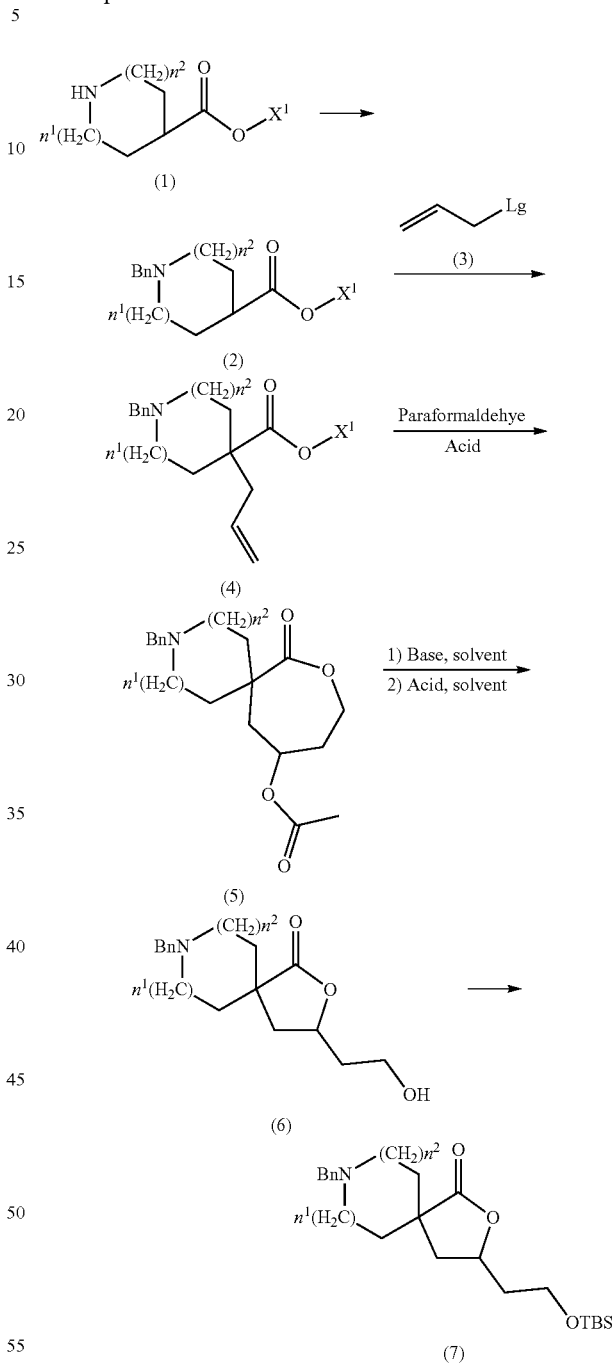

A suitably substituted compound of formula (1), a known compound or compound prepared by known methods wherein $X^1$ is an $C_{1-6}$ alkyl, is reacted with benzyl bromide in the presence of a base such as triethylamine, diisopropylethylamine, pyridine, 2,6-lutidine, and the like in the presence of a solvent such as ethanol, methanol, isopropanol, tetrahydrofuran, 1,4-dioxane, methylene chloride, N,N-dimethyl formamide, and the like, optionally with heating, optionally with microwave irradiation to provide a compound of the formula (2). A compound of the formula (2) is reacted with a compound of the formula (3), a known compound or a compound prepared by known methods in which LG is a leaving group such as chlorine, bromine, iodine, mesylate, tosylate, and the like, in the presence of a base such as lithium diisopropylamide, sodium diisopropylamide, potassium diisopropylamide, lithium bis(trimethylsilyl)amide, sodium bis(trimethylsilyl)amide, potassium bis(trimethylsilyl)amide, sodium hydride, and the like in an organic solvent such as tetrahydrofuran, 1,4-dioxane, 1,2-dimethoxyethane, dimethylformamide, dimethylacetamide, and the like, to provide a compound of the formula (4). A compound of the formula (4) is then treated with paraformaldehyde in the presence of an acid such as sulfuric acid, hydrochloric acid, and the like, in an the presence of acetic acid, and optionally in an organic solvent such as methanol, ethanol, tetrahydrofuran, 1,4-dioxane, 1,2-dimethoxyethane, N,N-dimethylformamide, N,N-dimethylacetamide, and the like, optionally with heating, optionally with microwave irradiation to provide a compound of the formula (5). A compound of the formula (5) is then treated with a base such as sodium hydroxide, potassium hydroxide, lithium hydroxide, and the like, in an solvent such as water, methanol, ethanol, isopropanol, and the like, optionally with heating, and then treated with an acid such as sulfuric acid, hydrochloric acid, and the like, in a solvent such as water, methanol, ethanol, isopropanol, and the like, to provide a compound of the formula (6). A compound of the formula (6) is reacted with tert-butyldimethylchlorosilane in the presence of imidazole, in the presence of a solvent such as methylene chloride, 1,2-dichloroethane, tetrahydrofuran, 1,4-dioxane, 1,2-dimethoxyethane, N,N-dimethylformamide, N,N-dimethylacetamide, and the like, optionally with heating, optionally with microwave irradiation to provide a compound of the formula (7). Alternatively, a compound of the formula (6) is reacted with tert-butyldimethylsilyl trifluoromethanesulfonate in the presence of a base such as pyridine, 2,6-lutidine, triethylamine, diisopropylethylamine, and the like, in a solvent such as methylene chloride, 1,2-dichloroethane, tetrahydrofuran, 1,4-dioxane, 1,2-dimethoxyethane, N,N-dimethylformamide, N,N-dimethylacetamide, and the like, optionally with heating, optionally with microwave irradiation to provide a compound of the formula (7)

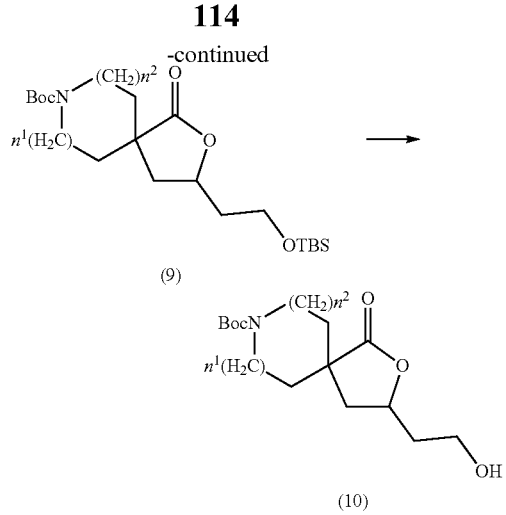

A compound of the formula (7) is reacted with hydrogen gas in the presence of a palladium catalyst such as palladium on carbon, palladium on barium sulfate, palladium (II) acetate, tetrakis(triphenylphosphine)palladium(0), dichlorobis(triphenylphosphine)palladium(II), palladium on carbon, bis(acetonitrile)dichloropalladium(II), and the like, in an organic solvent such as methanol, ethanol, ethyl acetate, tetrahydrofuran, 1,4-dioxane, dichloromethane, chloroform, 1,2-dichloroethane, N,N-dimethylformamide, and the like, to provide a compound of the formula (8). A compound of the formula (8) is reacted with Di-tert-butyl dicarbonate in the presence of a base such as such as pyridine, 2,6-lutidine, triethylamine, diisopropylethylamine, and the like, in a solvent such as methylene chloride, 1,2-dichloroethane, tetrahydrofuran, 1,4-dioxane, 1,2-dimethoxyethane, N,N-dimethylformamide, N,N-dimethylacetamide, methanol, ethanol, isopropanol, and the like, optionally with heating, optionally with microwave irradiation to provide a compound of the formula (9). A compound of the formula (9) is reacted with Tetra-n-butylammonium fluoride in the presence of solvent such as methylene chloride, 1,2-dichloroethane, tetrahydrofuran, 1,4-dioxane, 1,2-dimethoxyethane, N,N-dimethylformamide, N,N-dimethylacetamide, methanol, ethanol, isopropanol, and the like, optionally with heating, optionally with microwave irradiation to provide a compound of the formula (10).

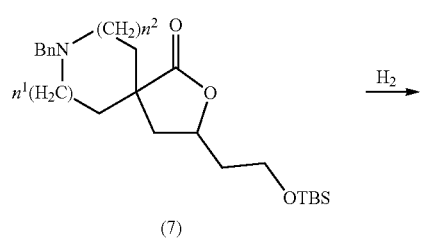

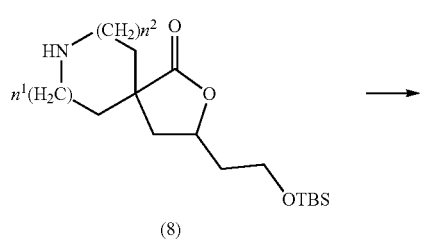

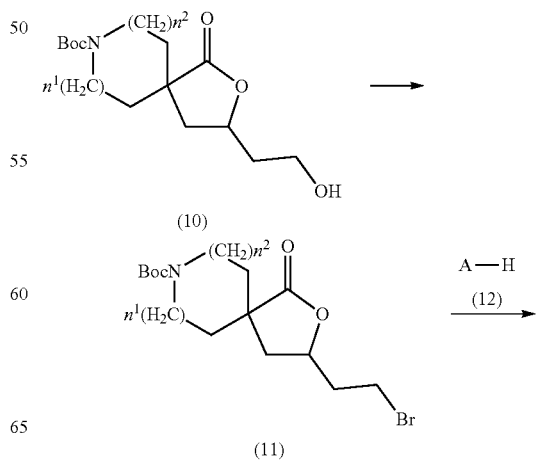

-continued

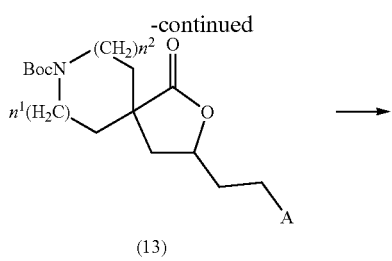

(13)

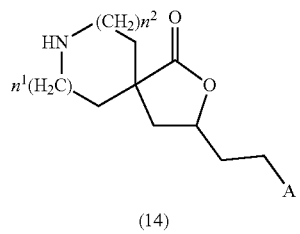

(14)

A compound of the formula (10) is treated with carbon tetrabromide in the presence of triphenylphosphine, in a solvent such as methylene chloride, 1,2-dichloroethane, tetrahydrofuran, 1,4-dioxane, 1,2-dimethoxyethane, N,N-dimethylformamide, N,N-dimethylacetamide, and the like, optionally with heating, optionally with microwave irradiation to provide a compound of the formula (11). A compound of the formula (11) is reacted with a compound of the formula (12), a known compound or a compound prepared by known methods, in the presence of a base such as sodium carbonate, potassium carbonate, lithium carbonate, sodium bicarbonate, potassium bicarbonate, lithium bicarbonate, triethylamine, diisopropylethylamine, pyridine, and the like, in a solvent such as methylene chloride, 1,2-dichloroethane, tetrahydrofuran, 1,4-dioxane, 1,2-dimethoxyethane, N,N-dimethylformamide, N,N-dimethylacetamide, acetonitrile, methanol, ethanol, isopropanol, and the like, optionally with heating, optionally with microwave irradiation to provide a compound of the formula (13). A compound of the formula (13) is reacted with an acid such as trifluoroacetic acid, formic acid, acetic acid, hydrochloric acid, sulfuric acid, and the like, optionally in a solvent such as methylene chloride, 1,2-dichloroethane, tetrahydrofuran, 1,4-dioxane, 1,2-dimethoxyethane, N,N-dimethylformamide, N,N-dimethylacetamide, acetonitrile, methanol, ethanol, isopropanol, and the like, optionally with heating, optionally with microwave irradiation to provide a compound of the formula (14).

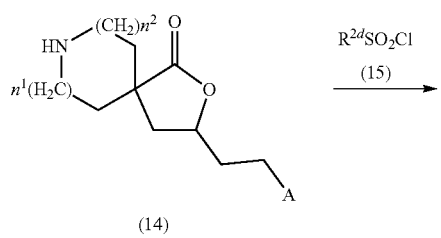

(14)

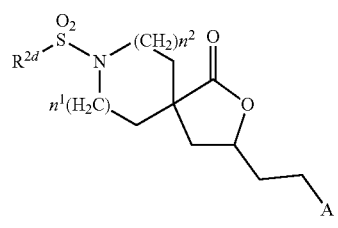

(16)

A compound of the formula (14) is reacted with a compound of the formula (15), a known compound or a compound prepared by known methods, in the presence of a base such as triethylamine, diisopropylethylamine, pyridine, and the like, in a solvent such as methylene chloride, 1,2-dichloroethane, tetrahydrofuran, 1,4-dioxane, 1,2-dimethoxyethane, N,N-dimethylformamide, N,N-dimethylacetamide, acetonitrile, and the like, optionally with heating, optionally with microwave irradiation to provide a compound of the formula (16).

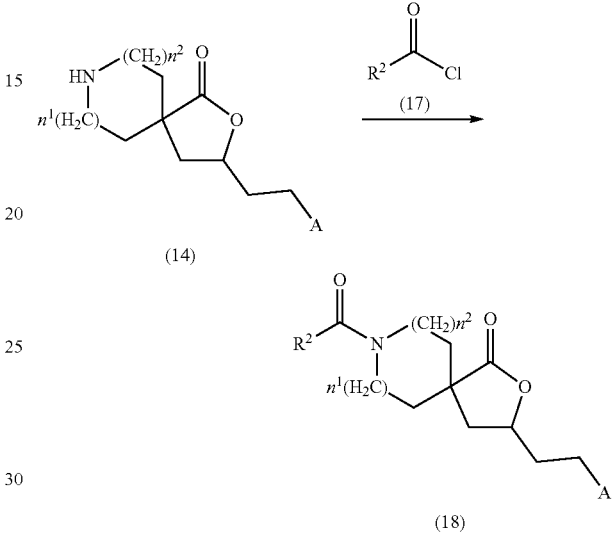

(14)

(18)

A compound of the formula (14) is reacted with a compound of the formula (17), a known compound or a compound prepared by known methods, in the presence of a base such as triethylamine, diisopropylethylamine, pyridine, and the like, in a solvent such as methylene chloride, 1,2-dichloroethane, tetrahydrofuran, 1,4-dioxane, 1,2-dimethoxyethane, N,N-dimethylformamide, N,N-dimethylacetamide, acetonitrile, and the like, optionally with heating, optionally with microwave irradiation to provide a compound of the formula (18).

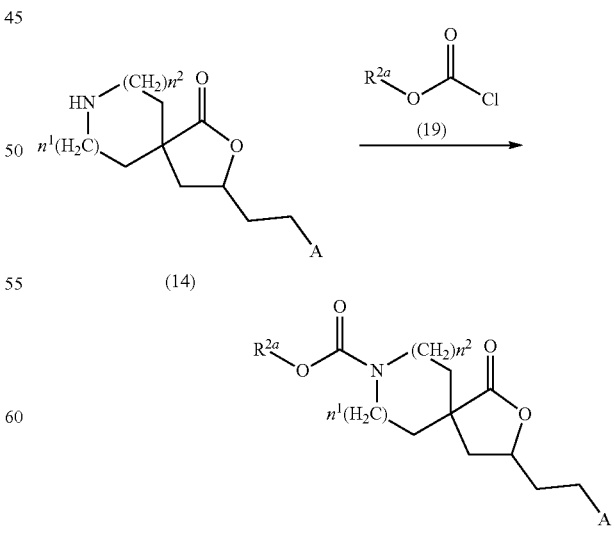

(14)

(20)

A compound of the formula (14) is reacted with a compound of the formula (19), a known compound or a compound prepared by known methods, in the presence of a base such as triethylamine, diisopropylethylamine, pyridine, and the like, in a solvent such as methylene chloride, 1,2-dichloroethane, tetrahydrofuran, 1,4-dioxane, 1,2-dimethoxyethane, N,N-dimethylformamide, N,N-dimethylacetamide, acetonitrile, and the like, optionally with heating, optionally with microwave irradiation to provide a compound of the formula (20).

(14)

(21)

(22)

A compound of the formula (14) is reacted with a compound of the formula (21), a known compound or a compound prepared by known methods, in the presence of a base such as triethylamine, diisopropylethylamine, pyridine, and the like, in a solvent such as methylene chloride, 1,2-dichloroethane, tetrahydrofuran, 1,4-dioxane, 1,2-dimethoxyethane, N,N-dimethylformamide, N,N-dimethylacetamide, acetonitrile, and the like, optionally with heating, optionally with microwave irradiation to provide a compound of the formula (22).

(14)

(23)

(24)

A compound of the formula (14) is reacted with a compound of the formula (23), a known compound or a compound prepared by known methods, in a solvent such as methylene chloride, 1,2-dichloroethane, tetrahydrofuran, 1,4-dioxane, 1,2-dimethoxyethane, N,N-dimethylformamide, N,N-dimethylacetamide, acetonitrile, and the like, optionally with heating, optionally with microwave irradiation to provide a compound of the formula (24).

(14)

(25)

(26)

A compound of the formula (14) is reacted with a compound of the formula (25), a known compound or a compound prepared by known methods, in the presence of a base such as triethylamine, diisopropylethylamine, pyridine, and the like, in a solvent such as methylene chloride, 1,2-dichloroethane, tetrahydrofuran, 1,4-dioxane, 1,2-dimethoxyethane, N,N-dimethylformamide, N,N-dimethylacetamide, acetonitrile, and the like, optionally with heating, optionally with microwave irradiation to provide a compound of the formula (26).

(27)

(28)

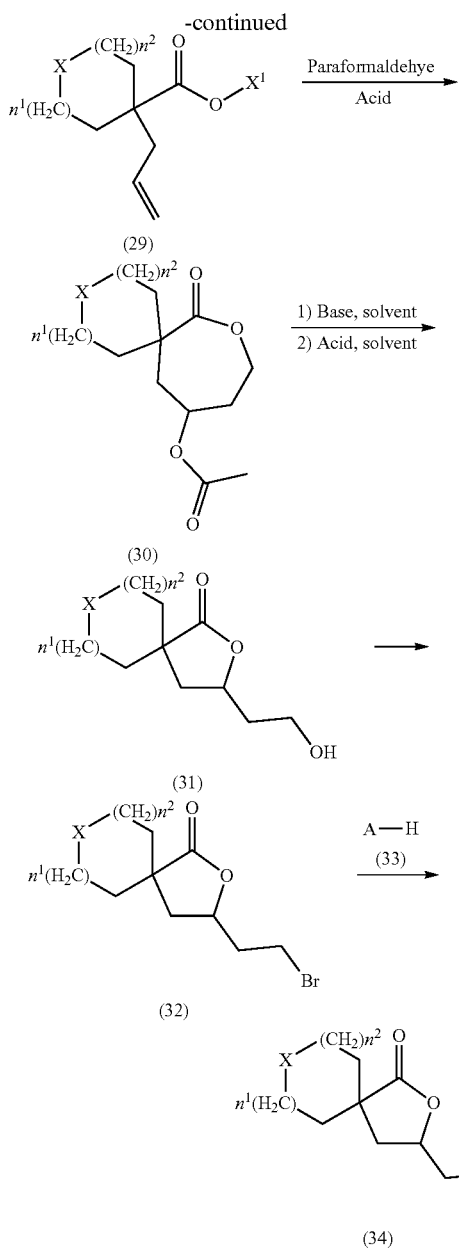

dioxane, 1,2-dimethoxyethane, N,N-dimethylformamide, N,N-dimethylacetamide, and the like, optionally with heating, optionally with microwave irradiation to provide a compound of the formula (30). A compound of the formula (30) is then treated with a base such as sodium hydroxide, potassium hydroxide, lithium hydroxide, and the like, in an solvent such as water, methanol, ethanol, isopropanol, and the like, optionally with heating, and then treated with an acid such as sulfuric acid, hydrochloric acid, and the like, in a solvent such as water, methanol, ethanol, isopropanol, and the like, to provide a compound of the formula (31). A compound of the formula (31) is treated with carbon tetrabromide in the presence of triphenylphosphine, in a solvent such as methylene chloride, 1,2-dichloroethane, tetrahydrofuran, 1,4-dioxane, 1,2-dimethoxyethane, N,N-dimethylformamide, N,N-dimethylacetamide, and the like, optionally with heating, optionally with microwave irradiation to provide a compound of the formula (32). A compound of the formula (32) is reacted with a compound of the formula (33), a known compound or a compound prepared by known methods, in the presence of a base such as sodium carbonate, potassium carbonate, lithium carbonate, sodium bicarbonate, potassium bicarbonate, lithium bicarbonate, triethylamine, diisopropylethylamine, pyridine, and the like, in a solvent such as methylene chloride, 1,2-dichloroethane, tetrahydrofuran, 1,4-dioxane, 1,2-dimethoxyethane, N,N-dimethylformamide, N,N-dimethylacetamide, acetonitrile, methanol, ethanol, isopropanol, and the like, optionally with heating, optionally with microwave irradiation to provide a compound of the formula (34).

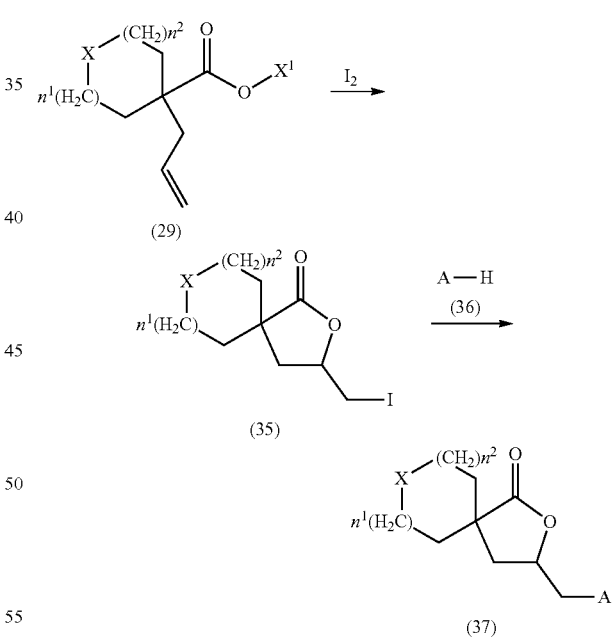

A suitably substituted compound of formula (27), a known compound or compound prepared by known methods wherein $X^1$ is an $C_{1-6}$ alkyl, is reacted with a compound of the formula (28), a known compound or a compound prepared by known methods in which LG is a leaving group such as chlorine, bromine, iodine, mesylate, tosylate, and the like, in the presence of a base such as lithium diisopropylamide, sodium diisopropylamide, potassium diisopropylamide, lithium bis(trimethylsilyl)amide, sodium bis(trimethylsilyl)amide, potassium bis(trimethylsilyl)amide, sodium hydride, and the like in an organic solvent such as tetrahydrofuran, 1,4-dioxane, 1,2-dimethoxyethane, dimethylformamide, dimethylacetamide, and the like, to provide a compound of the formula (29). A compound of the formula (29) is then treated with paraformaldehyde in the presence of an acid such as sulfuric acid, hydrochloric acid, and the like, in an the presence of acetic acid, and optionally in an organic solvent such as methanol, ethanol, tetrahydrofuran, 1,4-

A compound of the formula (29) is then reacted with iodine in the presence of a base such as sodium bicarbonate, potassium bicarbonate, lithium bicarbonate, sodium carbonate, potassium carbonate, lithium bicarbonate, sodium hydroxide, potassium hydroxide, lithium hydroxide, and the like, in the presence of a solvent such as tetrahydrofuran, ethyl ether, 1,4-dioxane, and the like to provide a compound of the formula (35). A compound of the formula (35) is reacted with a compound of the formula (36), a known compound or compound prepared by known methods, in an organic solvent such as tetrahydrofuran, 1,4-dioxane, 1,2-dimethoxyethane, dimethylformamide, dimethylacetamide, and the like, optionally in the presence of a base such as triethylamine, diisopropylethylamine, pyridine, 2,6 lutidine, and the like, optionally with heating, optionally with microwave irradiation to provide a compound of the formula (37)

acetate, tetrakis(triphenylphosphine)palladium(0), dichlorobis (triphenylphosphine)palladium(II), palladium on carbon, bis(acetonitrile)dichloropalladium(II), and the like, in an organic solvent such as methanol, ethanol, ethyl acetate, tetrahydrofuran, 1,4-dioxane, dichloromethane, chloroform, 1,2-dichloroethane, N,N-dimethylformamide, and the like, to provide a compound of the formula (41).

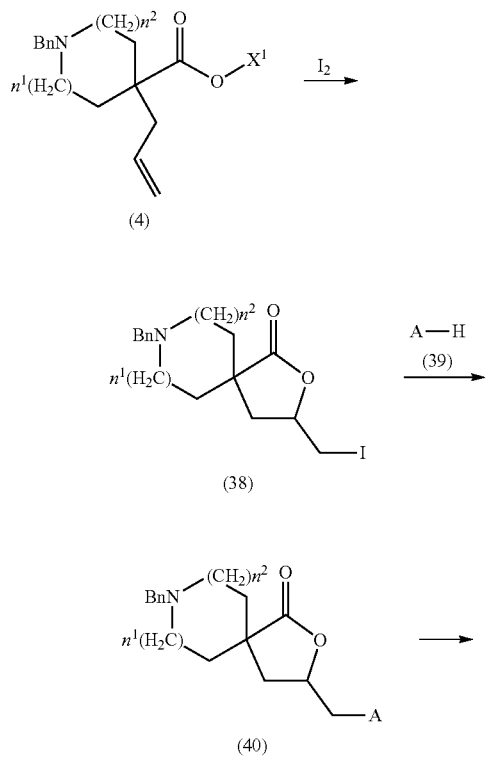

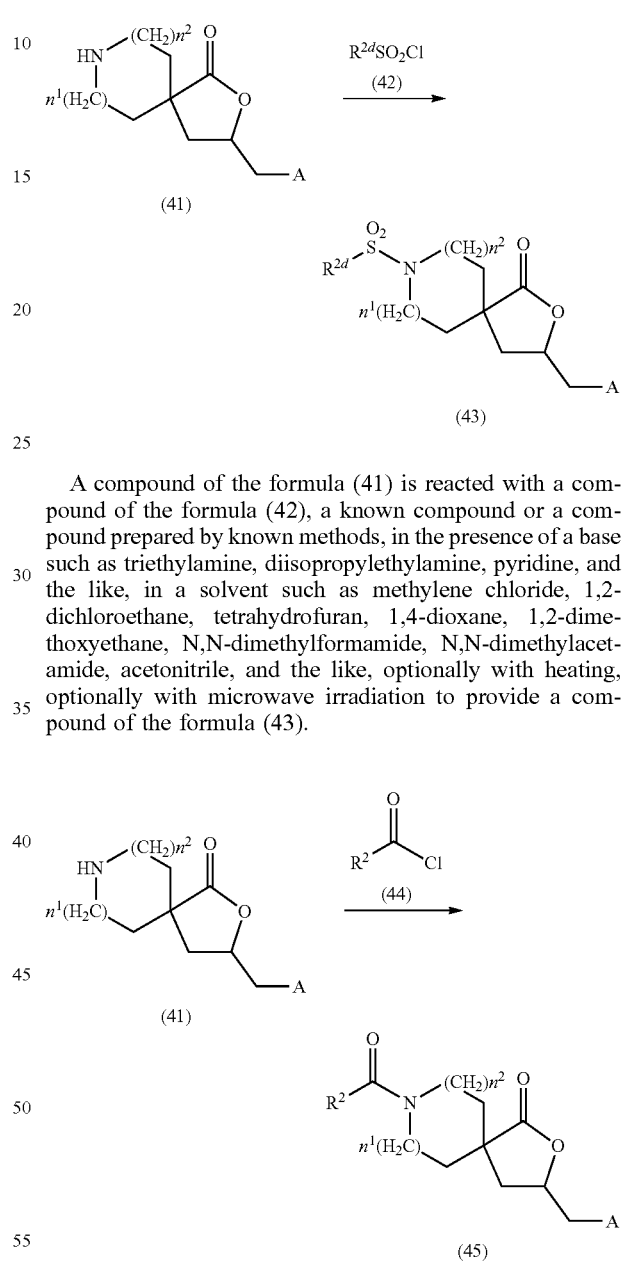

A compound of the formula (41) is reacted with a compound of the formula (42), a known compound or a compound prepared by known methods, in the presence of a base such as triethylamine, diisopropylethylamine, pyridine, and the like, in a solvent such as methylene chloride, 1,2-dichloroethane, tetrahydrofuran, 1,4-dioxane, 1,2-dimethoxyethane, N,N-dimethylformamide, N,N-dimethylacetamide, acetonitrile, and the like, optionally with heating, optionally with microwave irradiation to provide a compound of the formula (43).

A compound of the formula (4) is then reacted with iodine in the presence of a base such as sodium bicarbonate, potassium bicarbonate, lithium bicarbonate, sodium carbonate, potassium carbonate, lithium bicarbonate, sodium hydroxide, potassium hydroxide, lithium hydroxide, and the like, in the presence of a solvent such as tetrahydrofuran, ethyl ether, 1,4-dioxane, and the like to provide a compound of the formula (38). A compound of the formula (38) is reacted with a compound of the formula (39), a known compound or compound prepared by known methods, in an organic solvent such as tetrahydrofuran, 1,4-dioxane, 1,2-dimethoxyethane, dimethylformamide, dimethylacetamide, and the like, optionally in the presence of a base such as triethylamine, diisopropylethylamine, pyridine, 2,6 lutidine, and the like, optionally with heating, optionally with microwave irradiation to provide a compound of the formula (40). A compound of the formula (40) is reacted with hydrogen gas in the presence of a palladium catalyst such as palladium on carbon, palladium on barium sulfate, palladium (II)

A compound of the formula (41) is reacted with a compound of the formula (44), a known compound or a compound prepared by known methods, in the presence of a base such as triethylamine, diisopropylethylamine, pyridine, and the like, in a solvent such as methylene chloride, 1,2-dichloroethane, tetrahydrofuran, 1,4-dioxane, 1,2-dimethoxyethane, N,N-dimethylformamide, N,N-dimethylacetamide, acetonitrile, and the like, optionally with heating, optionally with microwave irradiation to provide a compound of the formula (45).

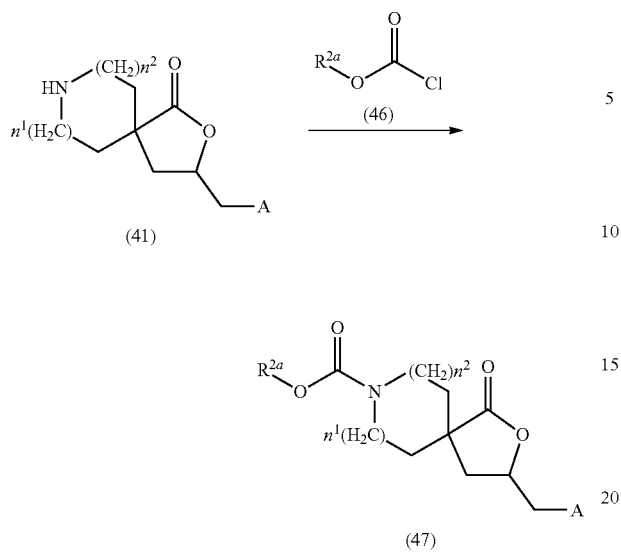

A compound of the formula (41) is reacted with a compound of the formula (46), a known compound or a compound prepared by known methods, in the presence of a base such as triethylamine, diisopropylethylamine, pyridine, and the like, in a solvent such as methylene chloride, 1,2-dichloroethane, tetrahydrofuran, 1,4-dioxane, 1,2-dimethoxyethane, N,N-dimethylformamide, N,N-dimethylacetamide, acetonitrile, and the like, optionally with heating, optionally with microwave irradiation to provide a compound of the formula (47).

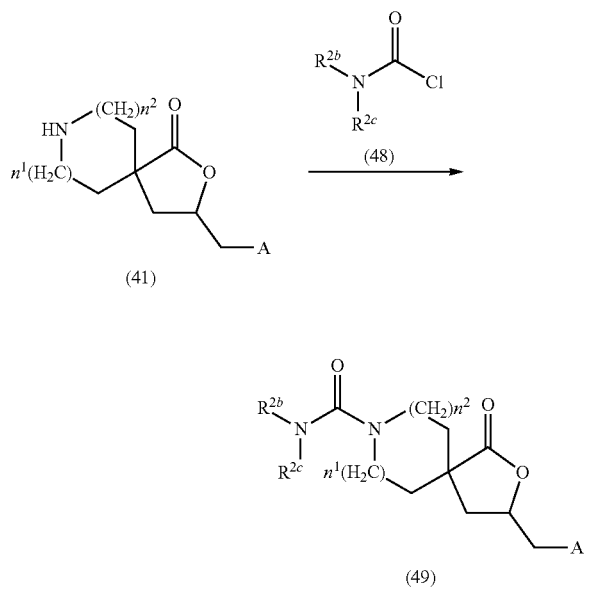

A compound of the formula (41) is reacted with a compound of the formula (48), a known compound or a compound prepared by known methods, in the presence of a base such as triethylamine, diisopropylethylamine, pyridine, and the like, in a solvent such as methylene chloride, 1,2-dichloroethane, tetrahydrofuran, 1,4-dioxane, 1,2-dimethoxyethane, N,N-dimethylformamide, N,N-dimethylacetamide, acetonitrile, and the like, optionally with heating, optionally with microwave irradiation to provide a compound of the formula (49).

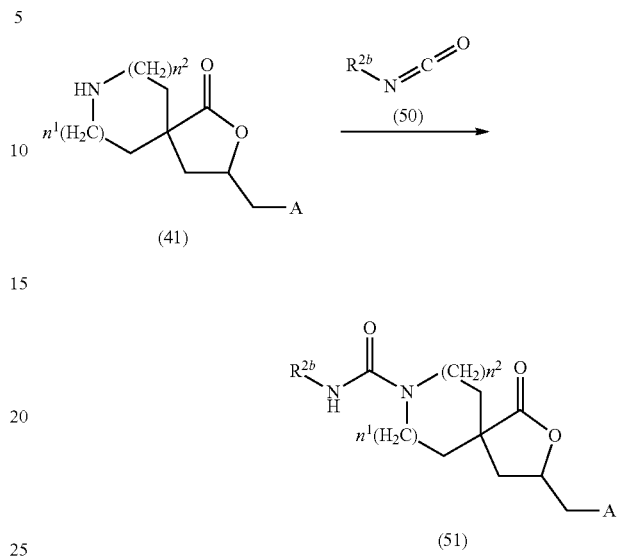

A compound of the formula (41) is reacted with a compound of the formula (50), a known compound or a compound prepared by known methods, in a solvent such as methylene chloride, 1,2-dichloroethane, tetrahydrofuran, 1,4-dioxane, 1,2-dimethoxyethane, N,N-dimethylformamide. N,N-dimethylacetamide, acetonitrile, and the like, optionally with heating, optionally with microwave irradiation to provide a compound of the formula (51).

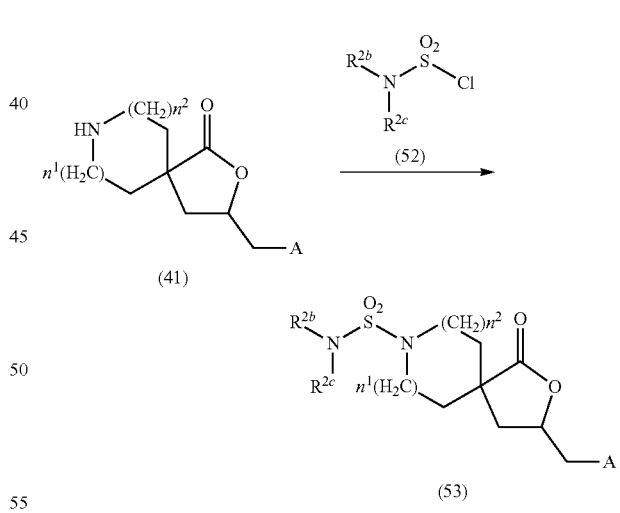

A compound of the formula (41) is reacted with a compound of the formula (52), a known compound or a compound prepared by known methods, in the presence of a base such as triethylamine, diisopropylethylamine, pyridine, and the like, in a solvent such as methylene chloride, 1,2-dichloroethane, tetrahydrofuran, 1,4-dioxane, 1,2-dimethoxyethane, N,N-dimethylformamide, N,N-dimethylacetamide, acetonitrile, and the like, optionally with heating, optionally with microwave irradiation to provide a compound of the formula (53).

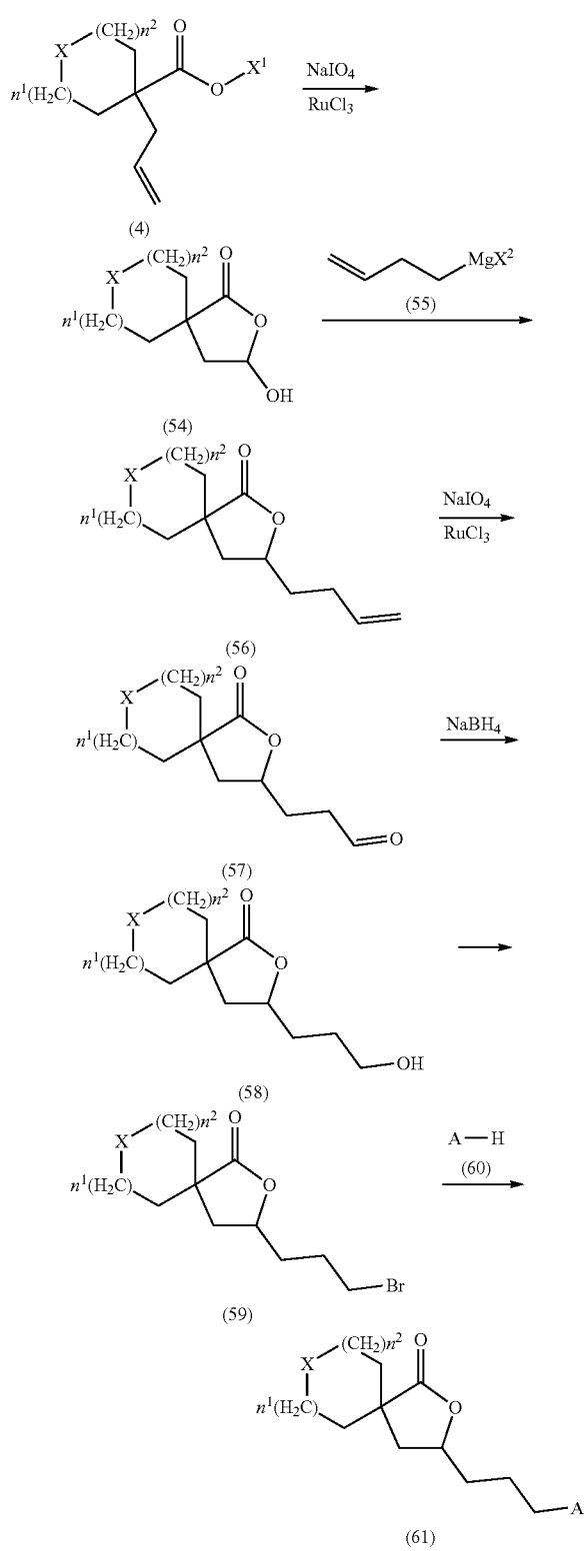

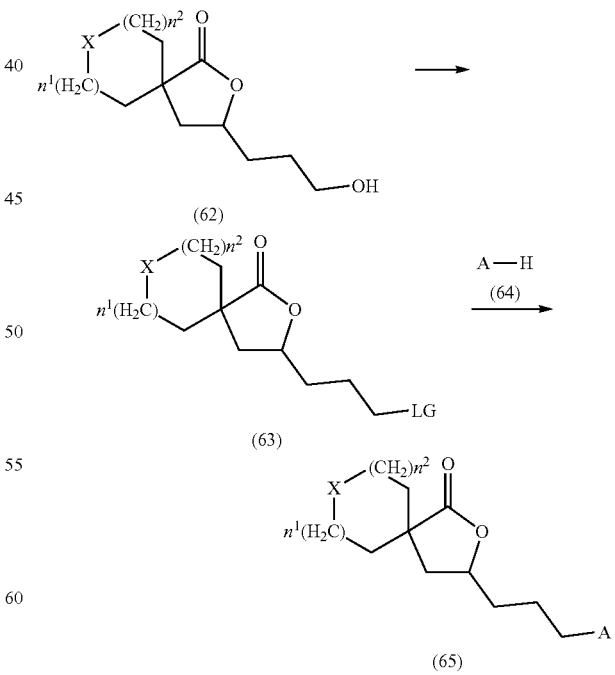

of the formula (55), a known compound or compound prepared by known methods, wherein $X^2$ is a halogen, in the presence of a solvent such as ethyl ether, tetrahydrofuran, 1,4-dioxane and the like, optionally with heating, optionally with microwave irradiation, to provide a compound of the formula (56). A compound of the formula (56) is reacted with ruthenium chloride in the presence of sodium periodate in a solvent such as acetonitrile, methanol, ethanol, isopropanol, and the like, optionally with heating, optionally with microwave irradiation, to provide a compound of the formula (57). A compound of the formula (57) is reacted with a reducing agent such as lithium borohydride, sodium borohydride, sodium cyanoborohydride and the like, in a solvent such as methanol, ethanol, isopropanol, acetonitrile, and the like, optionally with heating, optionally with microwave irradiation, to provide a compound of the formula (58). A compound of the formula (58) is treated with carbon tetrabromide in the presence of triphenylphosphine, in a solvent such as methylene chloride, 1,2-dichloroethane, tetrahydrofuran, 1,4-dioxane, 1,2-dimethoxyethane, N,N-dimethylformamide, N,N-dimethylacetamide, and the like, optionally with heating, optionally with microwave irradiation to provide a compound of the formula (59). A compound of the formula (59) is reacted with a compound of the formula (60), a known compound or a compound prepared by known methods, in the presence of a base such as sodium carbonate, potassium carbonate, lithium carbonate, sodium bicarbonate, potassium bicarbonate, lithium bicarbonate, triethylamine, diisopropylethylamine, pyridine, and the like, in a solvent such as methylene chloride, 1,2-dichloroethane, tetrahydrofuran, 1,4-dioxane, 1,2-dimethoxyethane, N,N-dimethylformamide, N,N-dimethylacetamide, acetonitrile, methanol, ethanol, isopropanol, and the like, optionally with heating, optionally with microwave irradiation to provide a compound of the formula (61).

A compound of the formula (4) is reacted with ruthenium chloride in the presence of sodium periodate in a solvent such as acetonitrile, methanol, ethanol, isopropanol, and the like, optionally with heating, optionally with microwave irradiation, to provide a compound of the formula (54). A compound of the formula (54) is reacted with a compound A compound of the formula (62) is then converted to a compound of the formula (63), wherein LG is a mesylate, tosylate, nosylate, and the like, using methods that are known to one skilled in the art. Thus, a compound of the formula (62) is treated with a sulfonyl chloride such as methanesulfonyl chloride, toluenesulfonyl chloride p-nitrophenyl sulfonyl chloride, and the like, in the presence of a base such as triethylamine, diisopropyl amine, pyridine, 2,6-lutidine, and the like, in an organic solvent such as methylene chloride, dichloroethane, tetrahydrofuran, 1,4-dioxane, N, N-dimethylformamide, tetrahydrofuran, 1,4-dioxane and the like to provide a compound of the formula (63). A compound of the formula (63) is reacted with a compound of the formula (64), a known compound or a compound prepared by known methods, in the presence of a base such as sodium carbonate, potassium carbonate, lithium carbonate, sodium bicarbonate, potassium bicarbonate, lithium bicarbonate, triethylamine, diisopropylethylamine, pyridine, and the like, in a solvent such as methylene chloride, 1,2-dichloroethane, tetrahydrofuran, 1,4-dioxane, 1,2-dimethoxyethane, N,N-dimethylformamide, N,N-dimethylacetamide, acetonitrile, methanol, ethanol, isopropanol, and the like, optionally with heating, optionally with microwave irradiation to provide a compound of the formula (65).

A compound of the formula (4) is reacted with ruthenium chloride in the presence of sodium periodate in a solvent such as acetonitrile, methanol, ethanol, isopropanol, and the like, optionally with heating, optionally with microwave irradiation, to provide a compound of the formula (66). A compound of the formula (66) is reacted with a compound of the formula (67), a known compound or compound prepared by known methods, wherein $X^2$ is a halogen, in the presence of a solvent such as ethyl ether, tetrahydrofuran, 1,4-dioxane and the like, optionally with heating, optionally with microwave irradiation, to provide a compound of the formula (68). A compound of the formula (68) is reacted with ruthenium chloride in the presence of sodium periodate in a solvent such as acetonitrile, methanol, ethanol, isopropanol, and the like, optionally with heating, optionally with microwave irradiation, to provide a compound of the formula (69). A compound of the formula (69) is reacted with a reducing agent such as lithium borohydride, sodium borohydride, sodium cyanoborohydride and the like, in a solvent such as methanol, ethanol, isopropanol, acetonitrile, and the like, optionally with heating, optionally with microwave irradiation, to provide a compound of the formula (70). A compound of the formula (70) is reacted with tert-butyldimethylchlorosilane in the presence of imidazole, in the presence of a solvent such as methylene chloride, 1,2-dichloroethane, tetrahydrofuran, 1,4-dioxane, 1,2-dimethoxyethane, N,N-dimethylformamide, N,N-dimethylacetamide, and the like, optionally with heating, optionally with microwave irradiation to provide a compound of the formula (71). Alternatively, a compound of the formula (70) is reacted with tert-butyldimethylsilyl trifluoromethanesulfonate in the presence of a base such as pyridine, 2,6-lutidine, triethylamine, diisopropylethylamine, and the like, in a solvent such as methylene chloride, 1,2-dichloroethane, tetrahydrofuran, 1,4-dioxane, 1,2-dimethoxyethane, N,N-dimethylformamide, N,N-dimethylacetamide, and the like, optionally with heating, optionally with microwave irradiation to provide a compound of the formula (71).

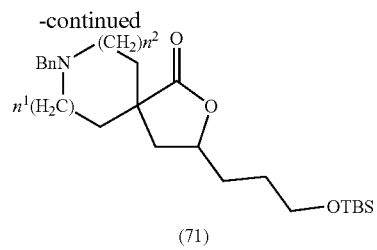

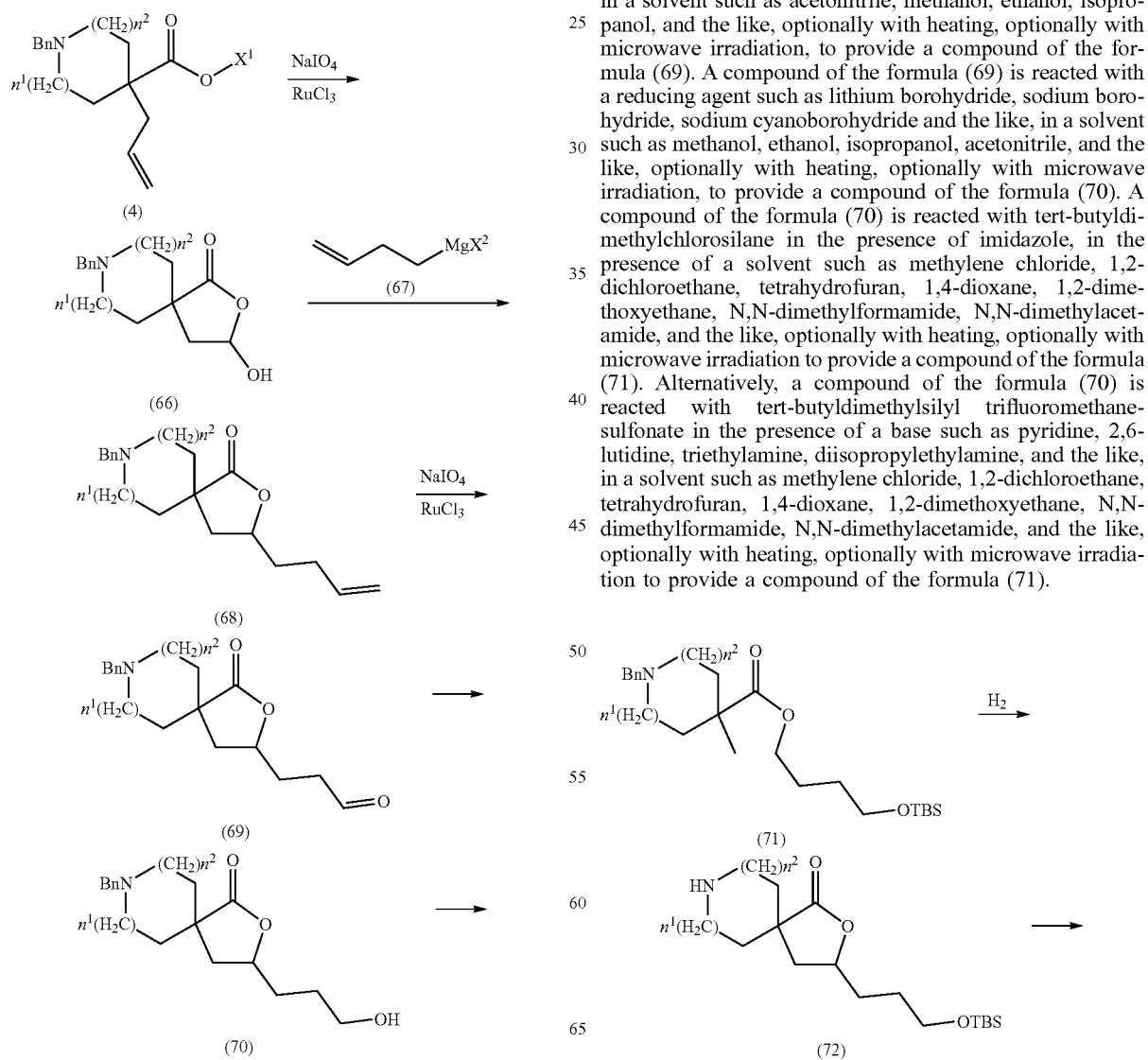

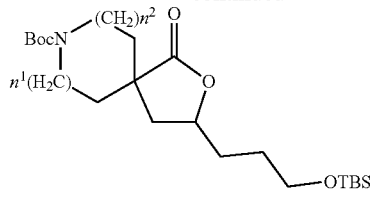

(73)

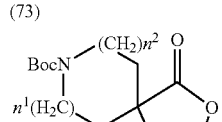

(74)

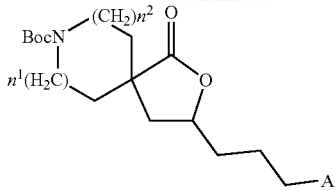

(77)

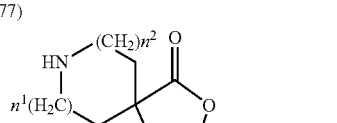

(78)

A compound of the formula (71) is reacted with hydrogen gas in the presence of a palladium catalyst such as palladium on carbon, palladium on barium sulfate, palladium (II) acetate, tetrakis(triphenylphosphine)palladium(0), dichlorobis (triphenylphosphine)palladium(II), palladium on carbon, bis(acetonitrile)dichloropalladium(II), and the like, in an organic solvent such as methanol, ethanol, ethyl acetate, tetrahydrofuran, 1,4-dioxane, dichloromethane, chloroform, 1,2-dichloroethane, N,N-dimethylformamide, and the like, to provide a compound of the formula (72). A compound of the formula (72) is reacted with Di-tert-butyl dicarbonate in the presence of a base such as such as pyridine, 2,6-lutidine, triethylamine, diisopropylethylamine, and the like, in a solvent such as methylene chloride, 1,2-dichloroethane, tetrahydrofuran, 1,4-dioxane, 1,2-dimethoxyethane, N,N-dimethylformamide, N,N-dimethylacetamide, methanol, ethanol, isopropanol, and the like, optionally with heating, optionally with microwave irradiation to provide a compound of the formula (73). A compound of the formula (73) is reacted with Tetra-n-butylammonium fluoride in the presence of solvent such as methylene chloride, 1,2-dichloroethane, tetrahydrofuran, 1,4-dioxane, 1,2-dimethoxyethane, N,N-dimethylformamide, N,N-dimethylacetamide, methanol, ethanol, isopropanol, and the like, optionally with heating, optionally with microwave irradiation to provide a compound of the formula (74).

A compound of the formula (74) is treated with carbon tetrabromide in the presence of triphenylphosphine, in a solvent such as methylene chloride, 1,2-dichloroethane, tetrahydrofuran, 1,4-dioxane, 1,2-dimethoxyethane, N,N-dimethylformamide, N,N-dimethylacetamide, and the like, optionally with heating, optionally with microwave irradiation to provide a compound of the formula (75). A compound of the formula (75) is reacted with a compound of the formula (76), a known compound or a compound prepared by known methods, in the presence of a base such as sodium carbonate, potassium carbonate, lithium carbonate, sodium bicarbonate, potassium bicarbonate, lithium bicarbonate, triethylamine, diisopropylethylamine, pyridine, and the like, in a solvent such as methylene chloride, 1,2-dichloroethane, tetrahydrofuran, 1,4-dioxane, 1,2-dimethoxyethane, N,N-dimethylformamide, N,N-dimethylacetamide, acetonitrile, methanol, ethanol, isopropanol, and the like, optionally with heating, optionally with microwave irradiation to provide a compound of the formula (77). A compound of the formula (77) is reacted with an acid such as trifluoroacetic acid, formic acid, acetic acid, hydrochloric acid, sulfuric acid, and the like, optionally in a solvent such as methylene chloride, 1,2-dichloroethane, tetrahydrofuran, 1,4-dioxane, 1,2-dimethoxyethane, N,N-dimethylformamide, N,N-dimethylacetamide, acetonitrile, methanol, ethanol, isopropanol, and the like, optionally with heating, optionally with microwave irradiation to provide a compound of the formula (78).

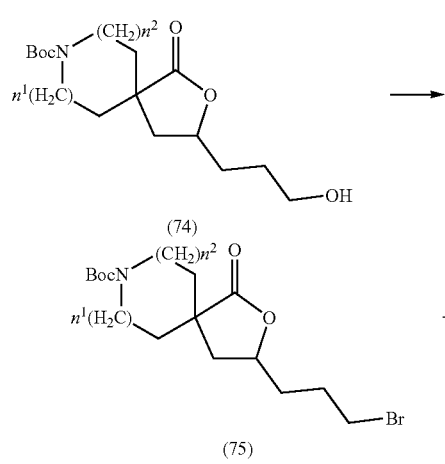

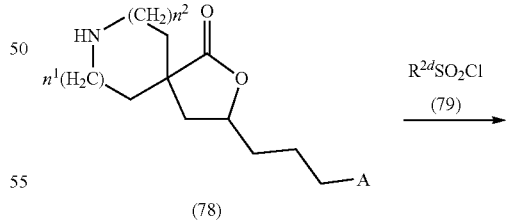

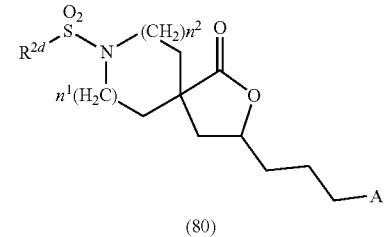

A compound of the formula (78) is reacted with a compound of the formula (79), a known compound or a compound prepared by known methods, in the presence of a base such as triethylamine, diisopropylethylamine, pyridinic, and the like, in a solvent such as methylene chloride, 1,2-dichloroethane, tetrahydrofuran, 1,4-dioxane, 1,2-dimethoxyethane, N,N-dimethylformamide, N,N-dimethylacetamide, acetonitrile, and the like, optionally with heating, optionally with microwave irradiation to provide a compound of the formula (80).

A compound of the formula (78) is reacted with a compound of the formula (83), a known compound or a compound prepared by known methods, in the presence of a base such as triethylamine, diisopropylethylamine, pyridine, and the like, in a solvent such as methylene chloride, 1,2-dichloroethane, tetrahydrofuran, 1,4-dioxane, 1,2-dimethoxyethane, N,N-dimethylformamide, N,N-dimethylacetamide, acetonitrile, and the like, optionally with heating, optionally with microwave irradiation to provide a compound of the formula (84).

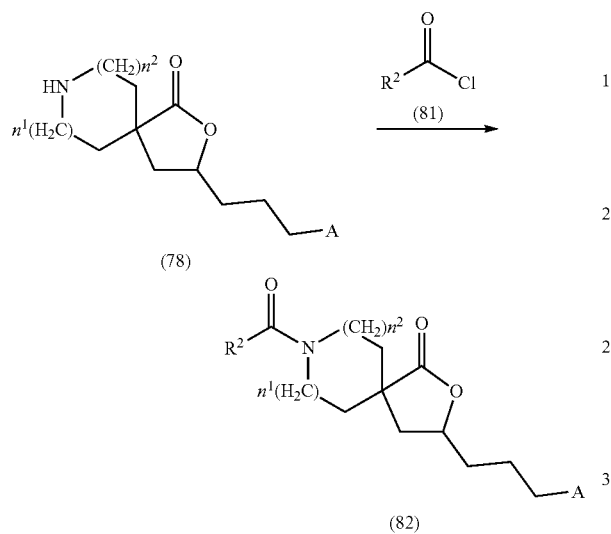

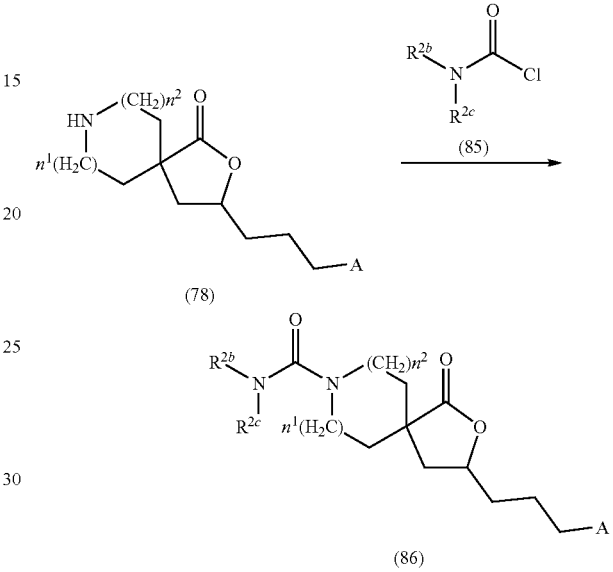

A compound of the formula (78) is reacted with a compound of the formula (81), a known compound or a compound prepared by known methods, in the presence of a base such as triethylamine, diisopropylethylamine, pyridine, and the like, in a solvent such as methylene chloride, 1,2-dichloroethane, tetrahydrofuran, 1,4-dioxane, 1,2-dimethoxyethane, N,N-dimethylformamide, N,N-dimethylacetamide, acetonitrile, and the like, optionally with heating, optionally with microwave irradiation to provide a compound of the formula (82).

A compound of the formula (78) is reacted with a compound of the formula (85), a known compound or a compound prepared by known methods, in the presence of a base such as triethylamine, diisopropylethylamine, pyridine, and the like, in a solvent such as methylene chloride, 1,2-dichloroethane, tetrahydrofuran, 1,4-dioxane, 1,2-dimethoxyethane, N,N-dimethylformamide, N,N-dimethylacetamide, acetonitrile, and the like, optionally with heating, optionally with microwave irradiation to provide a compound of the formula (86).

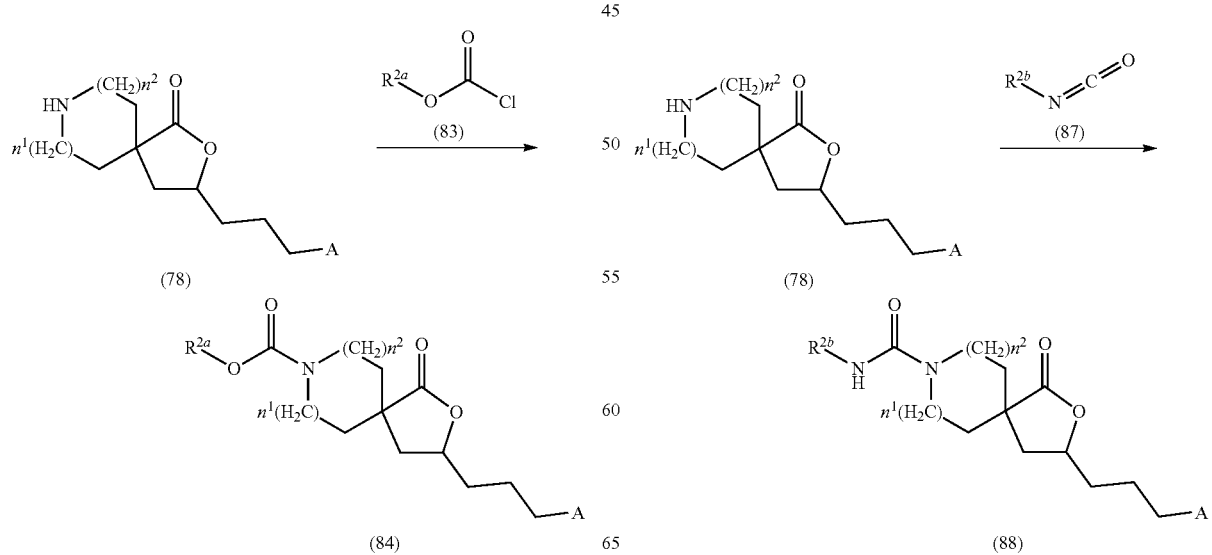

A compound of the formula (78) is reacted with a compound of the formula (87), a known compound or a compound prepared by known methods, in a solvent such as methylene chloride, 1,2-dichloroethane, tetrahydrofuran, 1,4-dioxane, 1,2-dimethoxyethane, N,N-dimethylformamide, N,N-dimethylacetamide, acetonitrile, and the like, optionally with heating, optionally with microwave irradiation to provide a compound of the formula (88).

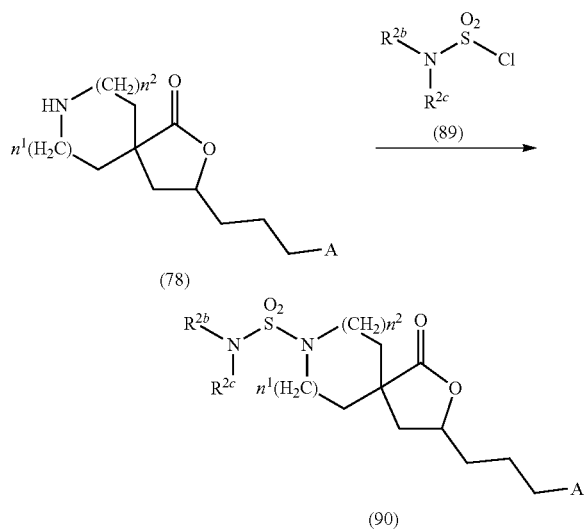

A compound of the formula (78) is reacted with a compound of the formula (89), a known compound or a compound prepared by known methods, in the presence of a base such as triethylamine, diisopropylethylamine, pyridine, and the like, in a solvent such as methylene chloride, 1,2-dichloroethane, tetrahydrofuran, 1,4-dioxane, 1,2-dimethoxyethane, N,N-dimethylformamide, N,N-dimethylacetamide, acetonitrile, and the like, optionally with heating, optionally with microwave irradiation to provide a compound of the formula (90).

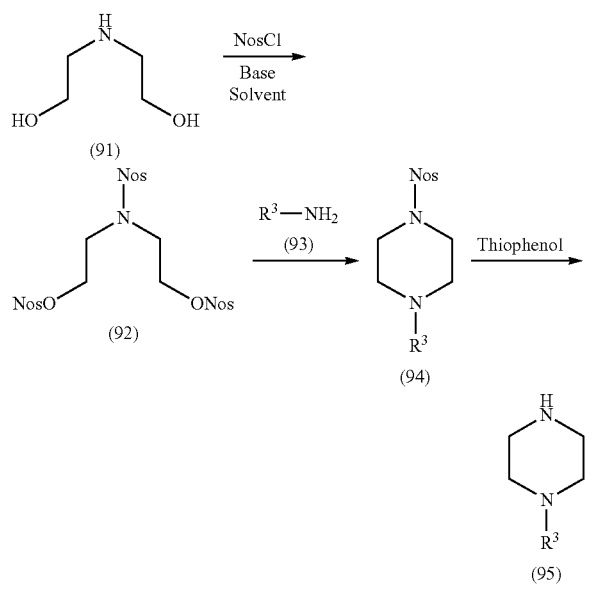

Diethanolamine (91) is reacted with 4-nitrobenzenesulfonyl chloride (NosCl) in the presence of a base such as triethylamine, diisopropylethylamine, pyridine, 2,6-lutidine, and the like in a solvent such as tetrahydrofuran, 1,4-dioxane, methylene chloride and the like to provide a compound of the formula (92). A compound of the formula (92) is then reacted with a compound of the formula (93), a known compound or one prepared by known methods, in the presence of a base such as triethylamine, diisopropylethylamine, pyridine, 2,6-lutidine, and the like, in a solvent such as acetonitrile, methanol, ethanol, dimethyl formamide, optionally with heating, optionally with microwave irradiation to provide a compound of the formula (94). A compound of the formula (94) is reacted with a thiophenol in the presence of a base such as sodium bicarbonate, potassium bicarbonate, lithium bicarbonate, sodium carbonate, potassium carbonate, lithium bicarbonate, sodium hydroxide, potassium hydroxide, lithium hydroxide, and the like, in the presence of a solvent such as tetrahydrofuran, ethyl ether, 1,4-dioxane, acetonitrile and the like, optionally in the presence of dimethylsulfoxide, optionally with heating, optionally with microwave irradiation, to provide a compound of the formula (95).

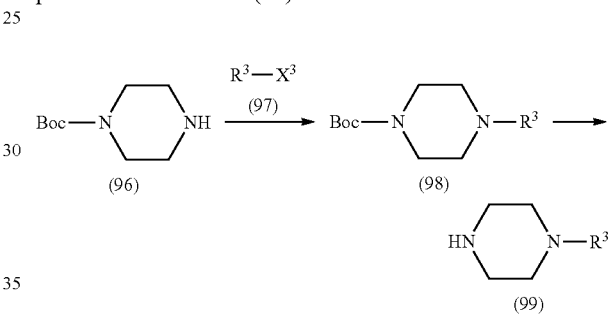

A compound of the formula (96), a known compound or a compound prepared by known methods, is reacted with a compound of the formula (97), a known compound or a compound prepared by known methods in which $X^3$ is selected from the group consisting of chlorine, bromine, iodine, and methanetrifluorosulfonate, in the presence of a base such as sodium tert-butoxide, lithium tert-butoxide, potassium tert-butoxide, and the like, optionally in the presence of a base such as triethylamine, diisopropylethyl amine, pyridine, 2,6-lutidine, and the like, in the presence of a palladium catalyst such as palladium (II) acetate, tetrakis (triphenylphosphine)palladium(0), dichlorobis (triphenylphosphine)palladium(II), palladium on carbon, bis(acetonitrile)dichloropalladium(II), tris(dibenzylideneacetone) dipalladium(0), and the like, in the presence of a solvent such as toluene, benzene, methylene chloride, 1,2-dichloraethan, tetrahydrofuran, 1,4-dioxane, N,N-dimethylformamide, and the like, optionally with heating, optionally with microwave irradiation, to provide a compound of the formula (98). A compound of the formula (98) is reacted with an acid such as trifluoroacetic acid, formic acid, acetic acid, hydrochloric acid, sulfuric acid, and the like, optionally in a solvent such as methylene chloride, 1,2-dichloroethane, tetrahydrofuran, 1,4-dioxane, 1,2-dimethoxyethane, N,N-dimethylformamide, N,N-dimethylacetamide, acetonitrile, methanol, ethanol, isopropanol, and the like, optionally with heating, optionally with microwave irradiation to provide a compound of the formula (99).

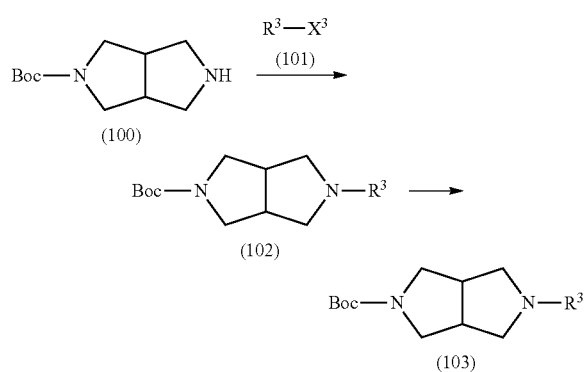

A compound of the formula (100), a known compound or a compound prepared by known methods, is reacted with a compound of the formula (101), a known compound or a compound prepared by known methods in which $X^3$ is selected from the group consisting of chlorine, bromine, iodine, and methanetrifluorosulfonate, in the presence of a base such as sodium tert-butoxide, lithium tert-butoxide, potassium tert-butoxide, and the like, optionally in the presence of a base such as triethylamine, diisopropylethyl amine, pyridine, 2,6-lutidine, and the like, in the presence of a palladium catalyst such as palladium (II) acetate, tetrakis (triphenylphosphine)palladium(0), dichlorobis (triphenylphosphine)palladium(II), palladium on carbon, bis(acetonitrile)dichloropalladium(II), tris(dibenzylideneacetone) dipalladium(0), and the like, in the presence of a solvent such as toluene, benzene, methylene chloride, 1,2-dichloroethane, tetrahydrofuran, 1,4-dioxane, N,N-dimethylformamide, and the like, optionally with heating, optionally with microwave irradiation, to provide a compound of the formula (102). A compound of the formula (102) is reacted with an acid such as trifluoroacetic acid, formic acid, acetic acid, hydrochloric acid, sulfuric acid, and the like, optionally in a solvent such as methylene chloride, 1,2-dichloroethane, tetrahydrofuran, 1,4-dioxane, 1,2-dimethoxyethane, N,N-dimethylformamide, N,N-dimethylacetamide, acetonitrile, methanol, ethanol, isopropanol, and the like, optionally with heating, optionally with microwave irradiation to provide a compound of the formula (103).

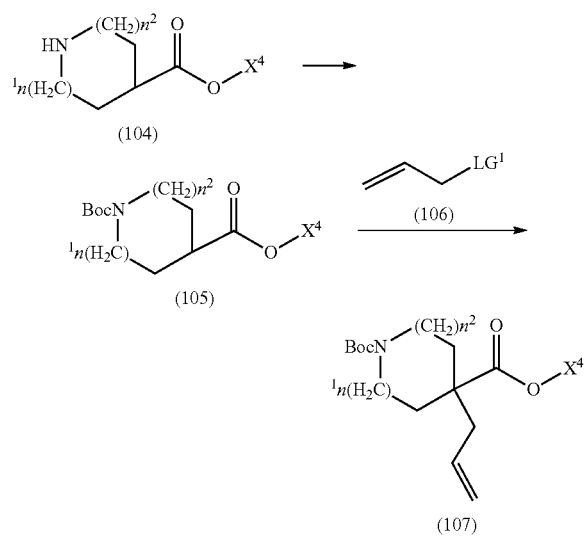

A compound of the formula (104), a known compound or a compound prepared by known methods in which $X^4$ is an $C_{1-6}$ alkyl, is reacted with di-tert-butyl dicarbonate in the presence of a base such as triethylamine, diisopropylethylamine, pyridine, 2,6-lutidine, and the like, in a solvent such as methanol, ethanol, methylene chloride, tetrahydrofuran, 1,4-dioxane, and the like, optionally with heating, optionally with microwave irradiation to provide a compound of the formula (105). A compound of the formula (105) is reacted with a compound of the formula (106), a known compound or a compound prepared by known methods where in $LG^1$ is a leaving group such as chlorine, bromine, iodine, mesylate, tosylate, and the like, in the presence of a base such as lithium diisopropylamide, sodium diisopropylamide, potassium diisopropylamide, lithium bis(trimethylsilyl)amide, sodium bis(trimethylsilyl)amide, potassium bis(trimethylsilyl)amide, sodium hydride, and the like in an organic solvent such as tetrahydrofuran, 1,4-dioxane, 1,2-dimethoxyethane, dimethylformamide, dimethylacetamide, and the like, to provide a compound of the formula (107).

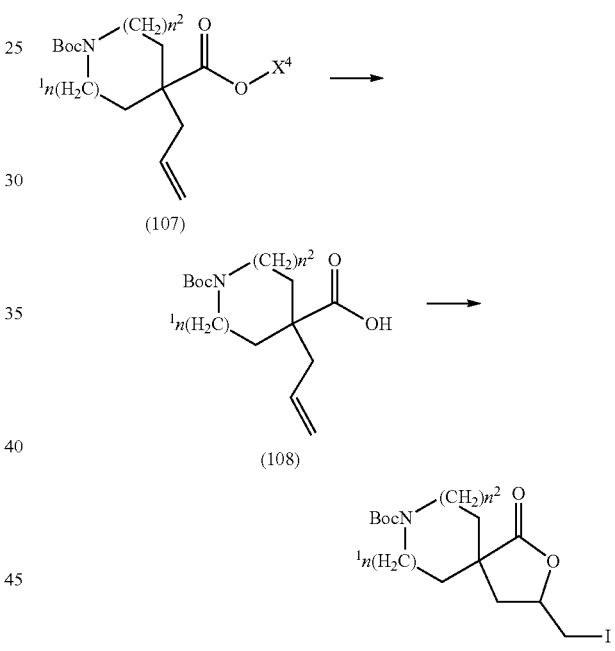

A compound of the formula (107) is reacted with a base such as sodium hydroxide, lithium hydroxide, potassium hydroxide, sodium carbonate, lithium carbonate, potassium carbonate, and the like in a solvent such as methanol, ethanol, isopropanol, tetrahydrofuran, 1,4-dioxane, N,N-dimethylformamide, and the like, optionally in the presence of water, optionally with heating, optionally with microwave irradiation to provide a compound of the formula (108). A compound of the formula (108) is then reacted with iodine in the presence of a base such as sodium bicarbonate, potassium bicarbonate, lithium bicarbonate, sodium carbonate, potassium carbonate, lithium bicarbonate, sodium hydroxide, potassium hydroxide, lithium hydroxide, and the like, in the presence of a solvent such as tetrahydrofuran, ethyl ether, 1,4-dioxane, and the like to provide a compound of the formula (109).

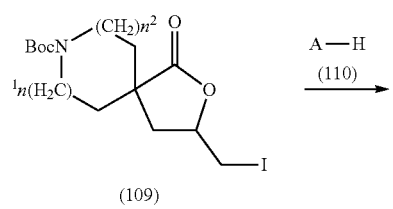

(109)

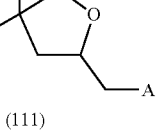

(111)

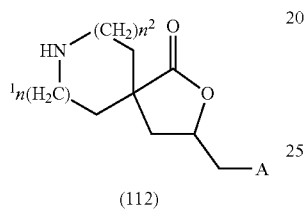

(112)

A compound of the formula (109) is reacted with a compound of the formula (110), a known compound or compound prepared by known methods, in an organic solvent such as tetrahydrofuran, 1,4-dioxane, 1,2-dimethoxyethane, dimethylformamide, dimethylacetamide, and the like, optionally in the presence of a base such as triethylamine, diisopropylethylamine, pyridine, 2,6 lutidine, and the like, optionally with heating, optionally with microwave irradiation to provide a compound of the formula (111). A compound of the formula (111) is reacted with an acid such as trifluoroacetic acid, formic acid, acetic acid, hydrochloric acid, sulfuric acid, and the like, optionally in a solvent such as methylene chloride, 1,2-dichloroethane, tetrahydrofuran, 1,4-dioxane, 1,2-dimethoxyethane, N,N-dimethylformamide, N,N-dimethylacetamide, acetonitrile, methanol, ethanol, isopropanol, and the like, optionally with heating, optionally with microwave irradiation to provide a compound of the formula (112).

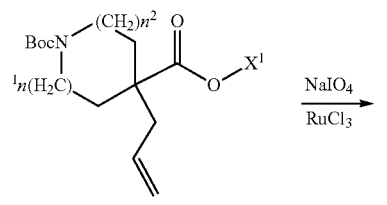

(113)

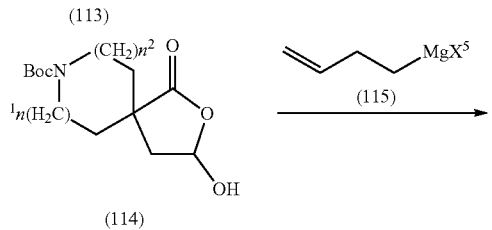

(114)

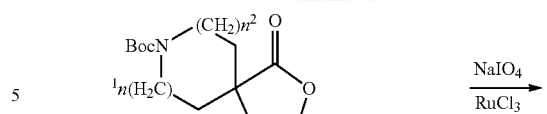

(116)

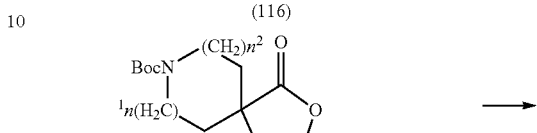

(117)

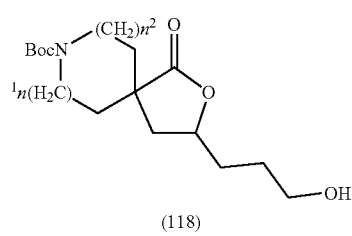

(118)

A compound of the formula (113) is reacted with ruthenium chloride in the presence of sodium periodate in a solvent such as acetonitrile, methanol, ethanol, isopropanol, and the like, optionally with heating, optionally with microwave irradiation, to provide a compound of the formula (114). A compound of the formula (114) is reacted with a compound of the formula (115), a known compound or compound prepared by known methods, wherein $X^5$ is a halogen, in the presence of a solvent such as ethyl ether, tetrahydrofuran, 1,4-dioxane and the like, optionally with heating, optionally with microwave irradiation, to provide a compound of the formula (116). A compound of the formula (116) is reacted with ruthenium chloride in the presence of sodium periodate in a solvent such as acetonitrile, methanol, ethanol, isopropanol, and the like, optionally with heating, optionally with microwave irradiation, to provide a compound of the formula (117). A compound of the formula (117) is reacted with a reducing agent such as lithium borohydride, sodium borohydride, sodium cyanoborohydride and the like, in a solvent such as methanol, ethanol, isopropanol, acetonitrile, and the like, optionally with heating, optionally with microwave irradiation to provide a compound of the formula (118).

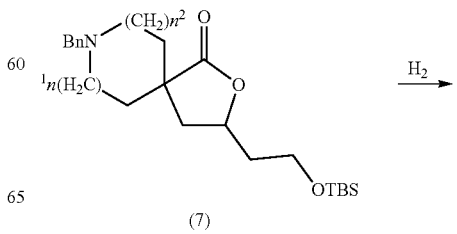

(7)

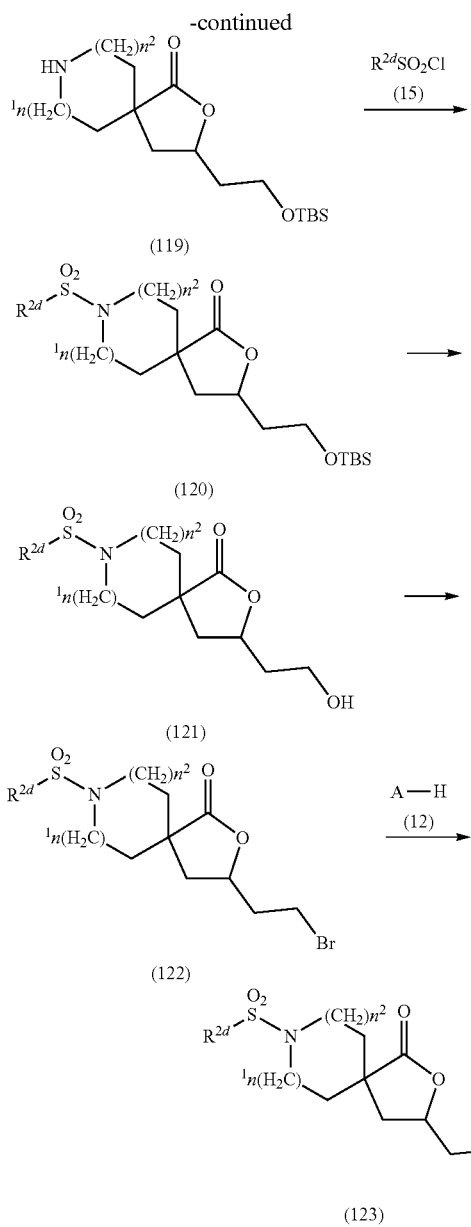

A compound of the formula (7) is reacted with hydrogen gas in the presence of a palladium catalyst such as palladium on carbon, palladium on barium sulfate, palladium (II) acetate, tetrakis(triphenylphosphine)palladium(0), dichlorobis (triphenylphosphine)palladium(II), palladium on carbon, bis(acetonitrile)dichloropalladium(II), and the like, in an organic solvent such as methanol, ethanol, ethyl acetate, tetrahydrofuran, 1,4-dioxane, dichloromethane, chloroform, 1,2-dichloroethane, N,N-dimethylformamide, and the like, to provide a compound of the formula (119). A compound of the formula (119) is reacted with a compound of the formula (15), a known compound or a compound prepared by known methods, in the presence of a base such as triethylamine, diisopropylethylamine, pyridine, and the like, in a solvent such as methylene chloride, 1,2-dichloroethane, tetrahydrofuran, 1,4-dioxane, 1,2-dimethoxyethane, N,N-dimethylformamide, N,N-dimethylacetamide, acetonitrile, and the like, optionally with heating, optionally with microwave irradiation to provide a compound of the formula (120). A compound of the formula (120) is reacted with tetra-n-butylammonium fluoride in the presence of solvent such as methylene chloride, 1,2-dichloroethane, tetrahydrofuran, 1,4-dioxane, 1,2-dimethoxyethane, N,N-dimethylformamide, N,N-dimethylacetamide, methanol, ethanol, isopropanol, and the like, optionally with heating, optionally with microwave irradiation to provide a compound of the formula (121). A compound of the formula (121) is treated with carbon tetrabromide in the presence of triphenylphosphine, in a solvent such as methylene chloride, 1,2-dichloroethane, tetrahydrofuran, 1,4-dioxane, 1,2-dimethoxyethane, N,N-dimethylformamide, N,N-dimethylacetamide, and the like, optionally with heating, optionally with microwave irradiation to provide a compound of the formula (122). A compound of the formula (122) is reacted with a compound of the formula (12), a known compound or a compound prepared by known methods, in the presence of a base such as sodium carbonate, potassium carbonate, lithium carbonate, sodium bicarbonate, potassium bicarbonate, lithium bicarbonate, triethylamine, diisopropylethylamine, pyridine, and the like, in a solvent such as methylene chloride, 1,2-dichloroethane, tetrahydrofuran, 1,4-dioxane, 1,2-dimethoxyethane, N,N-dimethylformamide, N,N-dimethylacetamide, acetonitrile, methanol, ethanol, isopropanol, and the like, optionally with heating, optionally with microwave irradiation to provide a compound of the formula (123).

The Examples provided below provide representative methods for preparing exemplary compounds of the present invention. The skilled practitioner will know how to substitute the appropriate reagents, starting materials and purification methods known to those skilled in the art, in order to prepare the compounds of the present invention.

EXAMPLES

The practice of the invention is illustrated by the following non-limiting examples. The Examples provided below provide representative methods for preparing exemplary compounds of the present invention. The skilled practitioner will know how to substitute the appropriate reagents, starting materials and purification methods known to those skilled in the art, in order to prepare the compounds of the present invention.

In the examples that follow, $^1$H-NMR spectra were obtained on a Varian Mercury 300-MHz NMR. Purity (%) and mass spectral data were determined with a Waters Alliance 2695 HPLC/MS (Waters Symmetry C18, 4.6×75 mm, 3.5 μm) with a 2996 diode array detector from 210-400 nm.

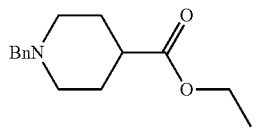 [SMILES: CCOC(=O)C1CCN(Cc2ccccc2)CC1]

Example 1: Preparation of ethyl 1-benzylpiperidine-4-carboxylate: To a solution of ethyl piperidine-4-carboxylate (5.0 g, 31.8 mmol, 1.0 eq) and ethanol (15.0 mL), benzyl bromide (7.07 g, mmol, 1.3 eq) was added dropwise at 0° C. Following, triethylamine (1.06 g, 10.5 mmol, 1.5 eq) was added in one portion while at 0° C. The resulting mixture was allowed to warm to RT and stir overnight. The reaction was concentrated in vacuo to remove the presence of ethanol. The resulting residue was suspended in a mixture of ethyl acetate: D.I. water (20 mL:20 mL). The organic layer was separated and the aqueous layer was extracted with ethyl acetate (2×10 mL). The combined extract was dried over Na$_2$SO$_4$, then filtered through a plug of silica gel and washed with ethyl acetate. The filtrated was concentrated in vacuo to give product that was used in the next step without further purification. $^1$H NMR (400 MHz, CDCl$_3$) δ 7.41-7.20 (m, 5H), 4.14 (q, J=7.2 Hz, 2H), 3.51 (s, 2H), 2.87 (dt, J=3.5, 11.8 Hz, 2H), 2.29 (m, 1H), 2.04 (td, J=2.5, 11.4 Hz, 2H), 1.95-1.85 (m, 2H), 1.85-1.70 (m, 2H), 1.26 (t, J=7.1 Hz, 3H).

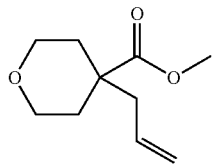

Example 2: Preparation of methyl 4-allyltetrahydro-2H-pyran-4-carboxylate: This reaction was performed in oven-dried glassware under a nitrogen atmosphere. To a solution of lithium diisopropylamide (1M, 1.20 equiv) in dry tetrahydrofuran (4.16 mL), methyl tetrahydro-2H-pyran-4-carboxylate (0.5 g, 3.47 mmol, 1.0 equiv), in 5 mL dry THF, was added dropwise during 0.5 hours at −78° C. The mixture was allowed to stir at this temperature for 1 hr followed by the addition of allyl bromide (0.457 g, 3.78 mmol, 1.1 eq) dropwise. The reaction mixture was allowed to warm to RT over a 1 hr period. The reaction was quenched with 10% HCl (while cooling in ice bath) until acidic (pH=2). The organic layer was separated and the aqueous layer was extracted with ethyl acetate (3×10 mL). The extract was dried over Na$_2$SO$_4$ and then concentrated in vacuo to give product that was used in the next step without further purification. $^1$H NMR (400 MHz, CDCl$_3$) δ 5.68-5.52 (m, 1H), 5.03-4.91 (m, 2H), 3.75 (dt, J=3.7, 11.8 Hz, 2H), 3.63 (s, 3H), 3.37 (td, J=2.1, 11.6 Hz, 2H), 2.21 (d, J=7.4 Hz, 2H), 2.03-1.95 (m, 2H), 1.53-1.40 (m, 21H).

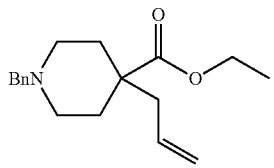 [SMILES: C=CCC1(C(=O)OCC)CCN(Cc2ccccc2)CC1]

Example 3: Preparation of ethyl 4-allyl-1-benzylpiperidine-4-carboxylate: This reaction was performed in oven-dried glassware under a nitrogen atmosphere. To a solution of ethyl 1-benzylpiperidine-4-carboxylate (6.24 g, 26.7 mmol, 1.0 eq) and dry THF (50 mL), lithium diisopropylamide (1M, 1.10 equiv) in dry tetrahydrofuran (29.3 mL) was added dropwise during 0.5 hours at −78° C. The mixture was allowed to stir at this temperature for 1 hr followed by the addition of allyl iodine (6.73 g, 3.78 mmol, 1.5 eq) dropwise. The reaction mixture was allowed to warm to RT and stir for 2 hr. The reaction was quenched with sat. aq. NH$_4$Cl until neutral pH (while cooling in ice bath). The organic layer was separated and the aqueous layer was extracted with ethyl acetate (2×50 mL). The combined extract was dried over Na$_2$SO$_4$, then filtered through a plug of silica gel and washed with ethyl acetate. The filtrated was concentrated in vacuo to give product that was used in the next step without further purification. $^1$H NMR (400 MHz, CDCl$_3$) δ 7.37-7.20 (m, 5H), 5.78-5.62 (m, 1H), 5.10-4.97 (m, 2H), 4.17 (q, J=7.1 Hz, 2H), 3.47 (s, 2H), 2.78-2.64 (m, 2H), 2.28 (d, J=7.4 Hz, 2H), 2.18-2.03 (m, 4H), 1.61-1.46 (m, 2H), 1.26 (t, J=7.1 Hz, 3H).

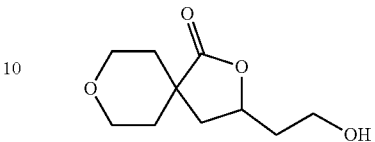

Example 4: Preparation of 3-(2-hydroxyethyl)-2,8-dioxaspiro[4.5]decan-1-one: A mixture of glacial acetic acid (10.9 g, 180 mmol, 53.6 eq), paraformaldehyde (0.309 g, 10.3 mmol, 3.0 eq) and H$_2$SO$_4$ (0.191 g, 1.95 mmol, 0.57 eq) was stirred for 30 min at 70° C. before methyl 4-allyltetrahydro-2H-pyran-4-carboxylate (0.632 g, 3.43 mmol, 1.0 equiv) was added dropwise during 10 min. The reaction mixture was then maintained at 70-80° C. and allowed to stir overnight. Acetic acid was removed under reduced pressure and the reaction was quenched with 10% NaHCO$_3$ solution. The mixture was then extracted with ethyl acetate (3×10 mL) and the combined organic phase was concentrated in vacuo to give a crude oil. The crude oil was used for next step without further purification.

A mixture of the crude oil (715 mg) and 30% NaOH (2.86 g NaOH, 4× crude oil) aqueous solution was refluxed for 2 hours. The mixture was cooled in an ice bath and excess 30% H$_2$SO$_4$ was added until acidic (pH<2). The resulting mixture was extracted with ethyl acetate (3×25 mL), the combined organic phase was washed with 10% NaHCO$_3$, (50 mL), brine (50 mL), dried over Na$_2$SO$_4$ and concentrated in vacuo to give a crude product which was used in the next step without further purification. $^1$H NMR (400 MHz, CDCl$_3$) δ 4.57 (m, 1H), 3.91 (dt, J=4.5, 11.8 Hz, 1H), 3.79 (dt, J=4.5, 12.0 Hz, H), 3.66 (t, J=6.0 Hz, 2H), 3.54-3.44 (m, 1H), 3.43-3.34 (m, 1H), 3.13 (b, 1H), 2.41 (dd, J=6.1, 13.2 Hz, 1H), 2.01-1.91 (m, 1H), 1.89-1.64 (m, 4H), 1.54-1.44 (m, 1H), 1.42-1.33 (m, 1H).

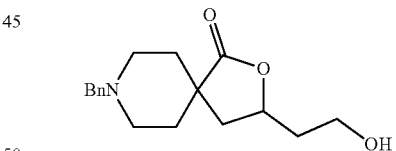

Example 5: Preparation of 8-benzyl-3-(2-hydroxyethyl)-2-oxa-8-azaspiro[4.5]decan-1-one: A mixture of glacial acetic acid (78.1 g, 1.3 mol, 53.6 eq), paraformaldehyde (2.21 g, 73.5 mmol, 3.0 eq) and H$_2$SO$_4$ (3.63 g, 37 mmol, 1.5 eq) was stirred for 30 min at 70° C. before ethyl 4-allyl-1-benzylpiperidine-4-carboxylate (7.03 g, 24.5 mmol, 1.0 equiv) was added dropwise during 10 min. The reaction mixture was then maintained at 70-80° C. and allowed to stir overnight. Acetic acid was removed under reduced pressure and the reaction was quenched with 10% NaHCO$_3$ solution. The mixture was then extracted with ethyl acetate (3×40 mL) and the combined organic phase was concentrated in vacuo to give a crude oil. The crude oil was used for next step without further purification.

A mixture of the crude oil (7.07 mg) and 30% NaOH (28 g NaOH, 4× crude oil) aqueous solution was refluxed for 2 hours. The mixture was cooled in an ice bath and excess 30% H$_2$SO$_4$ was added until acidic (pH<2). The resulting mixture was the neutralized (pH=8-9) with sat. aq. NaHCO$_3$ solution and then extracted with ethyl acetate (3×100 mL), the combined organic phase was dried over Na$_2$SO$_4$ and concentrated in vacuo to give a crude product which was used in the next step without further purification. $^1$H NMR (400 MHz, CDCl$_3$) δ 7.39-7.22 (m, 5H), 4.65 (m, 1H), 3.83 (t, J=5.6 Hz, 2H), 3.54 (s, 2H), 2.95-2.84 (m, 1H), 2.83-2.73 (m, 1H), 2.42 (dd, J=6.1, 13.0 Hz, 1H), 2.30-2.07 (m, 4H), 2.00-1.84 (m, 3H), 1.75-1.59 (m, 2H), 1.58-1.48 (m, 1H).

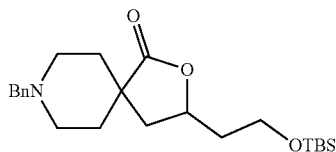 [SMILES: CC(C)(C)[Si](C)(C)OCCC1CC2(CCN(Cc3ccccc3)CC2)C(=O)O1]

Example 6: Preparation of 8-benzyl-3-(2-((tert-butyldimethylsilyl)oxy)ethyl)-2-oxa-8-azaspiro[4.5]decan-1-one: To a solution of 8-benzyl-3-(2-hydroxyethyl)-2-oxa-8-azaspiro[4.5]decan-1-one (10.0 g, 34.6 mmol, 1.0 eq.), imidazole (2.47 g, 36.3 mmol, 1.05 eq.) and dichloromethane (70 mL), was added a solution of tert-Butyldimethylsilyl chloride (1M, 5.47 g, 36.3 mmol, 1.05 eq.) in dichloromethane (36.3 mL). The reaction was allowed to stir at RT for 2 hr. before being quenched with D.I. water (50 mL). The organic layer was separated and the aqueous layer was extracted with dichloromethane (2×50 mL). The combined organic phase was dried over Na$_2$SO$_4$ and concentrated in vacuo to give a crude product which was further purified by column chromatography (Ethyl acetate/Hexanes, 0%-20%). $^1$H NMR (400 MHz, CDCl$_3$) δ 7.32-7.11 (m, 5H), 4.52 (m, 1H), 3.73-3.65 (m, 2H), 3.46 (s, 2H), 2.87-2.76 (m, 1H), 2.72 (dt, J=4.5, 11.8 Hz, 1H), 2.31 (dd, J=6.2, 12.9 Hz, 1H), 2.22-2.08 (m, 1H), 2.08-1.97 (m, 2H), 1.91-1.70 (m, 3H), 1.62 (dd, J=9.8, 12.8 Hz, 1H), 1.59-1.50 (m, 1H), 1.49-1.38 (m, 1H), 0.83 (s, 9H), 0.00 (s, 6H).

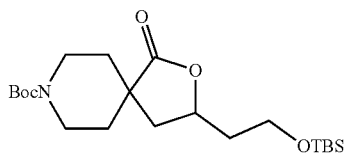 [SMILES: CC(C)(C)OC(=O)N1CCC2(CC1)CC(CCO[Si](C)(C)C(C)(C)C)OC2=O]

Example 7: Preparation of tert-butyl 3-(2-((tert-butyldimethylsilyl)oxy)ethyl)-1-oxo-2-oxa-8-azaspiro[4.5]decane-8-carboxylate: A mixture of 8-benzyl-3-(2-((tert-butyldimethylsilyl)oxy)ethyl)-2-oxa-8-azaspiro[4.5]decan-1-one (4.77 g, 11.8 mmol, 1 eq.), Pd/C (954 mg, 20% wt) and MeOH (79 mL) was stirred at RT under 1 atm of H$_2$ (filled balloon) overnight. The mixture was filtered through a plug of Celite, washed with MeOH (50 mL) and concentrated in vacuo to give a crude oil. The crude oil (3.78 g) was dissolved in dichloromethane (79 mL) and cooled to 0° C. before the addition of Di-tert-butyl dicarbonate (2.83 g, 13.0 mmol, 1.1 eq.) and trimethylamine (1.8 g, 17.7 mmol, 1.5 eq.). The reaction was allowed to warm to RT and stir for 45 min. At this point the reaction was diluted with sat. aq. NaHCO$_3$ solution and then extracted with ethyl acetate (3×50 mL), the combined organic phase was dried over Na$_2$SO$_4$ and concentrated in vacuo to give a crude product which was used in the next step without further purification.

$^1$H NMR (400 MHz, CDCl$_3$) δ 4.57 (m, 1H), 3.91 (b, 1H), 3.77 (b, 1H), 3.73-3.66 (m, 2H), 3.17-3.05 (m, 1H), 3.04-2.93 (m, 1H), 2.31 (dd, J=6.2, 13.0 Hz, 1H), 1.96-1.81 (m, 2H), 1.81-1.64 (m, 3H), 1.59-1.48 (m, 1H), 1.48-1.32 (m, 10H), 0.83 (s, 9H), 0.00 (s, 6H).

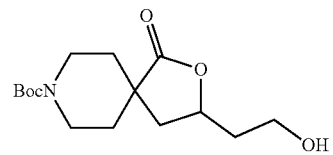 [SMILES: CC(C)(C)OC(=O)N1CCC2(CC1)CC(CCO)OC2=O]

Example 8: Preparation of tert-butyl 3-(2-hydroxyethyl)-1-oxo-2-oxa-8-azaspiro[4.5]decane-8-carboxylate: To a solution of tert-butyl 3-(2-((tert-butyldimethylsilyl)oxy)ethyl)-1-oxo-2-oxa-8-azaspiro[4.5]decane-8-carboxylate (4.88 g, 11.8 mmol, 1 eq.) and THF (70 mL) was added tetra-n-butylammonium fluoride (3.24 g, 12.4 mmol, 1.05 eq.): using THF (10 mL) to complete transfer. The resulting solution was allowed to stir at RT for 30 min before being concentrated in vacuo to give a crude product which was further purified by column chromatography (MeOH/DCM, 0%-10%). $^1$H NMR (400 MHz, CDCl$_3$) δ 4.67 (m, 1H), 3.95 (dt, J=5.0, 13.6 Hz, 11H), 3.87-3.73 (m, 3H), 3.23-3.10 (m, 1H), 3.09-2.98 (m, 1H), 2.39 (dd, J=6.0, 13.0 Hz, 1H), 1.99-1.84 (m, 4H), 1.83-1.68 (m, 2H), 1.63-1.53 (m, 1H), 1.53-1.36 (m, 10H).

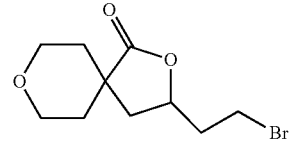 [SMILES: O=C1OC(CCBr)CC12CCOCC2]

Example 9: Preparation of 3-(2-bromoethyl)-2,8-dioxaspiro[4.5]decan-1-one: A solution of 3-(2-hydroxyethyl)-2,8-dioxaspiro[4.5]decan-1-one (0.320 g, 1.60 mmol, 1 eq.) and THF (15 mL) was cooled to 0° C. before triphenylphosphine (0.630 g, 2.4 mmol, 1.5 eq.) and carbon tetrabromide (0.795 g, 2.4 mmol, 1.5 eq.) were sequentially added to the solution. The reaction solution was allowed to warm to RT and stir overnight. The resulting mixture was then filtered and concentrated in vacuo to give a crude mixture. This mixture was suspended in diethyl ether (50 mL) and filtered 2× using diethyl ether to wash the filter cakes. The final filtrate was loaded onto Celite in vacuo and further purified by column chromatography (ethyl acetate/hexanes, 0%-40%). $^1$H NMR (400 MHz, CDCl$_3$) δ 4.67 (m, 1H), 4.04 (dt, J=4.6, 11.8 Hz, 1H), 3.91 (dt, J=4.6, 12.1 Hz, 1H), 3.60 (m, 1H), 3.56-3.45 (m, 3H), 2.50 (dd, J=6.1, 12.9 Hz, 1H), 2.30-2.02 (m, 3H), 1.91 (m, 1H), 1.76 (dd, J=9.8, 13.0 Hz, 1H), 1.64-1.55 (m, 1H), 1.52-1.44 (m, 1H).

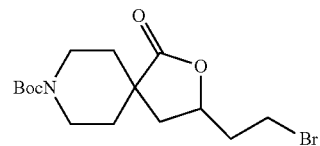 [SMILES: CC(C)(C)OC(=O)N1CCC2(CC1)CC(CCBr)OC2=O]

Example 10: Preparation of tert-butyl 3-(2-bromoethyl)-1-oxo-2-oxa-8-azaspiro[4.5]decane-8-carboxylate: The title compound was prepared according to the procedure for 3-(2-bromoethyl)-2,8-dioxaspiro[4.5]decan-1-one, except tert-butyl 3-(2-hydroxyethyl)-1-oxo-2-oxa-8-azaspiro[4.5]decane-8-carboxylate was substituted for 3-(2-hydroxyethyl)-2,8-dioxaspiro[4.5]decan-1-one: ¹H NMR (400 MHz, CDCl₃) δ 4.68 (m, 1H), 3.97 (dt, J=5.0, 13.5 Hz, 1H), 3.83 (dt, J=5.0, 13.7 Hz, 1H), 3.54 (dd, J=5.3, 7.5 Hz, 2H), 3.27-3.14 (m, 1H), 3.13-3.01 (m, 1H), 2.42 (dd, J=6.0, 13.0 Hz, 1H), 2.31-2.20 (m, 1H), 2.20-2.09 (m, 1H), 2.01-1.90 (m, 1H), 1.89-1.78 (m, 1H), 1.74 (dd, J=9.8, 12.8 Hz, 1H), 1.66-1.56 (m, 1H), 1.54-1.36 (m, 10H).

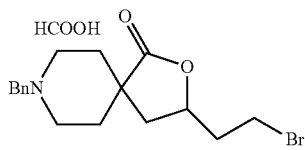

Example 11: Preparation of 8-benzyl-3-(2-bromoethyl)-2-oxa-8-azaspiro[4.5]decan-1-one formate: A solution of 3-(2-hydroxyethyl)-2,8-dioxaspiro[4.5]decan-1-one (2.07 g, 7.16 mmol, 1 eq.) and THF (70 mL) was cooled to 0° C. before triphenylphosphine (2.83 g, 10.8 mmol, 1.5 eq.) and carbon tetrabromide (3.58 g, 10.8 mmol, 1.5 eq.) were sequentially added to the solution. The reaction solution was allowed to warm to RT and stir overnight. The resulting mixture was then filtered and concentrated in vacuo to give a crude mixture. This mixture was suspended in diethyl ether (50 mL) and filtered 2× using diethyl ether to wash the filter cakes. The final filtrate was loaded onto Celite in vacuo and further purified by column chromatography on a C18 column. (ACN/H₂O, 0%~100%, w/ 0.1% formic acid). ¹H NMR (400 MHz, MeOD) δ 7.53 (b, 2H), 7.47 (b, 3H), 4.75 (m, 1H), 4.27 (s, 2H), 3.64-3.47 (m, 3H), 3.34 (m, 1H), 3.19 (b, 1H), 3.08 (b, 1H), 2.52 (m, 1H), 2.35-2.15 (m, 3H), 2.15-1.97 (m, 2H), 1.96-1.81 (m, 2H).

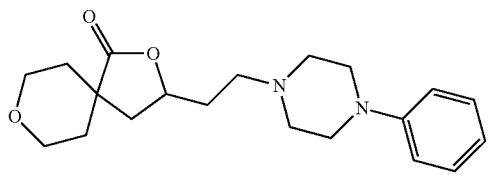 [SMILES: O=C1OC(CCN2CCN(c3ccccc3)CC2)CC12CCOCC2]

Example 12: Preparation of 3-(2-(4-phenylpiperazin-1-yl)ethyl)-2,8-dioxaspiro[4.5]decan-1-one: A solution of 3-(2-bromoethyl)-2,8-dioxaspiro[4.5]decan-1-one (0.050 g, 0.190 mmol, 1 eq.), THF (4 mL) and 1-phenylpiperazine (0.065 g, 0.399 mmol, 2.1 eq.) was heated and stirred at 60° C. for 3 days. The resulting mixture was then filtered and concentrated in vacuo to give a crude residue that was further purified by column chromatography (methanol/dichloromethane, 0%-10%). ¹H NMR (400 MHz, CDCl₃) δ 7.27 (m, 2H), 6.93 (d, J=8.3 Hz, 2H), 6.86 (t, J=7.3 Hz, 1H), 4.58 (m, 1H), 4.06 (dt, J=4.6, 11.9 Hz, 1H), 3.93 (dt, J=4.6, 12.0 Hz, 1H), 3.61 (m, 1H), 3.51 (m, 1H), 3.21 (t, J=5.0 Hz, 4H), 2.70-2.52 (m, 6H), 2.47 (dd, J=6.0, 12.8 Hz, 1H), 2.11 (m, 1H), 2.01-1.83 (m, 3H), 1.79 (dd, J=9.7, 13.1 Hz, 1H), 1.65-1.54 (m, 1H), 1.54-1.45 (m, 1H): MS (LC/MS, M+H⁺): 344.8.

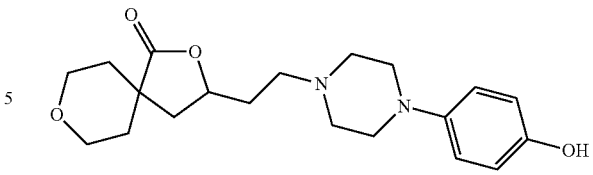

Example 13: Preparation of 3-(2-(4-(4-hydroxyphenyl)piperazin-1-yl)ethyl)-2,8-dioxaspiro[4.5]decan-1-one: The title compound was prepared according to the procedure for 3-(2-(4-phenylpiperazin-1-yl)ethyl)-2,8-dioxaspiro[4.5]decan-1-one, except 4-(piperazin-1-yl)phenol was substituted for 1-phenylpiperazine: ¹H NMR (400 MHz, CDCl₃) δ 6.74 (d, J=8.9 Hz, 2H), 6.63 (d, J=8.9 Hz, 2H), 4.45 (m, 1H), 3.97 (dt, J=4.6, 11.8 Hz, 1H), 3.83 (dt, J=4.5, 12.3 Hz, 1H), 3.51 (m, 1H), 3.42 (m, 1H), 3.00 (t, J=4.7 Hz, 4H), 2.67-2.42 (m, 6H), 2.35 (dd, J=6.1, 12.1 Hz, 1H), 2.00 (m, 1H), 1.92-1.74 (m, 3H), 1.67 (dd, J=9.6, 12.9 Hz, 1H), 1.52-1.43 (m, 1H), 1.43-1.34 (m, 1H): MS (LC/MS, M+H⁺): 360.8.

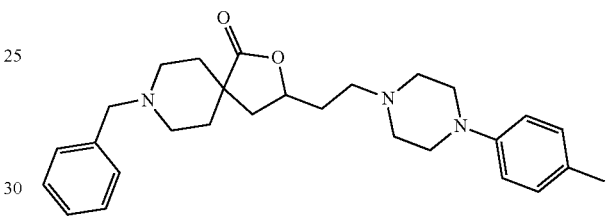

Example 14: Preparation of 8-benzyl-3-(2-(4-(p-tolyl)piperazin-1-yl)ethyl)-2-oxa-8-azaspiro[4.5]decan-1-one: A solution of 8-benzyl-3-(2-bromoethyl)-2-oxa-8-azaspiro[4.5]decan-1-one formate (0.545 g, 1.37 mmol, 1 eq.), THF (13.7 mL), 1-(p-tolyl)piperazine (0.507 g, 2.88 mmol, 2.1 eq.) and triethylamine (0.107 g, 1.5 mmol, 1.1 eq.) was heated and stirred at 60° C. for 3 days. The resulting mixture was then filtered and concentrated in vacuo to give a crude residue that was further purified by column chromatography (methanol/dichloromethane, 0%~ 10%). ¹H NMR (400 MHz, CDCl₃) δ 7.39-7.23 (m, 5H), 7.10 (d, J=8.3 Hz, 2H), 6.87 (d, J=8.6 Hz, 2H), 4.53 (m, 1H), 3.54 (s, 2H), 3.17 (t, J=5.0 Hz, 4H), 2.95-2.85 (m, 1H), 2.84-2.75 (m, 1H), 2.70-2.49 (m, 6H), 2.40 (dd, J=6.2, 12.8 Hz, 1H), 2.30 (s, 3H), 2.27-2.05 (m, 3H), 2.01-1.79 (m, 3H), 1.76-1.58 (m, 2H), 1.58-1.46 (m, 1H): MS (LC/MS, M+H⁺): 447.8.

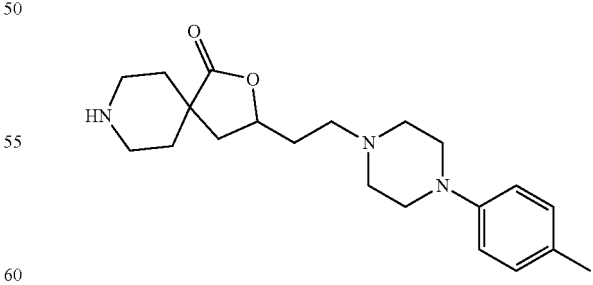

Example 15: Preparation of 3-(2-(4-(p-tolyl)piperazin-1-yl)ethyl)-2-oxa-8-azaspiro[4.5]decan-1-one: A mixture of 8-benzyl-3-(2-(4-(p-tolyl)piperazin-1-yl)ethyl)-2-oxa-8-azaspiro[4.5]decan-1-one (445 mg, 0.993 mmol, 1 eq.), Pd/C (90 mg, 20% wt) and EtOH (6.6 mL) was stirred at RT under 1 atm of H₂ (filled balloon) for 48 hrs. The mixture was filtered through a plug of Celite, washed with MeOH (50 mL) and concentrated in vacuo to give a crude oil. $^1$H NMR (400 MHz, MeOD) δ 6.95 (d, J=8.2 Hz, 2H), 6.77 (d, J=8.5 Hz, 2H), 4.56 (m, 1H), 3.47 (m, 1H), 3.28-3.18 (m, 1H), 3.17-3.09 (m, 1H), 3.08-2.96 (m, 5H), 2.66-2.46 (m, 6H), 2.42 (dd, J=6.0, 13.0 Hz, 1H), 2.14 (s, 3H), 2.10-2.00 (m, 1H), 2.00-1.91 (m, 1H), 1.91-1.80 (m, 4H), 1.80-1.70 (m, 1H); MS (LC/MS, M+H$^+$): 357.8.

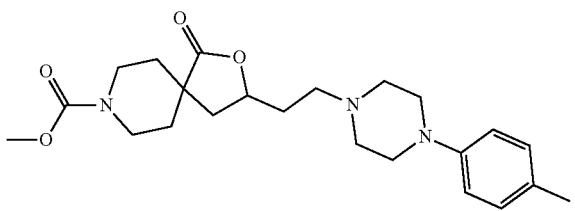

Example 16: Preparation of methyl 1-oxo-3-(2-(4-(p-tolyl)piperazin-1-yl)ethyl)-2-oxa-8-azaspiro[4.5]decane-8-carboxylate: A solution of 3-(2-(4-(p-tolyl)piperazin-1-yl)ethyl)-2-oxa-8-azaspiro[4.5]decan-1-one (0.05 g, 0.14 mmol, 1 eq.), dichloromethane (2 mL) and triethylamine (0.44 g, 0.41 mmol, 3 eq.) was cooled to 0° C. before methyl chloroformate (0.027 g, 0.28 mmol, 2 eq.) was added to the solution. The reaction solution was allowed to warm to RT and stir for 3 hours. The reaction was diluted with dichloromethane and loaded onto Celite in vacuo and further purified by column chromatography on a C18 column. (ACN/H$_2$O, 0%~ 100%, w/ 0.1% formic acid). The resulting formate acid salt was dissolved in MeOH (2 mL) and Amberlite IRA-400(OH) resin was added. This mixture was allowed to stir at RT for 30 min and then filtered and concentrated in vacuo to afford pure free based product. $^1$H NMR (400 MHz. CDCl$_3$) δ 7.08 (d, J=8.4 Hz, 2H), 6.85 (d, J=8.6 Hz, 2H), 4.59 (m, 1H), 4.02 (b, 1H), 3.85 (b, 1H), 3.72 (s, 3H), 3.35-3.24 (m, 1H), 3.23-3.10 (m, 5H), 2.71-2.50 (m, 6H), 2.38 (dd, J=6.0, 12.8 Hz, 1H), 2.28 (s, 3H), 2.07-1.72 (m, 5H), 1.69-1.47 (m, 2H): MS (LC/MS, M+H$^+$): 415.8.

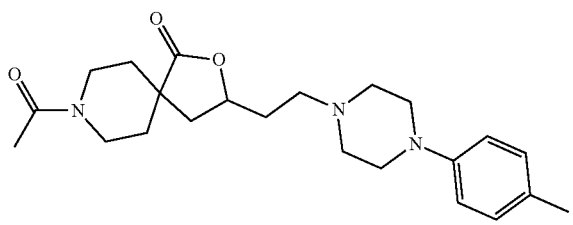 [SMILES: CC(=O)N1CCC2(CC1)CC(CCN1CCN(c3ccc(C)cc3)CC1)OC2=O]

Example 17: Preparation of 8-acetyl-3-(2-(4-(p-tolyl)piperazin-1-yl)ethyl)-2-oxa-8-azaspiro[4.5]decan-1-one: The title compound was prepared according to the procedure for methyl 1-oxo-3-(2-(4-(p-tolyl)piperazin-1-yl)ethyl)-2-oxa-8-azaspiro[4.5]decane-8-carboxylate, except acetic anhydride was substituted for methyl chloroformate: $^1$H NMR (400 MHz, CDCl$_3$) δ 7.08 (d, J=8.3 Hz, 2H), 6.85 (d, J=8.5 Hz, 2H), 4.60 (m, 1H), 4.19 (m, 0.5H), 4.04-3.84 (m, 1H), 3.72 (m, 0.5H), 3.45-3.22 (m, 2H), 3.15 (t, J=4.8 Hz, 4H), 2.70-2.49 (m, 6H), 2.43-2.32 (m, 1H), 2.27 (s, 3H), 2.10 (s, 3H), 2.05-1.72 (m, 5H), 1.69-1.49 (m, 2H): MS (LC/MS, M+H$^+$): 399.8.

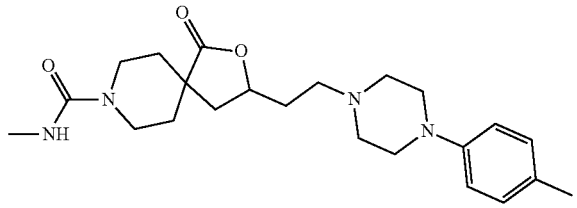

Example 18: Preparation of N-methyl-1-oxo-3-(2-(4-(p-tolyl)piperazin-1-yl)ethyl)-2-oxa-8-azaspiro[4.5]decane-8-carboxamide: The title compound was prepared according to the procedure for methyl 1-oxo-3-(2-(4-(p-tolyl)piperazin-1-yl)ethyl)-2-oxa-8-azaspiro[4.5]decane-8-carboxylate, except N-methyl-1H-imidazole-1-carboxamide was substituted for methyl chloroformate: $^1$H NMR (400 MHz, MeOD) δ 6.96 (d, J=8.3 Hz, 2H), 6.78 (d, J=8.2 Hz, 2H), 4.52 (m, 1H), 3.79 (dt, J=4.7, 13.8 Hz, 1H), 3.68 (dt, J=4.5, 13.8 Hz, 1H), 3.22 (m, 1H), 3.16-2.86 (m, 6H), 2.63 (s, 3H), 2.59-2.36 (m, 7H), 2.15 (s, 3H), 1.91-1.67 (m, 3H), 1.66-1.50 (m, 2H), 1.50-1.38 (m, 1H): MS (LC/MS, M+H$^+$): 414.8.

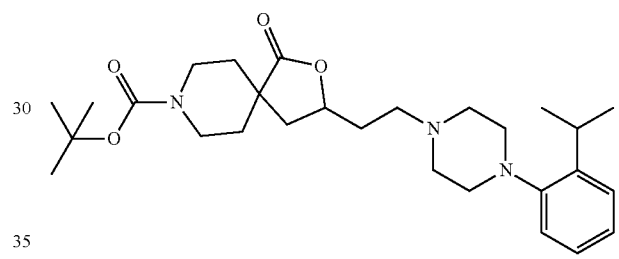

Example 20: Preparation of tert-butyl 3-(2-(4-(2-isopropylphenyl)piperazin-1-yl)ethyl)-1-oxo-2-oxa-8-azaspiro[4.5]decane-8-carboxylate: A mixture of tert-butyl 3-(2-bromoethyl)-1-oxo-2-oxa-8-azaspiro[4.5]decane-8-carboxylate (0.500 g, 1.38 mmol, 1 eq.), ACN (7 mL), 1-(2-isopropylphenyl)piperazine (0.337 g, 1.65 mmol, 1.2 eq.) and K$_2$CO$_3$ (0.954 g, 6.9 mmol, 5 eq.) was heated and stirred at 80° C. for 3 days. The resulting mixture was then filtered and concentrated in vacuo to give a crude residue that was further purified by column chromatography (methanol/dichloromethane, 0%~ 10%). $^1$H NMR (400 MHz, CDCl$_3$) δ 7.16 (dd, J=1.6, 7.4 Hz, 1H), 7.09-6.94 (m, 3H), 4.49 (m, 1H), 3.89 (b, 1H), 3.75 (b, 1H), 3.40 (sep, J=6.9 Hz, 1H), 3.09 (m, 1H), 2.98 (m, 1H), 2.81 (t, J=4.6 Hz, 4H), 2.65-2.39 (m, 5H), 2.30 (dd, J=6.1, 12.8 Hz, 1H), 1.99-1.60 (m, 5H), 1.51 (m, 1H), 1.46-1.29 (m, 1H), 1.12 (s, 3H), 1.10 (s, 6H): MS (LC/MS, M+H$^+$): 485.8

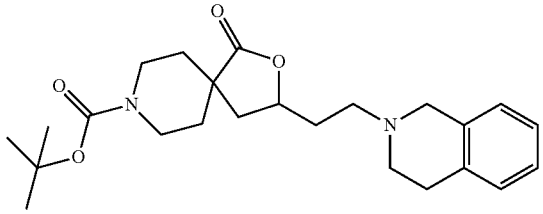 [SMILES: CC(C)(C)OC(=O)N1CCC2(CC1)CC(CCN1CCc3ccccc3C1)OC2=O]

Example 21: Preparation of tert-butyl 3-(2-(3,4-dihydroisoquinolin-2(1H)-yl)ethyl)-1-oxo-2-oxa-8-azaspiro

[4.5]decane-8-carboxylate: The title compound was prepared according to the procedure for tert-butyl 3-(2-(4-(2-isopropylphenyl)piperazin-1-yl)ethyl)-1-oxo-2-oxa-8-azaspiro[4.5]decane-8-carboxylate, except 1,2,3,4-tetrahydroisoquinoline hydrochloride was substituted for 1-(2-isopropylphenyl)piperazine: $^1$H NMR (400 MHz, CDCl$_3$) δ 7.07-6.96 (m, 3H), 6.95-6.87 (m, 1H), 4.53 (m, 1H), 3.87 (b, 1H), 3.72 (b, 1H), 3.60-3.46 (m, 2H), 3.06 (m, 1H), 2.95 (m, 1H), 2.80 (t, J=5.8 Hz, 2H), 2.64 (t, J=6.0 Hz, 2H), 2.58 (t, J=7.3 Hz, 2H), 2.28 (dd, J=6.1, 12.9 Hz, 1H), 1.97-1.75 (m, 3H), 1.74-1.58 (m, 2H), 1.54-1.26 (m, 11H): MS (LC/MS, M+H$^+$): 414.8

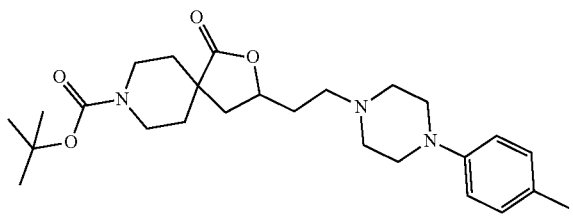 [SMILES: Cc1ccc(N2CCN(CCC3CC4(CCN(C(=O)OC(C)(C)C)CC4)C(=O)O3)CC2)cc1]

Example 22: Preparation of tert-butyl 1-oxo-3-(2-(4-(p-tolyl)piperazin-1-yl)ethyl)-2-oxa-8-azaspiro[4.5]decane-8-carboxylate: A solution of tert-butyl 3-(2-bromoethyl)-1-oxo-2-oxa-8-azaspiro[4.5]decane-8-carboxylate (1.5 g, 4.11 mmol, 1.1 eq.), THF (36 mL), 1-(p-tolyl)piperazine (0.660 g, 3.74 mmol, 1 eq.) and triethylamine (0.416 g, 4.11 mmol, 1.1 eq.) was heated and stirred at 70° C. for 3 days. The resulting mixture was then filtered and concentrated in vacuo to give a crude residue that was further purified by column chromatography (methanol/dichloromethane, 0%~10%). $^1$H NMR (400 MHz, CDCl$_3$) δ 7.05 (d, J=8.3 Hz, 2H), 6.82 (d, J=8.5 Hz, 2H), 4.55 (m, 1H), 3.96 (m, 1H), 3.81 (m, 1H), 3.22-2.98 (m, 6H), 2.67-2.45 (m, 6H), 2.36 (dd, J=6.2, 12.9 Hz, 1H), 2.25 (s, 31H), 2.00-1.66 (m, 5H), 1.57 (m, 1H), 1.53-1.34 (m, 10H); MS (LC/MS, M+H$^+$): 457.8

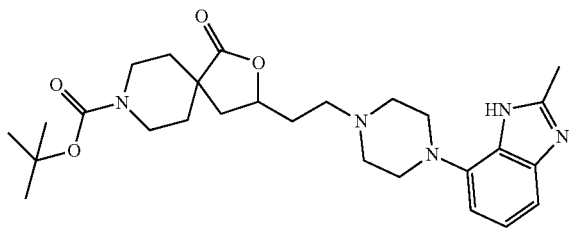 [SMILES: Cc1nc2cccc(N3CCN(CCC4CC5(CCN(C(=O)OC(C)(C)C)CC5)C(=O)O4)CC3)c2[nH]1]

Example 23: Preparation of tert-butyl 3-(2-(4-(2-methyl-1H-benzo[d]imidazol-7-yl)piperazin-1-yl)ethyl)-1-oxo-2-oxa-8-azaspiro[4.5]decane-8-carboxylate: A solution of tert-butyl 3-(2-bromoethyl)-1-oxo-2-oxa-8-azaspiro[4.5]decane-8-carboxylate (0.5 g, 1.38 mmol, 1. eq.), THE (12 mL), 2-methyl-7-(piperazin-1-yl)-1H-benzo[d]imidazole (0.549 g, 1.65 mmol, 1.2 eq.) and triethylamine (0.500 g, 4.95 mmol, 3.5 eq.) was heated and stirred at 70° C. for 3 days. The resulting mixture was then filtered and concentrated in vacuo to give a crude residue that was first purified by column chromatography (methanol/dichloromethane, 0%-10%). The resulting fractions were further purified by column chromatography on a C18 column. (ACN/H$_2$O, 0%~100%, w/ 0.1% NH$_4$OH) $^1$H NMR (400 MHz, CDCl$_3$) δ 7.16-6.97 (m, 2H), 6.65 (m, 1H), 4.54 (m, 1H), 3.98 (m, 1H), 3.83 (m, 1H), 3.40 (b, 4H), 3.17 (t, J=11.1 Hz, 1H), 3.06 (t, J=11.5 Hz, 1H), 2.68-2.42 (m, 9H), 2.36 (dd, J=6.2, 13.0 Hz, 1H), 1.99-1.66 (m, 5H), 1.58 (m, 1H), 1.54-1.33 (m, 10H): MS (LC/MS, M+H$^+$): 497.8

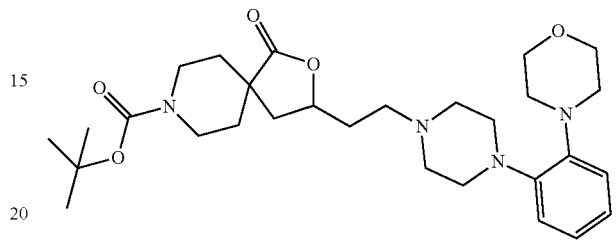

Example 24: Preparation of tert-butyl 3-(2-(4-(2-morpholinophenyl)piperazin-1-yl)ethyl)-1-oxo-2-oxa-8-azaspiro[4.5]decane-8-carboxylate: The title compound was prepared according to the procedure for tert-butyl 3-(2-(4-(2-methyl-1H-benzo[d]imidazol-7-yl)piperazin-1-yl)ethyl)-1-oxo-2-oxa-8-azaspiro[4.5]decane-8-carboxylate, except 4-(2-(piperazin-1-yl)phenyl)morpholine was substituted for 2-methyl-7-(piperazin-1-yl)-1H-benzo[d]imidazole: $^1$H NMR (400 MHz, CDCl$_3$) δ 6.94-6.87 (m, 2H), 6.87-6.78 (m, 2H), 4.51 (m, 1H), 3.90 (m, 1H), 3.81-3.66 (m, 5H), 3.34-2.84 (m, 10H), 2.67-2.37 (m, 6H), 2.31 (dd, J=6.2, 12.9 Hz, 1H), 1.93-1.59 (m, 5H), 1.52 (m, 1H), 1.47-1.30 (m, 10H); MS (LC/MS, M+H:528.8

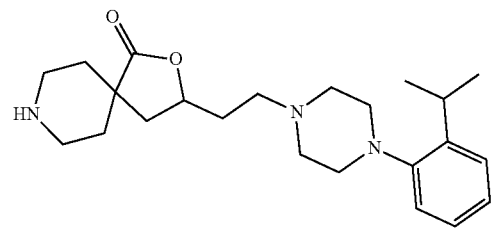 [SMILES: CC(C)c1ccccc1N1CCN(CCC2CC3(CCNCC3)C(=O)O2)CC1]

Example 25: Preparation of 3-(2-(4-(2-isopropylphenyl)piperazin-1-yl)ethyl)-2-oxa-8-azaspiro[4.5]decan-1-one: To a solution of tert-butyl 3-(2-(4-(2-isopropylphenyl)piperazin-1-yl)ethyl)-1-oxo-2-oxa-8-azaspiro[4.5]decane-8-carboxylate (0.450 g, 0.930 mmol, 1 eq.) in dichloromethane (3 mL) at 0° C. was added trifluoroacetic acid (3 mL). The reaction was allowed to stir at RT for 30 min before being diluted with MeOH and concentrated in vacuo to afford the product as a TFA salt. The resulting TFA salt was dissolved in MeOH (2 mL) and Amberlite IRA-400(OH) resin was added. This mixture was allowed to stir at RT for 30 min and then filtered and concentrated in vacuo to afford pure free based product. $^1$H NMR (400 MHz, MeOD) δ 7.16 (d, J=7.5 Hz, 1H), 7.07-6.93 (m, 3H), 4.50 (m, 1H), 3.44 (sep. J=6.9 Hz, 1H), 2.99 (dt, J=4.3, 12.6 Hz, 1H), 2.89 (dt, J=4.3, 13.2 Hz, 1H), 2.82 (t, J=4.7 Hz, 4H), 2.74-2.37 (m, 9H), 1.91-1.78 (m, 3H), 1.77-1.50 (m, 3H), 1.42 (m, 1H), 1.12 (s, 3H), 1.10 (s, 3H); MS (LC/MS, M+H$^+$): 385.8

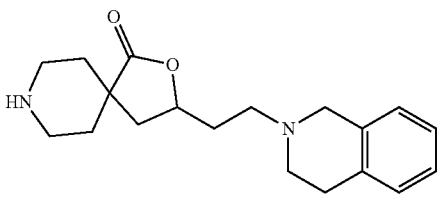 [SMILES: O=C1OC(CCN2CCc3ccccc3C2)CC12CCNCC2]

Example 26: Preparation of 3-(2-(3,4-dihydroisoquinolin-2(1H)-yl)ethyl)-2-oxa-8-azaspiro[4.5]decan-1-one: The title compound was prepared according to the procedure for 3-(2-(4-(2-isopropylphenyl)piperazin-1-yl)ethyl)-2-oxa-8-azaspiro[4.5]decan-1-one, except tert-butyl 3-(2-(3,4-dihydroisoquinolin-2(1H)-yl)ethyl)-1-oxo-2-oxa-8-azaspiro[4.5]decane-8-carboxylate was substituted for tert-butyl 3-(2-(4-(2-isopropylphenyl)piperazin-1-yl)ethyl)-1-oxo-2-oxa-8-azaspiro[4,5]decane-8-carboxylate: $^1$H NMR (400 MHz, MeOD) δ 7.18-7.09 (m, 3H), 7.09-7.03 (in, 1H), 4.64 (m, 1H), 3.68 (s, 2H), 3.25 (dt, J=5.0, 13.1 Hz, 1H), 3.10 (dt, J=5.0, 13.4 Hz, 1H), 2.99-2.88 (m, 3H), 2.85-2.61 (m, 5H), 2.55 (dd, J=6.1, 12.9 Hz, 1H), 2.09-1.95 (m, 3H), 1.90-1.70 (m, 3H), 1.63 (m, 1H); MS (LC/MS, M+H$^+$): 314.8

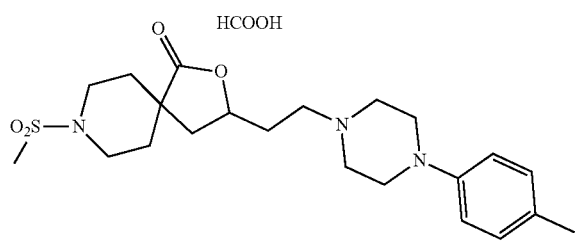

Example 27: Preparation of 8-(methylsulfonyl)-3-(2-(4-(p-tolyl)piperazin-1-yl)ethyl)-2-oxa-8-azaspiro[4.5]decan-1-one formate: A solution of 3-(2-(4-(p-tolyl)piperazin-1-yl)ethyl)-2-oxa-8-azaspiro[4.5]decan-1-one (0.05 g, 0.14 mmol, 1 eq.), dichloromethane (2 mL) and triethylamine (0.44 g, 0.41 mmol, 3 eq.) was cooled to 0° C. before methanesulfonyl chloride (0.032 g, 0.28 mmol, 2 eq.) was added to the solution. The reaction solution was allowed to warm to RT and stir for 3 hours. The reaction was diluted with dichloromethane and loaded onto Celite in vacuo and further purified by column chromatography on a C18 column. (ACN/H$_2$O, 0%~ 100%, w/ 0.1% formic acid). $^1$H NMR (400 MHz, DMSO) δ 7.01 (d, J=8.5 Hz, 2H), 6.82 (d, J=8.5 Hz, 2H), 4.59 (m, 1H), 3.58-3.45 (m, 1H), 3.44-3.33 (m, 1H), 3.13-2.95 (m, 5H), 2.88 (s, 3H), 2.86-2.78 (m, 1H), 2.62-2.31 (m, 7H), 2.19 (s, 3H), 1.97-1.57 (m, 7H): MS (LC/MS, M+H$^+$): 435.8

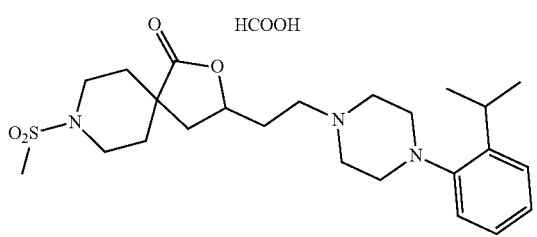 [SMILES: CC(C)c1ccccc1N1CCN(CCC2CC3(CCN(S(C)(=O)=O)CC3)C(=O)O2)CC1 ; "HCOOH"]

Example 28: Preparation of 3-(2-(4-(2-isopropylphenyl)piperazin-1-yl)ethyl)-8-(methylsulfonyl)-2-oxa-8-azaspiro[4.5]decan-1-one formate: The title compound was prepared according to the procedure for 8-(methylsulfonyl)-3-(2-(4-(p-tolyl)piperazin-1-yl)ethyl)-2-oxa-8-azaspiro[4.5]decan-1-one formate, except 3-(2-(4-(2-isopropylphenyl)piperazin-1-yl)ethyl)-2-oxa-8-azaspiro[4.5]decan-1-one was substituted for 3-(2-(4-(p-tolyl)piperazin-1-yl)ethyl)-2-oxa-8-azaspiro[4.5]decan-1-one: $^1$H NMR (400 MHz, MeOD) δ 7.34-7.27 (m, 1H), 7.23-7.08 (m, 3H), 4.67 (m, 1H), 3.70 (dt, J=4.8, 12.3 Hz, 1H), 3.61-3.47 (m, 2H), 3.40-3.09 (m, 11H), 3.04 (m, 1H), 2.88 (s, 3H), 2.56 (dd, J=6.4, 12.8 Hz, 11H), 2.29-2.10 (m, 2H), 2.05 (m, 1H), 1.96-1.80 (m, 3H), 1.75 (m, 1H), 1.24 (s, 3H), 1.22 (s, 3H); MS (LC/MS, M+H$^+$): 463.7

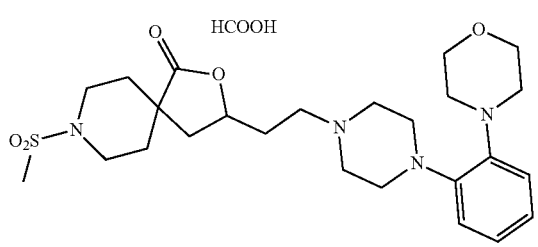 [SMILES: CS(=O)(=O)N1CCC2(CC1)CC(CCN1CCN(c3ccccc3N3CCOCC3)CC1)OC2=O ; "HCOOH"]

Example 29: Preparation of 8-(methylsulfonyl)-3-(2-(4-(2-morpholinophenyl)piperazin-1-yl)ethyl)-2-oxa-8-azaspiro[4,5]decan-1-one formate: The title compound was prepared according to the procedure for 8-(methylsulfonyl)-3-(2-(4-(p-tolyl)piperazin-1-yl)ethyl)-2-oxa-8-azaspiro[4.5]decan-1-one formate, except 3-(2-(4-(2-morpholinophenyl)piperazin-1-yl)ethyl)-2-oxa-X-azaspiro[4.5]decan-1-one was substituted for 3-(2-(4-(p-tolyl)piperazin-1-yl)ethyl)-2-oxa-8-azaspiro[4.5]decan-1-one: $^1$H NMR (400 MHz, MeOD) δ 7.13-6.90 (m, 4H), 4.67 (m, 1H), 3.86 (t, J=4.6 Hz, 4H), 3.70 (dt, J=4.7, 12.3 Hz, 1H), 3.61-3.08 (m, 6H), 3.04 (m, 1H), 2.88 (s, 3H), 2.56 (dd, J=5.9, 13.0 Hz, 1H), 2.29-2.11 (m, 2H), 2.05 (m, 1H), 1.97-1.81 (m, 3H), 1.75 (m, 1H); MS (LC/MS, M+H$^+$): 507.2

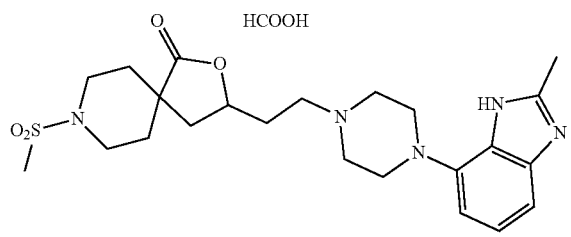 [SMILES: Cc1nc2cccc(N3CCN(CCC4CC5(CCN(S(C)(=O)=O)CC5)C(=O)O4)CC3)c2[nH]1 ; "HCOOH"]

Example 30: Preparation of 3-(2-(4-(2-methyl-1H-benzo[d]imidazol-7-yl)piperazin-1-yl)ethyl)-8-(methylsulfonyl)-2-oxa-8-azaspiro[4,5]decan-1-one formate: The title compound was prepared according to the procedure for 8-(methylsulfonyl)-3-(2-(4-(p-tolyl)piperazin-1-yl)ethyl)-2-oxa-8-azaspiro[4.5]decan-1-one formate, except 3-(2-(4-(2-methyl-1H-benzo[d]imidazol-7-yl)piperazin-1-yl)ethyl)-2-oxa-8-azaspiro[4.5]decan-1-one was substituted for 3-(2-(4-(p-tolyl)piperazin-1-yl)ethyl)-2-oxa-8-azaspiro[4.5]decan-1-one: $^1$H NMR (400 MHz, MeOD) δ 7.47-7.26 (m, 2H), 7.04 (d, J=6.7 Hz, 1H), 4.69 (m, 1H), 3.79-3.28 (m, 12H), 3.14 (m, 1H), 3.01 (m, 1H), 2.87 (s, 3H), 2.79 (s, 3H), 2.58 (dd, J=5.9, 12.9 Hz, 1H), 2.38-2.14 (m, 2H), 2.12-1.98 (m, 1H), 1.96-1.80 (m, 3H), 1.75 (m, 1H): MS (LC/MS, M+H$^+$): 476.2

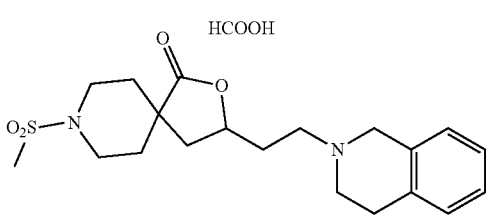 [SMILES: CS(=O)(=O)N1CCC2(CC1)CC(CCN1CCc3ccccc3C1)OC2=O ; "HCOOH"]

Example 31: Preparation of 3-(2-(3,4-dihydroisoquinolin-2(1H)-yl)ethyl)-8-(methylsulfonyl)-2-oxa-8-azaspiro[4.5]decan-1-one formate: The title compound was prepared according to the procedure for 8-(methylsulfonyl)-3-(2-(4-(p-tolyl)piperazin-1-yl)ethyl)-2-oxa-8-azaspiro[4.5]decan-1-one formate, except 3-(2-(3,4-dihydroisoquinolin-2(1H)-yl)ethyl)-2-oxa-8-azaspiro[4.5]decan-1-one was substituted for 3-(2-(4-(p-tolyl)piperazin-1-yl)ethyl)-2-oxa-8-azaspiro[4.5]decan-1-one: $^1$H NMR (400 MHz, MeOD) δ 7.31-7.21 (m, 3H), 7.20-7.15 (m, 1H), 4.67 (m, 1H), 4.26 (s, 2H), 3.70 (dt, J=4.9, 12.3 Hz, 1H), 3.53 (dt, J=5.2, 12.5 Hz, 1H), 3.39 (t, J=6.2 Hz, 2H), 3.31-3.10 (m, 5H), 3.03 (m, 1H), 2.88 (s, 3H), 2.56 (dd, J=6.0, 12.9 Hz, 1H), 2.30-2.12 (m, 2H), 2.05 (m, 1H), 1.97-1.80 (m, 3H), 1.75 (in, H); MS (LC/MS, M+H$^+$): 392.7.

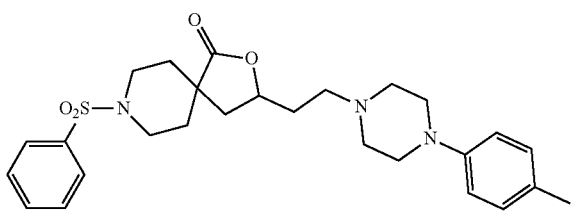 [SMILES: Cc1ccc(N2CCN(CCC3CC4(CCN(S(=O)(=O)c5ccccc5)CC4)C(=O)O3)CC2)cc1]

Example 32: Preparation of 8-(phenylsulfonyl)-3-(2-(4-(p-tolyl)piperazin-1-yl)ethyl)-2-oxa-8-azaspiro[4.5]decan-1-one: The title compound was prepared according to the procedure for 8-(methylsulfonyl)-3-(2-(4-(p-tolyl)piperazin-1-yl)ethyl)-2-oxa-8-azaspiro[4.5]decan-1-one formate, except benzenesulfonyl chloride was substituted for methanesulfonyl chloride and the title compound was purified by column chromatography on a silica gel column. (MeOH/DCM, 0%~10%): $^1$H NMR (400 MHz, CDCl$_3$) δ 7.69 (m, 2H), 7.53 (m, 1H), 7.46 (m, 2H), 7.00 (d, J=8.3 Hz, 2H), 6.75 (d, J=8.5 Hz, 2H), 4.44 (m, 1H), 3.46 (m, 1H), 3.22 (m, 1H), 3.10 (1, J=4.7 Hz, 4H), 2.97 (m, 1H), 2.87 (m, 1H), 2.75-2.44 (m, 6H), 2.19 (s, 3H), 2.12 (dd, J=6.1, 13.0 Hz, 1H), 2.02-1.77 (m, 4H), 1.72-1.53 (m, 3H): MS (LC/MS, M+H$^+$): 498.2.

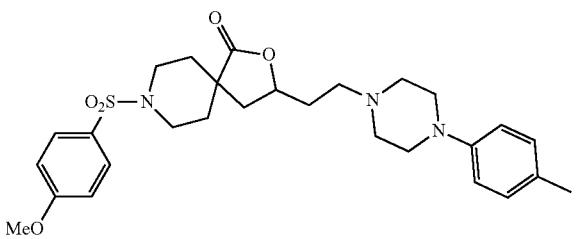 [SMILES: COc1ccc(S(=O)(=O)N2CCC3(CC2)CC(CCN2CCN(c4ccc(C)cc4)CC2)OC3=O)cc1]

Example 33: Preparation of 8-((4-methoxyphenyl)sulfonyl)-3-(2-(4-(p-tolyl)piperazin-1-yl)ethyl)-2-oxa-8-azaspiro[4.5]decan-1-one: The title compound was prepared according to the procedure for 8-(methylsulfonyl)-3-(2-(4-(p-tolyl)piperazin-1-yl)ethyl)-2-oxa-8-azaspiro[4.5]decan-1-one formate, except 4-methoxybenzenesulfonyl chloride was substituted for methanesulfonyl chloride and the title compound was purified by column chromatography on a silica gel column. (MeOH/DCM, 0%~10%): $^1$H NMR (400 MHz, CDCl$_3$) δ 7.62 (d, J=9.0 Hz, 2H), 6.99 (d, J=8.3 Hz, 2H), 6.91 (d, J=8.9 Hz, 2H), 6.75 (d, J=8.6 Hz, 2H), 4.45 (m, 11H), 3.80 (s, 3H), 3.42 (m, 1H), 3.18 (m, 1H), 3.04 (t, J=4.9 Hz, 4H), 2.95 (m, 1H), 2.86 (m, 1H), 2.57-2.39 (m, 6H), 2.19 (s, 3H), 2.11 (dd, J=6.1, 12.9 Hz, 1H), 2.01-1.86 (m, 2H), 1.86-1.50 (m, 5H); MS (LC/MS, M+H$^+$): 528.2.

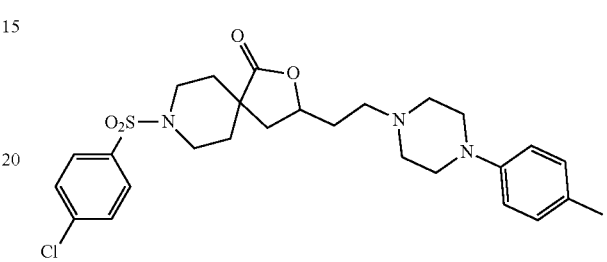

Example 34: Preparation of 8-((4-chlorophenyl)sulfonyl)-3-(2-(4-(p-tolyl)piperazin-1-yl)ethyl)-2-oxa-8-azaspiro[4.5]decan-1-one: The title compound was prepared according to the procedure for 8-(methylsulfonyl)-3-(2-(4-(p-tolyl)piperazin-1-yl)ethyl)-2-oxa-8-azaspiro[4.5]decan-1-one formate, except 4-chlorobenzenesulfonyl chloride was substituted for methanesulfonyl chloride and the title compound was purified by column chromatography on a silica gel column. (MeOH/DCM, 0%~10%): $^1$H NMR (400 MHz, CDCl$_3$) δ 7.56 (d, J=8.6 Hz, 2H), 7.37 (d, J=8.5 Hz, 2H), 6.93 (d, J=8.4 Hz, 2H), 6.69 (d, J=8.6 Hz, 2H), 4.40 (m, 1H), 3.37 (m, 1H), 3.10 (m, 1H), 3.02 (t, J=4.7 Hz, 4H), 2.96 (m, 1H), 2.87 (m, 1H), 2.59-2.34 (m, 6H), 2.13 (s, 3H), 2.06 (dd, J=5.9, 12.9 Hz, 1H), 1.95-1.81 (m, 2H), 1.81-1.67 (m, 2H), 1.66-1.49 (m, 3H): MS (LC/MS, M+H$^+$): 532.2.

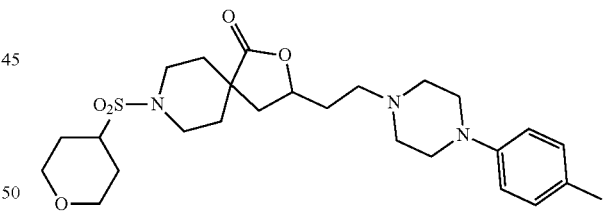

Example 35: Preparation of 8-((tetrahydro-2H-pyran-4-yl)sulfonyl)-3-(2-(4-(p-tolyl)piperazin-1-yl)ethyl)-2-oxa-8-azaspiro[4.5]decan-1-one: The title compound was prepared according to the procedure for 8-(methylsulfonyl)-3-(2-(4-(p-tolyl)piperazin-1-yl)ethyl)-2-oxa-8-azaspiro[4.5]decan-1-one formate, except tetrahydro-2H-pyran-4-sulfonyl chloride was substituted for methanesulfonyl chloride and the title compound was purified by column chromatography on a silica gel column. (MeOH/DCM, 0%~10%): $^1$H NMR (400 MHz, CDCl$_3$) δ 7.08 (d, J=8.3 Hz, 2H), 6.84 (d, J=8.5 Hz, 2H), 4.60 (m, 1H), 4.08 (dd, J=3.6, 11.5 Hz, 2H), 3.80 (m, 1H), 3.57-3.42 (m, 4H), 3.41-3.30 (m, 3H), 3.22-3.06 (m, 5H), 2.69-2.47 (m, 6H), 2.30 (dd, J=6.1, 12.9 Hz, 1H), 2.27 (s, 3H), 2.03-1.65 (m, 9H): MS (LC/MS, M+H$^+$): 506.2.

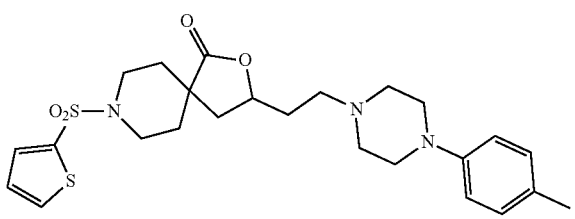 [SMILES: Cc1ccc(N2CCN(CCC3CC4(CCN(S(=O)(=O)c5cccs5)CC4)C(=O)O3)CC2)cc1]

Example 36: Preparation of 8-(thiophen-2-ylsulfonyl)-3-(2-(4-(p-tolyl)piperazin-1-yl)ethyl)-2-oxa-8-azaspiro[4.5]decan-1-one: The title compound was prepared according to the procedure for 8-(methylsulfonyl)-3-(2-(4-(p-tolyl)piperazin-1-yl)ethyl)-2-oxa-8-azaspiro[4,5]decan-1-one formate, except thiophene-2-sulfonyl chloride was substituted for methanesulfonyl chloride and the title compound was purified by column chromatography on a silica gel column. (MeOH/DCM, 0%~10%): $^1$H NMR (400 MHz, CDCl$_3$) δ 7.53 (dd, J=1.2, 5.0 Hz, 1H), 7.46 (dd, 1.3, 3.8 Hz, 1H), 7.06 (dd, J=3.8, 5.0 Hz, 1H), 6.99 (d, J=8.4 Hz, 21H), 6.75 (d, J=8.5 Hz, 2H), 4.46 (m, 1H), 3.49 (m, 1H), 3.24 (m, 1H), 3.12-2.97 (m, 5H), 2.92 (m, 1H), 2.61-2.41 (m, 6H), 2.19 (s, 3H), 2.14 (dd, J=6.0, 13.0 Hz, 1H), 2.04-1.88 (m, 2H), 1.88-1.73 (m, 2H), 1.73-1.57 (m, 31H): MS (LC/MS, M+H$^+$): 504.1.

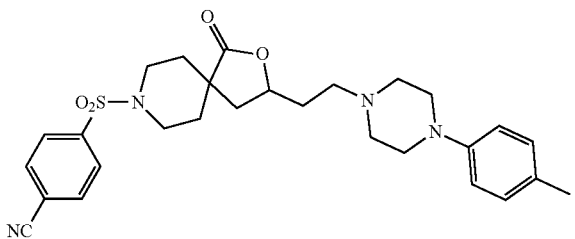 [SMILES: Cc1ccc(N2CCN(CCC3CC4(CCN(S(=O)(=O)c5ccc(C#N)cc5)CC4)C(=O)O3)CC2)cc1]

Example 37: Preparation of 4-((1-oxo-3-(2-(4-(p-tolyl)piperazin-1-yl)ethyl)-2-oxa-8-azaspiro[4.5]decan-8-yl)sulfonyl)benzonitrile: The title compound was prepared according to the procedure for 8-(methylsulfonyl)-3-(2-(4-(p-tolyl)piperazin-1-yl)ethyl)-2-oxa-8-azaspiro[4,5]decan-1-one formate, except 4-cyanobenzenesulfonyl chloride was substituted for methanesulfonyl chloride and the title compound was purified by column chromatography on a silica gel column. (MeOH/DCM, 0%~10%): $^1$H NMR (400 MHz, CDCl$_3$) δ 7.89 (d, J=8.1 Hz, 2H), 7.85 (d, 7.8 Hz, 2H), 7.08 (d, J=8.2 Hz, 2H), 6.84 (d, J=8.5 Hz, 2H), 4.57 (m, 1H), 3.53 (m, 1H), 3.24 (m, 2H), 3.20-3.07 (m, 51H), 2.68-2.48 (m, 6H), 2.28 (s, 3H), 2.21 (dd, J=6.0, 13.0 Hz, 1H), 2.08-1.97 (m, 2H), 1.97-1.65 (m, 5H): MS (LC/MS, M+H$^+$): 523.2.

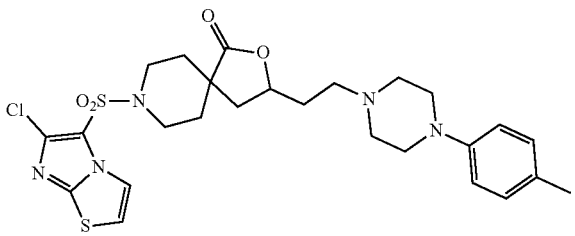 [SMILES: Cc1ccc(N2CCN(CCC3CC4(CCN(S(=O)(=O)c5c(Cl)nc6sccn56)CC4)C(=O)O3)CC2)cc1]

Example 38: Preparation of 8-((6-chloroimidazo[2,1-b]thiazol-5-yl)sulfonyl)-3-(2-(4-(p-tolyl)piperazin-1-yl)ethyl)-2-oxa-8-azaspiro[4.5]decan-1-one: The title compound was prepared according to the procedure for 8-(methylsulfonyl)-3-(2-(4-(p-tolyl)piperazin-1-yl)ethyl)-2-oxa-8-azaspiro[4.5]decan-1-one formate, except 6-chloro-imidazo[2,1-b]thiazole-5-sulfonyl chloride was substituted for methanesulfonyl chloride and the title compound was purified by column chromatography on a silica gel column. (MeOH/DCM, 0%~10%): $^1$H NMR (400 MHz, CDCl$_3$) δ 7.90 (d, J=4.5 Hz, 1H), 7.11-7.02 (m, 3H), 6.84 (d, J=8.6 Hz, 2H), 4.57 (m, 1H), 3.74 (m, 1H), 3.52 (m, 1H), 3.26 (m, 1H), 3.20-3.06 (m, 5H), 2.67-2.47 (m, 6H), 2.32-2.21 (m, 4H), 2.13-1.97 (m, 2H), 1.97-1.82 (m, 2H), 1.82-1.65 (m, 3H): MS (LC/MS, M+H$^+$): 578.1.

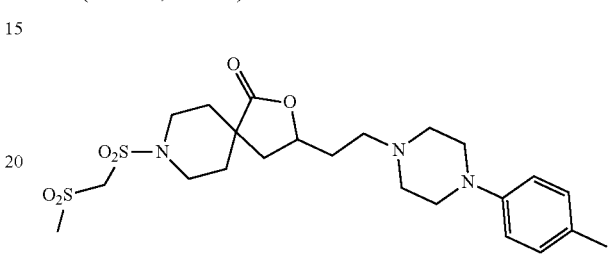

Example 39: Preparation of 8-(((methylsulfonyl)methyl)sulfonyl)-3-(2-(4-(p-tolyl)piperazin-1-yl)ethyl)-2-oxa-8-azaspiro[4.5]decan-1-one: The title compound was prepared according to the procedure for 8-(methylsulfonyl)-3-(2-(4-(p-tolyl)piperazin-1-yl)ethyl)-2-oxa-8-azaspiro[4.5]decan-1-one formate, except (methylsulfonyl)methanesulfonyl chloride was substituted for methanesulfonyl chloride and the title compound was purified by column chromatography on a silica gel column. (MeOH/DCM, 0%~10%): $^1$H NMR (400 MHz, CDCl$_3$) δ 7.09 (d, J=8.3 Hz, 2H), 6.86 (d, J=8.6 Hz, 2H), 4.61 (m, 1H), 4.45 (s, 2H), 3.89 (m, 1H), 3.66 (m, 1H), 3.45 (m, 1H), 3.34 (m, 1H), 3.23 (s, 3H), 3.17 (t, J=4.9 Hz, 4H), 2.73-2.52 (m, 6H), 2.37 (dd, J=6.1, 12.9 Hz, 1H), 2.28 (s, 3H), 2.15-1.85 (m, 4H), 1.85-1.65 (m, 3H); MS (LC/MS, M+H$^+$): 514.2.

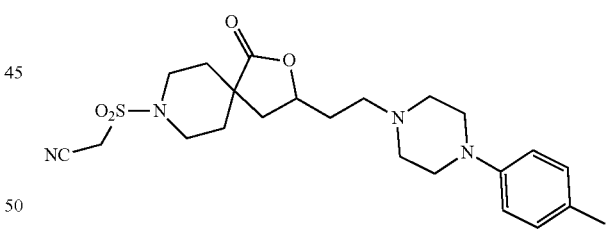

Example 40: Preparation of 2-((I-oxo-3-(2-(4-(p-tolyl)piperazin-1-yl)ethyl)-2-oxa-8-azaspiro[4.5]decan-8-yl)sulfonyl)acetonitrile: The title compound was prepared according to the procedure for 8-(methylsulfonyl)-3-(2-(4-(p-tolyl)piperazin-1-yl)ethyl)-2-oxa-8-azaspiro[4.5]decan-1-one formate, except cyanomethanesulfonyl chloride was substituted for methanesulfonyl chloride and the title compound was purified by column chromatography on a silica gel column. (MeOH/DCM, 0%~10%): $^1$H NMR (400 MHz, CDCl$_3$) δ 7.09 (d, J=8.3 Hz, 2H), 6.86 (d, J=8.5 Hz, 2H), 4.64 (in, 1H), 4.02-3.91 (m, 3H), 3.69 (m, 1H), 3.58 (m, 1H), 3.48 (m, 1H), 3.18 (t, J=4.9 Hz, 4H), 2.73-2.54 (m, 6H), 2.34 (dd, J=6.1, 13.0 Hz, 1H), 2.29 (s, 3H), 2.13-2.02 (m, 2H), 2.02-1.89 (m, 2H), 1.89-1.71 (m, 3H): MS (LC/MS, M+H$^+$): 461.2.

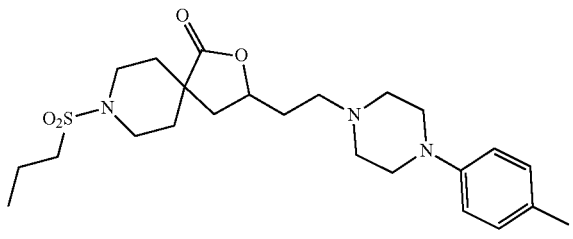 [SMILES: CCCS(=O)(=O)N1CCC2(CC1)CC(CCN1CCN(c3ccc(C)cc3)CC1)OC2=O]

Example 41: Preparation of 8-(propylsulfonyl)-3-(2-(4-(p-tolyl)piperazin-1-yl)ethyl)-2-oxa-8-azaspiro[4.5]decan-1-one: The title compound was prepared according to the procedure for 8-(methylsulfonyl)-3-(2-(4-(p-tolyl)piperazin-1-yl)ethyl)-2-oxa-8-azaspiro[4.5]decan-1-one formate, except 1-propanesulfonyl chloride was substituted for methanesulfonyl chloride and the title compound was purified by column chromatography on a silica gel column. (MeOH/DCM, 0%~10%): $^1$H NMR (400 MHz, CDCl$_3$) δ 7.09 (d, J=8.3 Hz, 2H), 6.85 (d, J=8.4 Hz, 2H), 4.61 (m, 1H), 3.73 (m, 1H), 3.48-3.35 (m, 2H), 3.34-3.25 (m, 1H), 3.16 (t, J=4.8 Hz, 4H), 2.92 (m, 2H), 2.69-2.50 (m, 6H), 2.30 (dd, J=6.0, 12.9 Hz, 1H), 2.28 (s, 3H), 2.07-1.65 (m, 9H), 1.07 (t, J=7.4 Hz, 3H); MS (LC/MS, M+H$^+$): 464

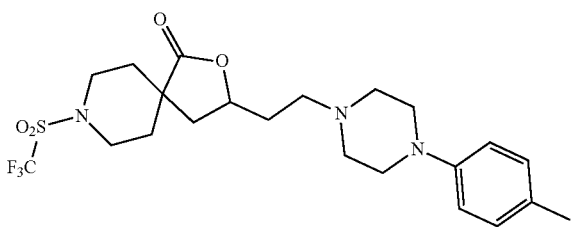 [SMILES: Cc1ccc(N2CCN(CCC3CC4(CCN(S(=O)(=O)C(F)(F)F)CC4)C(=O)O3)CC2)cc1]

Example 42: Preparation of 3-(2-(4-(p-tolyl)piperazin-1-yl)ethyl)-8-((trifluoromethyl)sulfonyl)-2-oxa-8-azaspiro[4.5]decan-1-one: The title compound was prepared according to the procedure for 8-(methylsulfonyl)-3-(2-(4-(p-tolyl)piperazin-1-yl)ethyl)-2-oxa-8-azaspiro[4.5]decan-1-one formate, except trifluoromethanesulfonyl chloride was substituted for methanesulfonyl chloride and the title compound was purified by column chromatography on a silica gel column. (MeOH/DCM, 0%~ 10%): $^1$H NMR (400 MHz, CDCl$_3$) δ 6.96 (d, J=8.3 Hz, 2H), 6.72 (d, J=8.5 Hz, 2H), 4.50 (m, 1H), 3.87 (m, 1H), 3.70-3.23 (b, 3H), 3.03 (t, J=4.9 Hz, 4H), 2.56-2.38 (m, 6H), 2.19 (dd, J=6.2, 12.9 Hz, 1H), 2.15 (s, 3H), 1.98-1.86 (m, 2H), 1.86-1.52 (m, 5H); MS (LC/MS, M+H$^+$): 490

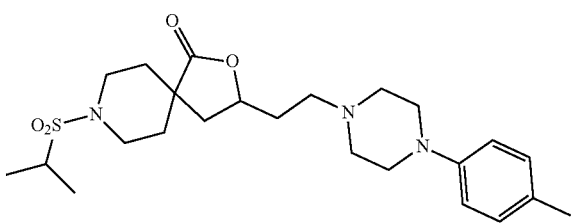 [SMILES: Cc1ccc(N2CCN(CCC3CC4(CCN(S(=O)(=O)C(C)C)CC4)C(=O)O3)CC2)cc1]

Example 43: Preparation of 8-(isopropylsulfonyl)-3-(2-(4-(p-tolyl)piperazin-1-yl)ethyl)-2-oxa-8-azaspiro[4.5]decan-1-one: The title compound was prepared according to the procedure for 8-(methylsulfonyl)-3-(2-(4-(p-tolyl)piper-azin-1-yl)ethyl)-2-oxa-8-azaspiro[4.5]decan-1-one formate, except 2-propanesulfonyl chloride was substituted for methanesulfonyl chloride and the title compound was purified by column chromatography on a silica gel column. (MeOH/DCM, 0%~10%): $^1$H NMR (400 MHz, CDCl$_3$) δ 6.95 (d, J=8.2 Hz, 2H), 6.72 (d, J=8.6 Hz, 2H), 4.47 (m, 1H), 3.67 (m, 1H), 3.44 (m, 1H), 3.35 (m, 1H), 3.25 (m, 1H), 3.12-2.94 (m, 5H), 2.58-2.36 (m, 6H), 2.18 (dd, J=6.0, 12.9 Hz, 1H), 2.14 (s, 3H), 1.92-1.71 (m, 4H), 1.71-1.45 (m, 3H): MS (LC/MS, M+H$^+$):

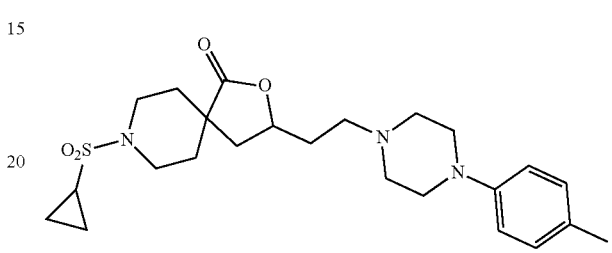

Example 44: Preparation of 8-(cyclopropylsulfonyl)-3-(2-(4-(p-tolyl)piperazin-1-yl)ethyl)-2-oxa-8-azaspiro[4,5]decan-1-one: The title compound was prepared according to the procedure for 8-(methylsulfonyl)-3-(2-(4-(p-tolyl)piperazin-1-yl)ethyl)-2-oxa-8-azaspiro[4.5]decan-1-one formate, except cyclopropanesulfonyl chloride was substituted for methanesulfonyl chloride and the title compound was purified by column chromatography on a silica gel column. (MeOH/DCM, 0%~ 10%): $^1$H NMR (400 MHz, CDCl$_3$) δ 7.08 (d, J=8.3 Hz, 2H), 6.85 (d, J=8.5 Hz, 2H), 4.61 (m, 1H), 3.78 (m, 1H), 3.50 (m, 1H), 3.37 (m, 1H), 3.28 (m, 1H), 3.16 (t, J=4.9 Hz, 4H), 2.70-2.50 (m, 6H), 2.36-2.25 (m, 5H), 2.10-1.98 (m, 2H), 1.98-1.65 (m, 5H), 1.23-1.11 (m, 2H), 1.07-0.95 (m, 2H); MS (LC/MS, M+H$^+$): 462

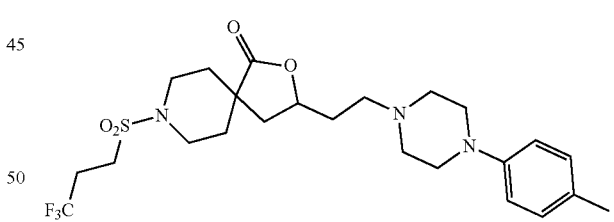

Example 45: Preparation of 3-(2-(4-(p-tolyl)piperazin-1-yl)ethyl)-8-((3,3,3-trifluoropropyl)sulfonyl)-2-oxa-8-azaspiro[4.5]decan-1-one: The title compound was prepared according to the procedure for 8-(methylsulfonyl)-3-(2-(4-(p-tolyl)piperazin-1-yl)ethyl)-2-oxa-8-azaspiro[4,5]decan-1-one formate, except 3,3,3-trifluoropropane-1-sulfonyl chloride was substituted for methanesulfonyl chloride and the title compound was purified by column chromatography on a silica gel column. (MeOH/DCM, 0%~ 10%): $^1$H NMR (400 MHz, CDCl$_3$) δ 6.95 (d, J=8.3 Hz, 2H), 6.72 (d, J=8.5 Hz, 2H), 4.49 (m, 1H), 3.64 (m, 1H), 3.38-3.27 (m, 2H), 3.23 (m, 1H), 3.09-2.93 (m, 6H), 2.59-2.36 (m, 8H), 2.17 (dd, J=5.9, 13.0 Hz, 1H), 2.15 (s, 3H), 1.96-1.85 (m, 2H), 1.85-1.56 (m, 5H); MS (LC/MS, M+H$^+$): 518

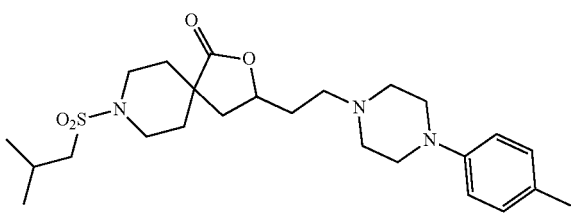 [SMILES: Cc1ccc(N2CCN(CCC3CC4(CCN(S(=O)(=O)CC(C)C)CC4)C(=O)O3)CC2)cc1]

Example 46: Preparation of 8-(isobutylsulfonyl)-3-(2-(4-(p-tolyl)piperazin-1-yl)ethyl)-2-oxa-8-azaspiro[4.5]decan-1-one: The title compound was prepared according to the procedure for 8-(methylsulfonyl)-3-(2-(4-(p-tolyl)piperazin-1-yl)ethyl)-2-oxa-8-azaspiro[4.5]decan-1-one formate, except isobutanesulfonyl chloride was substituted for methanesulfonyl chloride and the title compound was purified by column chromatography on a silica gel column. (MeOH/DCM, 0%~10%): $^1$H NMR (400 MHz, CDCl$_3$) δ 7.08 (d, J=8.3 Hz, 2H), 6.85 (d, J=8.5 Hz, 2H), 4.61 (m, 11H), 3.70 (m, 1H), 3.45-3.33 (m, 2H), 3.29 (in, 1H) 3.16 (t, J=4.8 Hz, 4H), 2.79 (dd, J=2.2, 6.6 Hz, 2H), 2.70-2.49 (m, 6H), 2.37-2.20 (m, 5H), 2.07-1.97 (m, 2H), 1.97-1.67 (m, 5H), 1.12 (d, J=6.7 Hz, 6H): MS (LC/MS, M+H$^+$): 478

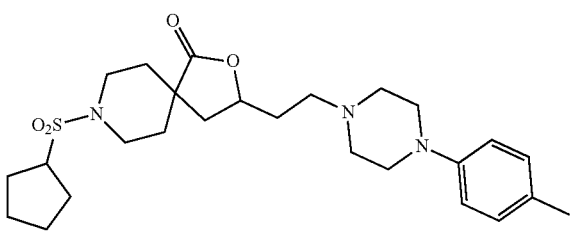 [SMILES: Cc1ccc(N2CCN(CCC3CC4(CCN(S(=O)(=O)C5CCCC5)CC4)C(=O)O3)CC2)cc1]

Example 47: Preparation of 8-(cyclopentylsulfonyl)-3-(2-(4-(p-tolyl)piperazin-1-yl)ethyl)-2-oxa-8-azaspiro[4.5]decan-1-one: The title compound was prepared according to the procedure for 8-(methylsulfonyl)-3-(2-(4-(p-tolyl)piperazin-1-yl)ethyl)-2-oxa-8-azaspiro[4.5]decan-1-one formate, except cyclopentanesulfonyl chloride was substituted for methanesulfonyl chloride and the title compound was purified by column chromatography on a silica gel column. (MeOH/DCM, 0%~10%): $^1$H NMR (400 MHz, CDCl$_3$) δ 6.95 (d, J=8.3 Hz, 2H), 6.72 (d, J=8.6 Hz, 2H), 4.47 (m, 1H), 3.64 (m, 1H), 3.42-3.22 (m, 3H), 3.18 (in, 1H) 3.03 (t, J=4.9 Hz, 4H), 2.57-2.37 (m, 6H), 2.18 (dd, J=6.1, 12.9 Hz, 1H), 2.15 (s, 3H), 1.95-1.42 (m, 15H); MS (LC/MS, M+H$^+$): 490

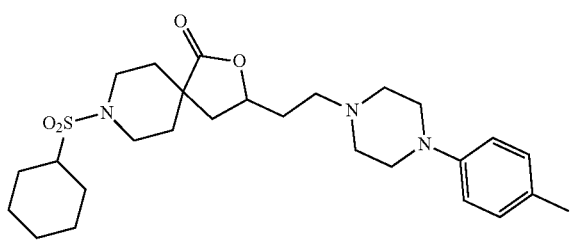 [SMILES: Cc1ccc(N2CCN(CCC3CC4(CCN(S(=O)(=O)C5CCCCC5)CC4)C(=O)O3)CC2)cc1]

Example 48: Preparation of 8-(cyclohexylsulfonyl)-3-(2-(4-(p-tolyl)piperazin-1-yl)ethyl)-2-oxa-8-azaspiro[4,5]decan-1-one: The title compound was prepared according to the procedure for 8-(methylsulfonyl)-3-(2-(4-(p-tolyl)piperazin-1-yl)ethyl)-2-oxa-8-azaspiro[4.5]decan-1-one formate, except cyclohexanesulfonyl chloride was substituted for methanesulfonyl chloride and the title compound was purified by column chromatography on a silica gel column. (MeOH/DCM, 0%~10%): $^1$H NMR (400 MHz, CDCl$_3$) δ 6.95 (d, J=8.3 Hz, 2H), 6.72 (d, J=8.4 Hz, 2H), 4.47 (in, 1H), 3.66 (m, 1H), 3.38 (m, 1H), 3.27 (m, 1H), 3.18 (m, 1H), 3.03 (t, J=4.9 Hz, 4H), 2.77 (tt, J=3.4, 12.0 Hz, 1H), 2.59-2.36 (m, 6H), 2.19 (dd, J=6.0, 12.9 Hz, 1H), 2.15 (s, 3H), 2.06-1.94 (b, 2H), 1.91-1.72 (m, 6H), 1.72-1.49 (m, 4H), 1.37 (qd, J=3.3, 12.3 Hz, 2H), 1.23-0.99 (m, 3H): MS (LC/MS, M+H$^+$): 504

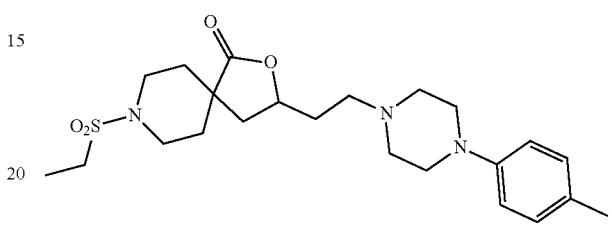

Example 49: Preparation of 8-(ethylsulfonyl)-3-(2-(4-(p-tolyl)piperazin-1-yl)ethyl)-2-oxa-8-azaspiro[4.5]decan-1-one: The title compound was prepared according to the procedure for 8-(methylsulfonyl)-3-(2-(4-(p-tolyl)piperazin-1-yl)ethyl)-2-oxa-8-azaspiro[4.5]decan-1-one formate, except ethanesulfonyl chloride was substituted for methanesulfonyl chloride and the title compound was purified by column chromatography on a silica gel column. (MeOH/DCM, 0%~10%): $^1$H NMR (400 MHz, CDCl$_3$) δ 7.08 (d, J=8.2 Hz, 2H), 6.85 (d, J=8.6 Hz, 2H), 4.61 (m, 1H), 3.75 (m, 1H), 3.51-3.35 (m, 2H), 3.30 (m, 1H), 3.15 (t, J=4.9 Hz, 4H), 2.98 (q, J=7.4 Hz, 2H), 2.70-2.48 (m, 6H), 2.31 (dd, J=6.2, 13.0 Hz, 1H), 2.28 (s, 3H), 2.07-1.96 (m, 2H), 1.96-1.66 (m, 5), 1.38 (t, J=7.4 Hz, 3H); MS (LC/MS, M+H$^+$): 450

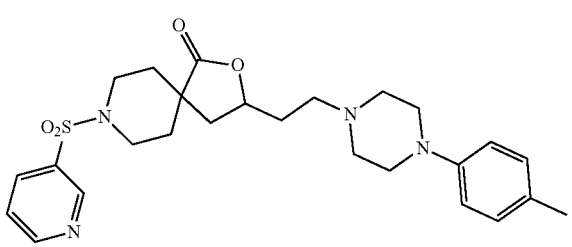 [SMILES: Cc1ccc(N2CCN(CCC3CC4(CCN(S(=O)(=O)c5cccnc5)CC4)C(=O)O3)CC2)cc1]

Example 50: Preparation of 8-(pyridin-3-ylsulfonyl)-3-(2-(4-(p-tolyl)piperazin-1-yl)ethyl)-2-oxa-8-azaspiro[4.5]decan-1-one: The title compound was prepared according to the procedure for 8-(methylsulfonyl)-3-(2-(4-(p-tolyl)piperazin-1-yl)ethyl)-2-oxa-8-azaspiro[4.5]decan-1-one formate, except pyridine-3-sulfonyl chloride was substituted for methanesulfonyl chloride and the title compound was purified by column chromatography on a silica gel column. (MeOH/DCM, 0%~10%): $^1$H NMR (400 MHz, CDCl$_3$) δ 9.00 (d, J=2.3 Hz, 1H), 8.84 (dd, J=1.5, 4.8 Hz, 1H), 8.06 (dt, J=1.9, 8.0 Hz, 1H), 7.5 (dd, J=4.9, 7.9 Hz, 1H), 7.08 (d, J=8.3 Hz, 2H), 6.84 (d, J=8.5 Hz, 2H), 4.55 (in, H), 3.56 (m, 1H), 3.29 (m, 1H), 3.24-3.05 (m, 6H), 2.66-2.47 (m, 6H), 2.27 (s, 3H) 2.09 (dd, J=6.0, 13.0 Hz, 1H), 2.09-1.96 (m, 2H), 1.96-1.64 (m, 5H): MS (LC/MS, M+H$^+$): 499

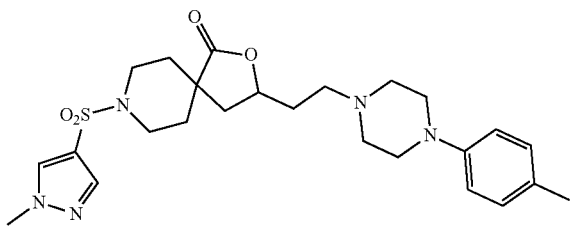

Example 51: Preparation of 8-((l-methyl-1H-pyrazol-4-yl)sulfonyl)-3-(2-(4-(p-tolyl)piperazin-1-yl)ethyl)-2-oxa-8-azaspiro[4.5]decan-1-one: The title compound was prepared according to the procedure for 8-(methylsulfonyl)-3-(2-(4-(p-tolyl)piperazin-1-yl)ethyl)-2-oxa-8-azaspiro[4,5]decan-1-one formate, except 1-methyl-1H-pyrazole-4-sulfonyl chloride was substituted for methanesulfonyl chloride and the title compound was purified by column chromatography on a silica gel column. (MeOH/DCM, 0%~ 10%): $^1$H NMR (400 MHz, CDCl$_3$) δ 7.75 (s, 1H), 7.71 (s, 1H), 7.07 (d, J=8.4 Hz, 2H), 6.84 (d, J=8.6 Hz, 2H), 4.55 (m, 1H), 3.95 (s, 3H), 3.48 (m, 1H), 3.23 (m, 1H), 3.13 (t, J=4.9 Hz, 4H), 3.02 (m, 1H), 2.93 (m, 1H), 2.67-2.48 (m, 6H), 2.27 (s, 3H), 2.22 (dd, J=6.1, 12.9 Hz, 1H), 2.11-1.96 (m, 2H), 1.96-1.64 (m, 5H): MS (LC/MS, M+H$^+$): 502

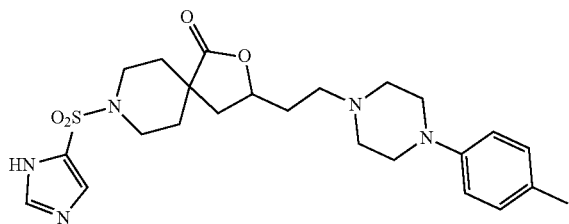 [SMILES: Cc1ccc(N2CCN(CCC3CC4(CCN(S(=O)(=O)c5cnc[nH]5)CC4)C(=O)O3)CC2)cc1]

Example 52: Preparation of 8-((1 H-imidazol-4-yl)sulfonyl)-3-(2-(4-(p-tolyl)piperazin-1-yl)ethyl)-2-oxa-8-azaspiro[4.5]decan-1-one formate: The title compound was prepared according to the procedure for 8-(methylsulfonyl)-3-(2-(4-(p-tolyl)piperazin-1-yl)ethyl)-2-oxa-8-azaspiro[4,5]decan-1-one formate, except 1H-imidazole-4-sulfonyl chloride was substituted for methanesulfonyl chloride: $^1$H NMR (400 MHz, MeOD) δ 7.88 (s, 1H), 7.74 (s, 1H), 7.09 (d, J=8.4 Hz, 2H), 6.90 (d, J=8.4 Hz, 2H), 4.58 (b, 1H), 3.67 (m, 1H), 3.53 (m, 1H), 3.40-3.05 (m, 10H), 2.99 (m, 1H), 2.85 (m, 1H), 2.38 (dd, J=5.7, 12.9 Hz, 1H), 2.26 (s, 3H), 2.19-1.91 (m, 3H), 1.90-1.72 (m, 3H), 1.72-1.58 (m, 1H): MS (LC/MS, M+H$^+$): 488

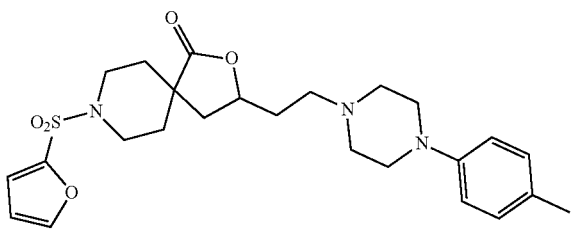 [SMILES: Cc1ccc(N2CCN(CCC3CC4(CCN(S(=O)(=O)c5ccco5)CC4)C(=O)O3)CC2)cc1]

Example 53: Preparation of 8-(furan-2-ylsulfonyl)-3-(2-(4-(p-tolyl)piperazin-1-yl)ethyl)-2-oxa-8-azaspiro[4,5]decan-1-one: The title compound was prepared according to the procedure for 8-(methylsulfonyl)-3-(2-(4-(p-tolyl)piper-azin-1-yl)ethyl)-2-oxa-8-azaspiro[4.5]decan-1-one formate, except furan-2-sulfonyl chloride was substituted for methanesulfonyl chloride and the title compound was purified by column chromatography on a silica gel column. (MeOH/DCM, 0%~10%): $^1$H NMR (400 MHz, CDCl$_3$) δ 7.59 (s, 1H), 7.07 (d, J=8.4 Hz, 2H), 7.02 (d, J=3.4 Hz, 1H), 6.84 (d, J=8.4 Hz, 2H), 6.52 (dd, J=1.7, 3.3 Hz, 1H), 4.56 (m, 1H), 3.70 (m, 1H), 3.47 (m, 1H), 3.24 (m, 1H), 3.19-3.07 (m, 5H), 2.68-2.46 (m, 6H), 2.33-2.18 (m, 4H), 2.07-1.79 (m, 4H), 1.79-1.60 (m, 3H): MS (LC/MS, M+H$^+$): 488

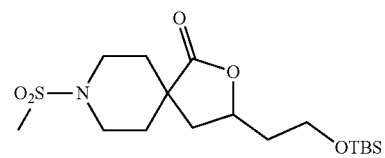 [SMILES: CC(C)(C)[Si](C)(C)OCCC1CC2(CCN(S(C)(=O)=O)CC2)C(=O)O1]

Example 54: Preparation of 3-(2-((tert-butyldimethylsilyl)oxy)ethyl)-8-(methylsulfonyl)-2-oxa-8-azaspiro[4.5]decan-1-one: A mixture of 8-benzyl-3-(2-((tert-butyldimethylsilyl)oxy)ethyl)-2-oxa-8-azaspiro[4.5]decan-1-one (3.25 g, 8.04 mmol, 1 eq.). Pd/C (0.65 g, 20% wt) and MeOH (54 mL) was stirred at RT under 1 atm of H$_2$ (filled balloon) overnight. The mixture was filtered through a plug of Celite, washed with MeOH (50 mL) and concentrated in vacuo to give a crude oil. The crude oil (2.43 g) was dissolved in dichloromethane (50 mL), followed by addition of triethylamine (5.55 mL, 38.8 mmol, 5 eq.). Cooled to 0° C. before the addition of methanesulfonyl chloride (2.83 g, 13.0 mmol, 1.1 eq.). The reaction was allowed to warm to RT and stir for 30 min. At this point the reaction was diluted with D.I. water and then extracted with dichloromethane (3×50 mL), the combined organic phase was dried over Na$_2$SO$_4$ and concentrated in vacuo to give a crude product which was further purified by column chromatography (EtOAc/DCM, 0%~ 10%). $^1$H NMR (400 MHz, CDCl$_3$) δ 4.61 (m, 1H), 3.75-3.65 (m, 2H), 3.60 (m, 1H), 3.37-3.18 (m, 3H), 2.75 (s, 3H), 2.21 (dd, J=6.0, 13.0 Hz, 1H), 2.02-1.91 (m, 2H), 1.91-1.62 (m, 5H), 0.83 (s, 9H), 0.00 (s, 6H).

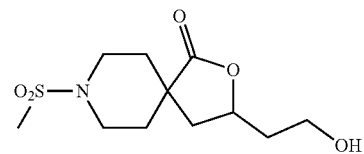 [SMILES: CS(=O)(=O)N1CCC2(CC1)CC(CCO)OC2=O]

Example 55: Preparation of 3-(2-hydroxyethyl)-8-(methylsulfonyl)-2-oxa-8-azaspiro[4.5]decan-1-one: The title compound was prepared according to the procedure for tert-butyl 3-(2-hydroxyethyl)-1-oxo-2-oxa-8-azaspiro[4.5]decane-8-carboxylate, except 3-(2-((tert-butyldimethylsilyl)oxy)ethyl)-8-(methylsulfonyl)-2-oxa-8-azaspiro[4.5]decan-1-one was substituted for tert-butyl 3-(2-((tert-butyldimethylsilyl)oxy)ethyl)-1-oxo-2-oxa-8-azaspiro[4.5]decane-8-carboxylate and the product was initially purified by column chromatography on a C18 column. (ACN/H$_2$O, 0%~ 100%, w/ 0.1% formic acid), followed by purification on a silica gel column (MeOH/DCM, 0%~10%). $^1$H NMR (400 MHz, CDCl$_3$) a 4.73 (m, 1H), 3.84 (t, J=5.5 Hz, 2H), 3.68 (m, 1H), 3.41-3.32 (m, 2H), 3.29 (m, 1H), 2.83 (s, 3H), 2.33 (dd, J=6.0, 13.0 Hz, 1H), 2.10-2.00 (m, 2H), 2.10-1.71 (m, 6H).

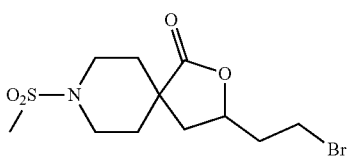 [SMILES: CS(=O)(=O)N1CCC2(CC1)CC(CCBr)OC2=O]

Example 56: Preparation of 3-(2-bromoethyl)-8-(methylsulfonyl)-2-oxa-8-azaspiro[4.5]decan-1-one: A solution of 3-(2-hydroxyethyl)-8-(methylsulfonyl)-2-oxa-8-azaspiro[4.5]decan-1-one (0.890 g, 3.21 mmol, 1 eq.) and dichloromethane (12 mL) was cooled to 0° C. before triphenylphosphine (1.26 g, 4.81 mmol, 1.5 eq.) and carbon tetrabromide (1.6 g, 4.81 mmol, 1.5 eq.) were sequentially added to the solution. The reaction solution was allowed to warm to RT and for 4 hrs. The resulting mixture was then filtered and concentrated in vacuo to give a crude mixture. This mixture was suspended in diethyl ether (50 mL) and filtered 2× using diethyl ether to wash the filter cakes. The final filtrate was loaded onto Celite in vacuo and further purified by column chromatography (EtOAc/DCM, 0%~40%). $^1$H NMR (400 MHz, MeOD) δ 4.72 (m, 1H), 3.67 (m, 1H), 3.54 (dd, J=5.3, 7.6 Hz, 2H), 3.44-3.25 (m, 3H), 2.82 (s, 3H), 2.34 (dd, J=6.0, 12.9 Hz, 1H), 2.31-2.21 (m, 1H), 2.21-2.10 (m, 1H), 2.10-1.98 (m, 2H), 1.88-1.71 (m, 3H).

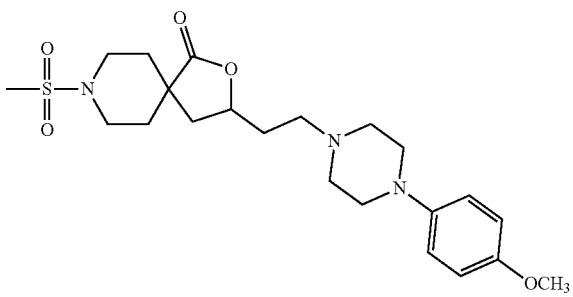 [SMILES: COc1ccc(N2CCN(CCC3CC4(CCN(S(C)(=O)=O)CC4)C(=O)O3)CC2)cc1]

Example 57: Preparation of 3-(2-(4-(4-methoxyphenyl)piperazin-1-yl)ethyl)-8-(methylsulfonyl)-2-oxa-8-azaspiro[4,5]decan-1-one: A solution of 3-(2-bromoethyl)-8-(methylsulfonyl)-2-oxa-8-azaspiro[4.5]decan-1-one (50 mg, 0.147 mmol, 1 eq.), 1-(4-methoxyphenyl)-piperazine (59.33 mg, 0.308 mmol, 2.1 eq.) and Acetonitrile (2 mL) was microwaved for 1 hour at 120° C. The solvent was then evaporated in vacuo and the product was suspended in 15 mL of saturated NaHCO$_3$ and extracted in dichloromethane (3×15 mL). The combined organic phase was dried over Na$_2$SO$_4$ and concentrated in vacuo to give a crude mixture that was then dissolved in dichloromethane and purified by column chromatography (methanol/dichloromethane, 0%~10%).

$^1$H NMR (400 MHz, CDCl$_3$) δ 7.4 (d, J=9.2 Hz, 2H), 6.5 (d, J=9.2 Hz, 2H), 4.61 (m, 1H), 3.77 (s, 3H), 3.67 (m, 1H), 3.36 (m, 2H), 3.29 (m, 1H), 3.1 (t, J=7.1 Hz, 4H), 2.8 (s, 3H), 2.62 (m, 4H), 2.56 (t, J=7.1 Hz, 2H), 2.29 (dd, J=7.2, 6 Hz, 1H), 2.05 (m, 2H), 1.99-1.71 (m, 6H): MS (LC/MS, M+H$^+$): 452.

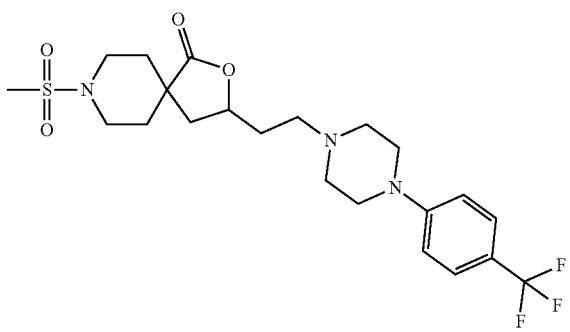 [SMILES: CS(=O)(=O)N1CCC2(CC1)CC(CCN1CCN(c3ccc(C(F)(F)F)cc3)CC1)OC2=O]

Example 58: Preparation of 3-(2-(4-(4-methoxyphenyl)piperazin-1-yl)ethyl)-8-(methylsulfonyl)-2-oxa-8-azaspiro[4.5]decan-1-one: The tittle compound was prepared and purified according to the procedure for 3-(2-(4-(4-methoxyphenyl)piperazin-1-yl)ethyl)-8-(methylsulfonyl)-2-oxa-8-azaspiro[4.5]decan-1-one except that 1-(4-trifluoromethylphenyl)-piperazine was substituted for 1-(4-methoxyphenyl)-piperazine. $^1$H NMR (400 MHz, CDCl$_3$) δ 7.5 (d, J=8.76 Hz, 2H), 6.94 (d, J=8.7 Hz, 2H), 4.64 (n, 1H), 3.68 (n, 1H), 3.46-3.28 (m, 7H), 2.83 (s, 3H), 2.67-2.55 (m, 6H), 2.3 (dd. J=7.1, 6.1 Hz, 1H), 2.11-2.01 (m, 2H), 2.0-1.74 (m, 5H); MS (LC/MS, M+H$^+$): 490

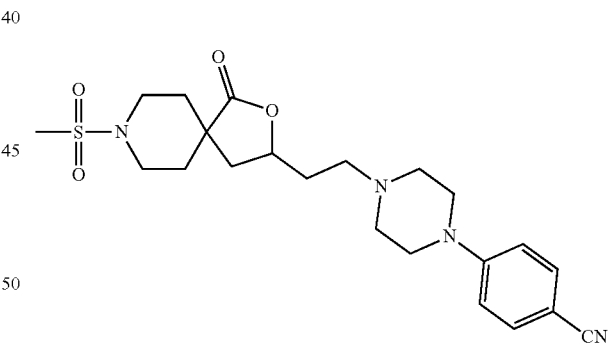

Example 59: Preparation of 4-(4-(2-(8-(methylsulfonyl)-1-oxo-2-oxa-8-azaspiro[4.5]decan-3-yl)ethyl)piperazin-1-yl)benzonitrile: The tittle compound was prepared and purified according to the procedure for 3-(2-(4-(4-methoxyphenyl)piperazin-1-yl)ethyl)-8-(methylsulfonyl)-2-oxa-8-azaspiro[4.5]decan-1-one except that triethylamine (0.06 mL, 0.44 mmol, 3 eq.) was added in the microwave mixture and 1-(4-cyanophenyl)-piperazine was substituted for 1-(4-methoxyphenyl)-piprazine: $^1$H NMR (400 MHz, CDCl$_3$) δ 7.49 (d, J=8.4 Hz, 2H), 6.85 (d, J=8.4 Hz, 2H), 4.61 (m, 1H), 3.65 (m, 1H), 3.43-3.26 (m, 7H), 2.81 (s, 3H), 2.64-2.52 (m, 6H), 2.28 (dd, J=6.8, 5.9 Hz, 1H), 2.02 (m, 2H), 1.96-1.74 (m, 5H); MS (LC/MS, M+H+): 447

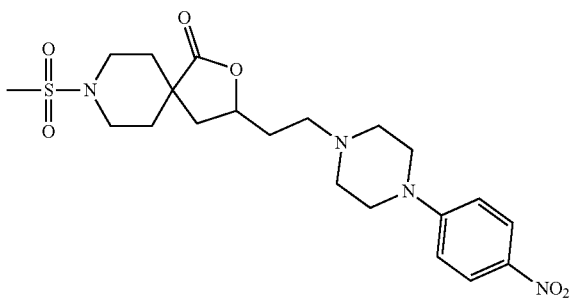 [SMILES: CS(=O)(=O)N1CCC2(CC1)CC(CCN1CCN(c3ccc([N+](=O)[O-])cc3)CC1)OC2=O]

Example 60: Preparation of 8-(methylsulfonyl)-3-(2-(4-(4-nitrophenyl)piperazin-1-yl)ethyl)-2-oxa-8-azaspiro[4.5]decan-1-one: The tittle compound was prepared and purified according to the procedure for 3-(2-(4-(4-methoxyphenyl)piperazin-1-yl)ethyl)-8-(methylsulfonyl)-2-oxa-8-azaspiro[4.5]decan-1-one except that it was microwaved for 1.5 hours at 120° C. and 1-(4-nitrophenyl)-piprazine was substituted for 1-(4-methoxyphenyl)-piprazine. $^1$H NMR (400 MHz, CDCl$_3$) δ 8.13 (d, J=9.3 Hz, 2H), 6.82 (d, J=9.3 Hz, 2H), 4.62 (m, 1H), 3.66 (m, 1H), 3.46-3.36 (m, 4H), 3.36-3.28 (m, 3H), 2.8 (s, 3H), 2.67-2.5 (b, 6H), 2.28 (dd, J=6.8, 5.9 Hz, 1H), 2.08-1.98 (m, 2H), 1.95-1.72 (m, 5H); MS (LC/MS, M+H+): 467

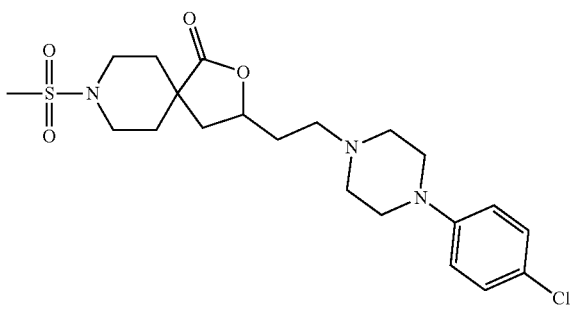 [SMILES: CS(=O)(=O)N1CCC2(CC1)CC(CCN1CCN(c3ccc(Cl)cc3)CC1)OC2=O]

Example 61: Preparation of 3-(2-(4-(4-chlorophenyl)piperazin-1-yl)ethyl)-8-(methylsulfonyl)-2-oxa-8-azaspiro[4,5]decan-1-one: The tittle compound was prepared and purified according to the procedure for 3-(2-(4-(4-methoxyphenyl)piperazin-1-yl)ethyl)-8-(methylsulfonyl)-2-oxa-8-azaspiro[4.5]decan-1-one except that it was microwaved for 2 hours at 120° C. and 1-(4-chlorophenyl)-piprazine was substituted for 1-(4-methoxyphenyl)-piprazine. $^1$H NMR (400 MHz, CDCl$_3$) δ 7.19 (d, J=8.9 Hz, 2H), 6.82 (d, J=8.9 Hz, 2H), 4.6 (m, 1H), 3.65 (m, 1H), 3.42-3.26 (m, 3H), 3.15 (t, J=4.9 Hz, 4H), 2.8 (s, 3H), 2.66-2.52 (m, 6H), 2.27 (dd, J=6.8, 5.9 Hz, 1H), 2.07-1.98 (m, 2H), 1.97-1.7 (m, 5H); MS (LC/MS, M+H+): 456

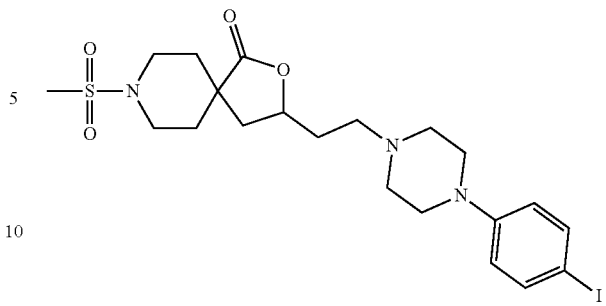

Example 62: Preparation of 3-(2-(4-(4-iodophenyl)piperazin-1-yl)ethyl)-8-(methylsulfonyl)-2-oxa-8-azaspiro[4,5]decan-1-one: The tittle compound was prepared and purified according to the procedure for 3-(2-(4-(4-chlorophenyl)piperazin-1-yl)ethyl)-8-(methylsulfonyl)-2-oxa-8-azaspiro[4.5]decan-1-one except that and 1-(4-iodophenyl)-piprazine was substituted for 1-(4-methoxyphenyl)-piprazine. $^1$H NMR (400 MHz, CDCl$_3$) δ 7.49 (d, J=8.8 Hz, 2H), 6.65 (d, J=8.8 Hz, 2H), 4.58 (m, 1H), 3.64 (m, 1H), 3.4-3.24 (m, 3H), 3.15 (t, J=4.8 Hz, 4H), 2.79 (s, 3H), 2.62-2.5 (m, 6H), 2.26 (dd, J=6.8, 6 Hz, 1H), 2.0-1.96 (m, 2H), 1.95-1.69 (m, 5H): MS (LC/MS, M+H+): 548

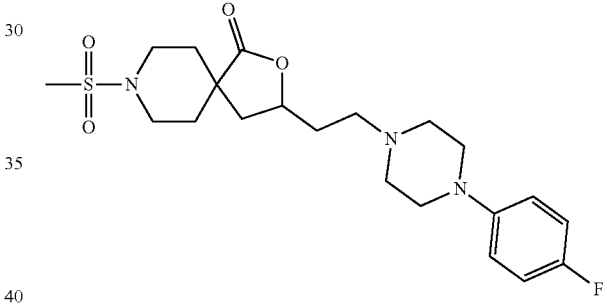

Example 63: Preparation of 3-(2-(4-(4-fluorophenyl)piperazin-1-yl)ethyl)-8-(methylsulfonyl)-2-oxa-8-azaspiro[4.5]decan-1-one: The tittle compound was prepared and purified according to the procedure for 3-(2-(4-(4-chlorophenyl)piperazin-1-yl)ethyl)-8-(methylsulfonyl)-2-oxa-8-azaspiro[4.5]decan-1-one except that and 1-(4-fluorophenyl)-piprazine was substituted for 1-(4-methoxyphenyl)-piprazine. $^1$H NMR (400 MHz, CDCl$_3$) δ 6.94 (m, 2H), 6.85 (m, 2H), 4.59 (m, 1H), 3.65 (m, 1H), 3.4-3.24 (m, 3H), 3.1 (t, J=4.8 Hz, 4H), 2.8 (s, 3H), 2.65-2.5 (m, 6H), 2.27 (dd, J=6.7, 5.9 Hz, 1H), 2.0 (m, 2H), 1.97-1.69 (m, 5H): MS (LC/MS, M+H+): 440.

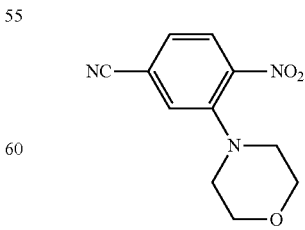

Preparation of 3-morpholino-4-nitrobenzonitrile: A solution of 3-fluoro-4-nitrobenzonitrile (0.6 g, 3.61 mmol, 1 eq.) and morpholine (0.629 g, 7.22 mmol, 2 eq.) in dimethyl sulfoxide (6.57 mL) was heated at 60° C. for 4 hours. The reaction solution was diluted with water 20 mL and extracted with ethyl acetate (3×20 mL). The combined organic phase was dried over Na$_2$SO$_4$ and concentrated in vacuo to give a crude product which was used in the next step without further purification. $^1$H NMR (400 MHz, CDCl$_3$) δ 7.82 (d, J=8.3 Hz, 1H), 7.40 (d, J=1.5 Hz, 1H), 7.33 (dd, J=1.6, 8.3 Hz, 1H), 3.86 (m, 4H), 3.11 (m, 4H); MS (LC/MS, M+H$^+$): 234

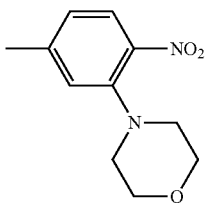

Preparation of 4-(5-methyl-2-nitrophenyl)morpholine: The title compound was prepared according to the procedure for 3-morpholino-4-nitrobenzonitrile, except 2-fluoro-4-methyl-1-nitrobenzene was substituted for 3-fluoro-4-nitrobenzonitrile. $^1$H NMR (400 MHz, CDCl$_3$) δ 7.76 (d, J=8.2 Hz, 1H), 6.93 (b, 1H), 6.88 (d, J=8.3H, 1H), 3.86 (m, 4H), 3.06 (m, 4H), 2.40 (s, 3H): MS (LC/MS, M+H$^+$): 223

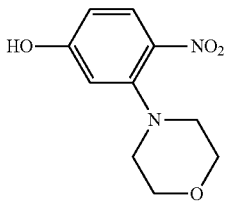 [SMILES: N#Cc1ccc([N+](=O)[O-])c(N2CCOCC2)c1]

Preparation of 3-morpholino-4-nitrophenol: The title compound was prepared according to the procedure for 3-morpholino-4-nitrobenzonitrile, except 3-fluoro-4-nitrophenol was substituted for 3-fluoro-4-nitrobenzonitrile. $^1$H NMR (400 MHz, MeOD) δ 7.90 (d, J=9.0 Hz, 1H), 6.56 (d, J=2.4 Hz, 1H), 6.49 (dd, J=2.5, 9.0 Hz, 1H), 3.83 (m, 4H), 3.02 (m, 4H): MS (LC/MS, M+H$^+$): 225

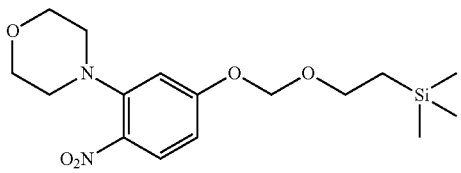 [SMILES: C[Si](C)(C)CCOCOc1ccc([N+](=O)[O-])c(N2CCOCC2)c1]

Preparation of 4-(2-nitro-5-((2-(trimethylsilyl)ethoxy)methoxy)phenyl)morpholine: A solution of 3-morpholino-4-nitrophenol (1.34 g, 5.98 mmol, 1 eq.), 2-(trimethylsilyl)ethoxymethyl chloride (1.05 g, 6.28 mmol, 1.05 eq.) and N,N-diisopropylethylamine (2.31 g, 17.9 mmol, 3 eq.) in dichloromethane (30.0 mL) was stirred at 25° C. for 16 hours. The reaction solution was diluted with 40 mL of water and extracted with dichloromethane (3×40 mL). The combined organic phase was dried over Na$_2$SO$_4$ and concentrated in vacuo to give a crude product which was used in the next step without further purification. $^1$H NMR (400 MHz, CDCl$_3$) δ 7.93 (d, J=9.7 Hz, 1H), 6.68 (m, 2H), 5.24 (s, 2H), 3.85 (m, 4H), 3.74 (m, 2H), 3.04 (m, 4H), 0.94 (m, 2H), 0.00 (s, 9H); MS (LC/MS, M+H$^+$): 355

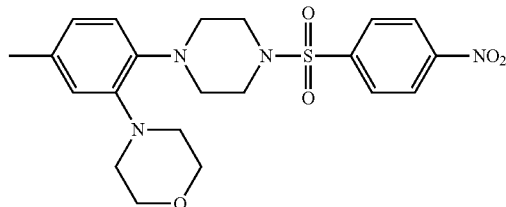

Preparation of 4-(5-methyl-2-(4-((4-nitrophenyl)sulfonyl)piperazin-1-yl)phenyl)morpholine: A mixture of 4-(5-methyl-2-nitrophenyl)morpholine (1.58 g, 7.11 mmol, 1 eq.), Pd on carbon (316 mg, 20% wt) and methanol (72 mL) was stirred at 25° C. under 1 atm of H$_2$ (filled balloon) for 48 hours. The mixture was filtered through a plug of Celite, washed with methanol (50 mL) and concentrated in vacuo to give the crude intermediate, 4-methyl-2-morpholinoaniline.

(((4-nitrophenyl)sulfonyl)azanediyl)bis(ethane-2,1-diyl) bis(4-nitrobenzenesulfonate) (1.0 g, 1.5 mmol, 1 eq.), 4-methyl-2-morpholinoaniline (0.346 g, 1.8 mmol, 1.2 eq.). N,N-diisopropylethylamine (1.55 g, 12.0 mmol, 4 eq.) and acetonitrile (4.7 mL) were mixed in a microwave reaction vial (10 mL) fitted with a no-invasive vial cap. The reaction vials containing the mixture were reacted in the microwave for 1 h at 175° C. After 1 h, the solvent was removed under reduced pressure. The residue was dissolved in dichloromethane and washed with HCl (10%, 3×30 mL) and saturated NaHCO$_3$ (40 mL). The organic phase was dried over Na$_2$SO$_4$ and concentrated in vacuo to afford the crude product. The title compound was purified by column chromatography on a silica gel column. (ethyl acetate/dichloromethane, 0%~10%): $^1$H NMR (400 MHz, CDCl$_3$) δ 8.44 (d, J=8.9 Hz, 2H), 8.02 (d, J=9.0 Hz, 2H), 6.82 (m, 2H), 6.74 (b, 1H), 3.71 (t, J=4.2 Hz, 4H), 3.24 (b, 8H), 3.05 (m, 4H), 2.29 (s, 3H); MS (LC/MS, M+H$^+$): 447

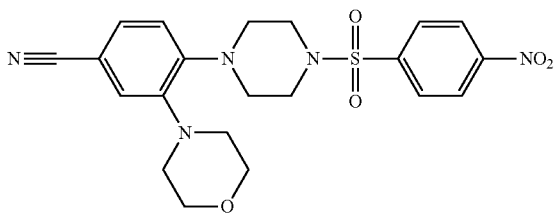 [SMILES: N#Cc1ccc(N2CCN(S(=O)(=O)c3ccc([N+](=O)[O-])cc3)CC2)c(N2CCOCC2)c1]

Preparation of 3-morpholino-4-(4-((4-nitrophenyl)sulfonyl)piperazin-1-yl)benzonitrile: The title compound was prepared according to the procedure for 4-(5-methyl-2-(4-((4-nitrophenyl)sulfonyl)piperazin-1-yl)phenyl)morpholine, except 3-morpholino-4-nitrobenzonitrile was substituted for 4-(5-methyl-2-nitrophenyl)morpholine and 4-amino-3-morpholinobenzonitrile for 4-methyl-2-morpholinoaniline. $^1$H NMR (400 MHz, CDCl$_3$) δ 8.43 (d, J=8.8 Hz, 2H), 8.01 (d, J=8.8 Hz, 2H), 7.30 (dd, J=1.8, 8.2 Hz, 1H), 7.14 (d, J=1.8 Hz, 1H), 6.90 (d, J=8.3 HZ, 1H), 3.73 (t, J=4.5 Hz, 4H), 3.36 (m, 4H), 3.26 (m, 4H), 3.02 (t, J=4.3 Hz, 4H): MS (LC/MS, M+H$^+$): 458

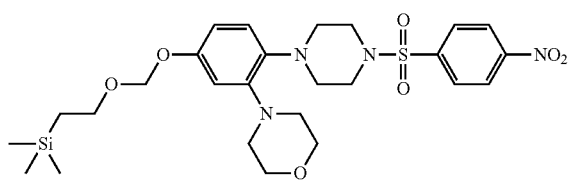

Preparation of 4-(2-(4-((4-nitrophenyl)sulfonyl)piperazin-1-yl)-5-((2-(trimethylsilyl)ethoxy)methoxy)phenyl)morpholine: The title compound was prepared according to the procedure for 4-(5-methyl-2-(4-((4-nitrophenyl)sulfonyl)piperazin-1-yl)phenyl)morpholine, except 4-(2-nitro-5-((2-(trimethylsilyl)ethoxy)methoxy)phenyl)morpholine was substituted for 4-(5-methyl-2-nitrophenyl)morpholine and 2-morpholine-4-((2-(trimethylsilyl)ethoxy)methoxy)aniline for 4-methyl-2-morpholinoaniline. $^1$H NMR (400 MHz, CDCl$_3$) δ 8.41 (d, J=8.8 Hz, 2H), 8.01 (d, J=8.7 Hz, 2H), 6.80 (d, 1=8.7 Hz, 1H), 6.67 (dd, J=2.7, 8.7 Hz, 1H), 6.60 (d, J=2.6 Hz, 1H), 5.14 (s, 2H), 3.74 (m, 2H), 3.68 (t, J=4.4 Hz, 4H), 3.23 (b, 4H), 3.16 (b, 4H), 3.03 (b, 4H), 0.95 (m, 2H), 0.00 (s, 9H): MS (LC/MS, M+H$^+$): 579

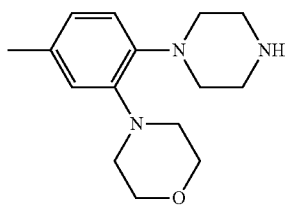 [SMILES: Cc1ccc(N2CCNCC2)c(N2CCOCC2)c1]

Preparation of 4-(5-methyl-2-(piperazin-1-yl)phenyl)morpholine: Potassium carbonate (1.5 g, 10.8 mmol 12 eq.) was added to a mixture of acetonitrile and dimethylsulfoxide (CH$_3$CN/DMSO 49:1, 2.4 mL) and heated to 50CC. Thiophenol (0.988 g, 8.96 mmol, 10 eq.) was added dropwise via syringe to the mixture with stirring. After 30 minutes a solution of 4-(5-methyl-2-(4-((4-nitrophenyl)sulfonyl)piperazin-1-yl)phenyl)morpholine (0.410 g, 0.896 mmol, 1 eq.) in acetonitrile and dimethyl sulfoxide (acetonitrile/dimethyl sulfoxide 49:1, 4.5 mL) was added dropwise. The reaction mixture was stirred for 3 hours, quenched with excess NaOH solution (40%) and concentrated under reduced pressure. The residue was extracted with dichloromethane (5×30 mL) and the organic phase was dried over MgSO$_4$, and concentrated in vacuo to give a crude oil. The oil was purified by reverse phase chromatography (acetonitrile in H$_2$O, gradient from 1%-100% with 0.1% formic acid) to afford the formic acid salt of the desired piperazine. The salt was dissolved in dichloromethane. washed with saturated NaHCO$_3$ solution, and the organic phase concentrated in vacuo to provide the product. $^1$H NMR (400 MHz, CDCl$_3$) δ 6.87-6.76 (m, 2H), 6.71 (s, 1H), 3.84 (t, J=4.5 Hz, 4H), 3.18 (b, 4H), 3.07 (b, 4H), 2.98 (b, 4H), 2.29 (s, 3H): MS (LC/MS, M+H$^+$): 262

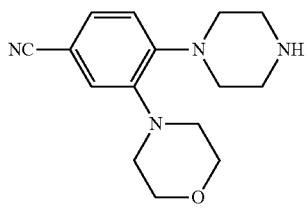 [SMILES: N#Cc1ccc(N2CCNCC2)c(N2CCOCC2)c1]

Preparation of 3-morpholino-4-(piperazin-1-yl)benzonitrile: The title compound was prepared according to the procedure for 4-(5-methyl-2-(piperazin-1-yl)phenyl)morpholine, except 3-morpholino-4-(4-((4-nitrophenyl)sulfonyl)piperazin-1-yl)benzonitrile was substituted for 4-(5-methyl-2-(4-((4-nitrophenyl)sulfonyl)piperazin-1-yl)phenyl)morpholine. $^1$H NMR (400 MHz, CDCl$_3$) δ 7.24 (dd, J=1.8, 8.2 Hz, 1H), 7.08 (d, J=1.8 Hz, 1H), 6.88 (d, J=8.4 Hz, 1H), 3.81 (t, J=4.6 Hz, 4H), 3.21 (b, 4H), 3.11 (b, 4H), 3.00 (b, 4H): MS (LC/MS, M+H$^+$): 273

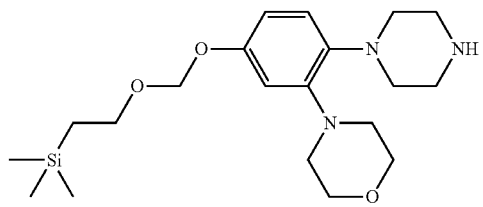 [SMILES: C[Si](C)(C)CCOCOc1ccc(N2CCNCC2)c(N2CCOCC2)c1]

Preparation of 4-(2-(piperazin-1-yl)-5-((2-(trimethylsilyl)ethoxy)methoxy)phenyl)morpholine: The title compound was prepared according to the procedure for 4-(5-methyl-2-(piperazin-1-yl)phenyl)morpholine, except 4-(2-(4-((4-nitrophenyl)sulfonyl)piperazin-1-yl)-5-((2-(trimethylsilyl)ethoxy)methoxy)phenyl)morpholine was substituted for 4-(5-methyl-2-(4-((4-nitrophenyl)sulfonyl)piperazin-1-yl)phenyl)morpholine. $^1$H NMR (400 MHz, CDCl$_3$) δ 6.83 (d, J=8.6 Hz, 1H), 6.67 (dd, J=2.7, 8.5 Hz, 1H), 6.59 (d, J=2.8 Hz, 1H), 3.82 (1, J=4.7 Hz, 4H), 3.74 (m, 2H), 3.18 (b, 4H), 3.10-2.92 (b, 8H), 0.95 (m, 2H), 0.00 (s, 9H); MS (LC/MS, M+H$^+$): 394

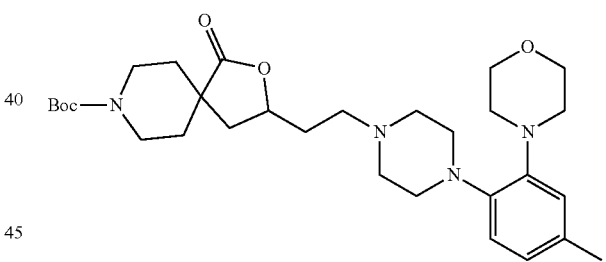

Preparation of tert-butyl 3-(2-(4-(4-methyl-2-morpholinophenyl)piperazin-1-yl)ethyl)-1-oxo-2-oxa-8-azaspiro[4.5]decane-8-carboxylate: A solution of tert-butyl 3-(2-bromoethyl)-1-oxo-2-oxa-8-azaspiro[4.5]decane-8-carboxylate (0.05 g, 0.138 mmol, 1 eq.), 4-(5-methyl-2-(piperazin-1-yl)phenyl)morpholine (0.044 g, 0.166 mmol, 1.2 eq.), and triethylamine (0.070 g, 0.69 mmol, 5 eq.) in acetonitrile (2 mL) was microwaved at 120° C. for 1 hour. The reaction mixture was filtered and the filtrate was concentrated in vacuo to give a crude product. The title compound was purified by column chromatography on a silica gel column. (methanol/dichloromethane, 0%~10%) $^1$H NMR (400 MHz, CDCl$_3$) δ 6.87-6.76 (m, 2H), 6.71 (s, 1H), 4.59 (m, 1H), 3.98 (m, 1H), 3.90-3.73 (m, 5H), 3.31-2.94 (m, 10H), 2.70-2.47 (m, 6H), 2.39 (dd, J=6.2, 12.8 Hz, 1H), 2.28 (s, 3H), 2.03-1.70 (m, 5H), 1.60 (m, 1H), 1.55-1.38 (m, 10H); MS (LC/MS, M+H$^+$): 543

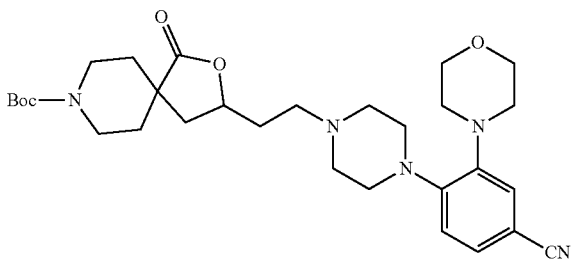 [SMILES: CC(C)(C)OC(=O)N1CCC2(CC1)CC(CCN1CCN(c3ccc(C#N)cc3N3CCOCC3)CC1)OC2=O]

Preparation o tert-butyl-(2-(4-(4-cyano-2-morpholinophenyl)piperazin-1-yl)ethyl)-1-oxo-2-oxa-8-azaspiro[4.5]decane-8-carboxylate: The title compound was prepared according to the procedure for tert-butyl 3-(2-(4-(4-methyl-2-morpholinophenyl)piperazin-1-yl)ethyl)-1-oxo-2-oxa-8-azaspiro[4.5]decane-8-carboxylate, except 3-morpholino-4-(piperazin-1-yl)benzonitrile was substituted for 4-(5-methyl-2-(piperazin-1-yl)phenyl)morpholine. $^1$H NMR (400 MHz, CDCl$_3$) δ 7.26 (dd, J=1.8, 8.3 Hz, 1H), 7.09 (d, J=1.6 Hz, 1H), 6.89 (d, J=8.3 Hz, 1H), 4.57 (m, 1H), 3.96 (m, 1H), 3.89-3.73 (m, 5H), 3.40-2.98 (m, 10H), 2.72-2.45 (m, 6H), 2.37 (dd, J=6.1, 12.8 Hz, 1H), 2.03-1.67 (m, 5H), 1.58 (m, 1H), 1.54-1.38 (m, 10H); MS (LC/MS, M+H$^+$): 554

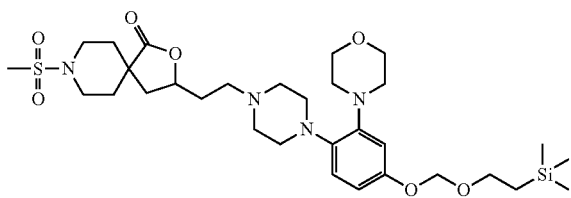

Preparation of 8-(methylsulfonyl)-3-(2-(4-(2-morpholino-4-((2-(trimethylsilyl)ethoxy)methoxy)phenyl)piperazin-1-yl)ethyl)-2-oxa-8-azaspiro[4.5]decan-1-one: The title compound was prepared according to the procedure for tert-butyl 3-(2-(4-(4-methyl-2-morpholinophenyl)piperazin-1-yl)ethyl)-1-oxo-2-oxa-8-azaspiro[4.5]decane-8-carboxylate, except 4-(2-(piperazin-1-yl)-5-((2-(trimethylsilyl)ethoxy)methoxy)phenyl)morpholine was substituted for 4-(5-methyl-2-(piperazin-1-yl)phenyl)morpholine and 3-(2-bromoethyl)-8-(methylsulfonyl)-2-oxa-8-azaspiro[4.5]decan-1-one for tert-butyl 3-(2-bromoethyl)-1-oxo-2-oxa-8-azaspiro[4.5]decane-8-carboxylate. $^1$H NMR (400 MHz, CDCl$_3$) δ 6.83 (d, J=8.6 Hz, 1H), 6.66 (dd, J=2.7, 8.6 Hz, 1H), 6.59 (d, J=2.7 Hz, 1H), 5.14 (s, 2H), 4.61 (m, 1H), 3.81 (t, J=4.4 Hz, 4H), 3.74 (m, 2H), 3.66 (m, 1H), 3.35 (m, 2H), 3.26 (m, 1H), 3.21-2.94 (b, 8H), 2.80 (s, 3H), 2.70-2.41 (m, 6H), 2.30 (dd, J=5.6, 12.9 Hz, 1H), 2.08-1.67 (m, 7H), 0.95 (m, 2H) 0.00 (s, 9H), MS (LC/MS, M+H$^+$): 653

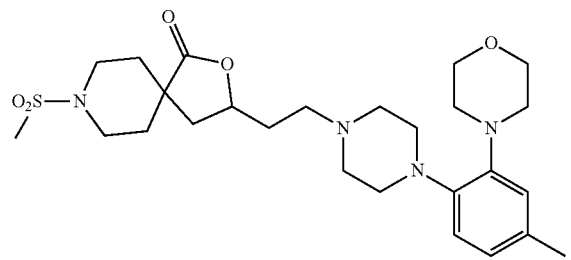

Preparation of 3-(2-(4-(4-methyl-2-morpholinophenyl)piperazin-1-yl)ethyl)-8-(methylsulfonyl)-2-oxa-8-azaspiro[4.5]decan-1-one: A solution of tert-butyl 3-(2-(4-(4-methyl-2-morpholinophenyl)piperazin-1-yl)ethyl)-1-oxo-2-oxa-8-azaspiro[4.5]decane-8-carboxylate (0.077 g, 0.142 mmol, 1 eq.) in trifluoroacetic acid:dichlroromethane (1:3, 2 mL) was allowed to stir at 25° C. for 30 minutes. The reaction solution was diluted with methanol (2 mL) and concentrated in vacuo to give a crude intermediate as a trifluoroacetic acid salt. The resulting material was dissolved in dichloromethane (10 mL) and washed with sat. NaHCO$_3$ (aq.) solution (10 mL). The aqueous layer was backwashed with dichloromethane (2×10 mL) and the combined organic layers were dried over Na$_2$SO$_4$ and concentrated in vacuo to give a crude intermediate as a free base.

The resulting free base (0.052 g, 0.114 mmol, 1 eq.) was dissolved in dichloromethane (2 mL) and cooled to 0° C., and trimethylamine (0.058 g, 0.57 mmol, 5 eq.) and methanesulfonyl chloride (0.026, 0.228 mmol, 2 eq.) were added. The reaction solution was allowed to stir at 25° C. for 30 minutes and then concentrated in vacuo to give a crude solid. The title compound was purified by column chromatography on a silica gel column. (methanol/dichloromethane, 0%~10%) $^1$H NMR (400 MHz, CDCl$_3$) δ 6.79-6.68 (m, 2H), 6.64 (s, 1H), 4.54 (m, 1H), 3.75 (t, J=4.4 Hz, 4H), 3.59 (m, 1H), 3.37-2.88 (b, 11H), 2.74 (s, 3H), 2.69-2.33 (b, 6H), 2.27-2.16 (m, 4H), 2.02-1.92 (m, 2H), 1.92-1.62 (m, 5H): MS (LC/MS, M+H$^+$): 521

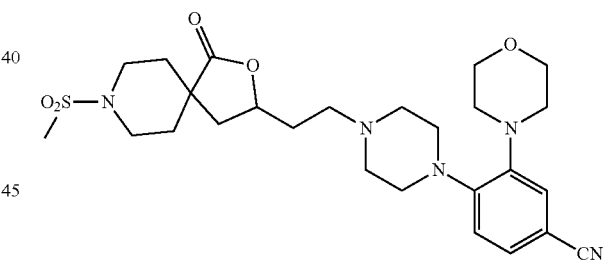

Preparation of 4-(4-(2-(8-(methylsulfonyl)-1-oxo-2-oxa-8-azaspiro[4.5]decan-3-yl)ethyl)piperazin-1-yl)-3-morpholinobenzonitrile: The title compound was prepared according to the procedure for 3-(2-(4-(4-methyl-2-morpholinophenyl)piperazin-1-yl)ethyl)-8-(methylsulfonyl)-2-oxa-8-azaspiro[4.5]decan-1-one, except tert-butyl 3-(2-(4-(4-cyano-2-morpholinophenyl)piperazin-1-yl)ethyl)-1-oxo-2-oxa-8-azaspiro[4.5]decane-8-carboxylate was substituted for 3-(2-(4-(4-methyl-2-morpholinophenyl)piperazin-1-yl)ethyl)-1-oxo-2-oxa-8-azaspiro[4.5]decane-8-carboxylate.
$^1$H NMR (400 MHz, CDCl$_3$) δ 7.29 (dd, J=1.8, 8.3 Hz, 1H), 7.12 (d, J=1.7 Hz, 1H), 6.91 (d, J=8.3 Hz, 1H), 4.63 (m, 1H), 3.85 (t, J=4.3 Hz, 4H), 3.67 (m, 1H), 3.55-2.96 (b, 11H), 2.83 (s, 3H), 2.75-2.40 (b, 6H), 2.30 (dd, J=6.0, 12.9H, 1H) 2.12-1.99 (m, 2H), 1.99-1.71 (m, 5H): MS (LC/MS, M+H$^+$): 532

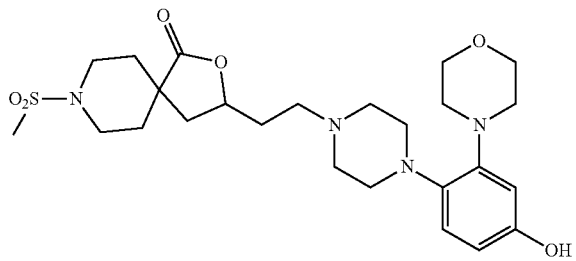 [SMILES: CS(=O)(=O)N1CCC2(CC1)CC(CCN1CCN(c3ccc(C#N)cc3N3CCOCC3)CC1)OC2=O]

Preparation of 3-(2-(4-(4-hydroxy-2-morpholinophenyl)piperazin-1-yl)ethyl)-8-(methylsulfonyl)-2-oxa-8-azaspiro[4.5]decan-1-one: To a small vial, 8-(methylsulfonyl)-3-(2-(4-(2-morpholino-4-((2-(trimethylsilyl)ethoxy)methoxy)phenyl)piperazin-1-yl)ethyl)-2-oxa-8-azaspiro [4.5]decan-1-one (0.190 g, 0.291 mmol, 1 eq.) was added and dissolved in hexamethylphosphoramide (1.5 mL). Tetra-n-butylammonium fluoride trihydrate (0.230 g, 0.873 mmol, 3 eq.) was added, followed by 300 mg of 4 A molecular sieves. The reaction mixture was stirred at 60° C. for 48 hours before being filtered and concentrated in vacuo to give a crude oil. The title compound was purified by column chromatography on a silica gel column (methanol/dichloromethane, 0%~10%) $^1$H NMR (400 MHz, CDCl$_3$) δ 6.70 (d, J=9.2 Hz, 1H), 6.40-6.32 (m, 2H), 4.53 (m, 1H), 3.75 (t, J=4.3 Hz, 4H), 3.58 (m, 1H), 3.38-2.84 (b, 11H), 2.74 (s, 3H), 2.70-2.33 (b, 6H), 2.21 (dd, J=5.9, 12.8 Hz, 1H), 2.01-1.80 (m, 4H), 1.79-1.60 (m, 3H): MS (LC/MS, M+H$^+$): 523.

Formulations

The present invention also relates to compositions or formulations which comprise the 5-hydroxytryptamine receptor 7 activity modulators according to the present invention. In general, the compositions of the present invention comprise an effective amount of one or more compounds of the disclosure and salts thereof according to the present invention which are effective for providing modulation of 5-hydroxytryptamine receptor 7 activity; and one or more excipients.

For the purposes of the present invention the term "excipient" and "carrier" are used interchangeably throughout the description of the present invention and said terms are defined herein as, "ingredients which are used in the practice of formulating a safe and effective pharmaceutical composition."

The formulator will understand that excipients are used primarily to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the fact the compounds of the present invention have improved cellular potency, pharmacokinetic properties, as well as improved oral bioavailability.

The present teachings also provide pharmaceutical compositions that include at least one compound described herein and one or more pharmaceutically acceptable carriers, excipients, or diluents. Examples of such carriers are well known to those skilled in the art and can be prepared in accordance with acceptable pharmaceutical procedures, such as, for example, those described in *Remington's Pharmaceutical Sciences,* 17th edition, ed. Alfonoso R. Gennaro, Mack Publishing Company, Easton, PA (1985), the entire disclosure of which is incorporated by reference herein for all purposes. As used herein, "pharmaceutically acceptable" refers to a substance that is acceptable for use in pharmaceutical applications from a toxicological perspective and does not adversely interact with the active ingredient. Accordingly, pharmaceutically acceptable carriers are those that are compatible with the other ingredients in the formulation and are biologically acceptable. Supplementary active ingredients can also be incorporated into the pharmaceutical compositions.

Compounds of the present teachings can be administered orally or parenterally, neat or in combination with conventional pharmaceutical carriers. Applicable solid carriers can include one or more substances which can also act as flavoring agents, lubricants, solubilizers, suspending agents, Fillers, glidants, compression aids, binders or tablet-disintegrating agents, or encapsulating materials. The compounds can be formulated in conventional manner, for example, in a manner similar to that used for known 5-hydroxytryptamine receptor 7 activity modulators. Oral formulations containing a compound disclosed herein can comprise any conventionally used oral form, including tablets, capsules, buccal forms, troches, lozenges and oral liquids, suspensions or solutions. In powders, the carrier can be a finely divided solid, which is an admixture with a finely divided compound. In tablets, a compound disclosed herein can be mixed with a carrier having the necessary compression properties in suitable proportions and compacted in the shape and size desired. The powders and tablets can contain up to 99% of the compound.

Capsules can contain mixtures of one or more compound(s) disclosed herein with inert filler(s) and/or diluent(s) such as pharmaceutically acceptable starches (e.g., corn, potato or tapioca starch), sugars, artificial sweetening agents, powdered celluloses (e.g., crystalline and microcrystalline celluloses), flours, gelatins, gums, and the like.

Useful tablet formulations can be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrrolidine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes, and ion exchange resins. Surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidal silicon dioxide, phosphates, sodium dodecylsulfate, magnesium aluminum silicate, and triethanolamine. Oral formulations herein can utilize standard delay or time-release formulations to alter the absorption of the compound(s). The oral formulation can also consist of administering a compound disclosed herein in water or fruit juice, containing appropriate solubilizers or emulsifiers as needed.

Liquid carriers can be used in preparing solutions, suspensions, emulsions, syrups, elixirs, and for inhaled delivery. A compound of the present teachings can be dissolved or suspended in a pharmaceutically acceptable liquid carrier such as water, an organic solvent, or a mixture of both, or a pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers, and osmo-regulators. Examples of liquid carriers for oral and parenteral administration include, but are not limited to, water (particularly containing additives as described herein, e.g., cellulose derivatives such as a sodium carboxymethyl cellulose solution), alcohols (including monohydric alcohols and polyhydric alcohols, e.g., glycols) and their derivatives, and oils (e.g., fractionated coconut oil and arachis oil). For parenteral administration, the carrier can be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellants.

Liquid pharmaceutical compositions, which are sterile solutions or suspensions, can be utilized by, for example, intramuscular, intraperitoneal or subcutaneous injection. Sterile solutions can also be administered intravenously. Compositions for oral administration can be in either liquid or solid form.

Preferably the pharmaceutical composition is in unit dosage form, for example, as tablets, capsules, powders, solutions, suspensions, emulsions, granules, or suppositories. In such form, the pharmaceutical composition can be sub-divided in unit dose(s) containing appropriate quantities of the compound. The unit dosage forms can be packaged compositions, for example, packeted powders, vials, ampoules, prefilled syringes or sachets containing liquids. Alternatively, the unit dosage form can be a capsule or tablet itself, or it can be the appropriate number of any such compositions in package form. Such unit dosage form can contain from about 1 mg/kg of compound to about 500 mg/kg of compound, and can be given in a single dose or in two or more doses. Such doses can be administered in any manner useful in directing the compound(s) to the recipient's bloodstream, including orally, via implants, parenterally (including intravenous, intraperitoneal and subcutaneous injections), rectally, vaginally, and transdermally.

When administered for the treatment or inhibition of a particular disease state or disorder, it is understood that an effective dosage can vary depending upon the particular compound utilized, the mode of administration, and severity of the condition being treated, as well as the various physical factors related to the individual being treated. In therapeutic applications, a compound of the present teachings can be provided to a patient already suffering from a disease in an amount sufficient to cure or at least partially ameliorate the symptoms of the disease and its complications. The dosage to be used in the treatment of a specific individual typically must be subjectively determined by the attending physician. The variables involved include the specific condition and its state as well as the size, age and response pattern of the patient.

In some cases it may be desirable to administer a compound directly to the airways of the patient, using devices such as, but not limited to, metered dose inhalers, breath-operated inhalers, multidose dry-powder inhalers, pumps, squeeze-actuated nebulized spray dispensers, aerosol dispensers, and aerosol nebulizers. For administration by intranasal or intrabronchial inhalation, the compounds of the present teachings can be formulated into a liquid composition, a solid composition, or an aerosol composition. The liquid composition can include, by way of illustration, one or more compounds of the present teachings dissolved, partially dissolved, or suspended in one or more pharmaceutically acceptable solvents and can be administered by, for example, a pump or a squeeze-actuated nebulized spray dispenser. The solvents can be, for example, isotonic saline or bacteriostatic water. The solid composition can be, by way of illustration, a powder preparation including one or more compounds of the present teachings intermixed with lactose or other inert powders that are acceptable for intrabronchial use, and can be administered by, for example, an aerosol dispenser or a device that breaks or punctures a capsule encasing the solid composition and delivers the solid composition for inhalation. The aerosol composition can include, by way of illustration, one or more compounds of the present teachings, propellants, surfactants, and co-solvents, and can be administered by, for example, a metered device. The propellants can be a chlorofluorocarbon (CFC), a hydrofluoroalkane (HFA), or other propellants that are physiologically and environmentally acceptable.]

Compounds described herein can be administered parenterally or intraperitoneally. Solutions or suspensions of these compounds or a pharmaceutically acceptable salts, hydrates, or esters thereof can be prepared in water suitably mixed with a surfactant such as hydroxyl-propylcellulose. Dispersions can also be prepared in glycerol, liquid polyethylene glycols, and mixtures thereof in oils. Under ordinary conditions of storage and use, these preparations typically contain a preservative to inhibit the growth of microorganisms.

The pharmaceutical forms suitable for injection can include sterile aqueous solutions or dispersions and sterile powders for the extemporaneous preparation of sterile injectable solutions or dispersions. In some embodiments, the form can sterile and its viscosity permits it to flow through a syringe. The form preferably is stable under the conditions of manufacture and storage and can be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Compounds described herein can be administered transdermally, i.e., administered across the surface of the body and the inner linings of bodily passages including epithelial and mucosal tissues. Such administration can be carried out using the compounds of the present teachings including pharmaceutically acceptable salts, hydrates, or esters thereof, in lotions, creams, foams, patches, suspensions, solutions, and suppositories (rectal and vaginal).

Transdermal administration can be accomplished through the use of a transdermal patch containing a compound, such as a compound disclosed herein, and a carrier that can be inert to the compound, can be non-toxic to the skin, and can allow delivery of the compound for systemic absorption into the blood stream via the skin. The carrier can take any number of forms such as creams and ointments, pastes, gels, and occlusive devices. The creams and ointments can be viscous liquid or semisolid emulsions of either the oil-in-water or water-in-oil type. Pastes comprised of absorptive powders dispersed in petroleum or hydrophilic petroleum containing the compound can also be suitable. A variety of occlusive devices can be used to release the compound into the blood stream, such as a semi-permeable membrane covering a reservoir containing the compound with or without a carrier, or a matrix containing the compound. Other occlusive devices are known in the literature.

Compounds described herein can be administered rectally or vaginally in the form of a conventional suppository. Suppository formulations can be made from traditional materials, including cocoa butter, with or without the addition of waxes to alter the suppository's melting point, and glycerin. Water-soluble suppository bases, such as polyethylene glycols of various molecular weights, can also be used.

Lipid formulations or nanocapsules can be used to introduce compounds of the present teachings into host cells either in viro or in vivo. Lipid formulations and nanocapsules can be prepared by methods known in the art.

To increase the effectiveness of compounds of the present teachings, it can be desirable to combine a compound with other agents effective in the treatment of the target disease. For example, other active compounds (i.e., other active ingredients or agents) effective in treating the target disease can be administered with compounds of the present teachings. The other agents can be administered at the same time or at different times than the compounds disclosed herein.

Compounds of the present teachings can be useful for the treatment or inhibition of a pathological condition or disorder in a mammal, for example, a human subject. The present teachings accordingly provide methods of treating or inhibiting a pathological condition or disorder by providing to a mammal a compound of the present teachings including its pharmaceutically acceptable salt) or a pharmaceutical composition that includes one or more compounds of the present teachings in combination or association with pharmaceutically acceptable carriers. Compounds of the present teachings can be administered alone or in combination with other therapeutically effective compounds or therapies for the treatment or inhibition of the pathological condition or disorder.

Non-limiting examples of compositions according to the present invention include from about 0.001 mg to about 1000 mg of one or more compounds of the disclosure according to the present invention and one or more excipients; from about 0.01 mg to about 100 mg of one or more compounds of the disclosure according to the present invention and one or more excipients: and from about 0.1 mg to about 10 mg of one or more compounds of the disclosure according to the present invention: and one or more excipients.

Procedures

The following procedures can be utilized in evaluating and selecting compounds as 5-hydroxytryptamine receptor 7 activity modulators.

Radiolabel Binding Studies for Scrotonin 5HT7 Receptors, Method 1:

A solution of the compound of the disclosure to be tested is prepared as a 1-mg/ml stock in Assay Buffer or DMSO according to its solubility. A similar stock of the reference compound chlorpromazine is also prepared as a positive control. Eleven dilutions (5× assay concentration) of the compound of the disclosure and chlorpromazine are prepared in the Assay Buffer by serial dilution to yield final corresponding assay concentrations ranging from 10 pM to 10 μM.

A stock concentration of 5 nM [$^3$H]LSD (lysergic acid diethyl amide) is prepared in 50 mM Tris-HCl, 10 mM $MgCl_2$, 1 mM EDTA, pH 7.4 (Assay Buffer). Aliquots (50 μl) of radioligand are dispensed into the wells of a 96-well plate containing 100 μl of Assay Buffer. Duplicate 50-μl aliquots of the compound of the disclosure test and chlorpromazine positive control reference compound serial dilutions are added.

Membrane fractions of cells expressing recombinant $5HT_7$ receptors (50 μL) are dispensed into each well. The membranes are prepared from stably transfected cell lines expressing $5HT_7$ receptors cultured on 10-cm plates by harvesting PBS-rinsed monolayers, resuspending and lysing in chilled, hypotonic 50 mM Tris-HCl. pH 7.4, centrifuging at 20,000×g, decanting the supernatant and storing at −80° C.; the membrane preparations are resuspended in 3 ml of chilled Assay Buffer and homogenized by several passages through a 26 gauge needle before using in the assay.

The 250-μl reactions are incubated at room temperature for 1.5 hours, then harvested by rapid filtration onto 0.3% polyethyleneimine-treated, 96-well filter mats using a 96-well Filtermate harvester. Four rapid 500-μl washes are performed with chilled Assay Buffer to reduce non-specific binding. The filter mats are dried, then scintillant is added to the filters and the radioactivity retained on the filters is counted in a Microbeta scintillation counter.

Raw data (dpm) representing total radioligand binding (i.e., specific+non-specific binding) are plotted as a function of the logarithm of the molar concentration of the competitor (i.e., test or reference compound). Non-linear regression of the normalized (i.e., percent radioligand binding compared to that observed in the absence of test or reference compound) raw data is performed in Prism 4.0 (GraphPad Software) using the built-in three parameter logistic model describing ligand competition binding to radioligand-labeled sites:

$$y=\text{bottom}+[(\text{top}-\text{bottom})/(1+10x-\log IC_{50})]$$

where bottom equals the residual radioligand binding measured in the presence of 10 μM reference compound (i.e., non-specific binding) and top equals the total radioligand binding observed in the absence of competitor. The log $IC_{50}$ (i.e., the log of the ligand concentration that reduces radioligand binding by 50%) is thus estimated from the data and used to obtain the Ki by applying the Cheng-Prusoff approximation:

$$Ki=IC_{50}/(1+[\text{ligand}]/KD)$$

where [ligand] equals the assay radioligand concentration and KD equals the affinity constant of the radioligand for the target receptor.

Compounds of the disclosure are also screened at a single concentration of 10 μM using the same method described for the Radiolabel Binding Studies for Serotonin $5HT_7$ receptors to determine the percent inhibition of [$^3$H]LSD binding.

Radiolabel Binding Studies for Serotonin 5-HT7 Receptors, Method 2:

A solution of the compound of the disclosure to be tested is prepared as a 1-mg/ml stock in Assay Buffer or DMSO according to its solubility. A similar stock of the reference compound chlorpromazine is also prepared as a positive control. Eleven dilutions (5× assay concentration) of the compound of the disclosure and chlorpromazine are prepared in the Assay Buffer by serial dilution to yield final corresponding assay concentrations ranging from 10 μM to 10 μM.

A stock concentration of 5 nM [$^1$H]-5-Hydroxytryptamine ([$^1$H]-5HT) is prepared in 50 mM Tris-HCl, 10 mM $MgCl_2$, 1 mM EDTA, pH 7.4 (Assay Buffer). Aliquots (50 μl) of radioligand are dispensed into the wells of a 96-well plate containing 100 μl of Assay Buffer. Duplicate 50-μl aliquots of the compound of the disclosure test and chlorpromazine positive control reference compound serial dilutions are added.

Membrane fractions of cells expressing recombinant 5HT$_7$ receptors (50 μL) are dispensed into each well. The membranes are prepared from stably transfected cell lines expressing 5HT$_7$ receptors cultured on 10-cm plates by harvesting PBS-rinsed monolayers, resuspending and lysing in chilled, hypotonic 50 mM Tris-HCl, pH 7.4, centrifuging at 20,000×g, decanting the supernatant and storing at −80° C.: the membrane preparations are resuspended in 3 ml of chilled Assay Buffer and homogenized by several passages through a 26 gauge needle before using in the assay.

The 250-μl reactions are incubated at room temperature for 1.5 hours, then harvested by rapid filtration onto 0.3% polyethyleneimine-treated, 96-well filter mats using a 96-well Filtermate harvester. Four rapid 500-μl washes are performed with chilled Assay Buffer to reduce non-specific binding. The filter mats are dried, then scintillant is added to the filters and the radioactivity retained on the filters is counted in a Microbeta scintillation counter.

Raw data (dpm) representing total radioligand binding (i.e., specific+non-specific binding) are plotted as a function of the logarithm of the molar concentration of the competitor (i.e., test or reference compound). Non-linear regression of the normalized (i.e., percent radioligand binding compared to that observed in the absence of test or reference compound) raw data is performed in Prism 4.0 (GraphPad Software) using the built-in three parameter logistic model describing ligand competition binding to radioligand-labeled sites:

$$y=\text{bottom}+((\text{top}-\text{bottom})/(1+10^{x-\log IC_{50}})]$$

where bottom equals the residual radioligand binding measured in the presence of 10 μM reference compound (i.e., non-specific binding) and top equals the total radioligand binding observed in the absence of competitor. The log IC$_{50}$ (i.e., the log of the ligand concentration that reduces radioligand binding by 50%) is thus estimated from the data and used to obtain the Ki by applying the Cheng-Prusoff approximation:

$$Ki=IC_{50}/(1+[\text{ligand}]/KD)$$

where [ligand] equals the assay radioligand concentration and KD equals the affinity constant of the radioligand for the target receptor.

Compounds of the disclosure are also screened at a single concentration of 10 μM using the same method described for the Radiolabel Binding Studies for Scrotonin 5HT$_7$ receptors to determine the percent inhibition of [$^3$H]-5HT binding.

Results for representative compounds according to the present invention are listed in Table 11.

TABLE 11

Radiolabel Binding Studies for Serotonin 5HT$_7$ receptors results for exemplary compounds of the disclosure

| Entry | Structure | 5-HT7 % inhib @10 uM | 5-HT$_7$ IC$_{50}$ (nm) |
|---|---|---|---|
| 1 | 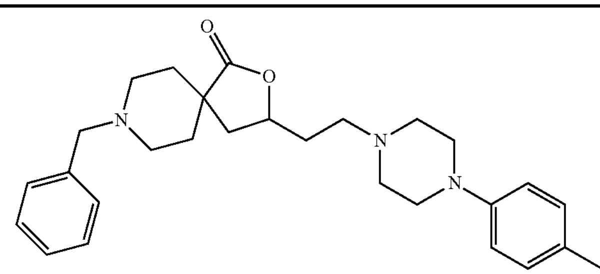 | 96.5 | 18 |
| 2 | 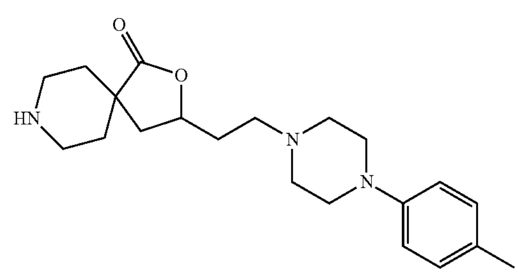 [SMILES: Cc1ccc(N2CCN(CCC3CC4(CCNCC4)C(=O)O3)CC2)cc1] | 88.8 | 149 |
| 3 | 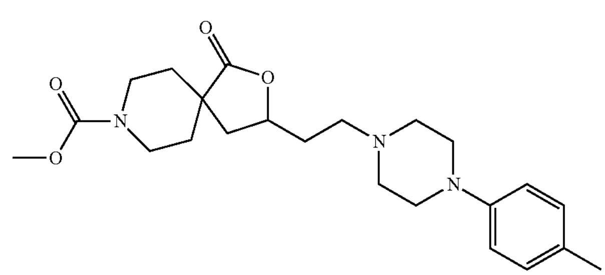 | 90 | 81 |

TABLE 11-continued

Radiolabel Binding Studies for Serotonin 5HT$_7$ receptors results for exemplary compounds of the disclosure

| Entry | Structure | 5-HT7 % inhib @10 uM | 5-HT$_7$ IC$_{50}$ (nm) |
|---|---|---|---|
| 4 | 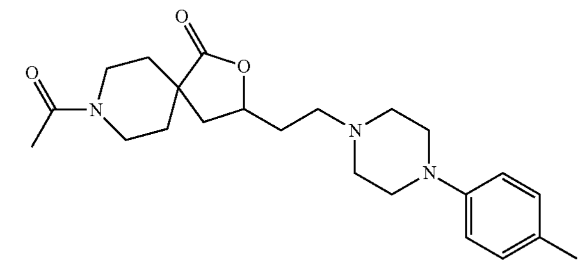 [SMILES: CC(=O)N1CCC2(CC1)CC(CCN1CCN(c3ccc(C)cc3)CC1)OC2=O] | 88.5 | 122 |
| 5 | 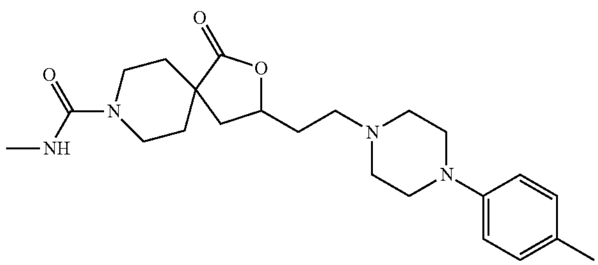 | 91.6 | 102 |
| 6 | 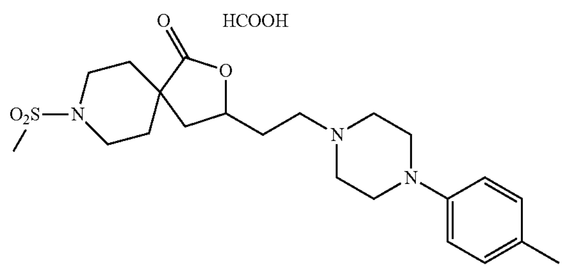 | 90.5 | 93 |
| 7 | 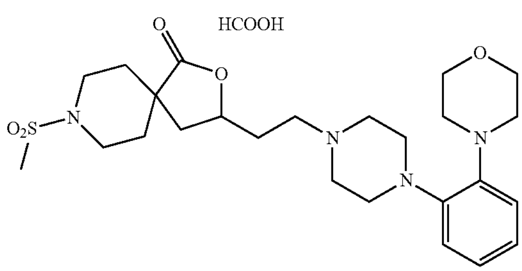 [SMILES: CS(=O)(=O)N1CCC2(CC1)CC(CCN1CCN(c3ccccc3N3CCOCC3)CC1)OC2=O ; "HCOOH"] | N.D. | 34 |
| 8 | 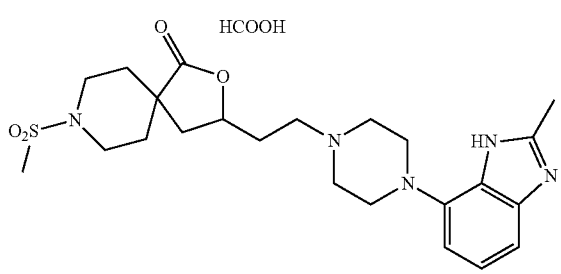 | 100 | 46 |

TABLE 11-continued

Radiolabel Binding Studies for Serotonin 5HT$_7$ receptors results for exemplary compounds of the disclosure

| Entry | Structure | 5-HT7 % inhib @10 uM | 5-HT$_7$ IC$_{50}$ (nm) |
|---|---|---|---|
| 9 | 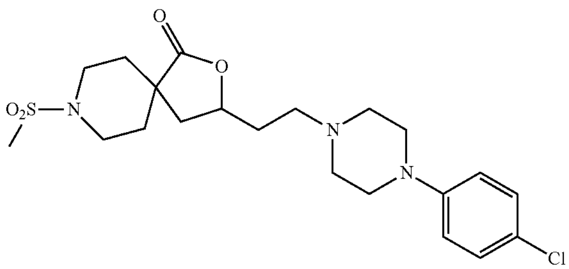 [SMILES: CS(=O)(=O)N1CCC2(CC1)CC(CCN1CCN(c3ccc(Cl)cc3)CC1)OC2=O] | N.D. | 303 |
| 10 | 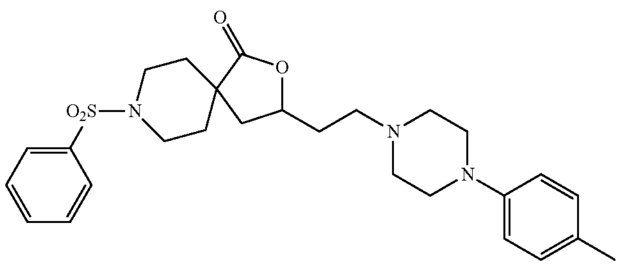 [SMILES: Cc1ccc(N2CCN(CCC3CC4(CCN(S(=O)(=O)c5ccccc5)CC4)C(=O)O3)CC2)cc1] | N.D. | 64 |
| 11 | 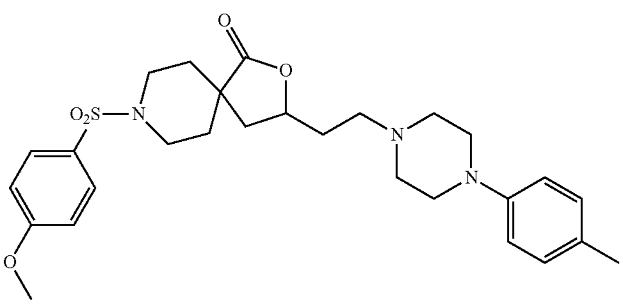 [SMILES: COc1ccc(S(=O)(=O)N2CCC3(CC2)CC(CCN2CCN(c4ccc(C)cc4)CC2)OC3=O)cc1] | N.D. | 77 |
| 12 | 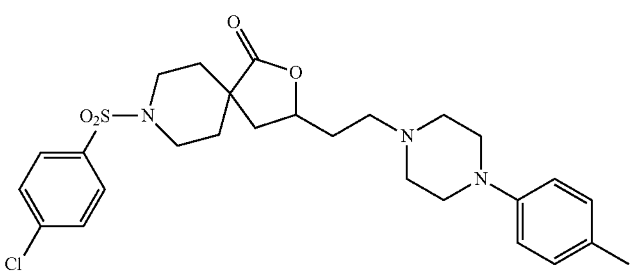 [SMILES: Cc1ccc(N2CCN(CCC3CC4(CCN(S(=O)(=O)c5ccc(Cl)cc5)CC4)C(=O)O3)CC2)cc1] | N.D. | 108 |
| 13 | (HCOOH) | N.D. | 96 |

TABLE 11-continued

Radiolabel Binding Studies for Serotonin 5HT$_7$ receptors results for exemplary compounds of the disclosure

| Entry | Structure | 5-HT7 % inhib @10 uM | 5-HT$_7$ IC$_{50}$ (nm) |
|---|---|---|---|
| 14 | 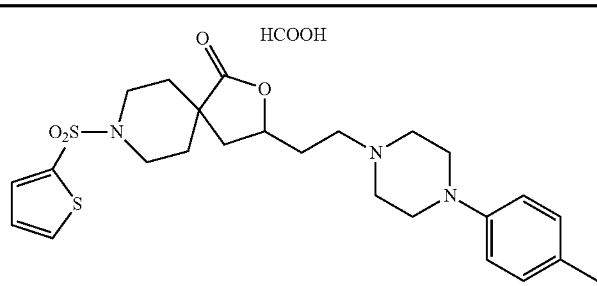 | N.D. | 47 |
| 15 | 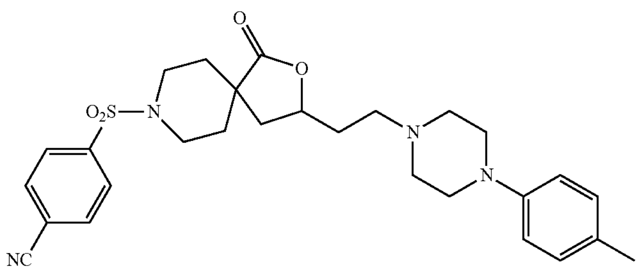 [SMILES: Cc1ccc(N2CCN(CCC3CC4(CCN(S(=O)(=O)c5ccc(C#N)cc5)CC4)C(=O)O3)CC2)cc1] | N.D. | 131 |
| 16 | 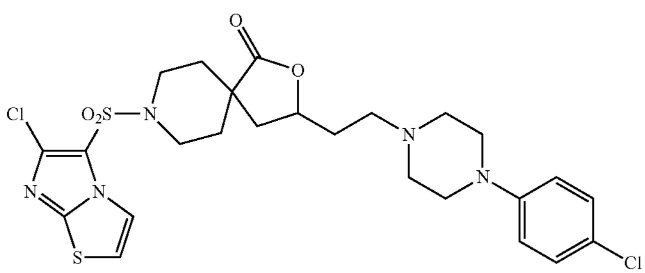 [SMILES: O=C1OC(CCN2CCN(c3ccc(Cl)cc3)CC2)CC12CCN(S(=O)(=O)c1c(Cl)nc3sccn13)CC2] | N.D. | 56 |
| 17 | 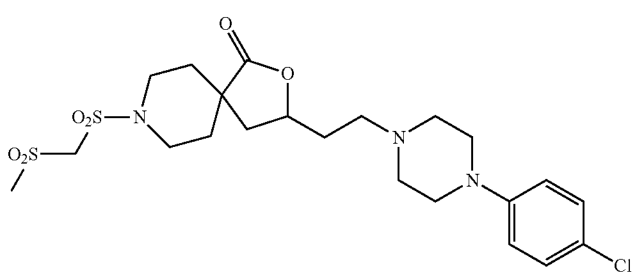 [SMILES: CS(=O)(=O)CS(=O)(=O)N1CCC2(CC1)CC(CCN1CCN(c3ccc(Cl)cc3)CC1)OC2=O] | N.D. | 116 |
| 18 | 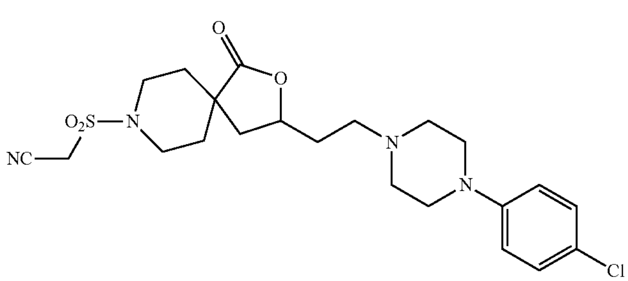 [SMILES: N#CCS(=O)(=O)N1CCC2(CC1)CC(CCN1CCN(c3ccc(Cl)cc3)CC1)OC2=O] | N.D. | 86 |

TABLE 11-continued

Radiolabel Binding Studies for Serotonin 5HT$_7$ receptors results for exemplary compounds of the disclosure

| Entry | Structure | 5-HT7 % inhib @10 uM | 5-HT$_7$ IC$_{50}$ (nm) |
|---|---|---|---|
| 19 | 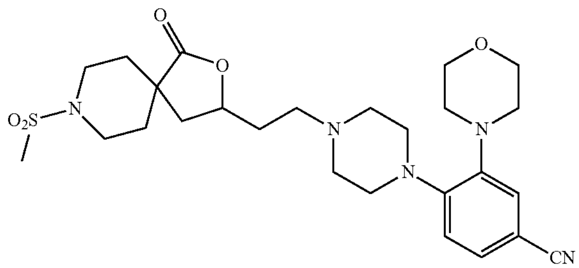 | N.D. | 461 |
| 20 | 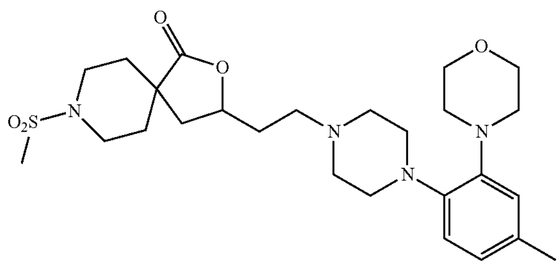 | N.D. | 67 |
| 21 | 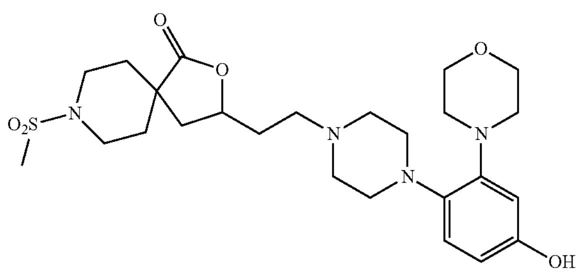 [SMILES: CS(=O)(=O)N1CCC2(CC1)CC(CCN1CCN(c3ccc(C#N)cc3N3CCOCC3)CC1)OC2=O] | N.D. | 75 |
| 22 | 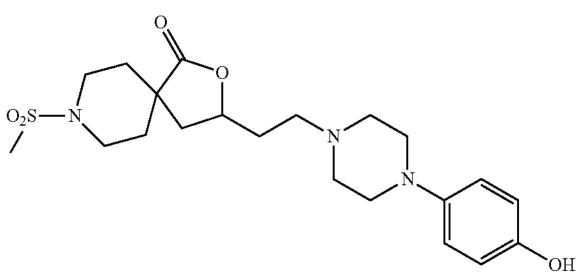 [SMILES: CS(=O)(=O)N1CCC2(CC1)CC(CCN1CCN(c3ccc(O)cc3)CC1)OC2=O] | N.D. | 202 |

N.D. = not determined

Functional Serotonin 5HT$_7$ Assay, Method 1:

Cell lines stably expressing human 5HT$_7$ receptors are seeded in 96-well, poly-L-lysine-coated plates 48 hours prior to the assay (40,000 cells per well) in Dulbecco's Modified Eagle Medium (DMEM) containing 5% dialyzed serum. Twenty hours prior to the assay, the medium is changed to scrum-free DMEM. On the day of the assay, the DMEM is washed and replaced with 30 µl of assay buffer (1× Krebs-Ringer bicarbonate glucose buffer, 0.75 mM IBMX, pH 7.4). A 10-min pre-incubation is performed in a 37-degree centigrade, humidified incubator. Then, the cells are stimulated by addition of 30 µl of 2× dilutions of compounds of the disclosure or chlorpromazine (final concentrations ranging from 0.1 nM to 10 µM, each concentration assayed in triplicate). A positive control (100 µM forskolin) is also included. Accumulation of cAMP is allowed to continue for 15 min, after which the buffer is removed and the cells are lysed with Cell Lysis Buffer (CatchPoint cAMP Assay Kit, Molecular Devices). Next, the lysates are transferred to 96-well, glass-bottom plates coated with goat anti-rabbit IgG and adsorbed with rabbit anti-cAMP (Molecular Devices). Following a 5 minute incubation, horseradish peroxidase-cAMP conjugate is added (Molecular Devices) and a 2-hour incubation is performed at room temperature. Then, after three washes with Wash Buffer (Molecular Devices), Stoplight Red substrate (Molecular Devices), reconstituted in Substrate Buffer (Molecular Devices) containing freshly-added 1 mM H$_2$O$_2$, is added and, after a 15-min incubation at room temperature, fluorescence is measured (excitation 510-545 nm, emission 565-625 nm). For each assay, a cAMP calibration curve is generated and controls without lysate and without antibody are included.

For agonist tests, raw data (maximum fluorescence, fluorescence units) for each concentration of the compounds of the disclosure or chlorpromazine are normalized to the basal (vehicle-stimulated) fluorescence (reported as fold increase over basal) and plotted as a function of the logarithm of the molar concentration of the drug (i.e., test or reference compound). Non-linear regression of the normalized data is performed in Prism 4.0 (GraphPad Software) using the built-in three parameter logistic model (i.e., sigmoidal concentration-response) describing agonist-stimulated activation of one receptor population:

$$y = \text{bottom} + [(\text{top} - \text{bottom})/(1 + 10x - \log EC50)]$$

where bottom equals the best-fit basal fluorescence and top equals the best-fit maximal fluorescence stimulated by the compound of the disclosure or chlorpromazine. The log $EC_{50}$ (i.e., the log of the drug concentration that increases fluorescence by 50% of the maximum fluorescence observed for the compound of the disclosure or chlorpromazine is thus estimated from the data, and the $EC_{50}$ (agonist potency) is obtained. To obtain an estimate of the relative efficacy of the test compound (Rel. Emax), its best-fit top is compared to and expressed as a ratio of that for the chlorpromazine (Rel. Emax of the reference agonist is 1.00).

To ascertain whether compounds of the disclosure are antagonists, a double-addition paradigm is employed. First, 30 μl of a compound of the disclosure (20 μM) is added (10 μM final concentration) and a 15 minute incubation is performed. Then, 30 μl of chlorpromazine (3×: $EC_{50}$) is added (final concentration of agonist is EC30) and cAMP accumulation is allowed to proceed for 15 minutes. The samples are then processed for cAMP measurements as detailed above. Measurements of chlorpromazine-induced cAMP accumulation are compared to the signals elicited by the chlorpromazine following addition of vehicle instead of test compound and expressed as a ratio. 'Hits' (compounds that antagonize chlorpromazine-stimulated increases in baseline-normalized fluorescence by at least 50%) are then characterized by a modified Schild analysis.

For modified Schild analysis, a family of chlorpromazine concentration-response isotherms is generated in the absence and presence of graded concentrations of test compound (added 15 min prior to reference agonist). Theoretically, compounds that are competitive antagonists cause a dextral shift of agonist concentration-response isotherms without reducing the maximum response to agonist (i.e., surmountable antagonism). However, on occasion, factors such as non-competitive antagonism, hemiequilibria, and/or receptor reserve cause apparent insurmountable antagonism. To account for such deviations, we apply the modified Lew-Angus method to ascertain antagonist potency (Christopoulos et al., 1999). Briefly, equieffective concentrations of agonist (concentrations of agonist that elicit a response equal to the ECs of the agonist control curve) are plotted as a function of the compound of the disclosure concentration present in the wells in which they were measured. Non-linear regression of the baseline-normalized data is performed in Prism 4.0 using the following equation:

$$pEC25\% = -\log([B] + 10 - pK) - \log c$$

where EC25% equals the concentration of agonist that elicits a response equal to 25% of the maximum agonist control curve response and [B] equals the antagonist concentration: K, c, and s are fit parameters. The parameter s is equal to the Schild slope factor. If s is not significantly different from unity, pK equals pKB: otherwise, pA2 is calculated (pA2=pK/s). The parameter c equals the ratio $EC_{2.5\%}/[B]$.

Functional Efficacy Assay for 5-HT7 Receptors Method 2:

Functional efficacy of the compounds of the disclosure on 5-HT7 serotonin receptors were measured in a cell based cAMP enzyme fragment complementation assay using the HitHunter cAMP assay (DiscoveRx). Cells stably expressing human 5HT7 receptors were plated in 96-well plates at 4000 cells/well, 16-20 hours prior to assay in growth media (Ultraculture medium, 2 mM GlutaMax and G418 1 mg/mL. Serial dilutions of the agonist, 5-Carboxamidotryptamine (5-CT), were prepared in a final concentration range of 10 μM to 10 nM. Compounds of the disclosure were prepared in 3-fold serial dilutions to obtain a final concentration range of 10 μM to 0.1 nM. Compounds of the disclosure are tested for agonist activity in the absence of 5-CT and antagonist activity in the presence of 5-CT. For the cAMP assay, the protocol was followed according to the instructions provided by the supplier. Briefly, cells were incubated with a compound of the disclosure for 30 minutes at 37° C. prior to addition of $EC_{70}$ concentration of 5-CT. After an additional 30 minutes, cAMP antibody/cell lysis solution was added (20 μL/well) and incubated for 60 minutes at room temperature. cAMP XS+EA reagent is added (20 μL/well) and incubated for 2 hours at room temperature. Luminescence was read on the Envision Multilabel plate reader.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A compound having formula (XXV):

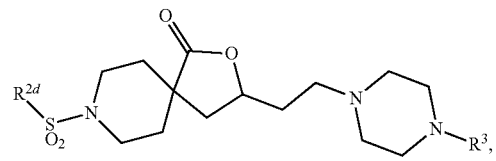

(XXV)

or a pharmaceutically acceptable salt thereof, wherein: $R^{2d}$ is

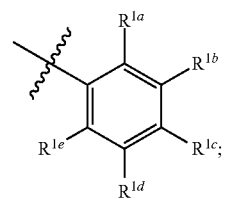

$R^{1a}$, $R^{1b}$, $R^{1c}$, $R^{1d}$, and $R^{1e}$ are at each occurrence independently selected from the group consisting of H, halogen, CN, $C_{1-6}$ linear alkyl, and $C_{1-6}$ linear alkoxy; and $R^3$ is optionally substituted phenyl.

2. The compound of claim 1, wherein $R^{2d}$ is unsubstituted phenyl, 4-methoxyphenyl, 4-chlorophenyl, or 4-cyanophenyl.

3. The compound of claim 1, wherein $R^3$ is selected from the group consisting of phenyl, 4-Me-phenyl, 2-morpholino-phenyl, 4-Cl-phenyl, 4-cyano-2-morpholino-phenyl, 4-methyl-2-morpholino-phenyl, 4-hydroxy-2-morpholino-phenyl, and 4-OH-phenyl.

4. A pharmaceutical composition comprising the compound of claim 1, or a pharmaceutically acceptable salt thereof, and a pharmaceutically acceptable excipient.

5. The compound of claim 1, wherein the compound is selected from the group consisting of:

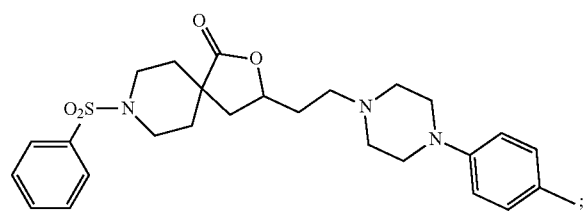

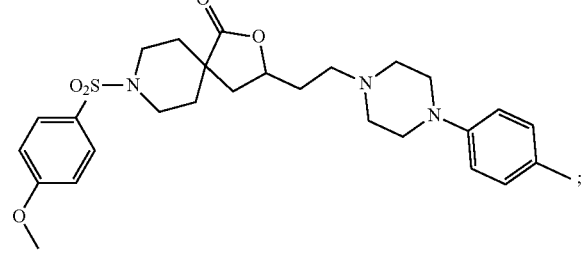

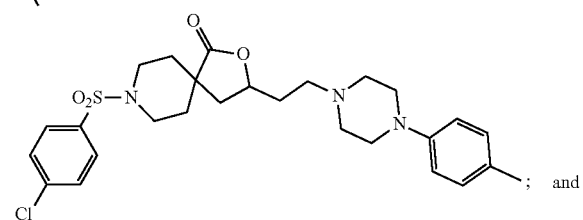

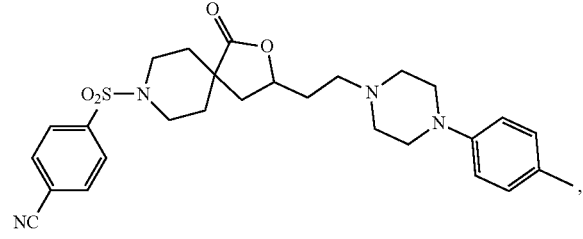

or a pharmaceutically acceptable salt thereof.

6. A compound having formula (XXV):

(XXV)

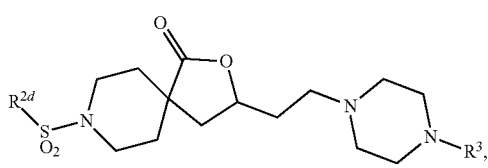

or a pharmaceutically acceptable salt thereof, wherein:
$R^{2d}$ is

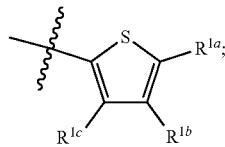

$R^{1a}$, $R^{1b}$, and $R^{1c}$ are at each occurrence independently selected from the group consisting of H, halogen, CN, $C_{1-6}$ linear alkyl, and $C_{1-6}$ linear alkoxy; and
$R^3$ is optionally substituted phenyl.

7. The compound of claim 6, wherein $R^{2d}$ is

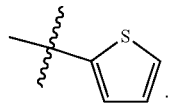

8. The compound of claim 6, wherein $R^3$ is selected from the group consisting of phenyl, 4-Me-phenyl, 2-morpholino-phenyl, 4-Cl-phenyl, 4-cyano-2-morpholino-phenyl, 4-methyl-2-morpholino-phenyl, 4-hydroxy-2-morpholino-phenyl, and 4-OH-phenyl.

9. A pharmaceutical composition comprising the compound of claim 6, or a pharmaceutically acceptable salt thereof, and a pharmaceutically acceptable excipient.

10. A compound having formula (XXV):

(XXV)

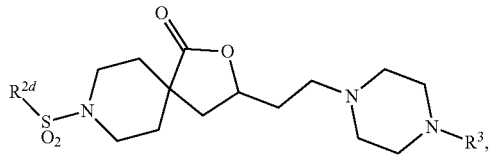

or a pharmaceutically acceptable salt thereof, wherein:
$R^{2d}$ is $C_{1-6}$ linear alkyl; and
$R^3$ is optionally substituted phenyl.

11. The compound of claim 10, wherein $R^{2d}$ is methyl.

12. The compound of claim 10, wherein $R^3$ is selected from the group consisting of phenyl, 4-Me-phenyl, 2-morpholino-phenyl, 4-Cl-phenyl, 4-cyano-2-morpholino-phenyl, 4-methyl-2-morpholino-phenyl, 4-hydroxy-2-morpholino-phenyl, and 4-OH-phenyl.

13. A pharmaceutical composition comprising the compound of claim 10, or a pharmaceutically acceptable salt thereof, and a pharmaceutically acceptable excipient.

14. The compound of claim 6, wherein the compound is

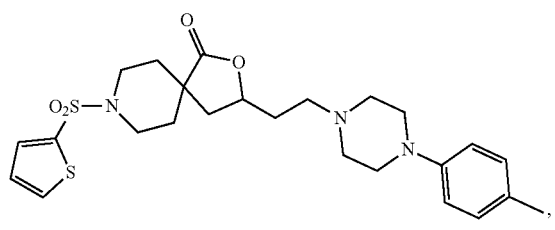

HCOOH or a pharmaceutically acceptable salt thereof.

15. The compound of claim 10, wherein the compound is selected from the group consisting of:
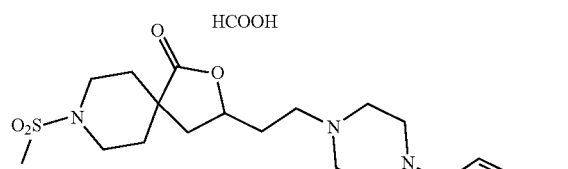
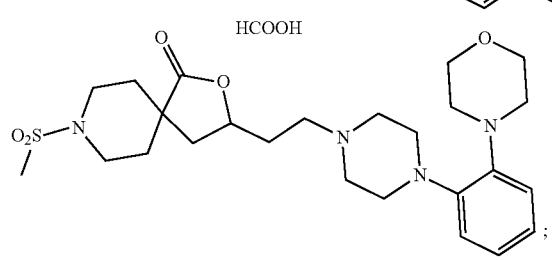
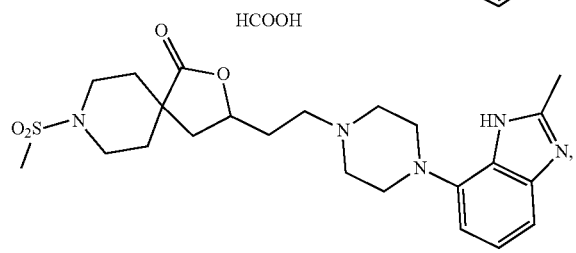
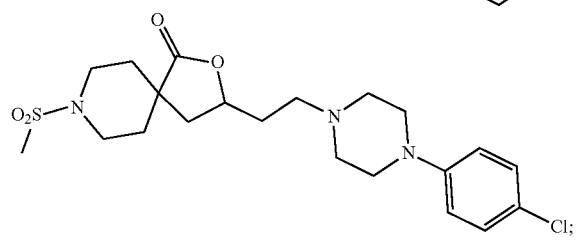
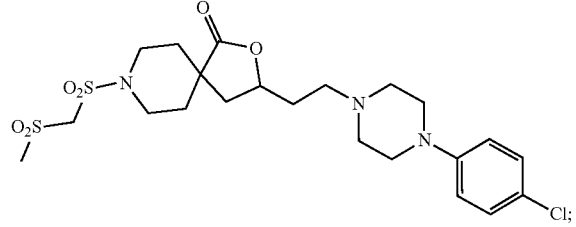
-continued
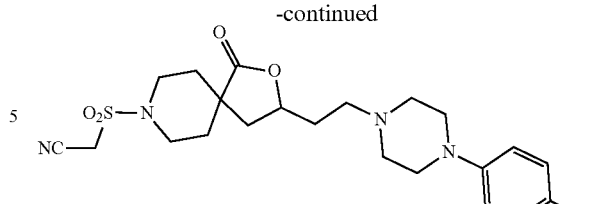
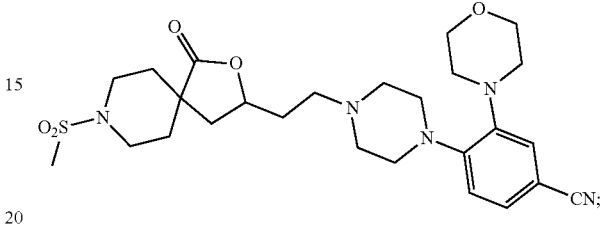
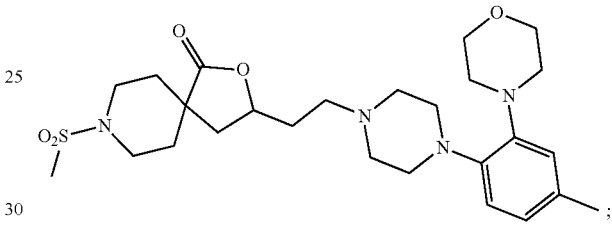
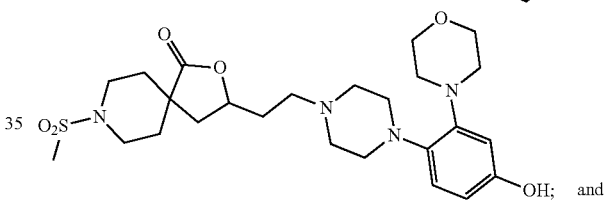
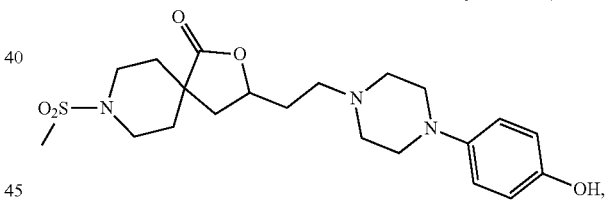
or a pharmaceutically acceptable salt thereof.
* * * * *